United States Patent
Sommadossi et al.

(10) Patent No.: US 9,249,173 B2
(45) Date of Patent: Feb. 2, 2016

(54) COMPOUNDS AND PHARMACEUTICAL COMPOSITIONS FOR THE TREATMENT OF VIRAL INFECTIONS

(71) Applicants: Idenix Pharmaceuticals, Inc., Cambridge, MA (US); Centre National de la Recherche Scientifique, Paris (FR); Universite Montpellier II, Montpellier (FR)

(72) Inventors: Jean-Pierre Sommadossi, Cambridge, MA (US); Gilles Gosselin, Montpellier (FR); Claire Pierra, Montramaud (FR); Christian Perigaud, Grabels (FR); Suzanne Peyrottes, Grabels (FR)

(73) Assignee: Idenix Pharmaceuticals, LLC, Cambridge, MA (US)

( * ) Notice: Subject to any disclaimer, the term of this patent is extended or adjusted under 35 U.S.C. 154(b) by 0 days.

(21) Appl. No.: 14/197,078

(22) Filed: Mar. 4, 2014

(65) Prior Publication Data

US 2014/0255339 A1    Sep. 11, 2014

Related U.S. Application Data

(60) Division of application No. 13/116,890, filed on May 26, 2011, now Pat. No. 8,691,788, which is a continuation of application No. 12/005,937, filed on Dec. 27, 2007, now Pat. No. 7,951,789.

(60) Provisional application No. 60/877,944, filed on Dec. 28, 2006, provisional application No. 60/936,290, filed on Jun. 18, 2007, provisional application No. 60/985,891, filed on Nov. 6, 2007.

(51) Int. Cl.
| | |
|---|---|
| *A61K 31/70* | (2006.01) |
| *C07H 17/02* | (2006.01) |
| *C07F 9/6558* | (2006.01) |
| *C07F 9/6561* | (2006.01) |
| *C07H 19/00* | (2006.01) |
| *A61K 31/675* | (2006.01) |
| *A61K 31/7056* | (2006.01) |
| *A61K 31/7064* | (2006.01) |
| *A61K 31/7068* | (2006.01) |
| *A61K 31/7072* | (2006.01) |
| *A61K 31/7076* | (2006.01) |
| *A61K 31/708* | (2006.01) |

(52) U.S. Cl.
CPC .............. *C07H 17/02* (2013.01); *A61K 31/675* (2013.01); *A61K 31/708* (2013.01); *A61K 31/7056* (2013.01); *A61K 31/7064* (2013.01); *A61K 31/7068* (2013.01); *A61K 31/7072* (2013.01); *A61K 31/7076* (2013.01); *C07F 9/65586* (2013.01); *C07F 9/65616* (2013.01); *C07H 19/00* (2013.01)

(58) Field of Classification Search
USPC .................................................. 514/50, 43
See application file for complete search history.

(56) References Cited

U.S. PATENT DOCUMENTS

| | | |
|---|---|---|
| 3,480,613 A | 11/1969 | Walton |
| 5,627,185 A | 5/1997 | Gosselin et al. |
| 6,174,868 B1 | 1/2001 | Anderson et al. |
| 6,284,458 B1 | 9/2001 | Anderson et al. |
| 6,348,587 B1 | 2/2002 | Schinazi et al. |
| 6,391,542 B1 | 5/2002 | Anderson et al. |
| 6,423,489 B1 | 7/2002 | Anderson et al. |
| 6,433,159 B1 | 8/2002 | Anderson |
| 6,455,513 B1 | 9/2002 | McGuigan et al. |
| 6,555,676 B2 | 4/2003 | Gosselin et al. |
| 6,566,365 B1 | 5/2003 | Storer |
| 6,573,247 B1 | 6/2003 | McGuigan et al. |
| 6,608,191 B1 | 8/2003 | Anderson et al. |
| 6,638,919 B2 | 10/2003 | McGuigan et al. |
| 6,653,296 B1 | 11/2003 | Holy et al. |
| 6,660,721 B2 | 12/2003 | Devos et al. |
| 6,752,981 B1 | 6/2004 | Erion et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,787,526 B1 | 9/2004 | Bryant et al. |
| 6,812,219 B2 | 11/2004 | LaColla et al. |
| 6,833,361 B2 | 12/2004 | Hong et al. |
| 6,846,810 B2 | 1/2005 | Martin et al. |
| 6,849,726 B2 | 2/2005 | Usman et al. |
| 6,852,535 B1 | 2/2005 | Thompson |
| 6,911,424 B2 | 6/2005 | Schinazi et al. |

(Continued)

FOREIGN PATENT DOCUMENTS

| | | |
|---|---|---|
| CN | 101333235 A | 12/2008 |
| EP | 1655033 A1 | 10/2006 |

(Continued)

OTHER PUBLICATIONS

Ariza, "Current Prodrug Strategies for the Delivery of Nucleotides into Cells," Drug Design Reviews-Online, 2005, 2, 373-87.

Ariza, "Current Prodrug Strategies for the Delivery of Nuleotides into Cells," Drug Design Reviews-Online, 2005, 2, 373-387.

Ballatore, et al., "Synthesis and Evaluation of Novel Amidate Prodrugs of PMEA and PMPA," Bioorganic & Medicinal Chemistry Letters 11, 2001 1053-1056.

Beltran, et al., "Rational Design of a New Series of Pronucleotide," Bioorganic & Medicinal Chemistry Letters, 11, 2001, 1775-1777.

Birkus, Cathepsin A Is the Major Hydrolase Catalyzing the Intracellular Hydrolysis of the Antiretroviral Nucleotide Phosphonoamidate Prodrugs GS-7340 and GS-9131, Antimicrobial Agents and Chemotherapy, 2007, 543-550.

Cahard, et al., "Aryloxy Phosphoramidate Triesters as Pro-Tides," Mini-Reviews in Medicinal Chemistry, 2004, 4, 371-382.

Chapman, et al., "Practical Synthesis, Separation, and Stereochemical Assignment of the PMPA Pro-Drub GS-7340," Nucleosides, Nucleotides & Nucleic Acids, 20(4-7), 621-628, 2001.

(Continued)

*Primary Examiner* — Rei-Tsang Shiao
(74) *Attorney, Agent, or Firm* — Jones Day

(57) ABSTRACT

Provided herein are compounds, compositions and methods for the treatment of liver disorder, including HCV and/or HBV infections. Specifically, compound and compositions of nucleoside derivatives are disclosed, which can be administered either alone or in combination with other anti-viral agents.

23 Claims, 2 Drawing Sheets

(56) References Cited

U.S. PATENT DOCUMENTS

| | | |
|---|---|---|
| 6,914,054 B2 | 7/2005 | Sommadossi et al. |
| 6,927,291 B2 | 8/2005 | Jin et al. |
| 6,984,634 B2 | 1/2006 | Cundy et al. |
| 6,995,146 B2 | 2/2006 | Anderson et al. |
| 7,018,989 B2 | 3/2006 | McGuigan et al. |
| 7,019,135 B2 | 3/2006 | McGuigan et al. |
| 7,022,828 B2 | 4/2006 | McSwiggen |
| 7,034,009 B2 | 4/2006 | Pavco et al. |
| 7,041,817 B2 | 5/2006 | Usman et al. |
| 7,094,770 B2 | 8/2006 | Watanabe et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,109,165 B2 | 9/2006 | Matulic-Adamic et al. |
| 7,125,855 B2 | 10/2006 | Bhat et al. |
| 7,138,376 B2 | 11/2006 | Gosselin et al. |
| 7,144,877 B2 | 12/2006 | Gallop et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,176,304 B2 | 2/2007 | McSwiggen et al. |
| 7,192,936 B2 | 3/2007 | LaColla et al. |
| 7,202,224 B2 | 4/2007 | Eldrup et al. |
| 7,285,658 B2 | 10/2007 | Cook et al. |
| 7,300,924 B2 | 11/2007 | Boojamra et al. |
| 7,307,065 B2 | 12/2007 | Schinazi et al. |
| 7,323,449 B2 | 1/2008 | Olsen et al. |
| 7,323,453 B2 | 1/2008 | Olsen et al. |
| 7,365,057 B2 | 4/2008 | LaColla et al. |
| 7,384,924 B2 | 6/2008 | LaColla et al. |
| 7,456,155 B2 | 11/2008 | Sommadossi et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,600 B2 | 10/2009 | Storer et al. |
| 7,625,875 B2 | 12/2009 | Gosselin et al. |
| 7,635,689 B2 | 12/2009 | LaColla et al. |
| 7,662,798 B2 | 2/2010 | LaColla et al. |
| 7,781,576 B2 | 8/2010 | Mayes et al. |
| 7,807,653 B2 | 10/2010 | Cook et al. |
| 7,824,851 B2 | 11/2010 | Sommadossi et al. |
| 7,879,815 B2 | 2/2011 | MacCoss et al. |
| 7,902,202 B2 | 3/2011 | Sommadossi et al. |
| 7,951,789 B2 | 5/2011 | Sommadossi et al. |
| 8,183,216 B2 | 5/2012 | DiFrancesco et al. |
| 8,299,038 B2 | 10/2012 | Sommadossi et al. |
| 8,507,460 B2 | 8/2013 | Surleraux et al. |
| 8,637,475 B1 | 1/2014 | Storer et al. |
| 8,680,071 B2 | 3/2014 | Surleraux et al. |
| 8,691,788 B2 | 4/2014 | Sommadossi et al. |
| 2003/0008841 A1 | 1/2003 | Devos et al. |
| 2003/0060400 A1 | 3/2003 | LaColla |
| 2003/0087873 A1 | 5/2003 | Stuyver et al. |
| 2003/0219727 A1 | 11/2003 | Becker et al. |
| 2004/0006002 A1 | 1/2004 | Sommadossi et al. |
| 2004/0014108 A1 | 1/2004 | Eldrup et al. |
| 2004/0023901 A1 | 2/2004 | Cook |
| 2004/0063658 A1 | 4/2004 | Roberts et al. |
| 2004/0110718 A1 | 6/2004 | Devos et al. |
| 2004/0121980 A1 | 6/2004 | Martin et al. |
| 2004/0209831 A1 | 10/2004 | McSwiggen et al. |
| 2004/0229839 A1 | 11/2004 | Babu et al. |
| 2004/0229840 A1 | 11/2004 | Bhat et al. |
| 2004/0266723 A1 | 12/2004 | Otto et al. |
| 2005/0009737 A1 | 1/2005 | Clark |
| 2005/0009775 A1 | 1/2005 | Howes et al. |
| 2005/0038240 A1 | 2/2005 | Connolly et al. |
| 2005/0124532 A1 | 6/2005 | Sommadossi et al. |
| 2005/0182252 A1 | 8/2005 | Reddy et al. |
| 2005/0191302 A1 | 9/2005 | Arthur et al. |
| 2005/0203243 A1 | 9/2005 | Polus |
| 2005/0215510 A1 | 9/2005 | Roberts et al. |
| 2006/0040890 A1 | 2/2006 | Martin et al. |
| 2006/0040944 A1 | 2/2006 | Gosselin et al. |
| 2006/0046980 A1 | 3/2006 | Erion et al. |
| 2006/0111324 A1 | 5/2006 | Choi et al. |
| 2006/0234962 A1 | 10/2006 | Olsen et al. |
| 2006/0264389 A1 | 11/2006 | Bhat et al. |
| 2006/0286615 A1 | 12/2006 | Lederkremer et al. |
| 2007/0004669 A1 | 1/2007 | Carroll et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037221 A1 | 2/2007 | Block et al. |
| 2007/0037735 A1 | 2/2007 | Gosselin et al. |
| 2007/0042939 A1 | 2/2007 | LaColla |
| 2007/0042940 A1 | 2/2007 | LaColla et al. |
| 2007/0042990 A1 | 2/2007 | Gosselin et al. |
| 2007/0042991 A1 | 2/2007 | LaColla et al. |
| 2007/0060498 A1 | 3/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0087960 A1 | 4/2007 | Storer et al. |
| 2007/0265222 A1 | 11/2007 | MacCoss et al. |
| 2008/0261913 A1 | 10/2008 | Sommadossi et al. |
| 2008/0280842 A1 | 11/2008 | MacCoss et al. |
| 2010/0279974 A1 | 11/2010 | Pierra et al. |
| 2010/0316594 A1 | 12/2010 | Sommadossi et al. |
| 2012/0251487 A1 | 10/2012 | Surleraux |
| 2013/0064794 A1 | 3/2013 | Surleraux et al. |
| 2013/0315862 A1 | 11/2013 | Sommadossi et al. |
| 2013/0315866 A1 | 11/2013 | Parsy et al. |
| 2013/0315867 A1 | 11/2013 | Parsy et al. |
| 2013/0315868 A1 | 11/2013 | Mayes et al. |
| 2013/0330297 A1 | 12/2013 | Storer et al. |
| 2014/0086873 A1 | 3/2014 | Mayes et al. |
| 2014/0099283 A1 | 4/2014 | Gosselin et al. |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0128339 A1 | 5/2014 | Girijavallabhan et al. |
| 2014/0140951 A1 | 5/2014 | Moussa et al. |
| 2014/0140952 A1 | 5/2014 | Moussa et al. |
| 2014/0154211 A1 | 6/2014 | Girijavallabhan et al. |
| 2014/0161770 A1 | 6/2014 | Girijavallabhan et al. |
| 2014/0178338 A1 | 6/2014 | Mayes et al. |
| 2014/0206640 A1 | 7/2014 | Girijavallabhan et al. |
| 2014/0248241 A1 | 9/2014 | Stewart et al. |
| 2014/0248242 A1 | 9/2014 | Dousson et al. |
| 2014/0271547 A1 | 9/2014 | Dukhan et al. |
| 2014/0294769 A1 | 10/2014 | Mayes et al. |
| 2014/0364446 A1 | 12/2014 | Dukhan et al. |
| 2015/0037282 A1 | 2/2015 | Mayes et al. |

FOREIGN PATENT DOCUMENTS

| | | |
|---|---|---|
| WO | WO 88/00201 | 1/1988 |
| WO | 93/17651 | 9/1993 |
| WO | WO 98/53813 | 12/1998 |
| WO | WO 01/32153 | 5/2001 |
| WO | WO 01/60315 | 8/2001 |
| WO | WO 01/79246 | 10/2001 |
| WO | WO 01/90121 | 11/2001 |
| WO | WO 01/92282 | 12/2001 |
| WO | WO 02/18404 | 3/2002 |
| WO | WO 02/32920 | 4/2002 |
| WO | WO 02/48165 | 6/2002 |
| WO | WO 02/057287 | 7/2002 |
| WO | WO 02/057425 A2 | 7/2002 |
| WO | WO 03/062256 A1 | 7/2003 |
| WO | WO 03/070750 | 8/2003 |
| WO | WO 03/105770 A2 | 12/2003 |
| WO | WO 2004/002422 A2 | 1/2004 |
| WO | WO 2004/002999 | 1/2004 |
| WO | WO 2004/003000 A2 | 1/2004 |
| WO | WO 2004/003138 A2 | 1/2004 |
| WO | WO 2004/009020 A2 | 1/2004 |
| WO | WO 2004/022999 | 3/2004 |
| WO | WO 2004/072090 A1 | 8/2004 |

(56) References Cited

FOREIGN PATENT DOCUMENTS

| | | |
|---|---|---|
| WO | WO 2004/096233 A2 | 11/2004 |
| WO | WO 2004/096234 A2 | 11/2004 |
| WO | WO 2004/096237 A2 | 11/2004 |
| WO | WO 2004/096285 A2 | 11/2004 |
| WO | WO 2004/096286 A2 | 11/2004 |
| WO | WO 2004/096287 A2 | 11/2004 |
| WO | WO 2004/100960 A2 | 11/2004 |
| WO | WO 2004/000858 A2 | 12/2004 |
| WO | WO 2005/012525 A1 | 2/2005 |
| WO | 2005/020884 | 3/2005 |
| WO | 2005/020885 | 3/2005 |
| WO | WO 2005/021568 | 3/2005 |
| WO | WO 2005/021568 A2 | 3/2005 |
| WO | WO 2005/044279 A2 | 5/2005 |
| WO | WO 2005/044308 A2 | 5/2005 |
| WO | WO 2005/087788 | 9/2005 |
| WO | WO 2006/012078 | 2/2006 |
| WO | WO 2006/012440 | 2/2006 |
| WO | WO 2006/116557 | 2/2006 |
| WO | WO 2006/063149 | 6/2006 |
| WO | WO 2006/093987 A1 | 9/2006 |
| WO | WO 2006/094347 A1 | 9/2006 |
| WO | WO 2006/116512 A1 | 11/2006 |
| WO | WO 2007/020193 A2 | 2/2007 |
| WO | 2007/027248 | 3/2007 |
| WO | WO 2007/095269 A2 | 8/2007 |
| WO | WO 2008/62206 | 5/2008 |
| WO | WO 2008/082602 | 7/2008 |
| WO | 2014/059901 | 4/2014 |
| WO | 2014/059902 | 4/2014 |
| WO | 2014/204831 | 12/2014 |

OTHER PUBLICATIONS

Chapman, et al., Purification of PMPA Amidate Prodrugs by SMB Chromatography and X-Ray Crystallography of the Diastereomerically Pure GS-7340, Nucleosides, Nucleotides & Nucleic Acids, 20(4-7), 1085-1090, 2001.

Chou et al., "Phosphoramidate Pronucleotides: A Comparison of the Phosphoramidase Substrate Specificity of Human and *Escherichia coli* Histidine Triad Nucleotide Binding Proteins," Molecular Pharmaceutics, vol. 4, No. 2, 208-217, 2006.

De Clercq, Erik, "The acyclic nucleoside phosphonates from inception to clinical use: Historical perspective," Antiviral Research, 2007, 75, 1-13.

Drontle, et al., Designing a Pronucleotide Stratagem: Lessons from Amino Acid Phosphoramidates of Anticancer and Antiviral Pyrimidines, Mini-Reviews in Medicinal Chemistry, vol. 4, No. 4, 409-419, 2004.

Egron et al., CAS, 139:350904 (2003).

Egron et al., CAS: 136:20199 (2001).

Egron, "Synthesis and study of antiviral S-acyl-2-thioethyl (SATE) phosphoramidate derivatives of B-L-ddA." Submitted for 14th International Conference on Antiviral Research, Seattle, WA; Apr. 8-13, 2001.

Egron, et al., "S-Acyl-2-thioethyl Phosphoramidate Diester Derivatives as Mononucleotide Prodrugs," J. Med. Chem., 46, 4564-4571, 2003.

Egron, et al., "Synthesis and Anti-HIV Activity of Some S-Acyl-2-Thioethyl (SATE) Phosphoramidate Derivatives of 3'-Azido-2',3'-Dideoxythymidine," Nucleosides and Nucleotides, 18(4&5), 981-982, 1999.

Egron, et al., "Synthesis and Study of a New Series of Phosphoramidate Derivatives as Mononucleotide Prodrugs," Nucleosides, Nucleotides, 20(4-7), 751-754, 2001.

Eisenberg, et al., "Metabolism of GS-7340, A Novel Phenyl Monophosphoramidate Intracellular Prodrub of PMPA, in Blood," Nucleosides, Nucleotides 20 (4-7), 1091-1098, 2001.

Ergon, D.; Gosselin, G.; Bryant M.; Sommadossi J.-P.; Imbach J.-L., "Synthesis and study of antiviral S-acyl-2-thioethyl (SATE) phosphoramidate derivatives of b-L-ddA", Antiviral Research, 2001, 50 (1), A45.

Erion, et al., "Targeting thyroid hormone receptor-B agonists to the liver reduces cholesterol and triglycerides and improves the therapeutic index," PNAS, vol. 104, No. 39, 15490-15495, 2007.

Hecker, et al., "Prodrugs of Phosphates and Phosphonates," J. Med. Chen, 51, 2328-2345, 2008.

Hirao, et al. Partial Synthesis of Leader Sequence of Phage fl Coat Protein mRNA, Chem Lett., 11, 1929-1932, 1986.

Huttunen, "Novel Cyclic Phosphate Prodrug Approach for Cytochrom P450-activated Drugs Containing an Alcohol Functionality," Pharmaceutical Research, vol. 24, No. 4, 679-687, 2007.

ISA/EP International Search Report dated Aug. 5, 2008 for International Application No. PCT/US2007/26408, filed Dec. 28, 2007.

ISA/EP Written Opinion of the International Searching Authority dated Aug. 5, 2008 for International Application No. PCT/US2007/26408, filed Dec. 28, 2007.

Jochum, et al., "Biolabile constructs for pronucleotide design," Journal of Organometallic Chemistry 690, 2614-2625, 2005.

Kruchkov, et al., "Influence of Solvent on the Strength of Cyclic Oxygen-Containing Phosphorus Acids," Academy of Sciences of the USSR, Division of Chemical Science, Plenum Publishing Corporation, vol. 36, No. 6, Part 1, 1145-1148, 1987.

Li, et al., "Synthesis of the Phosphoramidite Derivative of 2'-Deoxy-2'-C-B-methylcytidine," J. Org. Chem., 68, 6799-6802, 2003.

Ludwig, J., A New Route to Nucleoside 5'-triphosphates, Acta Biochim, Biophys. Acad. Sci. Hung., 16, 131-133, 1981.

Perrone, et al., "Application of the Phosphoramidate ProTide Approach to 4'-Azidouridine Confers Sub-micromolar Potency versus Hepatitis C Virus on an Inactive Nucleoside," J. Med. Chem 50, 1840-1849, 2007.

Petersen, et al., "Synthesis and Evaluation of Double-Prodrugs against HIV. Conjugation of D4T with 6-Benzyl-1-(ethoxymethyl)-5-isopropyluracil (MKC-442, Emivirine)-Type Reverse Transcriptase Inhibitors via the SATE Prodrug Approach," J. Med. Chem. 48, 1211-1220, 2005.

Peyrottes et al, "SATE pronucleotide approaches: an overview," *Mini Rev. Med. Chem.*, 2004, 4(4), 395-408.

Placidi, et al., "Antiviral activity and intracellular metabolism of Bis(tButylSATE) phosphotriester of B-L-2',3' dideoxyadenosine, a potent inhibitor of HIV and HBV replication," Antiviral Chemistry & Chemotherapy 12:41-50, 2001.

Poijarvi-Virta, et al., "Prodrug Approaches of Nucleotides and Oligonucleotides," Current Medicinal Chemistry, 13, 3441-3467, 2006.

Prakash, et al., "Synthesis and Evaluation of S-Acyl-2-thioethyl Esters of Modified Nucleoside 5'-Monophosphates as Inhibitors of Hepatitis C Virus RNA Replication," J. Med. Chem. 48, 1199-1210, 2005.

Saboulard, D. et al., "Characterization of the Activation Pathway of Phosphoramidate Triester Prodrug of Stavudine and Zidovudine," Molecular Pharmacology, 1999, 56: 693-704.

Tomassini et al, "Inhibitory Effect of 2'-Substituted Nucleotides on Hepatitis C Virus Replication Correlates with Metabolic Properties in Replicon Cells," Antimicrobial Agents and Chemotherapy, 49(5):2050-2058 (2005).

Wagner et al, "Pronucleotides: towards in vivo delivery of antiviral and anticancer nucleotides," *Med. Res. Rev.*, 2000, 20(6), 417-451.

Yoshimura, et al., Nucleosides and Nucleotides. 102. Stereoselective Radical Deoxygenation of *Tert*-Propargyl Alcohols in Sugar Moiety of Pyrimidine Nucleosides: Synthesis of 2'-C-Alkynyl-2'-Deoxy-1-B-D-Arabinofuranosylpyrimidines, Tetrahedron Lett., 32, 6003-6006, 1991.

Congiatu et al., Novel Potential Anticancer Naphthyl Phosphoramidates of BVdU: Separation of Diastereoisomers and Assignment of the Absolute Configuration of the Phosphorus Center (2006) Journal of Medicinal Chemistry 49:452-455.

Eldrup et al., Structure-Activity Relationship of Purine Ribonucleosides for Inhibition of Hepatitis C Virus RNA-Dependent RNA Polymerase (2004) Journal of Medicinal Chemistry 47:2283-2295.

Hollecker et al., Synthesis of β-enantiomers of N4-hydroxy-3'-deoxypyrimidine nucleosides and their evaluation against bovine viral diarrhoea virus and hepatitis C virus in cell culture (2004) Antiviral Chemistry & Chemotherapy 14:43-55.

(56) References Cited

OTHER PUBLICATIONS

Kakefuda et al., Nucleosides and nucleotides. 120. Stereoselective Radical Deoxygenation of tert-Alcohols in the Sugar Moiety of Nucleosides: Synthesis of 2',3'-Dideoxy-2'-C-methyl- and -2'-C-ethynyl-β-d-threo-pentofuranosyl Pyrimidines and Adenine as Potential Antiviral and Antitumor Agents (1993) Tetrahedron 49:8513-8528.

Kawana et al., The deoxygenations of tosylated adenosine derivatives with Grignard reagents (1986) Nucleic Acids Symp Ser. 17:37-40.

Kawana et al., The Synthesis of C-Methyl Branched-Chain Deoxy Sugar Nucleosides by the Deoxygenative Methylation of O-Tosylated Adenosines with Grignard Reagents (1988) Bull. Chem. Soc. Jpn. 61:2437-2442.

King et al., Inhibition of the replication of a hepatitis C virus-like RNA template by interferon and 3'-deoxycytidine (2002) Antiviral Chemistry & Chemotherapy 13:363-370.

Murakami et al., Mechanism of Activation of β-D-2'-Deoxy-2'-Fluoro-2'-C-Methylcytidine and Inhibition of Hepatitis C Virus NS5B RNA polymerase (2007) Antimicrobial Agents and Chemotherapy 51:503-509.

Olsen et al., A 7-Deaza-Adenosine Analog Is a Potent and Selective Inhibitor of Hepatitis C Virus Replication with Excellent Pharmacokinetic Properties (2004) Antimicrobial Agents and Chemotherapy 28:3944-3953.

Pierra et al., Synthesis of 2'-C-Methylcytidine and 2'-C-Methyluridine Derivatives Modified in the 3'-Position as Potential Antiviral Agents (2006) Collection of Czechoslovak Chemical Communications 71:991-1010.

Stein et al., Phosphorylation of Nucleoside Analog Antiretrovirals: A Review for Clinicians (2001) Pharmacotherapy 21:11-34.

Tomassini et al., Inhibitory Effect of 2'-Substituted Nucleosides on Hepatitis C Virus Replication Correlates with Metabolic Properties in Replicon Cells (2005) Antimicrobial Agents and Chemotherapy 49:2050-2058.

Tong et al., Nucleosides of thioguanine and other 2-amino-6-substituted purines from 2-acetamido-5-chloropurine (1967) J Org Chem. 32:859-62.

COMPOUNDS AND PHARMACEUTICAL COMPOSITIONS FOR THE TREATMENT OF VIRAL INFECTIONS

CROSS REFERENCE TO RELATED APPLICATIONS

This application is a divisional of U.S. application Ser. No. 13/116,890, filed on May 26, 2011, which is a continuation of U.S. application Ser. No. 12/005,937, filed on Dec. 27, 2007, now issued as U.S. Pat. No. 7,951,789, which claims priority to 1) U.S. Provisional Appl. No. 60/877,944, filed Dec. 28, 2006; 2) U.S. Provisional Appl. No. 60/936,290, filed Jun. 18, 2007; and 3) U.S. Provisional Application No. 60/985,891, filed Nov. 6, 2007. The disclosures of the above referenced applications are incorporated by reference in their entireties herein.

FIELD

Provided herein are compounds, methods and pharmaceutical compositions, for use in treatment of viral infections, including hepatitis C virus infection, and hepatitis B virus infection in a host in need thereof. In a particular embodiment, phosphoroamidate or phosphonoamidate nucleoside compounds are provided which allow concentration of the drug in the liver.

BACKGROUND

Flaviviridae Viruses

The Flaviviridae family of viruses comprises at least three distinct genera: *pestiviruses*, which cause disease in cattle and pigs; *Flaviviruses*, which are the primary cause of diseases such as dengue fever and yellow fever; and *hepaciviruses*, whose sole member is HCV. The *flavivirus* genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). *Flaviviruses* of global concern that are associated with human disease include the dengue hemorrhagic fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med.*, 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research*, 1996, 47, 53-118; Moennig V., et al, *Adv. Vir. Res.* 1992, 41, 53-98). Human *pestiviruses* have not been as extensively characterized as the animal *pestiviruses*. However, serological surveys indicate considerable pestivirus exposure in humans.

*Pestiviruses* and *hepaciviruses* are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are approximately 6 HCV genotypes and more than 50 subtypes. Due to the similarities between *pestiviruses* and *hepaciviruses*, combined with the poor ability of *hepaciviruses* to grow efficiently in cell culture, bovine viral diarrhea virus (BVDV) is often used as a surrogate to study the HCV virus.

The genetic organization of *pestiviruses* and *hepaciviruses* is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for *pestiviruses* and *hepaciviruses* is very similar. For both the *pestiviruses* and *hepaciviruses*, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of *pestiviruses* and *hepaciviruses* share sequence domains that are characteristic of specific protein functions. For example, the NS3 proteins of viruses in both groups possess amino acid sequence motifs characteristic of serine proteinases and of helicases (Gorbalenya et al. (1988) *Nature* 333:22; Bazan and Fletterick (1989) *Virology* 171: 637-639; Gorbalenya et al. (1989) *Nucleic Acid Res.* 17.3889-3897). Similarly, the NS5B proteins of *pestiviruses* and *hepaciviruses* have the motifs characteristic of RNA-directed RNA polymerases (Koonin, E. V. and Dolja, V. V. (1993) *Crit. Rev. Biochem. Molec. Biol.* 28:375-430).

The actual roles and functions of the NS proteins of *pestiviruses* and *hepaciviruses* in the lifecycle of the viruses are directly analogous. In both cases, the NS3 serine proteinase is responsible for all proteolytic processing of polyprotein precursors downstream of its position in the ORF (Wiskerchen and Collett (1991) *Virology* 184:341-350; Bartenschlager et al. (1993) *J. Virol.* 67:3835-3844; Eckart et al. (1993) *Biochem. Biophys. Res. Comm.* 192:399-406; Grakoui et al. (1993) *J. Virol.* 67:2832-2843; Grakoui et al. (1993) *Proc. Natl. Acad. Sci. USA* 90:10583-10587; Hijikata et al. (1993) *J. Virol.* 67:4665-4675; Tome et al. (1993) *J. Virol.* 67:4017-4026). The NS4A protein, in both cases, acts as a cofactor with the NS3 serine protease (Bartenschlager et al. (1994) *J. Virol.* 68:5045-5055; Failla et al. (1994) *J. Virol.* 68: 3753-3760; Lin et al. (1994) 68:8147-8157; Xu et al. (1997) *J. Virol.* 71:5312-5322). The NS3 protein of both viruses also functions as a helicase (Kim et al. (1995) *Biochem. Biophys. Res. Comm.* 215: 160-166; Jin and Peterson (1995) *Arch. Biochem. Biophys.*, 323:47-53; Warrener and Collett (1995) *J. Virol.* 69:1720-1726). Finally, the NS5B proteins of *pestiviruses* and *hepaciviruses* have the predicted RNA-directed RNA polymerases activity (Behrens et al. (1996) *EMBO J.* 15:12-22; Lchmann et al. (1997) *J. Virol.* 71:8416-8428; Yuan et al. (1997) *Biochem. Biophys. Res. Comm.* 232:231-235; Hagedorn, PCT WO 97/12033; U.S. Pat. Nos. 5,981,247; 6,248,589 and 6,461,845 Zhong et al. (1998) *J. Virol.* 72.9365-9369).

Hepatitis C Virus

The hepatitis C virus (HCV) is the leading cause of chronic liver disease worldwide. (Boyer, N. et al. *J. Hepatol.* 32:98-112, 2000). HCV causes a slow growing viral infection and is the major cause of cirrhosis and hepatocellular carcinoma (Di Besceglie, A. M. and Bacon, B. R., *Scientific American, Octo-* ber: 80-85, (1999); Boyer, N. et al. *J. Hepatol.* 32:98-112, 2000). An estimated 170 million persons are infected with HCV worldwide. (Boyer, N. et al. *J. Hepatol.* 32:98-112, 2000). Cirrhosis caused by chronic hepatitis C infection accounts for 8,000-12,000 deaths per year in the United States, and HCV infection is the leading indication for liver transplantation.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed to the development of improved methods of treatment of chronic HCV infections in humans (Di Besceglie, A. M. and Bacon, B. R., *Scientific American*, October: 80-85, (1999)).

In light of the fact that HCV infection has reached epidemic levels worldwide, and has tragic effects on the infected patient, there remains a strong need to provide new effective pharmaceutical agents to treat hepatitis C that have low toxicity to the host.

Further, given the rising threat of other flaviviridae infections, there remains a strong need to provide new effective pharmaceutical agents that have low toxicity to the host.

Hepatitis B

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. Chronic persistent hepatitis can cause fatigue, cirrhosis of the liver and hepatocellular carcinoma, a primary liver cancer. In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

Daily treatments with α-interferon, a genetically engineered protein, have shown promise. A human serum-derived vaccine has also been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

An essential step in the mode of action of purine and pyrimidine nucleosides against viral diseases, and in particular, HBV and HCV is their metabolic activation by cellular kinases, to yield the mono-, di- and triphosphate derivatives. The biologically active species of many nucleosides is the triphosphate form, which inhibits viral DNA polymerase, RNA polymerase, or reverse transcriptase, or causes chain termination.

In light of the fact that hepatitis B and C viruses have reached epidemic levels worldwide, and has severe and often tragic effects on the infected patient, there remains a strong need to provide new effective pharmaceutical agents to treat humans infected with the virus that have low toxicity to the host.

Therefore, there is a continuing need for effective treatments of HCV and HBV infections.

SUMMARY

Phosphoramidate and phosphonoamidate compounds of a variety of therapeutic agents are provided, as well as methods for their manufacture and use in the treatment of a variety of disorders including liver disorders. Such compounds can be used in some embodiments to permit concentration of the therapeutic agent in the liver. In one embodiment, the compound is a S-pivaloyl-2-thioethyl phosphoramidate, S-pivaloyl-2-thioethyl phosphonoamidate, S-hydroxypivaloyl-2-thioethyl phosphoramidate or S-hydroxypivaloyl-2-thioethyl phosphonoamidate.

Phosphoramidate or phosphonoamidate compounds of a variety of therapeutic agents are provided. As used herein, a "phosphoramidate or phosphonoamidate compound of a therapeutic agent" includes a therapeutic agent derivatized to include a phosphoramidate or phosphonoamidate group. The therapeutic agent is, for example, an anti-viral agent that includes, or has been derivatized to include, a reactive group, such as a hydroxyl, for attachment of the phosphoramidate or phosphonoamidate moiety. Such therapeutic agents include, but are not limited to nucleosides and nucleoside analogs including acyclic nucleosides. In some embodiments, phosphoramidates of nucleotides and nucleotide analogs are also provided, such as phosphoramidates of 1',2',3'-branched and 4'-branched nucleosides. Such compounds can be administered in an effective amount for the treatment of liver disorders, including infectious diseases, such as hepatitis B and hepatitis C infection, including resistant strains thereof.

In certain embodiments, while not being limited to any theory, it is possible that the parent drug is obtained from selective metabolism of the phosphoramidate or phosphonoamidate compound in the liver, and thus the parent drug is capable of accumulating in the liver of a host. By selectively targeting and activating compounds in the liver, potentially undesired distribution of active compound in the gastrointestinal tract can be reduced. Moreover, therapeutic amounts of active compound at the site of infection in the liver can be increased.

In certain embodiments, a 5'-monophosphate or phosphonate of a parent nucleoside (or nucleoside derivative) drug is formed from metabolism of the phosphoramidate or phosphonoamidate compound in the liver, allowing the monophosphate or phosphonate to form and accumulate in the liver of a host. Thus, in certain embodiments, the phosphoramidate in effect provides a stabilized phosphate on the nucleoside or nucleoside analogue. In certain embodiments, where the compound needs to be triphosphorylated to be active, this advantageously can eliminate the requirement for the initial phosphorylation step, and promote more ready formation of the active triphosphate, which inhibits the target enzyme, and can enhance the overall activity of the nucleoside or nucleoside analog.

Without being limited to any theory, in one embodiment, a phosphoramidate of a nucleoside, such as a 2'-C-methylribonucleoside, is provided, that is selectively concentrated in the liver after oral administration, and metabolized in the liver cell to yield a 5'-monophosphate that can be enzymatically converted to the active form of the 5'-triphosphate, which inhibits the HCV polymerase. Thus potentially therapeutic doses can be reduced in comparison to administering the nucleoside parent molecule.

Thus, in some embodiments, after oral administration of the phosphoramidate and phosphonamidate compounds described herein, the compounds can advantageously concentrate in the liver cells at the site of infection and convert to the phosphate or phosphonate in the liver cell, which then is optionally further phosphorylated to implement its therapeutic effect.

Since these methods allow accumulation of the phosphoramidate or phosphonoamidate compounds disclosed herein in the liver of a host, the methods described herein can be useful, for example, for the treatment and/or prophylaxis of diseases or disorders of the liver, such as hepatitis B or C.

In certain embodiments, the compounds provided herein are useful in the prevention and treatment of Flaviviridae infections and other related conditions such as anti-Flaviviridae antibody positive and Flaviviridae-positive conditions, chronic liver inflammation caused by HCV, cirrhosis, fibrosis, acute hepatitis, fulminant hepatitis, chronic persistent hepatitis, and fatigue. These compounds or formulations can also be used prophylactically to prevent or retard the progression of clinical illness in individuals who are anti-Flaviviridae antibody or Flaviviridae-antigen positive or who have been exposed to a Flaviviridae. In one specific embodiment, the Flaviviridae is hepatitis C. In certain embodiments, the compound is used to treat any virus that replicates through an RNA-dependent RNA polymerase.

A method for the treatment of a Flaviviridae infection in a host, including a human, is also provided that includes administering an effective amount of a compound provided herein, administered either alone or in combination or alternation with another anti-Flaviviridae agent, optionally in a pharmaceutically acceptable carrier.

In certain embodiments, a method for treatment and/or prophylaxis of hepatitis B infections and other related conditions such as anti-HBV antibody positive and HBV-positive conditions, chronic liver inflammation caused by HBV, fibrosis, cirrhosis, acute hepatitis, fulminant hepatitis, chronic persistent hepatitis, and fatigue are provided herein.

In certain embodiments, phosphoramidate or phosphonoamidate compounds of a variety of pharmaceutical agents can be made and used therapeutically as described herein, to enhance delivery of the drug to the liver. In one embodiment, the compound is an S-acyl-2-thioethyl phosphoramidate or an S-acyl-2-thioethyl phosphonoamidate derivative, e.g., a S-pivaloyl-2-thioethyl phosphoramidate or a S-hydroxypivaloyl-2-thioethyl phosphonoamidate derivative.

The phosphoramidate or phosphonoamidate compounds, as well as salts thereof, and compositions comprising the compounds, provided herein are useful for treatment of disorders of the liver, such as HBV and/or HCV infections. In one embodiment, the compound provided herein is a compound of Formula I:

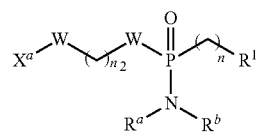

I or a pharmaceutically acceptable salt, solvate, a stereoisomeric, tautomeric or polymorphic form thereof, wherein
$X^a$ is

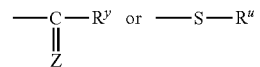

Z is O or S;
each W is independently O or S;
$R^y$ and $R^u$ each independently represent alkyl, alkenyl, alkynyl, aryl, aryl alkyl, cycloalkyl, cycloalkenyl, amino, aminoalkyl, hydroxyalkyl, alkoxy, heterocyclyl, or heteroaryl, all optionally substituted;
$R^a$ and $R^b$ are selected as follows:
i) $R^a$ and $R^b$ are each independently hydrogen, alkyl, carboxyalkyl, hydroxyalkyl, hydroxyarylalkyl, acyloxyalkyl, aminocarbonylalkyl, alkoxycarbonylalkyl, aryl, aryl alkyl, cycloalkyl, aryl, heteroaryl or heterocyclyl, all optionally substituted; or
ii) $R^a$ and $R^b$ together with the nitrogen atom on which they are substituted form a 3-7 membered heterocyclic or heteroaryl ring;
n is 0-3; $n_2$ is 1-4; and
$R^1$ is a moiety derivable by removal of a hydrogen from a hydroxy group of an anti-viral drug.
In another embodiment,
$X^a$ is

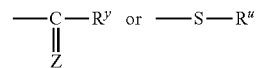

Z is O, S, NH or $NR^W$, where $R^w$ is, e.g., alkyl, alkyl, alkenyl, alkynyl, aryl, aryl alkyl, cycloalkyl, cycloalkenyl, amino, aminoalkyl, alkoxy, heterocyclyl, or heteroaryl, all optionally substituted;

each W is O, S, NH or NR$^W$, where R$^w$ is, e.g., alkyl, alkyl, alkenyl, alkynyl, aryl, aryl alkyl, cycloalkyl, cycloalkenyl, amino, aminoalkyl, alkoxy, heterocyclyl, or heteroaryl, all optionally substituted;

R$^y$ and R$^u$ each independently represent alkyl, alkenyl, alkynyl, aryl, aryl alkyl, cycloalkyl, cycloalkenyl, amino, aminoalkyl, alkoxy, heterocyclyl, or heteroaryl, all optionally substituted;

R$^a$ and R$^b$ are selected as follows:

i) R$^a$ and R$^b$ are each independently hydrogen, alkyl, carboxyalkyl, hydroxyalkyl, hydroxyarylalkyl, acyloxyalkyl, aminocarbonylalkyl, alkoxycarbonylalkyl, aryl, aryl alkyl, cycloalkyl, heteroaryl or heterocyclyl, all optionally substituted; or ii) R$^a$ and R$^b$ together with the nitrogen atom on which they are substituted form a 3-7 membered heterocyclic or heteroaryl ring;

n is 0-3; n$_2$ is 1-4; and

R$^1$ is as described herein.

Those of skill in the art will recognize that compounds of Formula I can be designed or prepared by reaction, e.g., at a hydroxy group of said anti-viral drug, for example, via condensation or dehydration. For convenience, in the description herein when substituents, such as exemplary R$^1$ groups are identified as a drug, those of skill in the art will recognize that the compound e.g. of Formula I comprises a derivative, e.g. a radical of the anti-viral drug. Those derivatives can for example be prepared by elimination of a hydrogen radical from a hydroxy group of the drug, for instance in a dehydration reaction. Where appropriate, certain derivatives can be prepared by modification of a phosphate or phosphonate of an anti-viral drug to yield a compound of formula I.

In certain embodiments of Formula I, R$^1$ is a nucleoside comprising a cyclic or acyclic sugar or an analog thereof.

In certain embodiments, R$^1$ is an anti-viral nucleoside analog useful for treatment of HCV virus infection selected from ribavirin, viramidine, 2'-C-methylcytidine, 2'-C-methylguanosine, valopicitabine (NM 283), MK-0608 and PSI-6130.

In certain embodiments, R$^1$ is an anti-viral nucleoside analog useful for treatment of HBV virus infection selected from lamivudine (Epivir-HBV, Zeffix, or Heptodin), adefovir, entecavir (Baraclude), telbivudine (Tyzeka, Sebivo), emtricitabine (FTC), clevudine (L-FMAU), viread (Tenofovir), torcitabine, valtorcitabine (monoval LdC), amdoxovir (DAPD) and RCV (Racivir).

In certain embodiments, R$^1$ is a non-nucleoside anti-viral useful for treatment of HBV virus infection selected from resiquimod or celgosivir.

In certain embodiments according to Formula I, R$^y$ is substituted alkyl, e.g. hydroxyalkyl or aminoalkyl; and R$^a$ and R$^b$ are each independently hydrogen, alkyl, substituted alkyl, benzyl or substituted benzyl, for instance hydroxy- or amino-substituted alkyl or benzyl. In another embodiment, R$^y$ is —OR$^c$, —C(R$^c$)$_3$ or —NHR$^c$ where each R$^c$ is independently alkyl, substituted alkyl, aryl or substituted aryl, for instance hydroxy- or amino-substituted alkyl or aryl; and R$^a$ and R$^b$ are independently hydrogen, alkyl, substituted alkyl, benzyl or substituted benzyl, for instance hydroxy- or amino-substituted alkyl or benzyl. In a further embodiment, R$^a$ and R$^b$ are independently benzyl or substituted alkyl. In a further embodiment, R$^y$ is selected from the group consisting of alkyl and hydroxyalkyl. In certain embodiments, R$^y$ is —C(CH$_3$)$_2$CH$_2$OH.

In certain embodiments, the compounds provided herein are selected such that R$^1$ is not 3'-azido-2',3'-dideoxythymidine.

In another embodiment, the compound provided herein is a compound of Formula IIa or IIb:

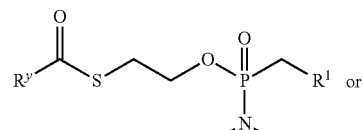

IIa

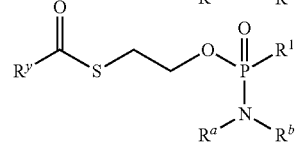

IIb or a pharmaceutically acceptable salt, solvate, a stereoisomeric, tautomeric or polymorphic form thereof, wherein R$^y$ is alkyl, alkenyl, alkynyl, aryl, aryl alkyl, cycloalkyl, cycloalkenyl, amino, aminoalkyl, hydroxyalkyl, heterocyclyl or heteroaryl, all optionally substituted;

R$^a$ and R$^b$ are selected as follows:

i) R$^a$ and R$^b$ are each independently hydrogen, alkyl, carboxyalkyl, hydroxyalkyl, hydroxyarylalkyl, acyloxyalkyl, aminocarbonylalkyl, alkoxycarbonylalkyl, aryl, aryl alkyl, cycloalkyl, aryl, heteroaryl or heterocyclyl, all optionally substituted; or ii) R$^a$ and R$^b$ together with the nitrogen atom on which they are substituted form a 3-7 membered heterocyclic or heteroaryl ring; and R$^1$ is an antiviral drug (as used herein where R$^1$ is an antiviral drug, that embodiment includes a moiety derivable by removal of a hydrogen from a hydroxy group of an antiviral drug), such as a nucleoside or nucleoside analog.

In certain embodiments according to Formula IIa or IIb, R$^y$ is substituted alkyl, e.g. hydroxyalkyl or aminoalkyl; and R$^a$ and R$^b$ are independently hydrogen, alkyl, substituted alkyl, benzyl or substituted benzyl, for instance hydroxy- or amino-substituted alkyl or benzyl. In another embodiment, R$^y$ is —OR$^c$, —C(R$^c$)$_3$ or —NHR$^c$ where each R$^c$ is independently alkyl, substituted alkyl, aryl or substituted aryl, for instance hydroxy- or amino-substituted alkyl or aryl; and R$^a$ and R$^b$ are independently hydrogen, alkyl, substituted alkyl, benzyl or substituted benzyl, for instance hydroxy- or amino-substituted alkyl or benzyl. In a further embodiment, R$^a$ and R$^b$ are independently benzyl or substituted alkyl. In a further embodiment, R$^y$ is selected from the group consisting of alkyl and hydroxyalkyl. In certain embodiments, R$^y$ is —C(CH$_3$)$_2$CH$_2$OH.

In another embodiment, the compound provided herein is a compound of Formula:

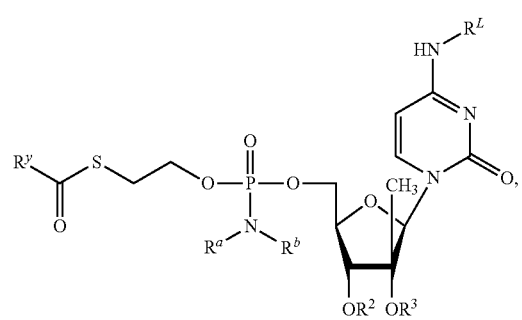

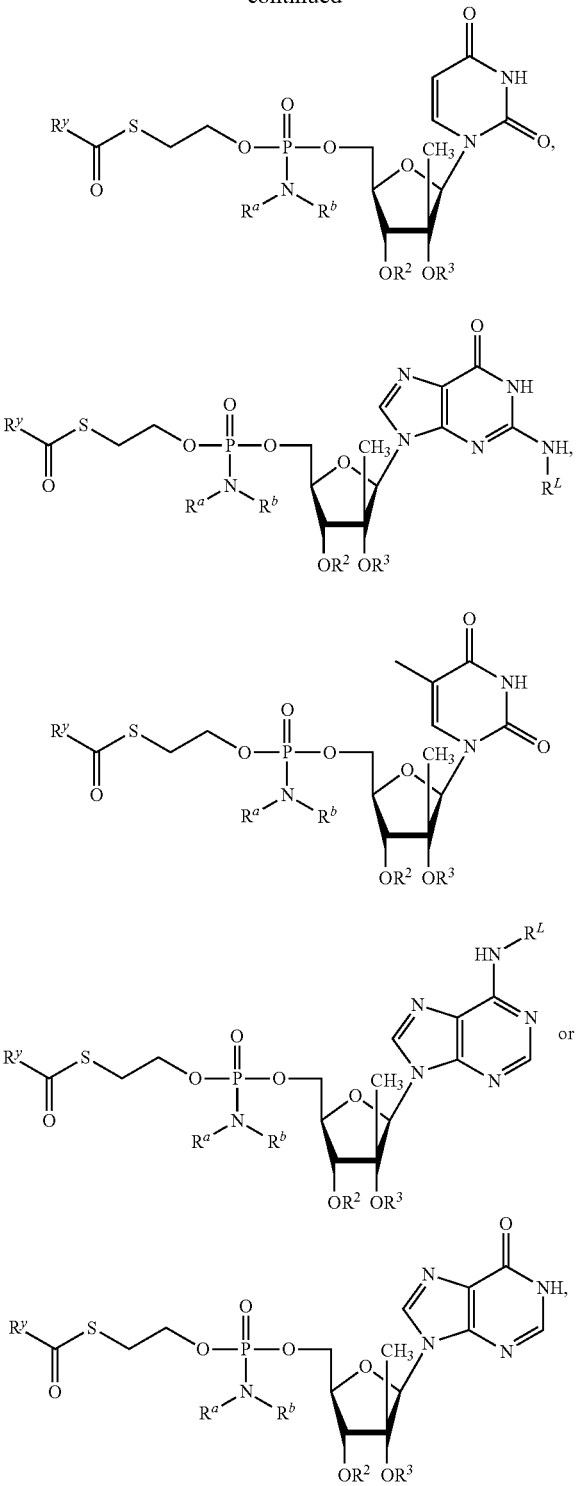

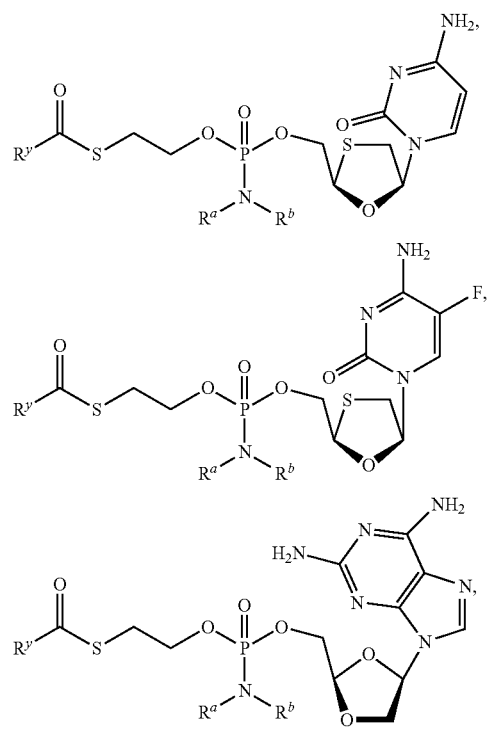

wherein $R^a$, $R^b$ and $R^y$ are as described in Formula I and
 wherein $R^2$ and $R^3$ are each independently H, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, aryl alkylsulfonyl, a lipid, such as a phospholipid; an amino acid; and amino acid residue, a carbohydrate; a peptide; cholesterol; or other pharmaceutically acceptable leaving group which is capable of providing a compound wherein $R^2$ and/or $R^3$ is independently H, for example when administered in vivo; or $R^2$ and $R^3$ are linked to form a cyclic group by an alkyl, ester or carbamate linkage; and wherein each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, aryl alkylsulfonyl, a lipid, such as a phospholipid; an amino acid; an amino acid residue; or a carbohydrate. In certain embodiments according to this paragraph, $R^2$ and $R^3$ are each H; $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^2$ and $R^3$ are each H; $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^2$ and $R^3$ are each H; $R^a$ and $R^b$ are independently benzyl or substituted alkyl. In a further embodiment, $R^2$ and $R^3$ are each H; $R^y$ is selected from the group consisting of alkyl and hydroxyalkyl. In certain embodiments, $R^2$ and $R^3$ are each H; $R^y$ is —$C(CH_3)_2CH_2OH$. In certain embodiments according to this paragraph, $R^2$ and $R^3$ are each hydrogen, $R^a$ is hydrogen, $R^b$ is —$CH_2$—$C_6H_5$ and $R^y$ is —$C(CH_3)_2CH_2OH$.

In another embodiment, the compound provided herein is a compound of formula:

-continued

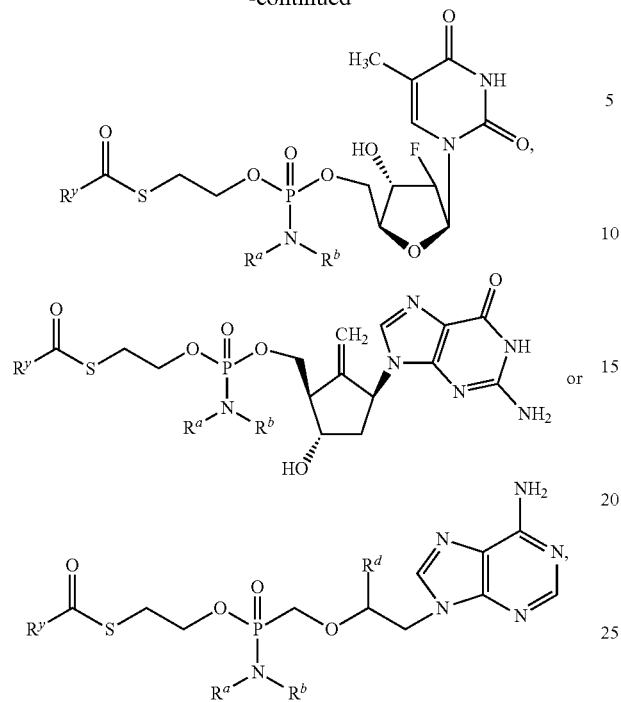

wherein $R^a$, $R^b$ and $R^y$ are as described in Formula I. $R^d$ is selected from the group consisting of hydrogen, alkyl and alkoxy. In certain embodiments, $R^d$ is hydrogen, methyl or methoxy. In certain embodiments according to this paragraph, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^y$ is —$C(CH_3)_2CH_2OH$. In certain embodiments according to this paragraph, $R^2$ and $R^3$ are each hydrogen, $R^a$ is hydrogen, $R^b$ is —$CH_2$—$C_6H_5$ and $R^y$ is —$C(CH_3)_2CH_2OH$ In certain embodiments according to this paragraph, $R^a$ is hydrogen, $R^b$ is —$CH_2$—$C_6H_5$ and $R^y$ is —$C(CH_3)_2CH_2OH$.

In one embodiment, the nucleosides that can be derivatized to include a phosphoramidate or phosphonoamidate, e.g. at the 5' position include:

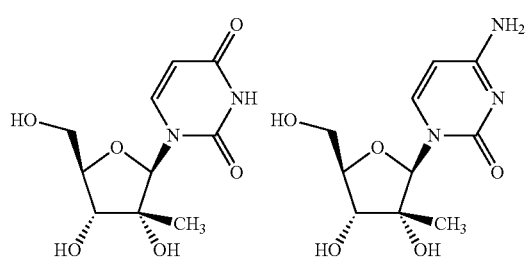

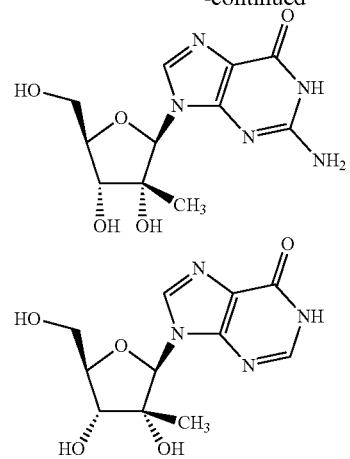

Examples of phosphoramidate or phosphonoamidate nucleoside compounds include:

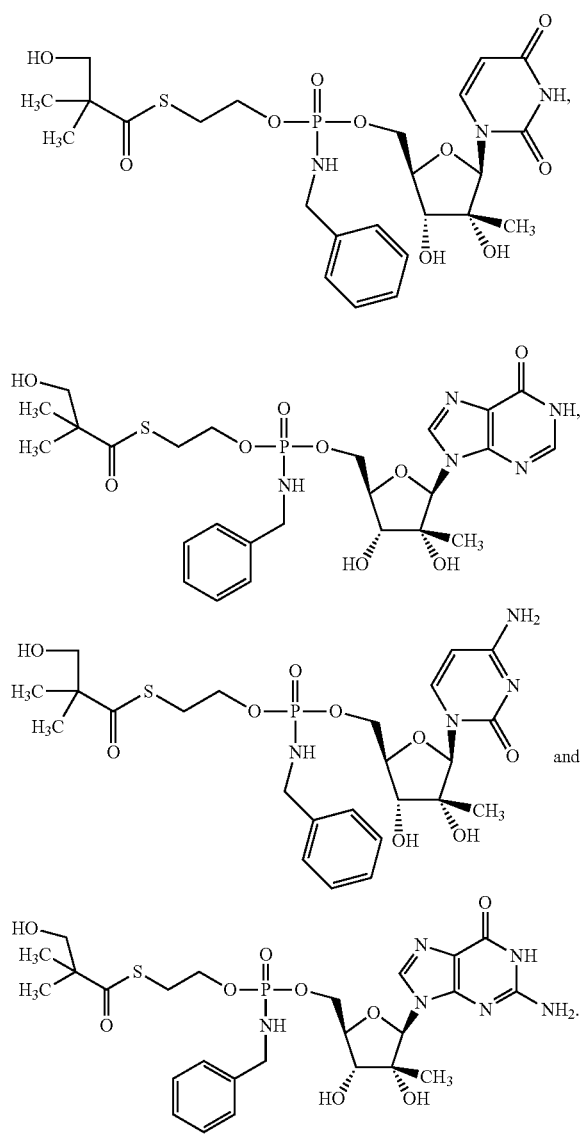

In one embodiment, the nucleosides that can be derivatized to include a phosphoramidate or phosphonoamidate, e.g. at the 5' position include:

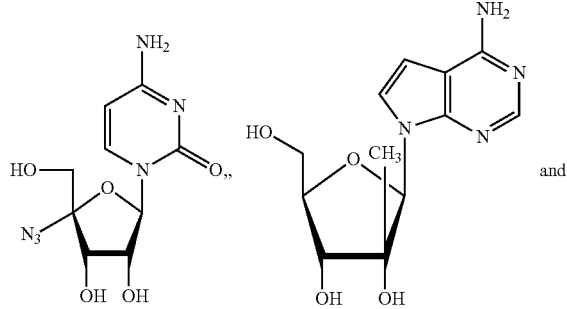

and

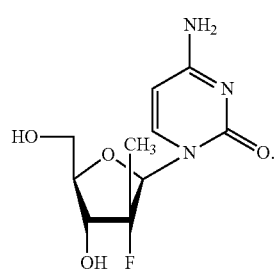

In one embodiment, phosphoramidate or phosphonoamidate nucleoside compounds include:

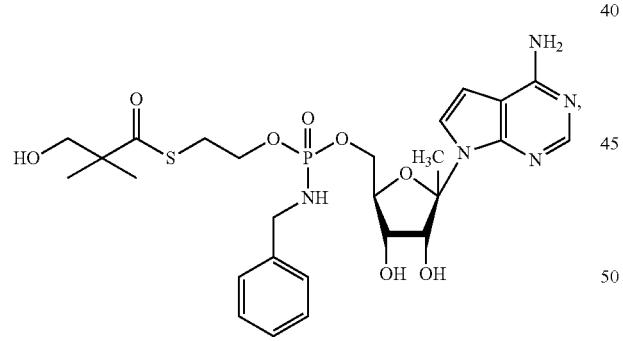

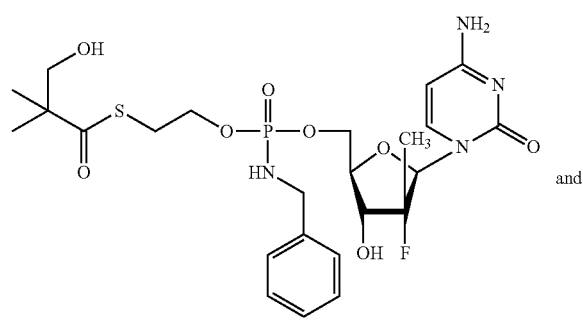

and

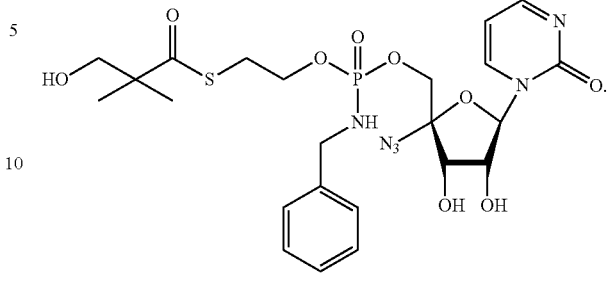

In one embodiment, the nucleosides that can be derivatized to include a phosphoramidate or phosphonoamidate, e.g. at the 5' position include:

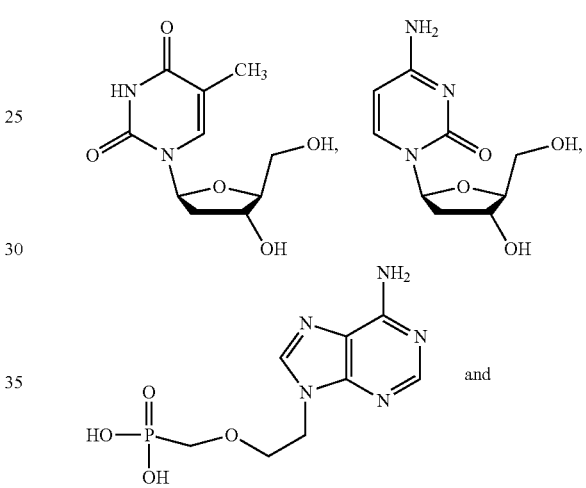

In one embodiment, phosphoramidate or phosphonoamidate nucleoside compounds include:

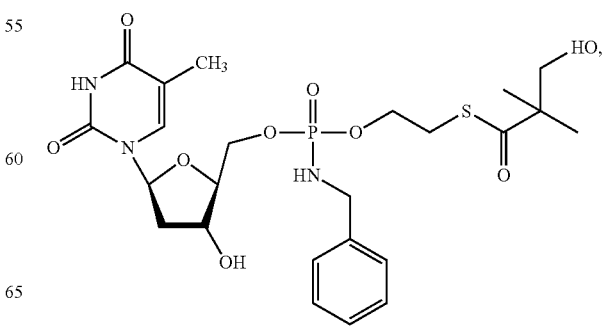

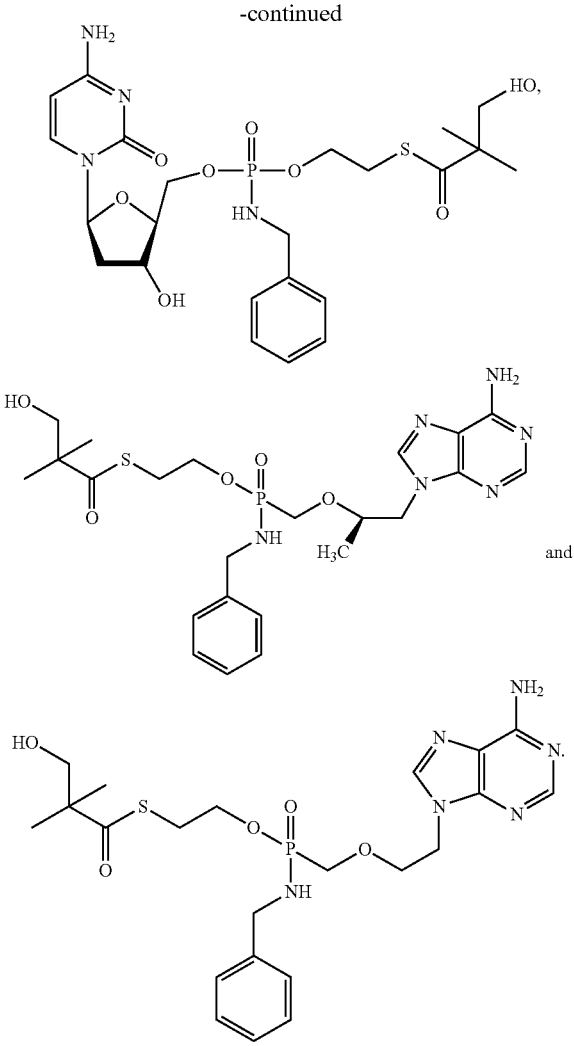

In one aspect, the compounds described herein are provided or administered in combination with a second therapeutic agent, such as one useful for the treatment or prevention of HBV and/or HCV infections. Exemplary therapeutic agents are described in detail in the sections below.

In another aspect, provided are pharmaceutical compositions, single unit dosage forms, and kits suitable for use in treating or preventing disorders such as HBV and/or HCV infections which comprise a therapeutically or prophylactically effective amount of a compound described herein, e.g. of Formula I, IIa or IIb, and a therapeutically or prophylactically effective amount of a second therapeutic such as one useful for the treatment or prevention of HBV and/or HCV infections.

In certain embodiments, a method of treatment of a liver disorder is provided comprising administering to an individual in need thereof a treatment effective amount of a phosphoramidate or phosphonoamidate derivative of a nucleoside or nucleoside analogue, wherein optionally the derivative is a S-pivaloyl-2-thioethyl phosphoramidate or S-pivaloyl-2-thioethyl phosphonoamidate derivative. The derivative is optionally selected from the compounds disclosed herein.

In some embodiments, provided herein are:
(a) compounds as described herein, e.g. of Formula I, IIa or IIb, and pharmaceutically acceptable salts and compositions thereof;
(b) compounds as described herein, e.g. of Formula I, IIa or IIb, and pharmaceutically acceptable salts and compositions thereof for use in the treatment and/or prophylaxis of a liver disorder including Flaviviridae infection, especially in individuals diagnosed as having a Flaviviridae infection or being at risk of becoming infected by hepatitis C;
(c) processes for the preparation of compounds as described herein, e.g. of Formula I, IIa or IIb, as described in more detail below;
(d) pharmaceutical formulations comprising a compound as described herein, e.g. of Formula I, IIa or IIb, or a pharmaceutically acceptable salt thereof together with a pharmaceutically acceptable carrier or diluent;
(e) pharmaceutical formulations comprising a compound as described herein, e.g. of Formula I, IIa or IIb, or a pharmaceutically acceptable salt thereof together with one or more other effective anti-HCV agents, optionally in a pharmaceutically acceptable carrier or diluent;
(f) a method for the treatment and/or prophylaxis of a host infected with Flaviviridae that includes the administration of an effective amount of a compound as described herein, e.g. of Formula I, IIa or IIb, its pharmaceutically acceptable salt or composition;
(g) a method for the treatment and/or prophylaxis of a host infected with Flaviviridae that includes the administration of an effective amount of a compounds as described herein, e.g. of Formula I, IIa or IIb, its pharmaceutically acceptable salt or composition in combination and/or alternation with one or more effective anti-HCV agent;
(h) compounds as described herein, e.g. of Formula I, IIa or IIb, and pharmaceutically acceptable salts and compositions thereof for use in the treatment and/or prophylaxis of a HBV infection, especially in individuals diagnosed as having an HBV infection or being at risk of becoming infected by hepatitis B;
(i) pharmaceutical formulations comprising a compound as described herein, e.g. of Formula I, IIa or IIb, or a pharmaceutically acceptable salt thereof together with one or more other effective anti-HBV agents, optionally in a pharmaceutically acceptable carrier or diluent;
(j) a method for the treatment and/or prophylaxis of hepatitis B infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue that includes administering an effective amount of a compound as described herein, e.g. of Formula I, IIa or IIb, or its pharmaceutically acceptable salt or composition.
(k) a prophylactic method to prevent or retard the progression of clinical illness in individuals who are anti-HBV antibody or HBV-antigen positive or who have been exposed to HBV.

Flaviviridae which can be treated are, e.g., discussed generally in *Fields Virology*, Editors: Fields, B. N., Knipe, D. M., and Howley, P. M., Lippincott-Raven Publishers, Philadelphia, Pa., Chapter 31, 1996. In a particular embodiment of the invention, the Flaviviridae is HCV. In an alternate embodiment, the Flaviviridae is a *flavivirus* or pestivirus. Specific *flaviviruses* include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

*Pestiviruses* which can be treated are discussed generally in *Fields Virology*, Editors: Fields, B. N., Knipe, D. M., and Howley, P. M., Lippincott-Raven Publishers, Philadelphia, Pa., Chapter 33, 1996. Specific *pestiviruses* include, without limitation: bovine viral diarrhea virus ("BVDV"), classical swine fever virus ("CSFV," also called hog cholera virus), and border disease virus ("BDV").

DESCRIPTION OF EXEMPLARY EMBODIMENTS

Figure 1:
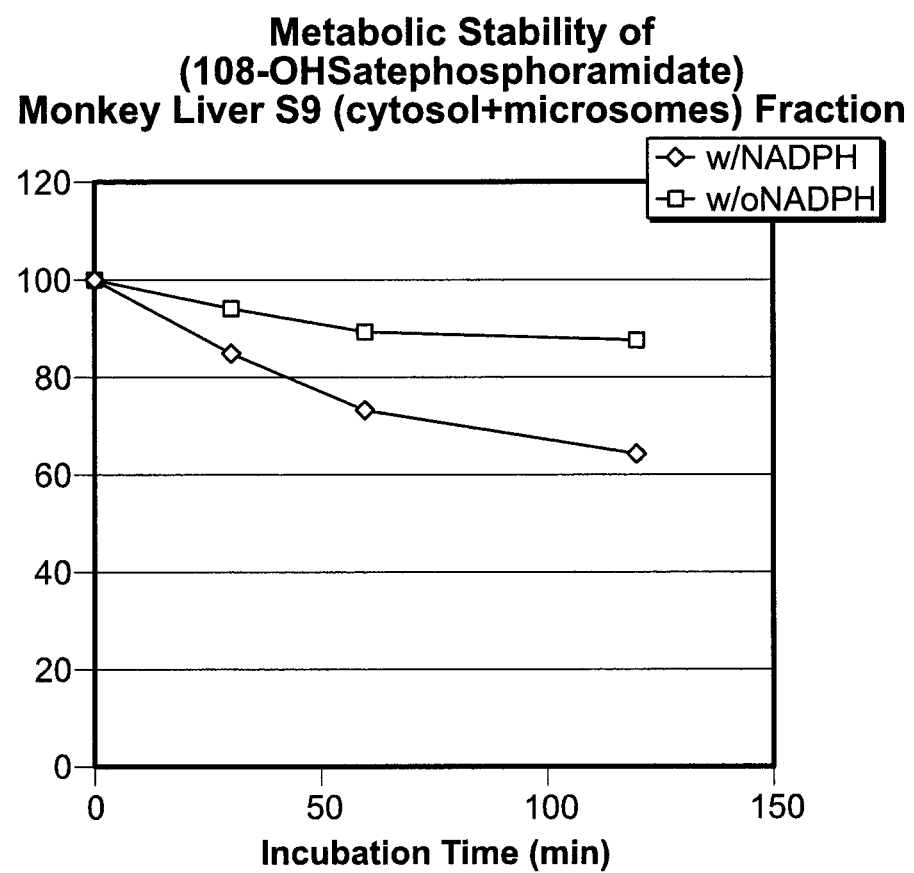
FIG. 1 depicts depletion of NM108 hydroxySATE phosphoramidate (B299) after incubation with and without NADPH in monkey liver S9.

Provided herein are compounds, compositions and methods useful for treating liver disorders such as HBV and/or HCV infection in a subject. Further provided are dosage forms useful for such methods.

Definitions

When referring to the compounds provided herein, the following terms have the following meanings unless indicated otherwise.

The term "alkyl", as used herein, unless otherwise specified, includes a saturated straight, branched, or cyclic, primary, secondary, or tertiary hydrocarbon of typically $C_1$ to $C_{10}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, secbutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups, and even more particularly fluorinated alkyl groups. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "lower alkyl", as used herein, and unless otherwise specified, includes a $C_1$ to $C_4$ saturated straight, branched, or if appropriate, a cyclic (for example, cyclopropyl) alkyl group, including both substituted and unsubstituted moieties.

"Alkylene" includes divalent saturated aliphatic hydrocarbon groups particularly having up to about 11 carbon atoms and more particularly 1 to 6 carbon atoms which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" includes monovalent olefinically unsaturated hydrocarbon groups, in certain embodiment, having up to about 11 carbon atoms, from 2 to 8 carbon atoms, or from 2 to 6 carbon atoms, which can be straight-chained or branched and having at least 1 or from 1 to 2 sites of olefinic unsaturation. Exemplary alkenyl groups include ethenyl (—CH=$CH_2$), n-propenyl (—$CH_2$CH=$CH_2$), isopropenyl (—C($CH_3$)=$CH_2$), vinyl and substituted vinyl, and the like.

"Alkenylene" includes divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—CH=CH—), the propenylene isomers (e.g., —CH=CH$CH_2$— and —C($CH_3$)=CH— and —CH=C($CH_3$)—) and the like.

"Alkynyl" includes acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—$CH_2$C≡CH), and the like.

The term "aryl", as used herein, and unless otherwise specified, includes phenyl, biphenyl, or naphthyl, and preferably phenyl. The term includes both substituted and unsubstituted moieties. The aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

"Alkoxy" includes the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" includes a radical —C(O)-alkoxy where alkoxy is as defined herein.

"Amino" includes the radical —$NH_2$.

"Carboxyl" includes the radical —C(O)OH.

The term "alkylamino" or "arylamino" includes an amino group that has one or two alkyl or aryl substituents, respectively. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

"Halogen" or "halo" includes chloro, bromo, fluoro or iodo.

"Monoalkylamino" includes the group alkyl-NR'—, wherein R' is selected from hydrogen and alkyl.

"Thioalkoxy" includes the group —SR where R is alkyl.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

"Pharmaceutically acceptable salt" includes any salt of a compound provided herein which retains its biological properties and which is not toxic or otherwise undesirable for pharmaceutical use. Such salts may be derived from a variety of organic and inorganic counter-ions well known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl) benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "alkaryl" or "alkylaryl" includes an aryl group with an alkyl substituent. The term aralkyl or arylalkyl includes an alkyl group with an aryl substituent.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 7-deazaguanine, 7-deazaadenine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" includes a group of the formula C(O)R', wherein R' is an straight, branched, or cyclic alkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxy-trityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoro-heptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoroethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

As used herein, the term "substantially free of" or "substantially in the absence of" with respect to a nucleoside composition includes a nucleoside composition that includes at least 85 or 90% by weight, preferably 95%, 98%, 99% or 100% by weight, of the designated enantiomer of that nucleoside. In a preferred embodiment, in the methods and compounds of this invention, the compounds are substantially free of enantiomers.

Similarly, the term "isolated" with respect to a nucleoside composition includes a nucleoside composition that includes at least 85, 90%, 95%, 98%, 99% to 100% by weight, of the nucleoside, the remainder comprising other chemical species or enantiomers.

"Solvate" includes a compound provided herein or a salt thereof, that further includes a stoichiometric or non-stoichiometric amount of solvent bound by non-covalent intermolecular forces. Where the solvent is water, the solvate is a hydrate.

The term "host", as used herein, includes any unicellular or multicellular organism in which the virus can replicate, including cell lines and animals, and preferably a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In one embodiment, the subject is refractory or non-responsive to current treatments for hepatitis C infection. In another embodiment, the subject is a farm animal (e.g., a horse, a cow, a pig, etc.) or a pet (e.g., a dog or a cat). In one embodiment, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In one embodiment, a therapeutic agent is an agent which is known to be useful for, or has been or is currently being used for the treatment or prevention of a disorder or one or more symptoms thereof.

"Therapeutically effective amount" includes an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to the prevent or impede the onset, development, progression and/or severity of a disorder.

As used herein, the phrase "prophylactically effective amount" includes the amount of a therapy (e.g., prophylactic agent) which is sufficient to result in the prevention or reduction of the development, recurrence or onset of one or more symptoms associated with a disorder), or to enhance or improve the prophylactic effect(s) of another therapy (e.g., another prophylactic agent).

Compounds

Phosphoramidate and phosphonoamidate compounds of a variety of therapeutic agents can be formed using methods available in the art and those disclosed herein. Such compounds can be used in some embodiments to enhance delivery of the drug to the liver. In one embodiment, the compound is an S-acyl-2-thioethyl phosphoramidate or an S-acyl-2-thioethyl phosphonoamidate derivative, e.g., an S-pivaloyl-2-thioethyl phosphoroamidate, an S-hydroxypivaloyl-2-thioethyl phosphoroamidate, an S-pivaloyl-2-thioethyl phosphonoamidate or an S-hydroxypivaloyl-2-thioethyl phosphonoamidate. Therapeutic agents that can be derivatized to compound form include an anti-viral agent that includes, or has been derivatized to include a reactive group for attachment of the phosphoramidate or phosphonoamidate moiety, including but not limited to nucleosides and nucleoside analogues including acyclic nucleosides. Therapeutic agents that can be derivatized to compound form also include an anti-viral agent that includes, or has been derivatized to include a phosphate or phorphonate group that can be derivatized to form a phosphoramidate or phosphonoamidate moiety, including but not limited to nucleosides and nucleoside analogues including acyclic nucleosides.

Nucleosides that can be derivatized include any $R^1$ as disclosed herein. Examples of nucleosides that can be derivatized to include a phosphoramidate or phosphonoamidate, e.g. at the 5',3' or 2' position include:

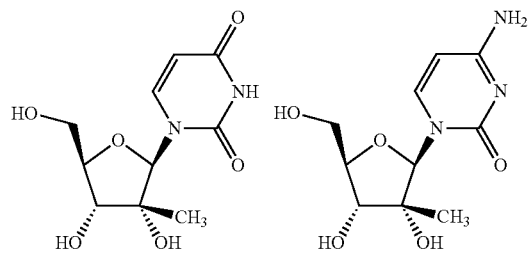

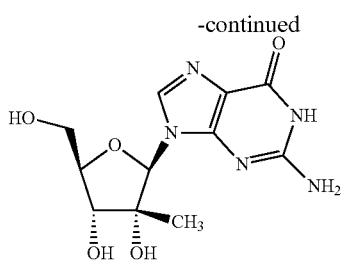

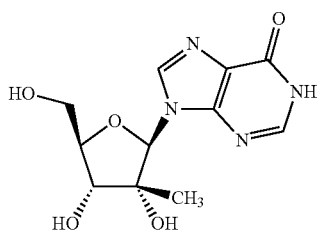

Examples of phosphoramidate or phosphonoamidate nucleoside compounds include:

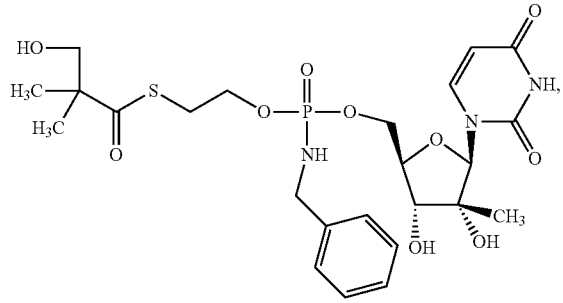

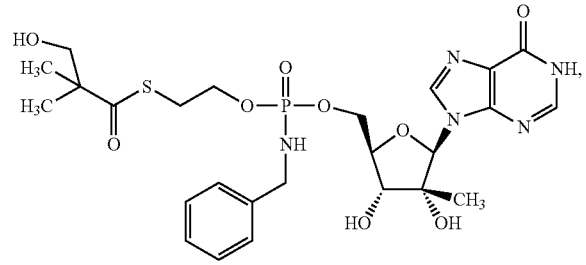

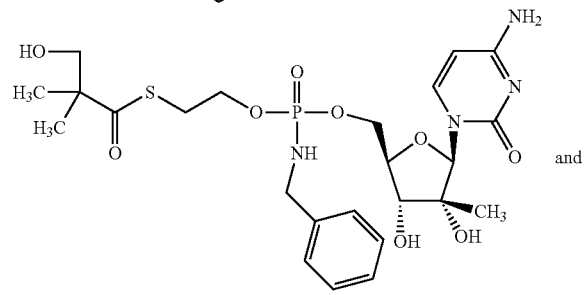

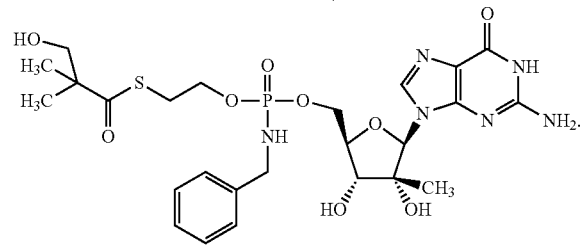

Phosphoramidate or phosphonoamidate compounds of other nucleosides and nucleoside analogues described herein and known in the art can be formed as described herein and used for the treatment of liver disorders. The phosphoramidate or phosphonoamidate moiety can be e.g., at the 5' position.

In one embodiment, provided herein are compounds, as well as salts thereof, and compositions comprising the compounds, that are useful for treatment of disorders of the liver, including HBV and/or HCV infections. In one embodiment, the phosphoramidate or phosphonoamidate compound provided herein is a compound of Formula IIa or IIb:

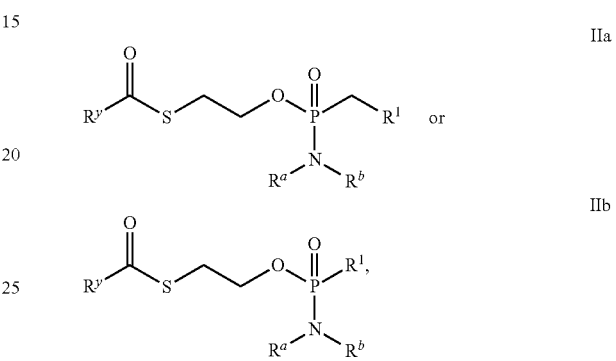

or a pharmaceutically acceptable salt, solvate, a stereoisomeric, tautomeric or polymorphic form thereof, wherein;

$R^y$ is alkyl, alkenyl, alkynyl, aryl, arylalkyl, cycloalkyl, cycloalkenyl, amino, heterocyclyl or heteroaryl, all optionally substituted;

$R^a$ and $R^b$ are selected as follows:

i) $R^a$ and $R^b$ are each independently hydrogen, alkyl, carboxyalkyl, hydroxyalkyl, hydroxyarylalkyl, acyloxyalkyl, aminocarbonylalkyl, alkoxycarbonylalkyl, aryl, arylalkyl, cycloalkyl, heteroaryl or heterocyclyl, all optionally substituted; or ii) $R^a$ and $R^b$ together with the nitrogen atom on which they are substituted form a 3-7 membered heterocyclic or heteroaryl ring; and $R^1$ is an anti-viral drug (which includes a moiety derivable by removal of a hydrogen from a hydroxy group of an anti-viral drug).

In certain embodiments, the compound of Formula IIa or IIb is selected with a proviso that when $R^y$ is tert-butyl or hydroxy-tert-butyl, then $R^1$ is not 3'-azido-2',3'-dideoxythymidine.

In certain embodiments, $R^1$, $R^a$, $R^b$ and $R^y$ are optionally substituted with one or more substituents as defined in the definitions.

In certain embodiments, the compounds are of Formula IIa or IIb, wherein $R^y$ is alkyl, alkenyl, alkynyl, aryl, arylalkyl, cycloalkyl, cycloalkenyl, amino, heterocyclyl or heteroaryl;

$R^a$ and $R^b$ are each independently hydrogen, alkyl, carboxyalkyl, hydroxyalkyl, hydroxyarylalkyl, acyloxyalkyl, aminocarbonylalkyl, alkoxycarbonylalkyl, aryl, arylalkyl, cycloalkyl, heteroaryl or heterocyclyl, all optionally substituted; and $R^1$ is an anti-viral drug (which is meant to include a moiety derivable by removal of a hydrogen from a hydroxy group of an anti-viral drug).

In one embodiment, $R^1$ is a nucleoside comprising a cyclic or acyclic sugar or analog thereof, including any nucleoside or analogue thereof described herein or known in the art.

Exemplary nucleoside drugs useful in the treatment of hepatitis C infection that can be derivatized as described herein are:

| Name | Structure |
| --- | --- |
| Ribavirin | (structure) |
| Viramidine | (structure) |
| Valopicitabine (NM283) | (structure) |
| 2'-C-methylcytidine (NM107) | (structure) |
| PSI-6130 | (structure) |
| MK-0608 | (structure) |
| 7-Fluoro-MK-0608 | (structure) |
| NM108 | (structure) |
| | (structure) |

Exemplary non-nucleoside drugs that can be derivatized as described herein are:

| Name | Structure |
| --- | --- |
| Resiquimod | (structure) |

| Name | Structure |
|---|---|
| Celgosivir | 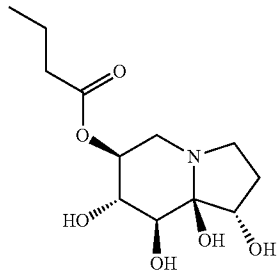 [SMILES: CCCC(=O)O[C@H]1CN2CC[C@H](O)[C@]2(O)[C@@H](O)[C@@H]1O] |
| Gliotoxin | 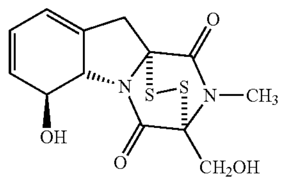 |

Exemplary nucleoside drugs useful in the treatment of hepatitis B infection that can be derivatized as described herein are:

| Name | Structure |
|---|---|
| Lamivudine or 3TC or Epivir ® | |
| Entecavir | |
| Telbivudine or L-dT | |
| Racivir | |
| Emtricitabine or (−)FTC | 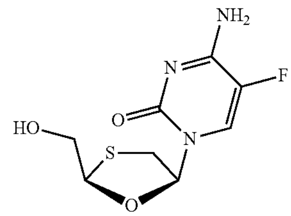 [SMILES: Nc1nc(=O)n([C@@H]2CS[C@H](CO)O2)cc1F] |
| Clevudine or L-FMAU | 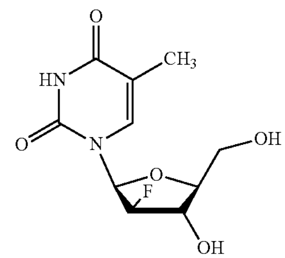 |
| Amdoxovir | 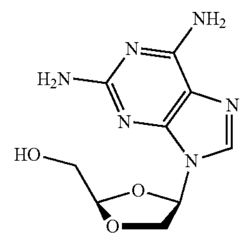 |
| Valtorcitabine | 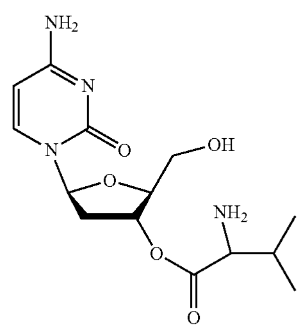 |
| Torcitabine (L-dC) | 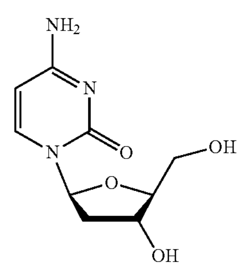 |
| Tenofovir or PMPA | 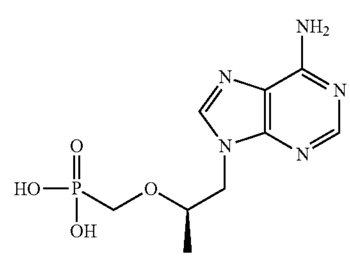 [SMILES: C[C@H](Cn1cnc2c(N)ncnc21)OCP(=O)(O)O] |

| Name | Structure |
|---|---|
| Adefovir or PMEA | 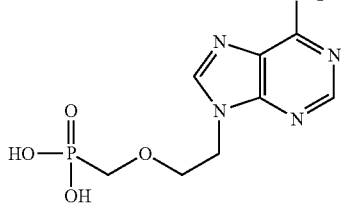 |
| L-cytidine | 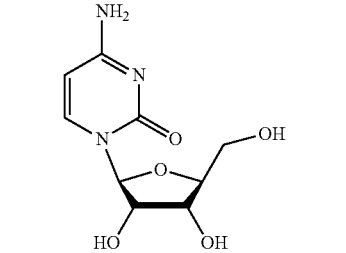 |

A phosphoramidate or phosphonoamidate compound of acyclovir, L-ddA or D-ddA can be administered for treatment of Hepatitis B, an example of which is shown below:

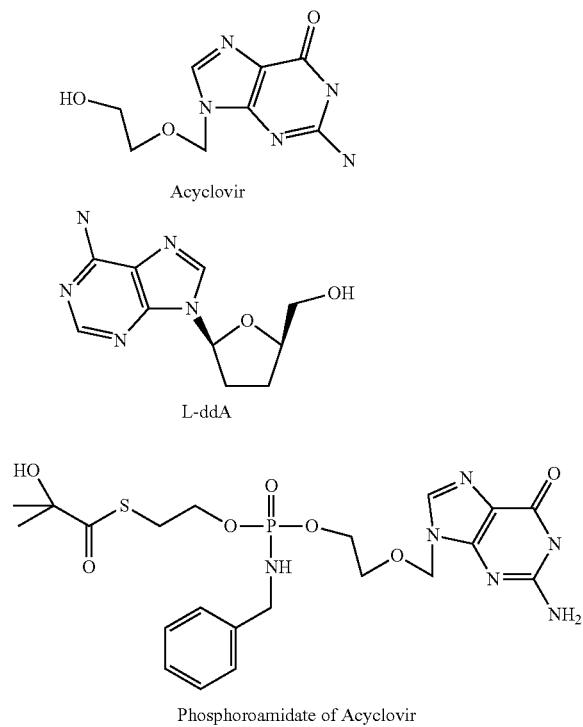

Acyclovir

L-ddA

Phosphoroamidate of Acyclovir

Where the nucleoside analog already includes a phosphonate, that phosphonate group can be incorporated in the phosphonoamidate moiety shown in the formulas herein, as shown by way of example in the phosphonoamidate of adefovir:

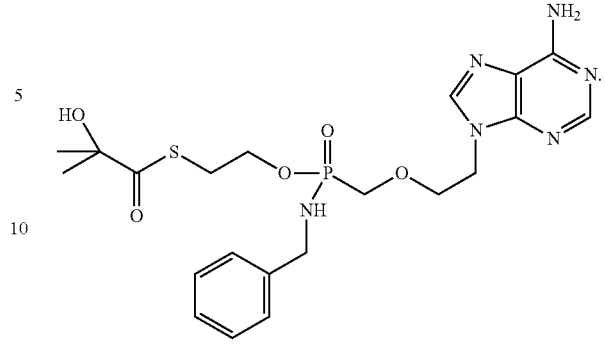

Thus, in certain embodiments of the compounds of Formula IIa below:

IIa

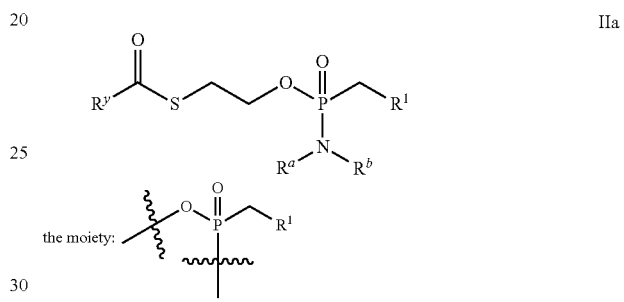

the moiety: 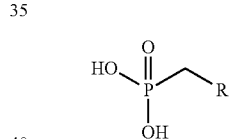

is derived from a drug that is an acyclic nucleoside phosphonate, i.e.:

$$HO-\overset{O}{\underset{OH}{P}}-R$$

which is e.g. PMEA (9-[2-(phosphonomethoxy)ethyl]adenine (adefovir).

In certain embodiments according to Formula IIa or IIb, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl.

In a further embodiment, $R^a$ and $R^b$ are independently benzyl or substituted alkyl. In a further embodiment, $R^y$ is selected from the group consisting of alkyl and hydroxyalkyl. In certain embodiments, $R^y$ is —$C(CH_3)_2CH_2OH$. In certain embodiments according to this paragraph, $R^2$ and $R^3$ are each hydrogen, $R^a$ is hydrogen, $R^b$ is —$CH_2$—$C_6H_5$ and $R^y$ is —$C(CH_3)_2CH_2OH$.

In one embodiment, $R^y$ is alkyl or hydroxyalkyl. In one embodiment, $R^y$ is methyl, tert-butyl, hydroxy-tert-butyl or hydroxyethyl. In certain embodiments, $R^y$ is —$C(CH_3)_2CH_2OH$.

In one embodiment, $R^a$ and $R^b$ are each independently hydrogen, alkyl, carboxyalkyl, hydroxyalkyl, hydroxyarylalkyl, acyloxyalkyl, aminocarbonylalkyl, alkoxycarbonylalkyl, aryl or arylalkyl, wherein the alkyl groups can be further substituted with one or more substitutents. In one embodiment, at least one of $R^a$ or $R^b$ is other than hydrogen. In one embodiment, $R^a$ and $R^b$ are each independently hydrogen, methyl or benzyl.

In certain embodiments, $R^y$ is —$C(CH_3)_2CH_2OH$ and $R^a$ and $R^b$ are each independently hydrogen, methyl or benzyl. In certain embodiments, $R^y$ is —$C(CH_3)_2CH_2OH$ and $R^a$ is hydrogen and $R^b$ is benzyl.

In another embodiment, the compound provided herein is a compound of formula:

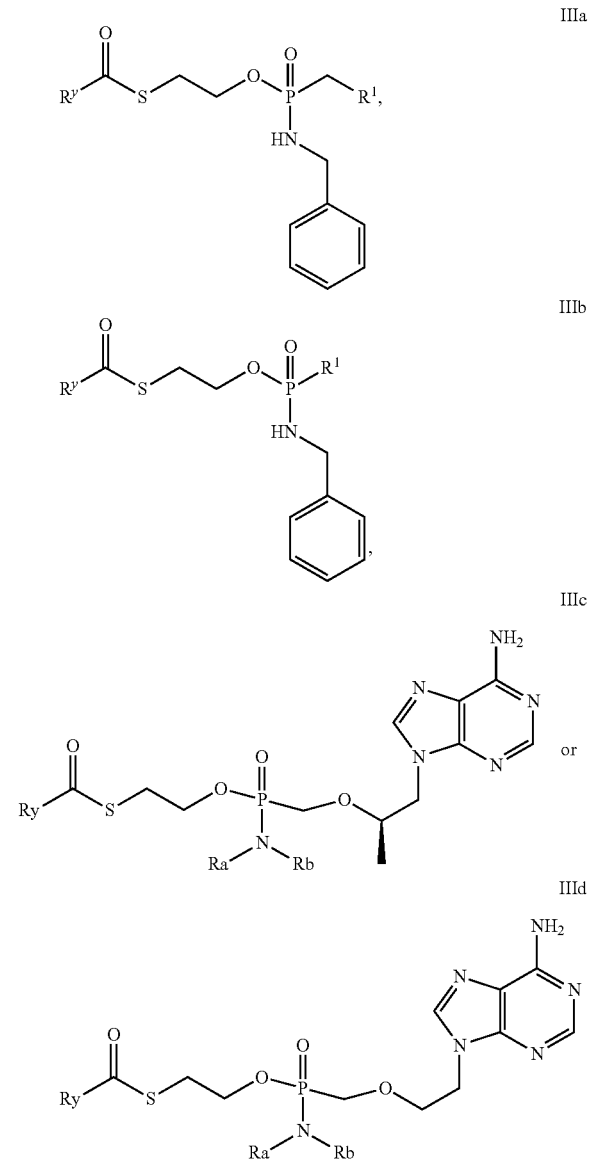

wherein $R^1$ and $R^y$ are as defined in Formula IIa or IIb.

In certain embodiments of Formula IIIa, b, c or d:

$R^y$ is substituted alkyl, e.g., hydroxyalkyl or aminoalkyl; and

In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or hydroxy-, amino-, alkyl-, haloalkyl- or trifluoromethyl-substituted benzyl. In certain embodiments, $R^a$ and $R^b$ together with the nitrogen atom on which they are substituted form a 3-7 membered heterocyclic or heteroaryl ring.

In one embodiment, $R^y$ is alkyl or hydroxyalkyl. In one embodiment, $R^y$ is methyl, tert-butyl, hydroxy-tert-butyl or hydroxyethyl. In one embodiment, $R^y$ is —$C(CH_3)_2CH_2OH$.

In certain embodiments according to Formula IIIa or IIIb, $R^y$ is substituted alkyl, e.g. hydroxyalkyl or aminoalkyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl. In a further embodiment, $R^y$ is selected from the group consisting of alkyl and hydroxyalkyl. In certain embodiments, $R^y$ is —$C(CH_3)_2CH_2OH$.

In another embodiment, the compound provided herein is a compound of formula:

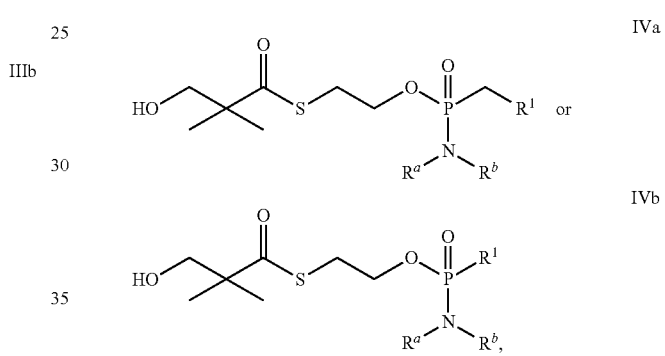

wherein $R^1$, $R^a$ and $R^b$ are e.g. as defined in Formula IIa or IIb.

In certain embodiments of Formula IVa or IVb:

$R^1$ is an antiviral drug, such as a nucleoside or nucleoside derivative; and $R^a$ and $R^b$ are each independently hydrogen, alkyl, substituted alkyl, benzyl or substituted benzyl, for instance hydroxy- or amino-substituted alkyl or hydroxy-, amino-, alkyl-, haloalkyl- or trifluoromethyl-substituted benzyl. In a further embodiment, $R^a$ and $R^b$ are independently H, benzyl or substituted alkyl. In certain embodiments, $R^a$ and $R^b$ together with the nitrogen atom on which they are substituted form a 3-7 membered heterocyclic or heteroaryl ring.

In certain embodiments of Formula IVa or IVb:

$R^1$ is an antiviral drug, such as a nucleoside or nucleoside derivative; and $R^a$ and $R^b$ are each independently hydrogen, alkyl, carboxyalkyl, hydroxyalkyl, hydroxyarylalkyl, acyloxyalkyl, aminocarbonylalkyl, alkoxycarbonylalkyl, aryl, arylalkyl, cycloalkyl, heteroaryl, or heterocyclyl, all optionally substituted; and wherein, in one embodiment, one of $R^a$ and $R^b$ is H and the other is alkyl optionally substituted with aryl, benzyl, or heteroaryl, each optionally substituted.

In another embodiment, the compound provided herein is a compound of formula:

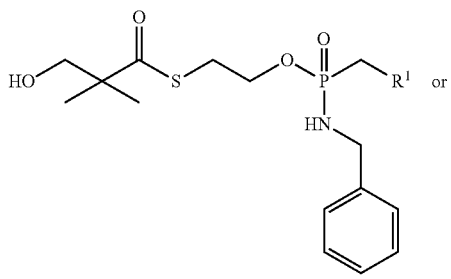

Va

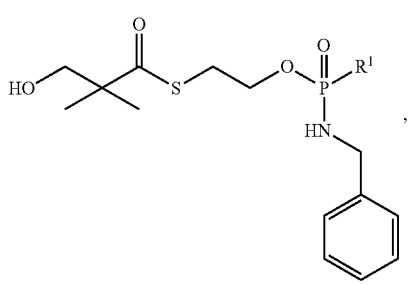

Vb wherein R¹ is as defined in Formula IIa or IIb.

In certain embodiments, R¹ is an anti-viral nucleoside analog useful for treatment of HCV virus infection selected from ribavirin, viramidine, 2'-C-methylcytidine, 2'-C-methylguanosine, valopicitabine (NM 283), MK-0608 and PSI-6130. As used herein, where R¹ is an analogue of a nucleoside, such as acyclovir, that itself includes a phosphonate group, that phosphonate can be in the form of the phosphonoamidate in the formulas disclosed herein. Thus, e.g., in formula Va or Vb, the R¹P(O)O— fragment is derived from the nucleoside analog that includes a phosphonate.

In certain embodiments, R¹ is an anti-viral nucleoside analog useful for treatment of HBV virus infection selected from lamivudine (Epivir-HBV, Zeffix, or Heptodin), adefovir, entecavir (Baraclude), telbivudine (Tyzeka, Sebivo), emtricitabine (FTC), clevudine (L-FMAU), viread (Tenofovir), torcitabine, valtorcitabine (monoval LdC), amdoxovir (DAPD) and RCV (Racivir).

Further exemplary anti-viral nucleoside analogs that can be used as R¹ are disclosed in International Publication Nos. WO2005021568; WO2006094347 and WO2006093987 and US Patent Publication No. US20050215510.

In certain embodiments, R¹ is a non-nucleoside anti-viral useful for treatment of HBV virus infection selected from resiquimod or celgosivir.

In one embodiment, R¹ is an immunosuppressant, such as combretastatin A-4, mycophenolic acid, pentostatin, nelarabine or mitoxantrone.

In one embodiment, R¹ is an interfering RNA (iRNA) based antivirals, including short interfering RNA (siRNA) based antivirals. Such compounds are described in International Patent Publication Nos. WO/03/070750 and WO 2005/012525, U.S. Pat. Nos. 7,176,304; 7,109,165; 7,041,817; 7,034,009; 7,022,828; 6,852,535 and 6,849,726 and US Patent Publication No. US 2004/0209831.

In another embodiment, the compound provided herein is a compound of formula:

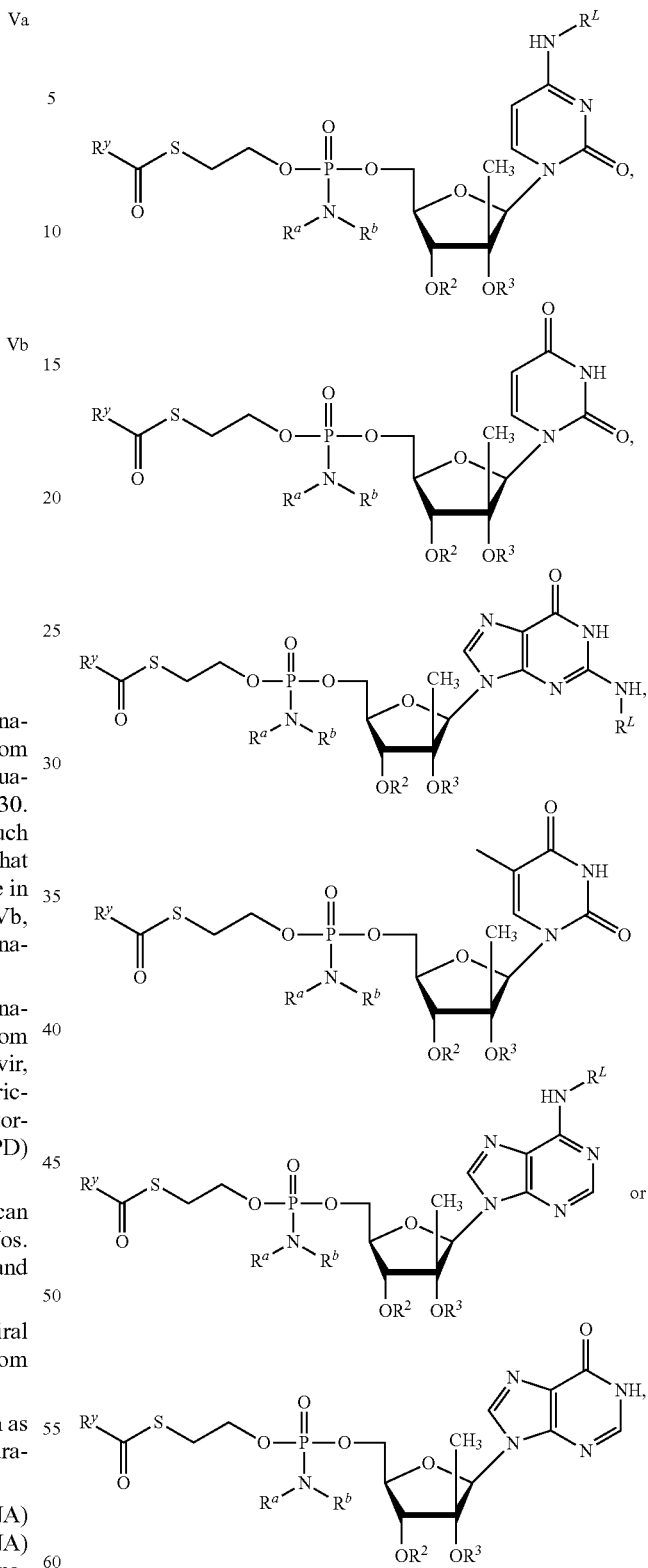

wherein $R^a$, $R^b$ and $R^y$ are as defined in Formula IIa or IIb and $R^2$ and $R^3$ are each independently H; straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, aralkylsulfonyl, a lipid, such as a phospholipid; an amino acid; and amino acid residue, a carbohydrate; a peptide; cholesterol; or other pharmaceutically acceptable leaving group which is capable of providing a compound wherein $R^2$ and/or $R^3$ is independently H or phosphate (including mono-, di- or triphosphate), for example when administered in vivo; or $R^2$ and $R^3$ are linked to form a cyclic group by an alkyl, ester or carbamate linkage. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments, $R^2$ and $R^3$ are each hydrogen, $R^a$ is hydrogen, $R^b$ is —$CH_2$—$C_6H_5$ and $R^y$ is —$C(CH_3)_2CH_2OH$. In certain embodiments according to this paragraph, $R^2$ and $R^3$ are each H; $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^2$ and $R^3$ are each H; $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^2$ and $R^3$ are each H; $R^a$ and $R^b$ are independently benzyl or substituted alkyl. In a further embodiment, $R^2$ and $R^3$ are each H; $R^y$ is selected from the group consisting of alkyl and hydroxyalkyl. In certain embodiments, $R^2$ and $R^3$ are each H; $R^y$ is —$C(CH_3)_2CH_2OH$.

In another embodiment, the compound provided herein is a compound of formula:

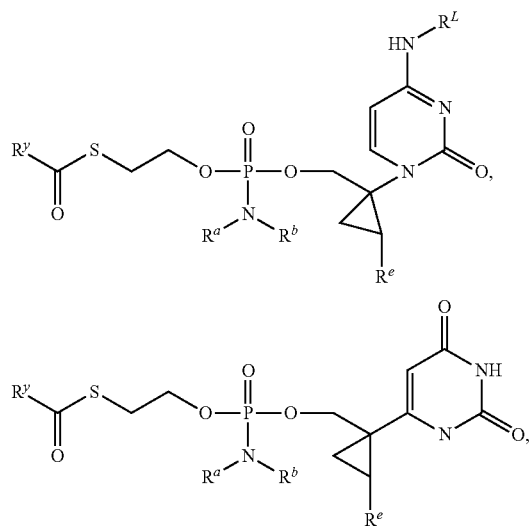

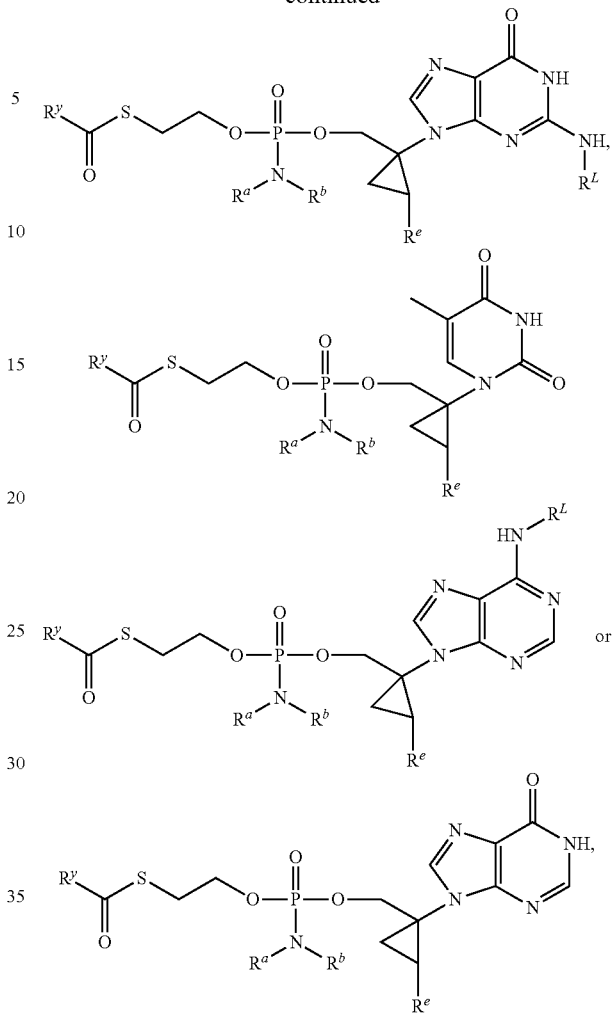

wherein $R^a$, $R^b$ and $R^y$ are as defined in Formula IIa or IIb and $R^e$ is hydrogen or alkyl. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, aralkylsulfonyl, a lipid, such as a phospholipid; an amino acid; an amino acid residue; or a carbohydrate. In certain embodiments, $R^e$ is methyl, ethyl or propyl, $R^a$ is hydrogen, $R^b$ is —$CH_2$—$C_6H_5$ and $R^y$ is —$C(CH_3)_2CH_2OH$. In certain embodiments according to this paragraph, $R^2$ and $R^3$ are each H; $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^e$ is methyl, ethyl or propyl; $R^2$ and $R^3$ are each H; $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^e$ is methyl, ethyl or propyl; $R^2$ and $R^3$ are each H; $R^a$ and $R^b$ are independently benzyl or substituted alkyl. In a further embodiment, $R^2$ and $R^3$ are each H; $R^y$ is selected from the group consisting of alkyl and hydroxyalkyl. In certain embodiments, $R^e$ is methyl, ethyl or propyl; $R^2$ and $R^3$ are each H; $R^y$ is —C(CH$_3$)$_2$CH$_2$OH. In certain embodiments according to this paragraph, $R^1$ is chosen from nucleosides described in U.S. Patent Application Publication No. US 2006/0111324 A1, the content of which is hereby incorporated by reference in its entirety.

In another embodiment, the compound provided herein is a compound of formula:

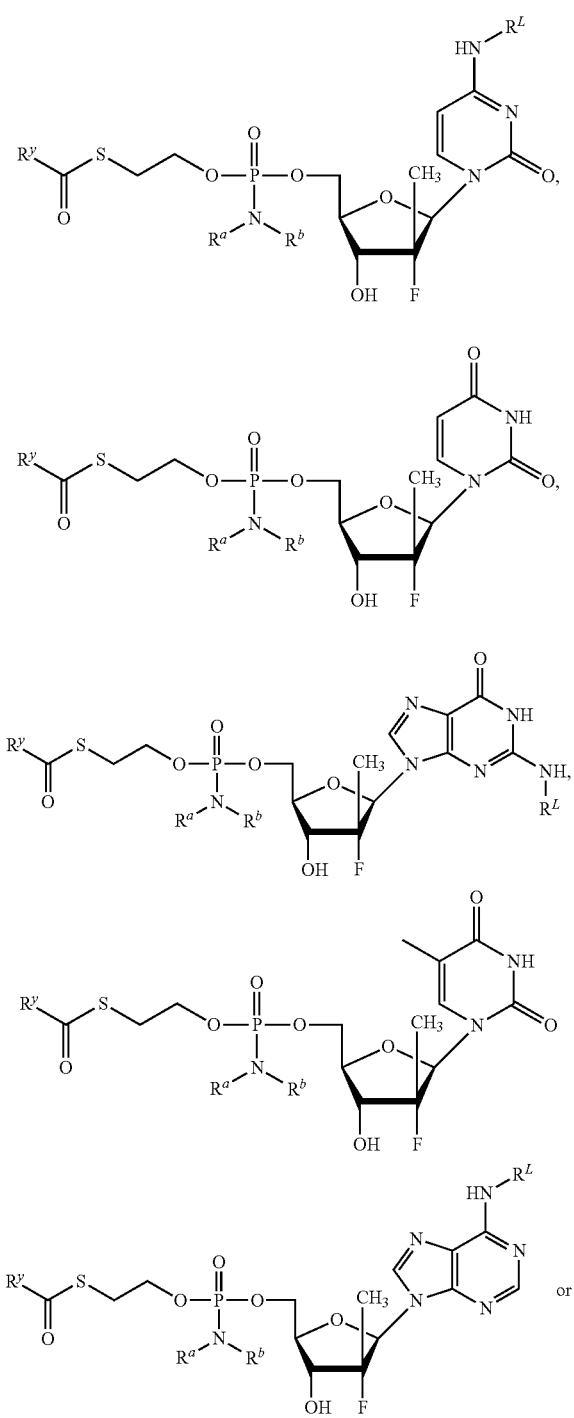

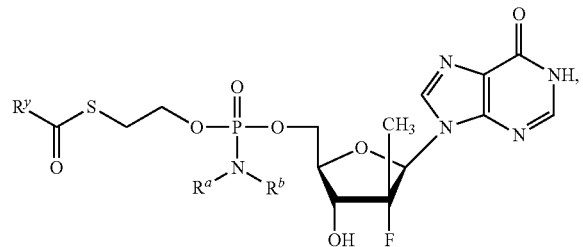

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —OR$^e$, —C(R$^e$)$_3$ or —NHR$^e$ where each $R^e$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —C(CH$_3$)$_2$CH$_2$OH.

In another embodiment, the compound provided herein is a compound of formula:

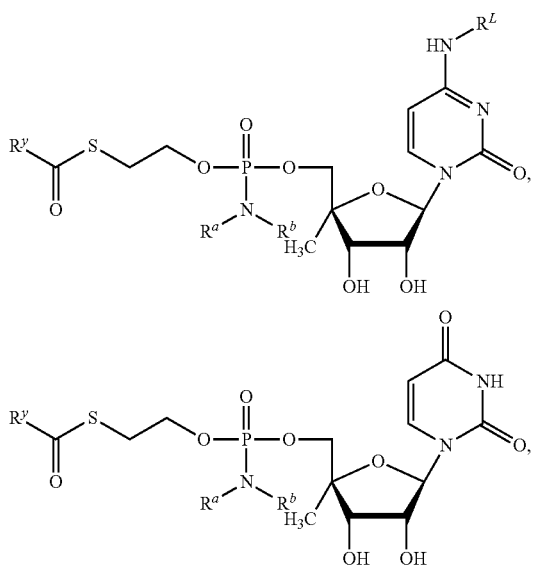

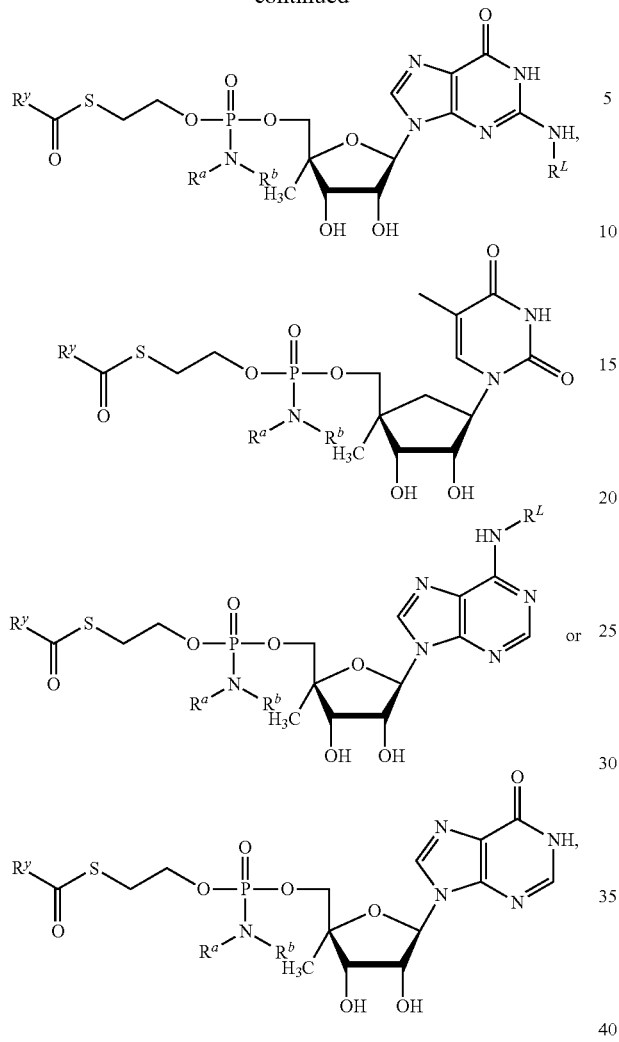

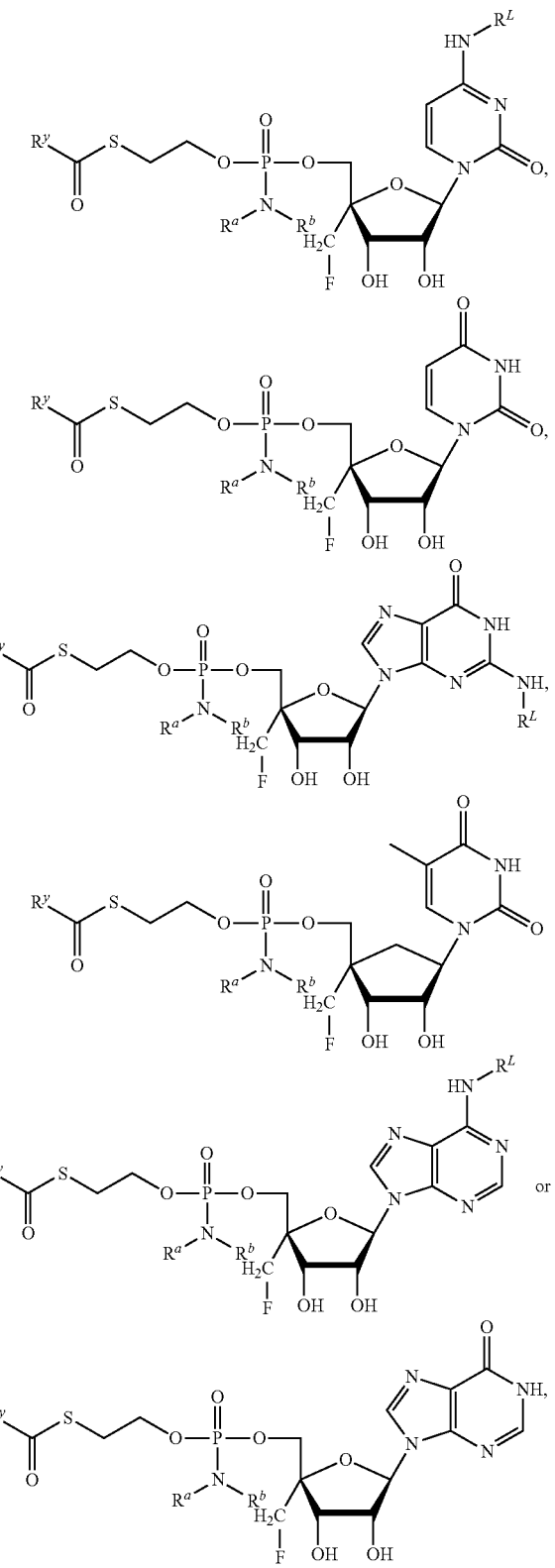

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$. In another embodiment, the compound provided herein is a compound of formula:

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$.

In another embodiment, the compound provided herein is a compound of formula:

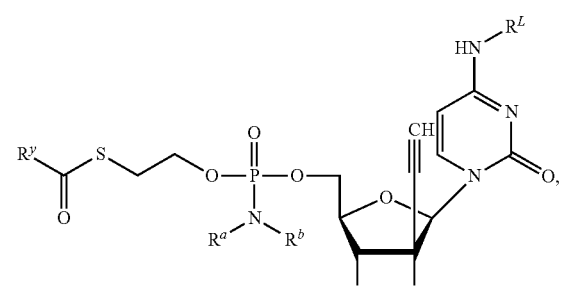

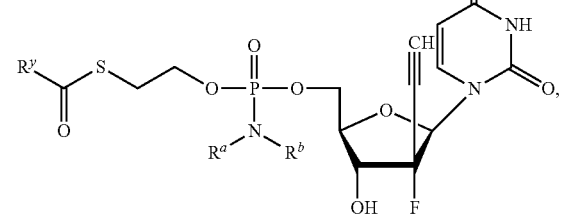

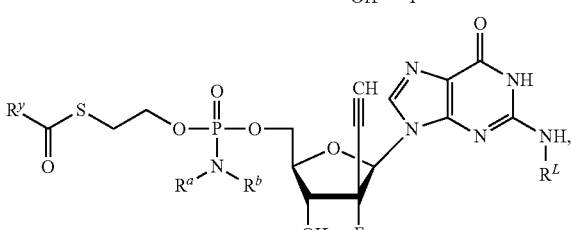

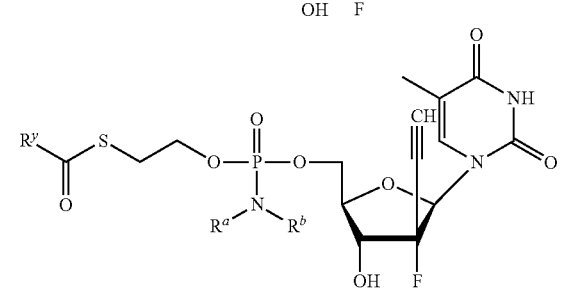

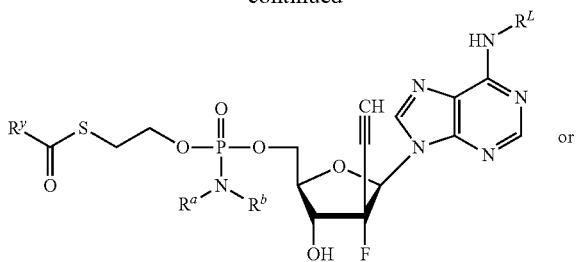

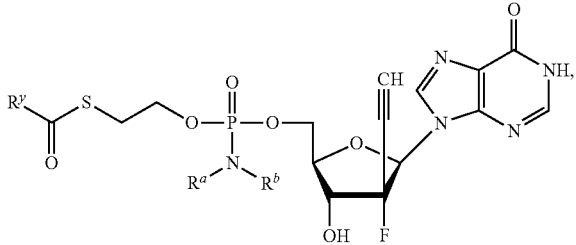

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$.

In another embodiment, the compound provided herein is a compound of formula:

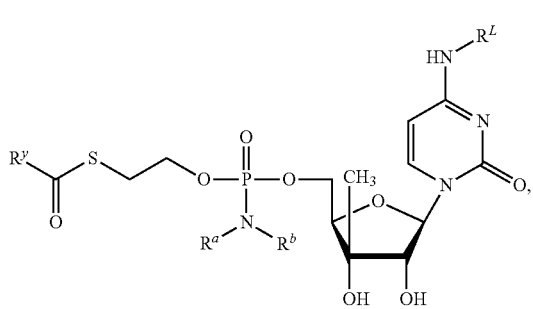

-continued

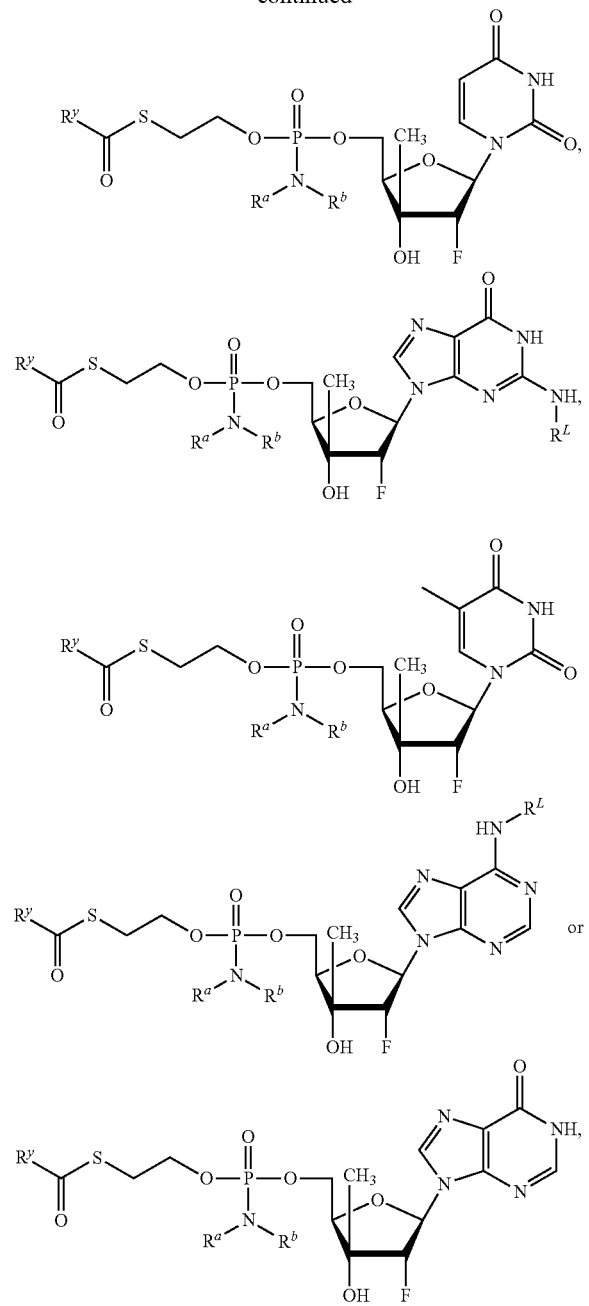

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$.

In another embodiment, the compound provided herein is a compound of formula:

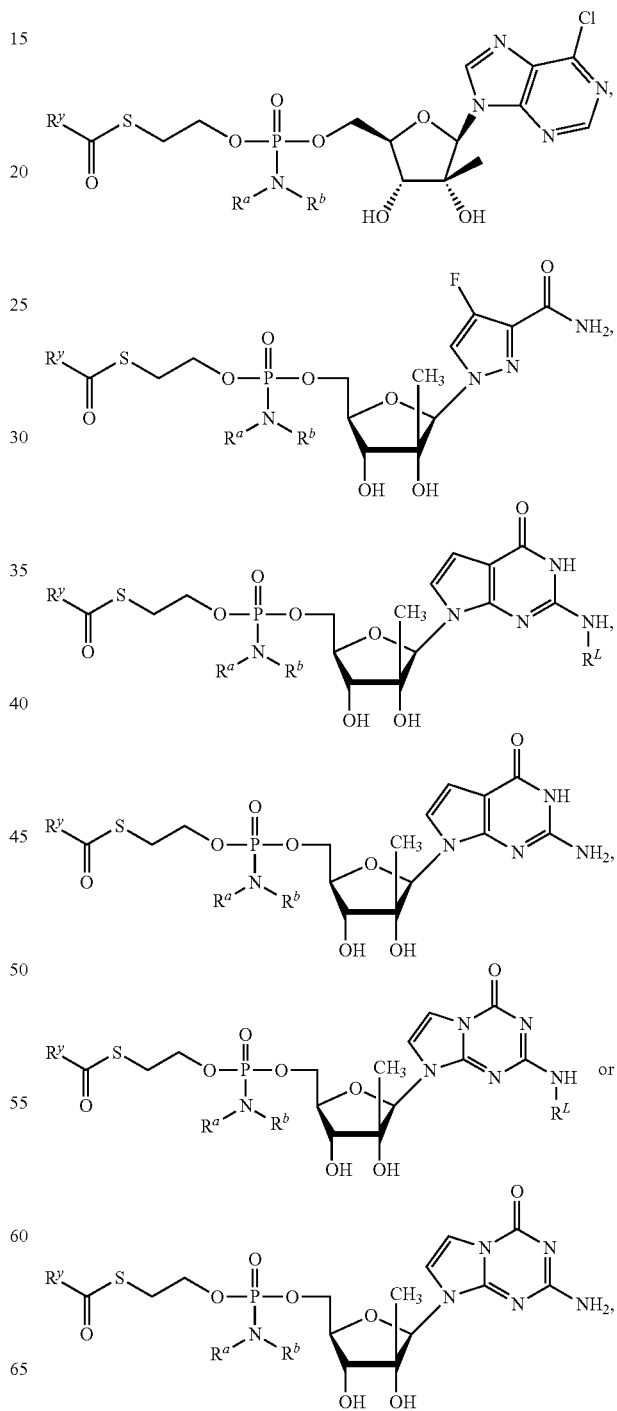

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$.

In another embodiment, the compound provided herein is a compound of formula:

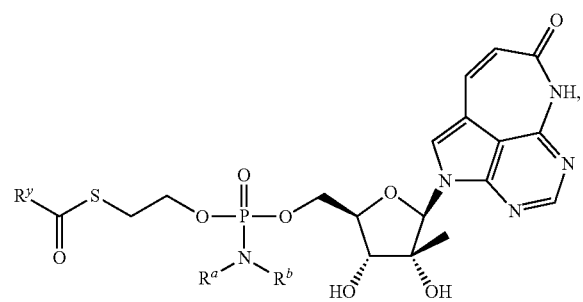

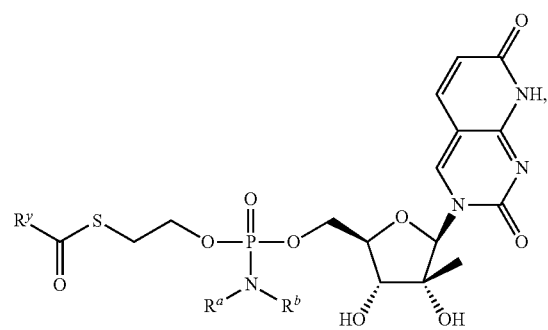

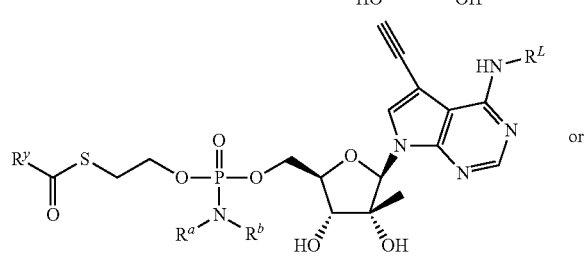

or

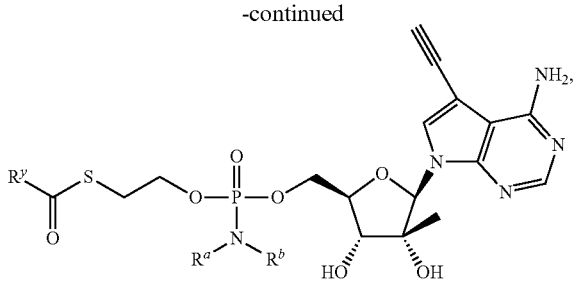

wherein $R^a$, $R^b$ and $R^y$ are as defined in Formula IIa or IIb. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$.

In certain embodiments, 2-deoxy-2-fluoro-2-C-ethynyl-β-D-nucleosides can be formed and derived into phosphoramidate compounds to potentiate delivery of an active monophosphate to the liver of an individual inflicted with HCV, such as the compounds described herein by way of example. In certain embodiments, a compound of the following formula is provided:

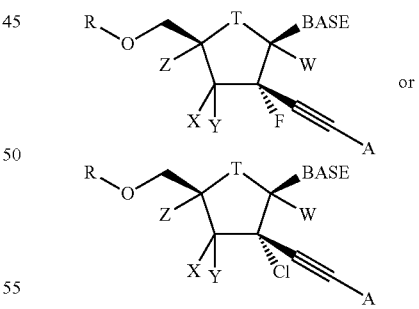

wherein:
T=O, S, $CH_2$, CH(hal) or $CH(hal)_2$, S(O)n;
n=1, 2;
hal=halogen;
R=H, acyl (with lower linear and non linear alkyl —C1 to 6-, aminoacid), monophosphate, diphosphate, triphosphate, monophosphate prodrug such as (alkyl-O)$_2$PO, (tBuSate-O)$_2$ PO, cyclic monophosphate prodrug, phosphoramidate prodrug (aromatic amine, aminoacid);
X and Y are independently H, OH, O-alkyl (lower), O-acyl, F, $NH_2$, NH-alkyl, N-dialkyl, NH-acyl, N-diacyl, or azido;

Z is H, alkyl, alkenyl, alkynyl, hydroxymethyl, fluoromethyl, or azido;

W is H, alkyl, alkenyl, alkynyl, hydroxymethyl, fluoromethyl, azido, carboxylic acid, $CO_2$-alkyl, cyano, or carboxamide;

A is H, alkyl, alkenyl, alkynyl, hydroxymethyl, fluoromethyl, azido, carboxylic acid, $CO_2$-alkyl, cyano, or carboxamide; and Base is a natural or modified base.

Optionally the compounds include a chlorine atom at the 2'-position.

In another embodiment, the compound provided herein is a compound of formula:

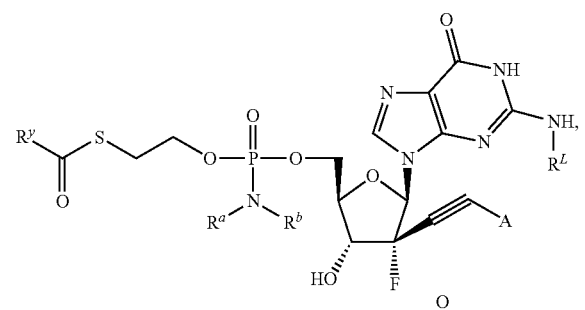

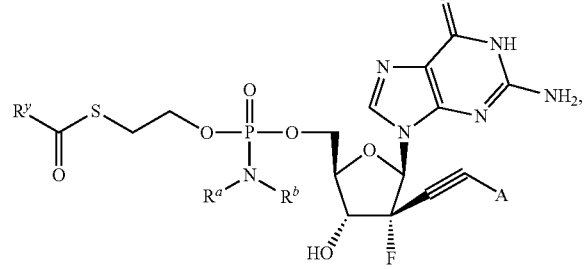

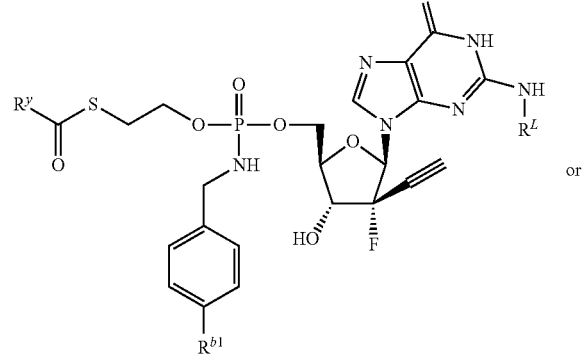

or

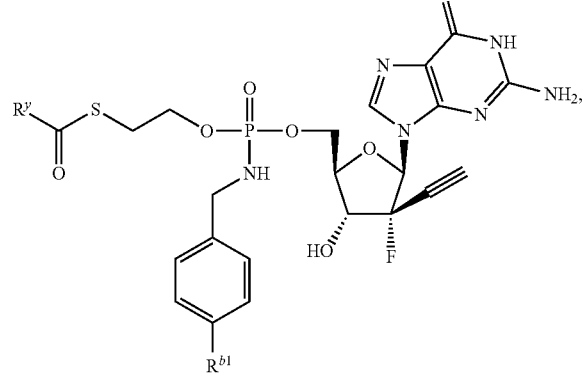

wherein $R^a$, $R^b$ and $R^y$ are as defined in Formula IIa or IIb; A is H, alkyl, alkenyl, alkynyl, hydroxymethyl, fluoromethyl, azido, carboxylic acid, $CO_2$-alkyl, cyano, or carboxamide; and $R^{b1}$ is halo, alkoxy or haloalkyl. Each $R^L$ is independently H, carbamyl, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; an amino acid residue; or a carbohydrate. In certain embodiments according to this paragraph, each $R^L$ is hydrogen, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, each $R^L$ is hydrogen, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, each $R^L$ is hydrogen, $R^a$ and $R^b$ are independently benzyl or substituted alkyl. In a further embodiment, $R^y$ is selected from the group consisting of alkyl and hydroxyalkyl. In certain embodiments, each $R^L$ is hydrogen and $R^y$ is —$C(CH_3)_2CH_2OH$.

In another embodiment, the compound provided herein is a compound of formula:

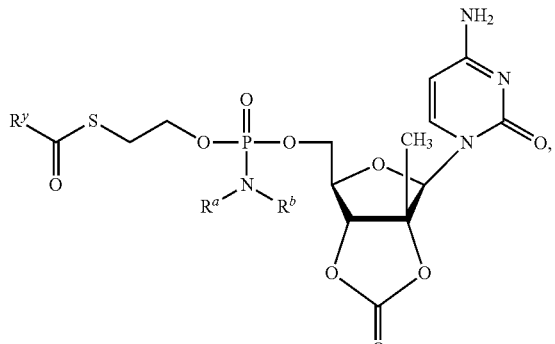

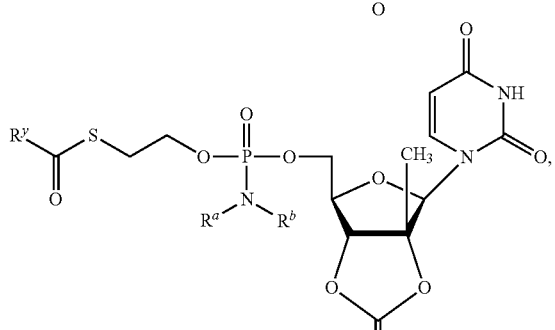

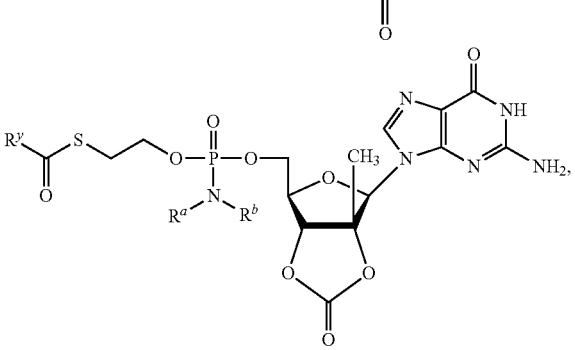

-continued

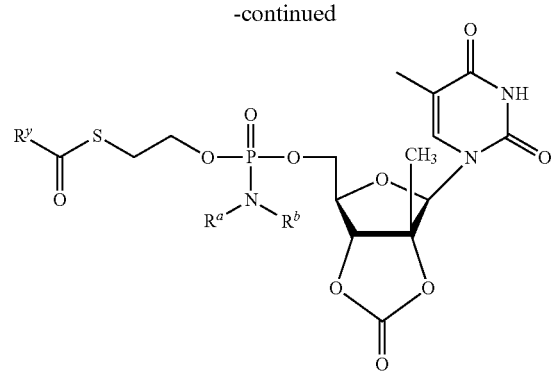

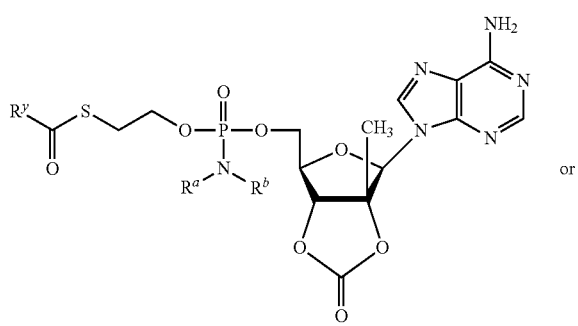

or

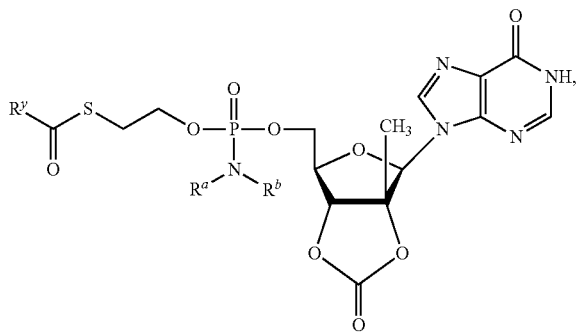

wherein $R^a$, $R^b$ and $R^y$ are as defined in Formula IIa or IIb. In certain embodiments, $R^a$ is hydrogen, $R^b$ is —CH$_2$—C$_6$H$_5$ and $R^y$ is —C(CH$_3$)$_2$CH$_2$OH. In certain embodiments according to this paragraph, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —OR$^c$, —C(R$^c$)$_3$ or —NHR$^c$ where each R$^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^y$ is —C(CH$_3$)$_2$CH$_2$OH.

In another embodiment, the compound provided herein is a compound of formula:

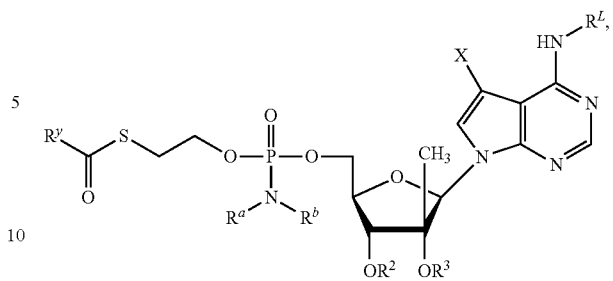

wherein X is halogen, $R^a$, $R^b$ and $R^y$ are as defined in Formula IIa or IIb and $R^2$ and $R^3$ are each independently H, straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, aralkylsulfonyl, a lipid, such as a phospholipid; an amino acid; and amino acid residue, a carbohydrate; a peptide; cholesterol; or other pharmaceutically acceptable leaving group which is capable of providing a compound wherein $R^2$ and/or $R^3$ is independently H or phosphate (including mono-, di- or triphosphate), for example when administered in vivo; or $R^2$ and $R^3$ are linked to form a cyclic group by an alkyl, ester or carbamate linkage. $R^L$ is hydrogen or any lipophillic group known to those of skill in the art. In certain embodiments, $R^2$ and $R^3$ are each hydrogen, $R^a$ is hydrogen, $R^b$ is —CH$_2$—C$_6$H$_5$ and $R^y$ is —C(CH$_3$)$_2$CH$_2$OH. In certain embodiments said lipophilic group is selected from alkyl, alkenyl, cycloalkyl, aryl, heteroaryl, arylalkyl and heteroarylalkyl. In certain embodiments according to this paragraph, X is fluoro, $R^L$ is hydrogen, $R^2$ and $R^3$ are each H, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, X is fluoro, $R^L$ is hydrogen, $R^2$ and $R^3$ are each H, $R^y$ is —OR$^c$, —C(R$^c$)$_3$ or —NHR$^c$ where each R$^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, X is fluoro, $R^L$ is hydrogen, $R^2$ and $R^3$ are each H, $R^a$ and $R^b$ are independently benzyl or substituted alkyl. In a further embodiment, X is fluoro, $R^L$ is hydrogen, $R^2$ and $R^3$ are each H, $R^y$ is selected from the group consisting of alkyl and hydroxyalkyl. In certain embodiments, X is fluoro, $R^L$ is hydrogen, $R^2$ and $R^3$ are each H, $R^y$ is —C(CH$_3$)$_2$CH$_2$OH.

In another embodiment, the compound provided herein is a compound of formula:

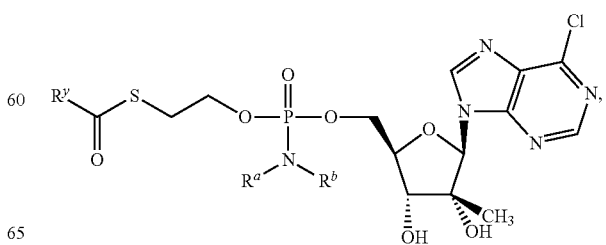

wherein $R^a$, $R^b$ and $R^y$ are as defined in Formula IIa or IIb. In certain embodiments, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^a$ is hydrogen, $R^b$ is —$CH_2$—$C_6H_5$ and $R^y$ is —$C(CH_3)_2CH_2OH$.

In another embodiment, the compound provided herein is a compound of formula:

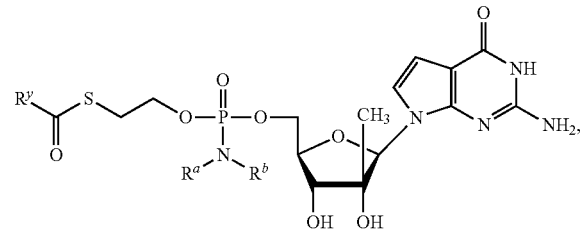

wherein $R^a$, $R^b$ and $R^y$ are as defined in Formula IIa or IIb. In certain embodiments, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^a$ is hydrogen, $R^b$ is —$CH_2$—$C_6H_5$ and $R^y$ is —$C(CH_3)_2CH_2OH$.

In another embodiment, the compound provided herein is a compound of formula:

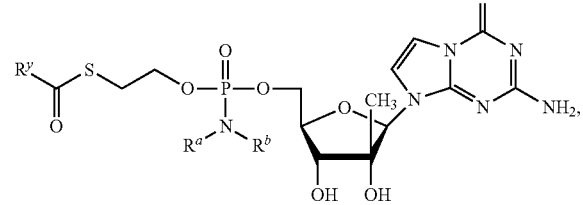

wherein $R^a$, $R^b$ and $R^y$ are as defined in Formula IIa or IIb. In certain embodiments, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^a$ is hydrogen, $R^b$ is —$CH_2$—$C_6H_5$ and $R^y$ is —$C(CH_3)_2CH_2OH$.

In another embodiment, the compound provided herein is a compound of formula:

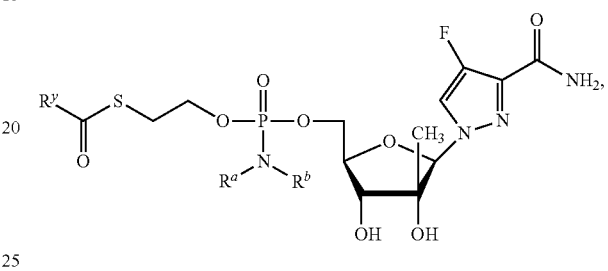

wherein $R^a$, $R^b$ and $R^y$ are as defined in Formula IIa or IIb. In certain embodiments, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —$OR^c$, —$C(R^c)_3$ or —$NHR^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^a$ is hydrogen, $R^b$ is —$CH_2$—$C_6H_5$ and $R^y$ is —$C(CH_3)_2CH_2OH$.

In another embodiment, the compound provided herein is a compound of formula:

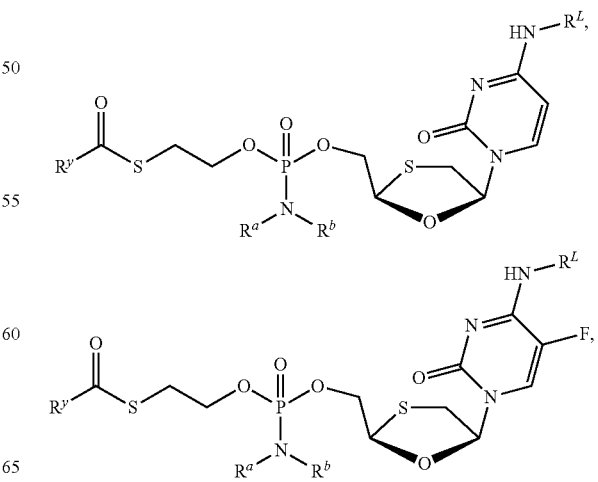

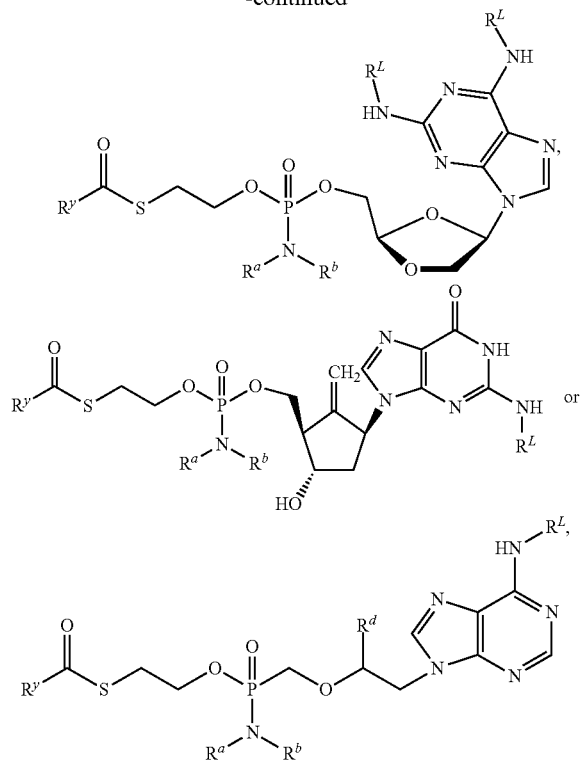

wherein $R^a$, $R^b$ and $R^y$ are as defined in Formula IIa or IIb. $R^L$ is hydrogen or any lipophillic group known to those of skill in the art. In certain embodiments, $R^a$ is hydrogen, $R^b$ is —CH$_2$—C$_6$H$_5$ and $R^y$ is —C(CH$_3$)$_2$CH$_2$OH. In certain embodiments said lipophilic group is selected from alkyl, alkenyl, cycloalkyl, aryl, heteroaryl, arylalkyl and heteroarylalkyl. In certain embodiments according to this paragraph, $R^y$ is substituted alkyl, e.g. hydroxyalkyl or aminoalkyl; and $R^a$ and $R^b$ are independently hydrogen, alkyl, substituted alkyl, benzyl or substituted benzyl, for instance hydroxy- or amino-substituted alkyl or benzyl. In another embodiment, $R^y$ is —C(R$^c$)$_3$ or —NHR$^c$ where each $R^c$ is independently alkyl, substituted alkyl, aryl or substituted aryl, for instance hydroxy- or amino-substituted alkyl or aryl; and $R^a$ and $R^b$ are independently hydrogen, alkyl, substituted alkyl, benzyl or substituted benzyl, for instance hydroxy- or amino-substituted alkyl or benzyl. In a further embodiment, $R^a$ and $R^b$ are independently benzyl or substituted alkyl. In a further embodiment, $R^y$ is selected from the group consisting of alkyl and hydroxyalkyl. In certain embodiments, $R^y$ is —C(CH$_3$)$_2$CH$_2$OH.

In another embodiment, the compound provided herein is a compound of formula:

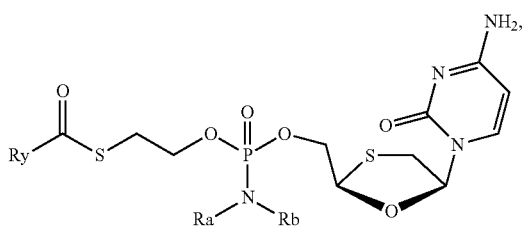

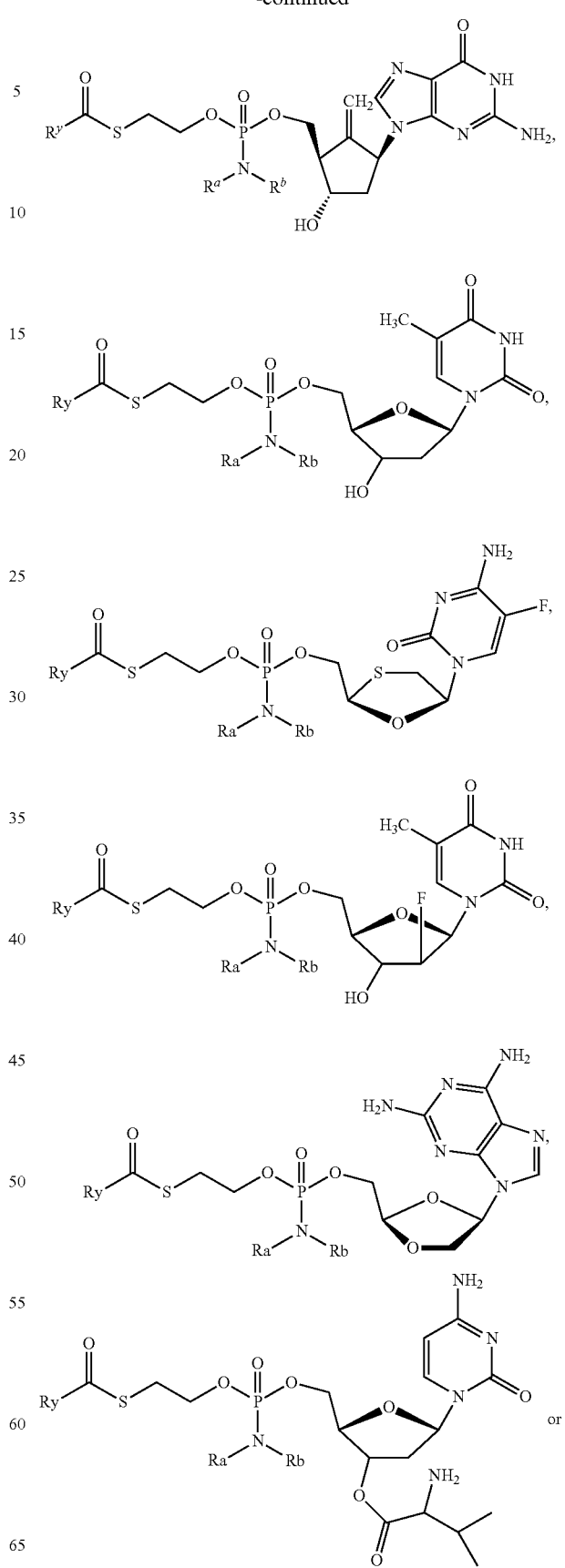

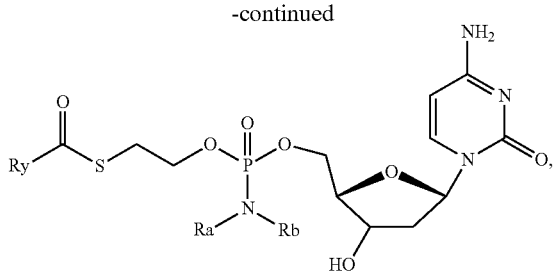

wherein the variables are as described above.

In another embodiment, the compound provided herein is a compound of formula:

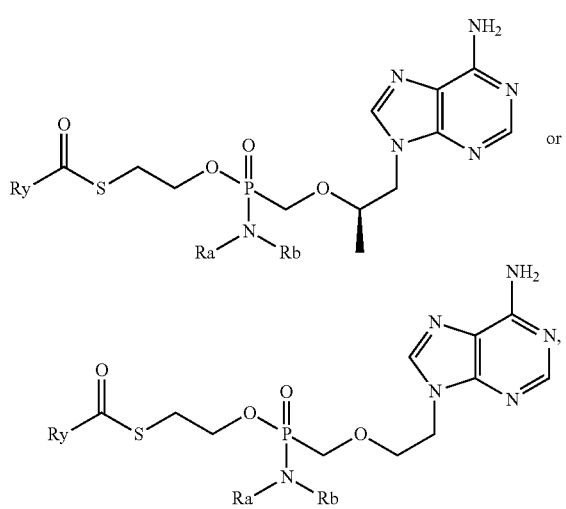

wherein the variables are as described above.

In one embodiment, $R^1$ is a natural nucleoside. In one embodiment, $R^1$ is a 2'- or 3'-prodrug of biologically active 1', 2', 3' or 4'C-branched β-D or β-L nucleoside. The term 1', 2', 3' or 4'C-branched, as used in this specification, includes a nucleoside that has an additional non-natural substituent in the 1', 2', 3' or 4'-position (i.e., carbon is bound to four non-hydrogen substituents). The term 2'-prodrug, as used herein, includes a 1', 2', 3' or 4' C-branched-β-D or β-L nucleoside that has a biologically cleavable moiety at the 2'-position, including, but not limited to acyl, and in one embodiment, a natural or synthetic D or L amino acid, in one embodiment, an L-amino acid. The term 3'-prodrug, as used herein, includes a 1', 2', 3' or 4' C-branched-β-D or β-L nucleoside that has a biologically cleavable moiety at the 3'-position, including, but not limited to acyl, and in one embodiment, a natural or synthetic D or L amino acid, in one embodiment, an L-amino acid. In one embodiment, the amino acid is valine.

Examples of prodrugs (that can be further derivatized as described herein to include a phosphoramidate or phosphonoamidate moiety, for example, at the 5' position) include 2'-L-valine ester of β-D-2'-C-methyl-cytidine; 2'-L-valine ester of β-D-2'-C-methyl-thymidine; 2'-L-valine ester of β-D-2'-C-methyl-adenosine; 2'-L-valine ester of β-D-2'-C-methyl-guanosine; 2'-L-valine ester of β-D-2'-C-methyl-5-fluorocytidine; 2'-L-valine ester of β-D-2'-C-methyl-uridine; 2'-acetyl ester of β-D-2'-C-methyl-cytidine; 2'-acetyl ester of β-D-2'-C-methyl-thymidine; 2'-acetyl ester of β-D-2'-C-methyl-adenosine; 2'-acetyl ester of β-D-2'-C-methyl-guanosine; 2'-acetyl ester of β-D-2'-C-methyl-5-fluoro-cytidine; and 2'-esters of β-D-2'-C-methyl-(cytidine, 5-fluorocytidine, guanosine, uridine, adenosine, or thymidine) wherein (i) the 2' ester is an amino acid ester; or (ii) the 2' ester is an alkyl or aryl ester.

Further examples of prodrugs are 3'-L-valine ester of β-D-2'-C-methyl-cytidine; 3'-L-valine ester of β-D-2'-C-methyl-thymidine; 3'-L-valine ester of β-D-2'-C-methyl-adenosine; 3'-L-valine ester of β-D-2'-C-methyl-guanosine; 3'-L-valine ester of β-D-2'-C-methyl-5-fluorocytidine; 3'-L-valine ester of β-D-2'-C-methyl-uridine; 3'-acetyl ester of β-D-2'-C-methyl-cytidine; 3'-acetyl ester of β-D-2'-C-methyl-thymidine; 3'-acetyl ester of β-D-2'-C-methyl-adenosine; 3'-acetyl ester of β-D-2'-C-methyl-guanosine; 3'-acetyl ester of β-D-2'-C-methyl-5-fluoro-cytidine; and 3'-esters of β-D-2'-C-methyl-(cytidine, 5-fluorocytidine, guanosine, uridine, adenosine, or thymidine) wherein (i) the 3' ester is an amino acid ester; or (ii) the 3' ester is an alkyl or aryl ester.

Additional examples of prodrugs include 2',3'-L-divaline ester of β-D-2'-C-methyl-cytidine (dival-2'-Me-L-dC); 2',3'-L-divaline ester of β-D-2'-C-methyl-thymidine; 2',3'-L-divaline ester of β-D-2'-C-methyl-adenosine; 2',3'-L-divaline ester of β-D-2'-C-methyl-guanosine; 2',3'-L-divaline ester of β-D-2'-C-methyl-5-fluoro-cytidine; 2',3'-L-divaline ester of β-D-2'-C-methyl-uridine; 2',3'-diacetyl ester of β-D-2'-C-methyl-cytidine; 2',3'-diacetyl ester of β-D-2'-C-methyl-thymidine; 2',3'-diacetyl ester of β-D-2'-C-methyl-adenosine; 2',3'-diacetyl ester of β-D-2'-C-methyl-guanosine; 2',3'-diacetyl ester of β-D-2'-C-methyl-5-fluoro-cytidine; and 2',3'-diesters of β-D-2'-C-methyl-(cytidine, 5-fluorocytidine, guanosine, uridine, adenosine, or thymidine) wherein (i) the 2' ester is an amino acid ester and the 3'-ester is an alkyl or aryl ester; (ii) both esters are amino acid esters; (iii) both esters are independently alkyl or aryl esters; or (iv) the 2' ester is an alkyl or aryl ester and the 3'-ester is an amino acid ester.

In one embodiment, $R^1$ is:

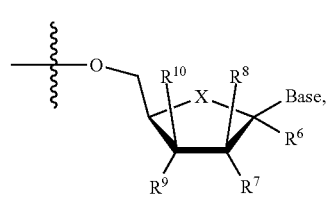

X

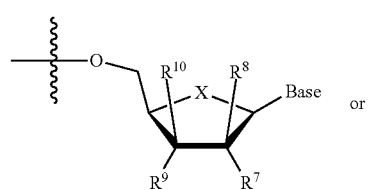

XI

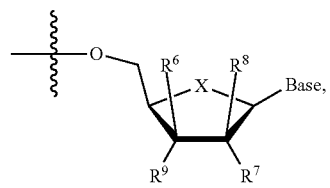

XII wherein Base is a natural or non-natural purine or pyrimidine base as defined herein;

$R^6$ is hydrogen, hydroxy, alkyl, alkenyl, alkynyl, azido, cyano, Br-vinyl, alkoxy, acyloxy, alkoxycarbonyl, alkenyloxy, halo, $NO_2$ or $NR^{6a}R^{6b}$;

$R^{6a}$ and $R^{6b}$ are each independently hydrogen, alkyl, alkenyl, alkynyl, cycloalkyl, acyl, aryl, heteroaryl or heterocyclyl;

$R^7$, $R^9$, $R^8$ and $R^{10}$ are selected as follows:

i) $R^7$ and $R^9$ are each independently hydrogen, $OR^{7a}$, hydroxy, alkyl, alkenyl, alkynyl, azido, cyano, Br-vinyl, alkyloxycarbonyl, acyloxy, halo, $NO_2$ or $NR^{6a}R^{6b}$;

ii) $R^8$ and $R^{10}$ are each independently H, alkyl or halo; or iii) each $R^7$ and $R^9$, $R^7$ and $R^{10}$, $R^8$ and $R^9$ or $R^8$ and $R^{10}$ together form a double bond;

$R^{7a}$ is H; straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester including alkyl or arylalkyl sulfonyl including methanesulfonyl and benzyl, wherein the phenyl group is optionally substituted with one or more substituents as described in the definition of aryl given herein; alkylsulfonyl, arylsulfonyl, arylalkylsulfonyl, a lipid, including a phospholipid; an amino acid; and amino acid residue, a carbohydrate; a peptide; cholesterol; or other pharmaceutically acceptable leaving group which is capable of providing a compound wherein $R^{7a}$ is H or phosphate (including mono-, di- or triphosphate), for example, when administered in vivo; wherein in one embodiment $R^{7a}$ is not phosphate (including mono-, di- or triphosphate or a stabilized phosphate prodrug), or two $R^{7a}$ groups are linked to form a cyclic group by an alkyl, ester or carbamate linkage; and X is O, S, $SO_2$ or $CH_2$.

In one embodiment, $R^1$ has formula:

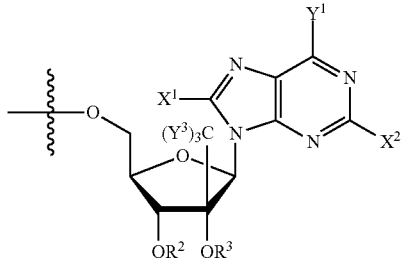

XIII wherein and $R^2$ and $R^3$ are each independently H; straight chained, branched or cyclic alkyl; acyl (including lower acyl); CO-alkyl, CO-aryl, CO-alkoxyalkyl, CO-aryloxyalkyl, CO-substituted aryl, sulfonate ester such as alkyl or arylalkyl sulfonyl including methanesulfonyl and benzyl, wherein the phenyl group is optionally substituted; alkylsulfonyl, arylsulfonyl, arylalkylsulfonyl, a lipid, such as a phospholipid; an amino acid; and amino acid residue, a carbohydrate; a peptide; cholesterol; or other pharmaceutically acceptable leaving group which is capable of providing a compound wherein $R^2$ and/or $R^3$ is independently H or phosphate (including mono-, di- or triphosphate), for example when administered in vivo; or $R^2$ and $R^3$ are linked to form a cyclic group by an alkyl, ester or carbamate linkage;

wherein $Y^1$ is hydrogen, bromo, chloro, fluoro, iodo, CN, OH, $OR^4$, $NH_2$, $NHR^4$, $NR^4R^5$, SH or SW;

$X^1$ is a straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-alkyl, COO-aryl, CO-Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH or $SR^5$; and $X^2$ is H, straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-alkyl, COO-aryl, CO-Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH or $SR^5$; and wherein each $Y^3$ is independently H, F, Cl, Br or I;

each $R^4$ and $R^5$ is independently hydrogen, acyl (including lower acyl), alkyl (including but not limited to methyl, ethyl, propyl and cyclopropyl), lower alkyl, alkenyl, alkynyl or cycloalkyl.

In the embodiments described herein, $R^2$ and/or $R^3$ may be a pharmaceutically acceptable leaving group which is capable of providing a compound wherein $R^2$ and/or $R^3$ is independently H or phosphate (including mono-, di- or triphosphate), for example when administered in vivo.

In another embodiment, each $R^2$ and $R^3$ is independently hydrogen or acyl. In another embodiment, $R^2$ and $R^3$ are linked to form a cyclic group by an alkyl, ester or carbamate linkage.

In another embodiment, $R^1$ is:

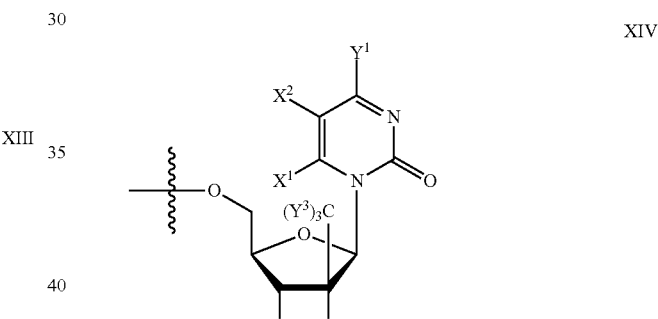

XIV wherein $R^2$, $R^3$, $Y^1$, $Y^3$, $X^1$ and $X^2$ are as defined in Formula XIII.

In one embodiment, $R^1$ is:

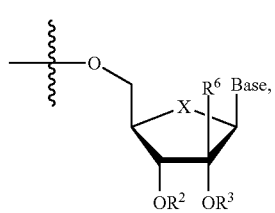

XX

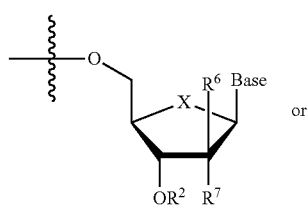

XXI or

-continued
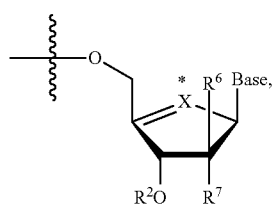
XXII
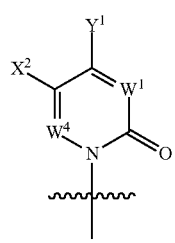
(F)
wherein Base is selected from the group consisting of
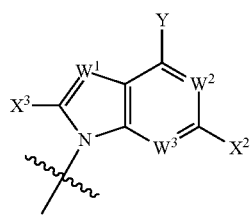
(A)
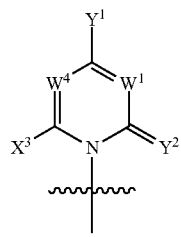
(G)
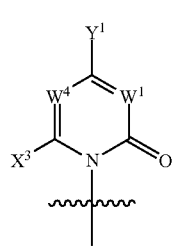
(H)
(B)
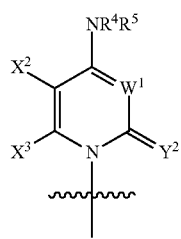
(I)
(C)
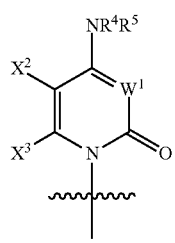
(J)
(D)
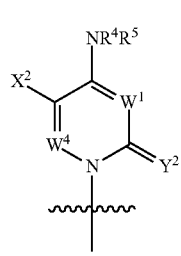
(K)
(E)

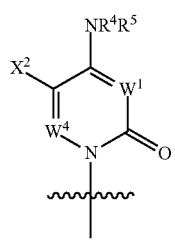
(L)
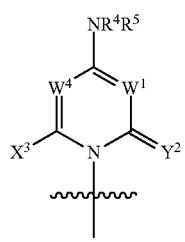
(M)
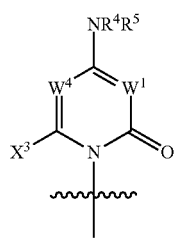
(N)
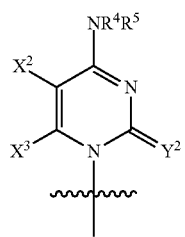
(O)
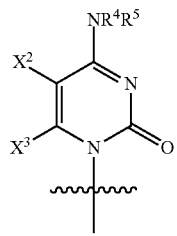
(P)
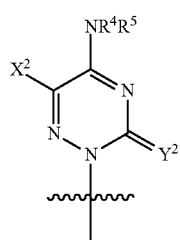
(Q)
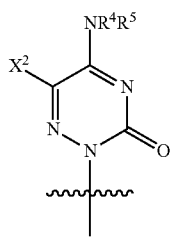
(R)
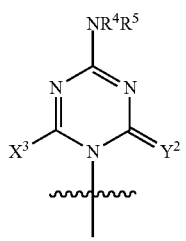
(S)
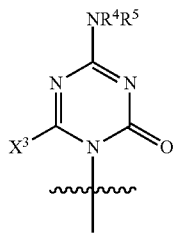
(T)
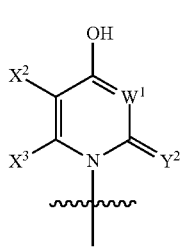
(U)
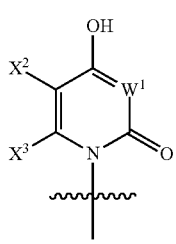
(V)
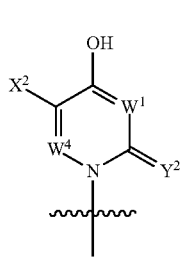
(W)

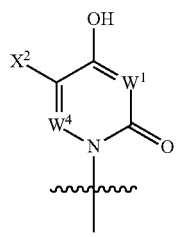 (X)
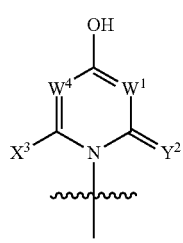 (Y)
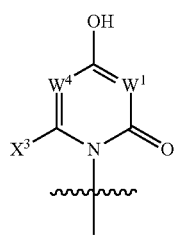 (Z)
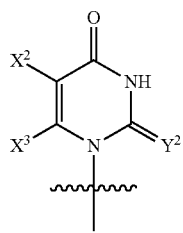 (AA)
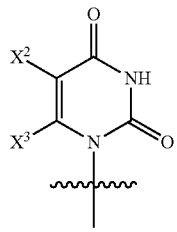 (AB)
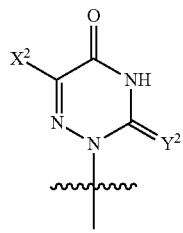 (AC)

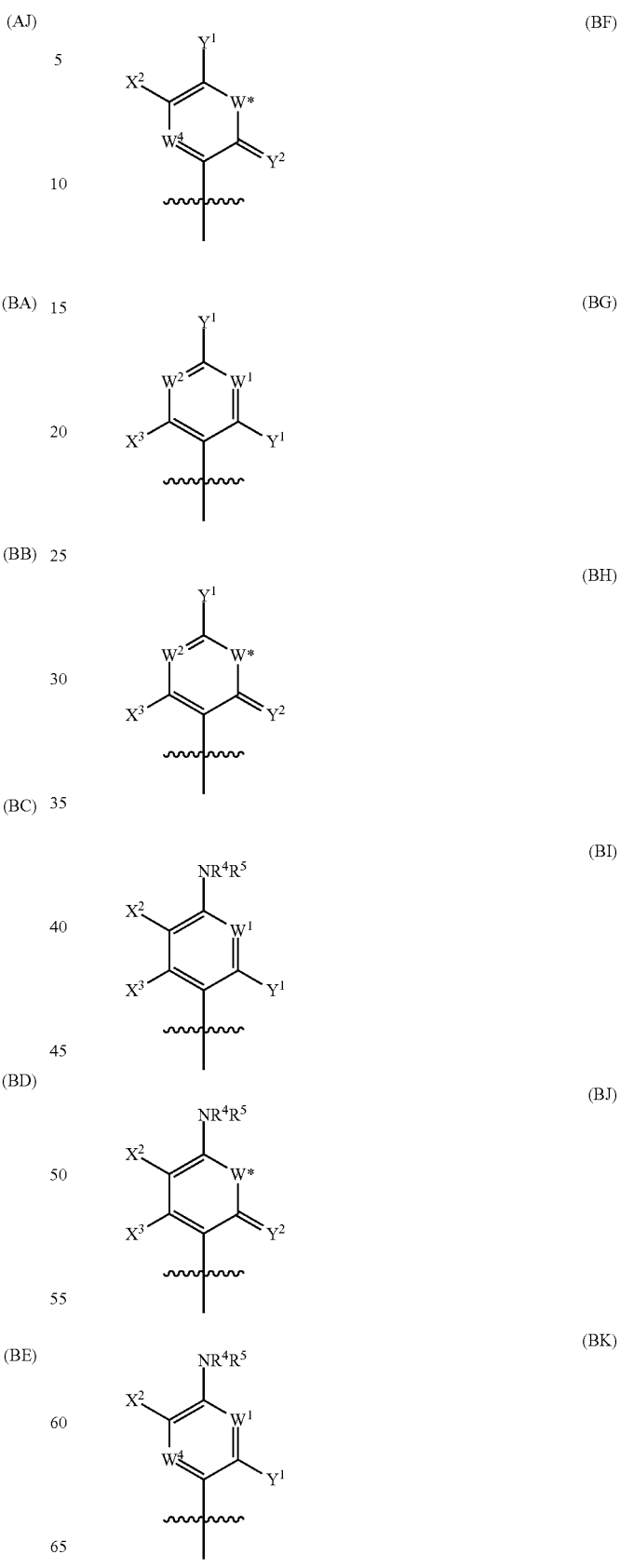

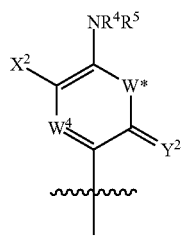 (BL)
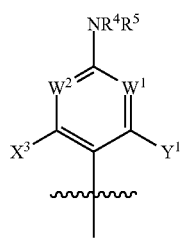 (BM)
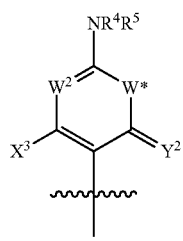 (BN)
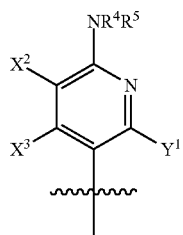 (BO)
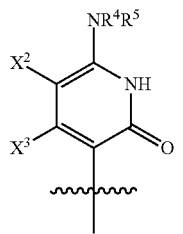 (BP)
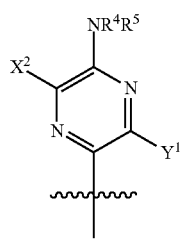 (BQ)
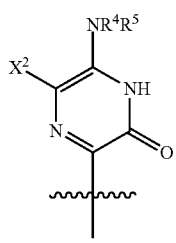 (BR)
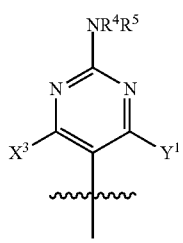 (BS)
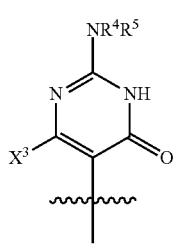 (BT)
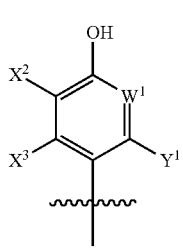 (BU)
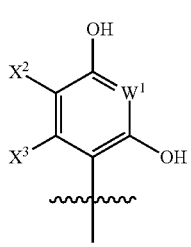 (BV)
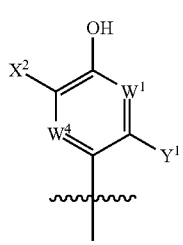 (BW)

-continued

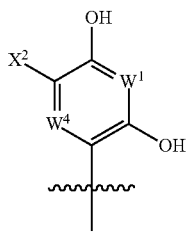
(BX)

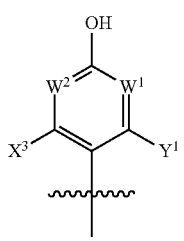
(BY)

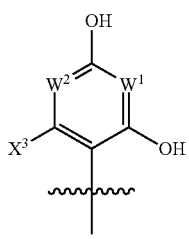
(BZ)

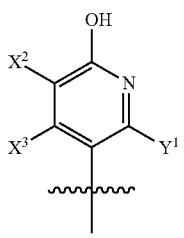
(BAA)

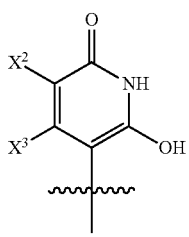
(BAB)

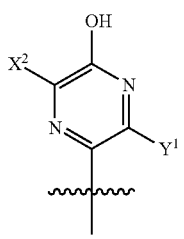
(BAC)

-continued

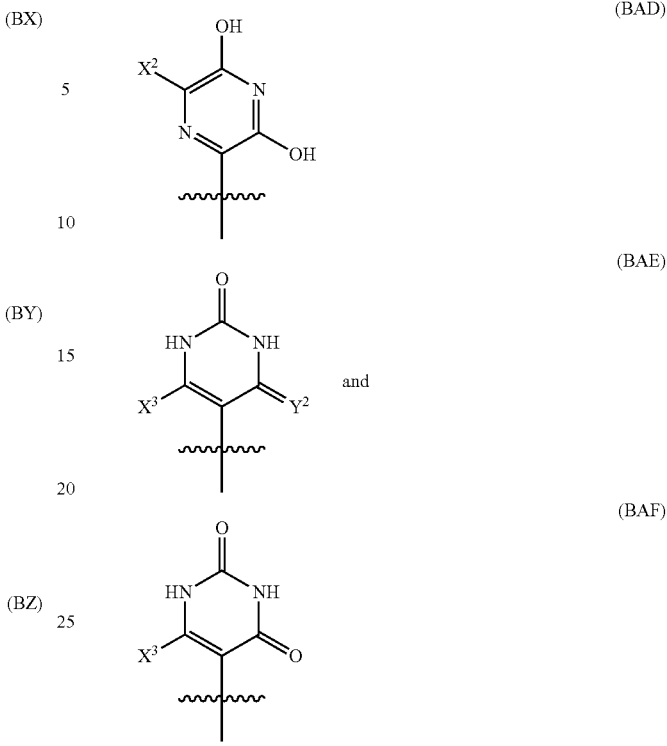

wherein each $W^1$, $W^2$, $W^3$ and $W^4$ is independently N, CH, CF, CI, CBr, CCl, CCN, CCH$_3$, CCF$_3$, CCH$_2$CH$_3$, CC(O)NH$_2$, CC(O)NHR$^4$, CC(O)N(R$^4$)$_2$, CC(O)OH, CC(O)OR$^4$ or CX$^3$;

each W* is independently O, S, NH or NR$^4$;

X is O, S, SO$_2$, CH$_2$, CH$_2$OH, CHF, CF$_2$, C(Y$^3$)$_2$, CHCN, C(CN)$_2$, CHR$^4$ or C(R$^4$)$_2$;

X* is CH, CF, CY$^3$ or CR$^4$;

$X^2$ is H, straight chained, branched or cyclic optionally substituted alkyl, CH$_3$, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, CH$_2$OH, optionally substituted alkenyl, optionally substituted alkynyl, COOH, COOR$^4$, COO-alkyl, COO-aryl, CO-Oalkoxyalkyl, CONH$_2$, CONHR$^4$, CON(R$^4$)$_2$, chloro, bromo, fluoro, iodo, CN, N$_3$, OH, OR$^4$, NH$_2$, NHR$^4$, NR$^4$R$^5$, SH or SR$^5$;

each $X^3$ is independently a straight chained, branched or cyclic optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, N$_3$, CN, —C(O)OH, —C(O)OR$^4$, —C(O)O (lower alkyl), —C(O)NH$_2$, —C(O)NHR$^4$, —C(O)NH(lower alkyl), —C(O)N(R$^4$)$_2$, —C(O)N(lower alkyl)$_2$, OH, OR$^4$, —O(acyl), —O(lower acyl), —O(alkyl), —O(lower alkyl), —O(alkenyl), —O(alkynyl), —O(arylalkyl), —O(cycloalkyl), —S(acyl), —S(lower acyl), —S(R$^4$), —S(lower alkyl), —S(alkenyl), —S(alkynyl), —S(arylalkyl), —S(cycloalkyl), chloro, bromo, fluoro, iodo, NH$_2$, —NH(lower alkyl), —NHR$^4$, —NR$^4$R$^5$, —NH(acyl), —N(lower alkyl)$_2$, —NH(alkenyl), —NH(alkynyl), —NH(arylalkyl), —NH(cycloalkyl), —N(acyl)$_2$;

each Y is independently selected from the group consisting of H, optionally substituted lower alkyl, cycloalkyl, alkenyl, alkynyl, CH$_2$OH, CH$_2$NH$_2$, CH$_2$NHCH$_3$, CH$_2$N(CH$_3$)$_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCO-OH$, $(CH_2)_mCOOR$, $(CH_2)_mCONH_2$, $(CH_2)_mCONR_2$, and $(CH_2)_mCONHR$;

wherein R is H, alkyl or acyl;

$Y^1$ is hydrogen, bromo, chloro, fluoro, iodo, CN, OH, $OR^4$, $NH_2$, $NHR^4$, $NR^4R^5$, SH or $SR^4$;

each $Y^2$ is independently O, S, NH or $NR^4$;

each $Y^3$ is independently H, F, Cl, Br or I;

each $R^4$ and $R^5$ is independently hydrogen, acyl (including lower acyl), alkyl (including but not limited to methyl, ethyl, propyl and cyclopropyl), lower alkyl, alkenyl, alkynyl or cycloalkyl;

each $R^6$ is independently an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, $-CH_2C(O)OH$, $-CH_2C(O)OR^4$, $-CH_2C(O)O(lower\ alkyl)$, $-CH_2C(O)NH_2$, $-CH_2C(O)NHR^4$, $-CH_2C(O)NH(lower\ alkyl)$, $-CH_2C(O)N(R^4)_2$, $-CH_2C(O)N(lower\ alkyl)_2$, $-(CH_2)_mC(O)OH$, $-(CH_2)_mC(O)OR^4$, $-(CH_2)_mC(O)O(lower\ alkyl)$, $-(CH_2)_mC(O)NH_2$, $-(CH_2)_mC(O)NHR^4$, $-(CH_2)_mC(O)NH(lower\ alkyl)$, $-(CH_2)_mC(O)N(R^4)_2$, $-(CH_2)_mC(O)N(lower\ alkyl)_2$, $-C(O)OH$, $-C(O)OR^4$, $-C(O)O(lower\ alkyl)$, $-C(O)NH_2$, $-C(O)NHR^4$, $-C(O)NH(lower\ alkyl)$, $-C(O)N(R^4)_2$, $-C(O)N(lower\ alkyl)_2$ or cyano;

each $R^7$ is independently H, OH, $OR^2$, optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle (for example, a 3-7 membered carbocyclic ring), optionally substituted heterocycle (for example, a 3-7 membered heterocyclic ring having one or more O, S and/or N), optionally substituted heteroaryl (for example, a 3-7 membered heteroaromatic ring having one or more O, S and/or N), $-CH_2C(O)OH$, $-CH_2C(O)OR^4$, $-CH_2C(O)O(lower\ alkyl)$, $-CH_2C(O)SH$, $-CH_2C(O)SR^4$, $-CH_2C(O)S(lower\ alkyl)$, $-CH_2C(O)NH_2$, $-CH_2C(O)NHR^4$, $-CH_2C(O)NH(lower\ alkyl)$, $-CH_2C(O)N(R^4)_2$, $-CH_2C(O)N(lower\ alkyl)_2$, $-(CH_2)_mC(O)OH$, $-(CH_2)_mC(O)OR^4$, $-(CH_2)_mC(O)O(lower\ alkyl)$, $-(CH_2)_mC(O)SH$, $-(CH_2)_mC(O)SR^4$, $-(CH_2)_mC(O)S(lower\ alkyl)$, $-(CH_2)_mC(O)NH_2$, $-(CH_2)_mC(O)NHR^4$, $-(CH_2)_mC(O)NH(lower\ alkyl)$, $-(CH_2)_mC(O)N(R^4)_2$, $-(CH_2)_mC(O)N(lower\ alkyl)_2$, $-C(O)OH$, $-C(O)OR^4$, $-C(O)O(lower\ alkyl)$, $-C(O)SH$, $-C(O)SR^4$, $-C(O)S(lower\ alkyl)$, $-C(O)NH_2$, $-C(O)NHR^4$, $-C(O)NH(lower\ alkyl)$, $-C(O)N(R^4)_2$, $-C(O)N(lower\ alkyl)_2$, $-O(acyl)$, $-O(lower\ acyl)$, $-O(R^4)$, $-O(alkyl)$, $-O(lower\ alkyl)$, $-O(alkenyl)$, $-O(alkynyl)$, $-O(arylalkyl)$, $-O(cycloalkyl)$, $-S(acyl)$, $-S(lower\ acyl)$, $-S(R^4)$, $-S(lower\ alkyl)$, $-S(alkenyl)$, $-S(alkynyl)$, $-S(arylalkyl)$, $-S(cycloalkyl)$, $NO_2$, $NH_2$, $-NH(lower\ alkyl)$, $-NHR^4$, $-NR^4R^5$, $-NH(acyl)$, $-N(lower\ alkyl)_2$, $-NH(alkenyl)$, $-NH(alkynyl)$, $-NH(arylalkyl)$, $-NH(cycloalkyl)$, $-N(acyl)_2$, azido, cyano, SCN, OCN, NCO or halo (fluoro, chloro, bromo, iodo);

alternatively, $R^6$ and $R^7$ can come together to form a spiro compound selected from the group consisting of optionally substituted carbocycle (for example, a 3-7 membered carbocyclic ring) or optionally substituted heterocycle (for example, a 3-7 membered heterocyclic ring having one or more O, S and/or N);

each m is independently 0, 1 or 2.

In one embodiment, the base is

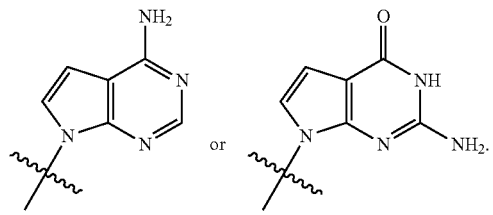 [SMILES: *n1ccc2c(N)ncnc21 ; "or" ; *n1ccc2c(=O)[nH]c(N)nc21]

In one embodiment, the base is

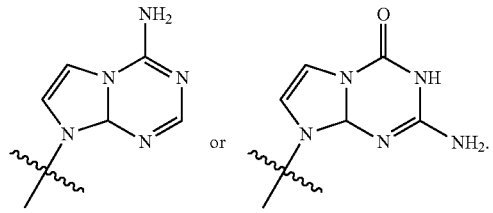 [SMILES: *N1C=CN2C(N)=NC=NC12 ; "or" ; *N1C=CN2C(=O)NC(N)=NC12]

In another embodiment, $R^1$ is

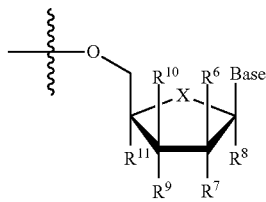

XXX

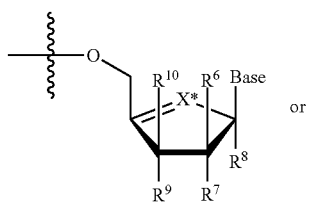

XXXI

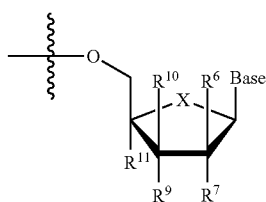

XXXII wherein each $R^6$ and $R^7$ is as defined in Formulae XX, XXI or XXII above;

wherein each $R^8$ and $R^{11}$ is independently hydrogen, an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, $-CH_2C(O)OH$, $-CH_2C(O)OR^4$, $-CH_2C(O)O(lower\ alkyl)$, $-CH_2C(O)NH_2$, $-CH_2C(O)NHR^4$, $-CH_2C(O)NH(lower\ alkyl)$, $-CH_2C(O)N(R^4)_2$, $-CH_2C$ (O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$ C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, cyano, azido, NH-acyl or N(acyl)$_2$;

each R$^9$ and R$^{10}$ are independently hydrogen, OH, OR$^2$, optionally substituted alkyl (including lower alkyl), CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, optionally substituted carbocycle (for example, a 3-7 membered carbocyclic ring), optionally substituted heterocycle (for example, a 3-7 membered heterocyclic ring having one or more O, S and/or N), optionally substituted heteroaryl (for example, a 3-7 membered heteroaromatic ring having one or more O, S and/or N), —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(arylalkyl), —O(cycloalkyl), —S(acyl), —S(lower acyl), —S(R$^4$), —S(lower alkyl), —S(alkenyl), —S(alkynyl), —S(arylalkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(arylalkyl), —NH(cycloalkyl), —N(acyl)$_2$, azido, cyano, SCN, OCN, NCO or halo (fluoro, chloro, bromo, iodo);

each m is independently 0, 1 or 2;

alternatively, R$^6$ and R$^{10}$, R$^7$ and R$^9$, R$^8$ and R$^7$ or R$^9$ and R$^{11}$ can come together to form a bridged compound selected from the group consisting of optionally substituted carbocycle (for example, a 3-7 membered carbocyclic ring) or optionally substituted heterocycle (for example, a 3-7 membered heterocyclic ring having one or more O, S and/or N); or alternatively, R$^6$ and R$^7$ or R$^9$ and R$^{10}$ can come together to form a spiro compound selected from the group consisting of optionally substituted carbocycle (for example, a 3-7 membered carbocyclic ring) or optionally substituted heterocycle (for example, a 3-7 membered heterocyclic ring having one or more O, S and/or N).

In another embodiment, R$^1$ is:

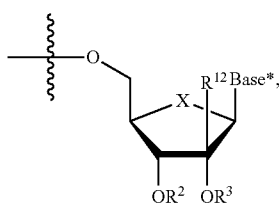

XL

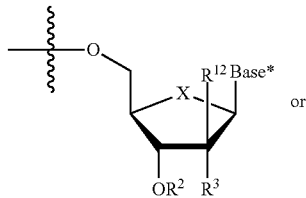

XLI or

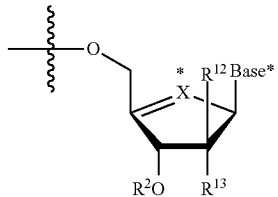

XLII wherein Base* is a purine or pyrimidine base as defined herein;

each R$^{12}$ is independently a substituted alkyl (including lower alkyl), CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, substituted alkenyl, haloalkenyl (but not Br-vinyl), substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)NH$_2$, —C(O)NHR$^4$, —C(O)NH(lower alkyl), —C(O)N(R$^4$)$_2$, —C(O)N(lower alkyl)$_2$;

each R$^{13}$ is independently substituted alkyl (including lower alkyl), CH$_2$CN, CH$_2$N$_3$, CH$_2$NH$_2$, CH$_2$NHCH$_3$, CH$_2$N(CH$_3$)$_2$, CH$_2$OH, halogenated alkyl (including halogenated lower alkyl), CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, substituted alkenyl, haloalkenyl (but not Br-vinyl), substituted alkynyl, haloalkynyl, optionally substituted carbocycle (for example, a 3-7 membered carbocyclic ring), optionally substituted heterocycle (for example, a 3-7 membered heterocyclic ring having one or more O, S and/or N), optionally substituted heteroaryl (for example, a 3-7 membered heteroaromatic ring having one or more O, S and/or N), —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$ C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(R$^4$), —O(alkynyl), —O(arylalkyl), —O(cycloalkyl), —S(acyl), —S(lower acyl), —S(R$^4$), —S(lower alkyl), —S(alkenyl), —S(alkynyl), —S(arylalkyl), —S(cycloalkyl), —NHR$^4$, —NR$^4$R$^5$, —NH(alkenyl), —NH(alkynyl), —NH(arylalkyl), —NH(cycloalkyl), SCN, OCN, NCO or fluoro;

alternatively, $R^{12}$ and $R^{13}$ can come together to form a spiro compound selected from the group consisting of optionally substituted carbocycle (for example, a 3-7 membered carbocyclic ring) or optionally substituted heterocycle (for example, a 3-7 membered heterocyclic ring having one or more O, S and/or N);

$R^2$ and $R^3$ are according to Formula XII; and each m is independently 0, 1 or 2.

In another embodiment, R is:

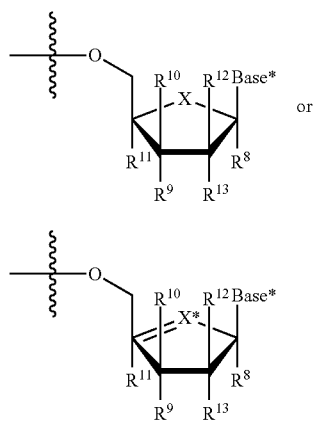

wherein Base* is a purine or pyrimidine base as described herein; and each $R^8$ and $R^{11}$ is independently hydrogen, an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, cyano, NH-acyl or N(acyl)$_2$;

each $R^9$ and $R^{10}$ are independently hydrogen, OH, OR$^2$, optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle (for example, a 3-7 membered carbocyclic ring), optionally substituted heterocycle (for example, a 3-7 membered heterocyclic ring having one or more O, S and/or N), optionally substituted heteroaryl (for example, a 3-7 membered heteroaromatic ring having one or more O, S and/or N), —$CH_2C(O)OH$, —$CH_2C(O)OR^4$, —$CH_2C(O)O$(lower alkyl), —$CH_2C(O)SH$, —$CH_2C(O)SR^4$, —$CH_2C(O)S$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)SH$, —$(CH_2)_mC(O)SR^4$, —$(CH_2)_mC(O)S$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(arylalkyl), —O(cycloalkyl), —S(acyl), —S(lower acyl), —S(R$^4$), —S(lower alkyl), —S(alkenyl), —S(alkynyl), —S(arylalkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(arylalkyl), —NH(cycloalkyl), —N(acyl)$_2$, azido, cyano, SCN, OCN, NCO or halo (fluoro, chloro, bromo, iodo);

each $R^{12}$ is independently a substituted alkyl (including lower alkyl), $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —C(O)OR$^4$, —C(O)NH$_2$, —C(O)NHR$^4$, —C(O)NH(lower alkyl), —C(O)N(R$^4$)$_2$, —C(O)N(lower alkyl)$_2$;

each m is independently 0, 1 or 2;

alternatively, $R^8$ and $R^{13}$, $R^9$ and $R^{13}$, $R^9$ and $R^{11}$ or $R^{10}$ and $R^{12}$ can come together to form a bridged compound selected from the group consisting of optionally substituted carbocycle (for example, a 3-7 membered carbocyclic ring) or optionally substituted heterocycle (for example, a 3-7 membered heterocyclic ring having one or more O, S and/or N); or alternatively, $R^{12}$ and $R^{13}$ or $R^9$ and $R^{10}$ can come together to form a spiro compound selected from the group consisting of optionally substituted carbocycle (for example, a 3-7 membered carbocyclic ring) or optionally substituted heterocycle (for example, a 3-7 membered heterocyclic ring having one or more O, S and/or N).

In one aspect, $R^1$ is:

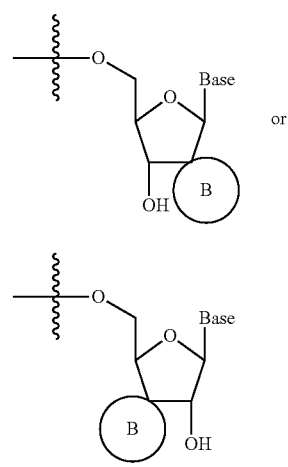

B indicates a spiro compound selected from the group consisting of optionally substituted carbocycle (for example, a 3-7 membered carbocyclic ring) or optionally substituted heterocycle (for example, a 3-7 membered heterocyclic ring having one or more O, S and/or N);

Base is selected from the group consisting of:

(a)
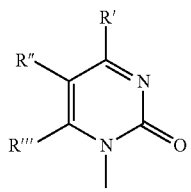

(b)
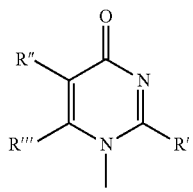

(c)
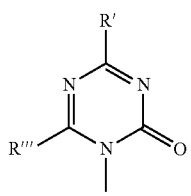

(d)
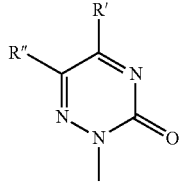

(e)
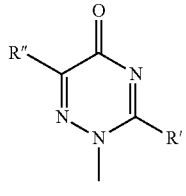

(f)
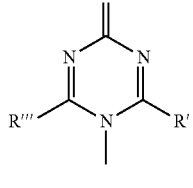

(g)
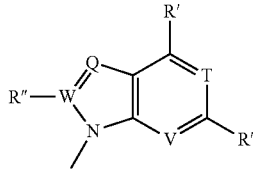

(h)
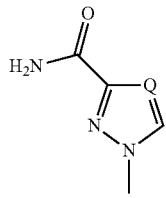

(i)
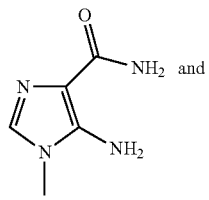

(j)
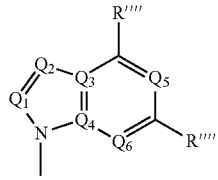

wherein each R', R'', R''' and R'''' are independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-arylalkyl, —O-acyl, O-cycloalkyl, $NH_2$, NH-alkyl, N-dialkyl, NH-acyl, N-aryl, N-arylalkyl, NH-cycloalkyl, SH, S-alkyl, S-acyl, S-aryl, S-cycloalkyl, S-arylalkyl, F, Cl, Br, I, CN, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$ and $(CH_2)_mCONH_2$;

m is 0 or 1;

each W is independently C—R'' or N;

T and V independently are CH or N;

Q is CH, —CCl, —CBr, —CF, —CI, —CCN, —C—COOH, —C—$CONH_2$, or N;

$Q_1$ and $Q_2$ independently are N or C—R;

$Q_3$, $Q_4$, $Q_5$ and $Q_6$ independently are N or CH; and tautomeric forms thereof.

In another aspect, $R^1$ is:

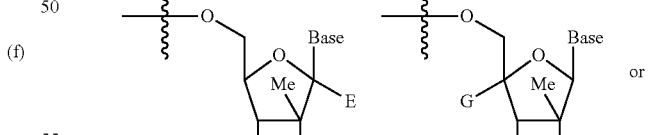

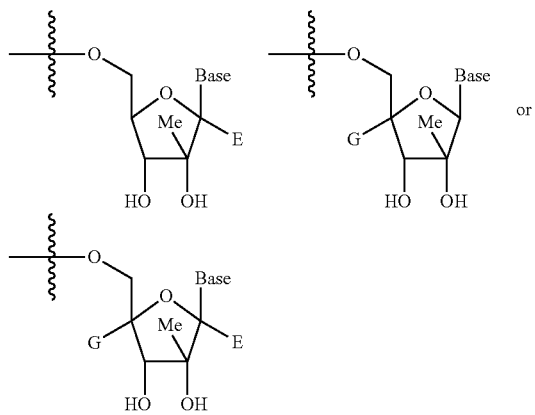

G and E independently are selected from the group consisting of $CH_3$, $CH_2OH$, $CH_2F$, $CH_2N_3$, $CH_2CN$, $(CH_2)_m$ COOH, $(CH_2)_mCOOR$, $(CH_2)_mCONH_2$, $(CH_2)_mCONR_2$, $(CH_2)_mCONHR$, $N_3$ and N-acyl;

m is 0 or 1;

R is H, alkyl or acyl; and

Base is as defined for Formula (XIII).

In one embodiment, at most one of G and E can further be hydrogen.

In another embodiment, $R^1$ is:

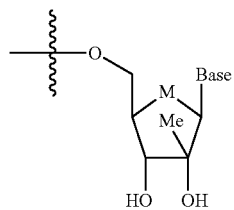

wherein M is selected from the group consisting of O, S, SO, and $SO_2$; and Base is as defined for Formula (XIII).

In certain embodiments, $R^1$ is:

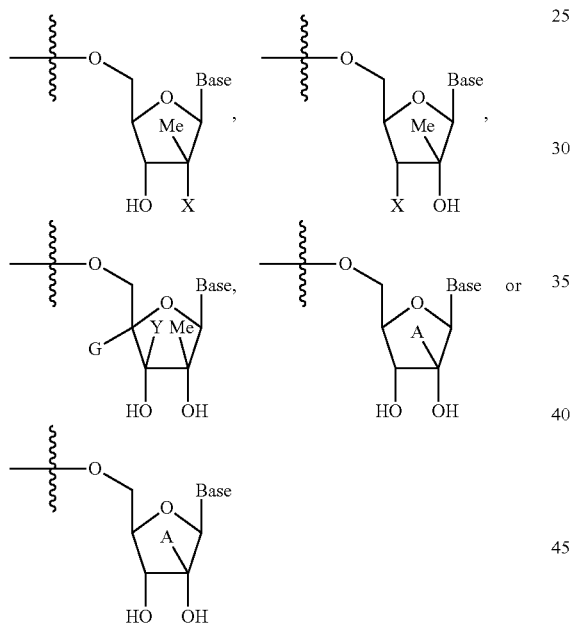

wherein A is selected from the group consisting of optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, and $(CH_2)_mCONHR$;

Y is selected from the group consisting of H, optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, and $(CH_2)_mCONHR$;

X is selected from the group consisting of H, —OH, optionally substituted alkyl, cycloalkyl, alkenyl, alkynyl, —O-alkyl, —O-alkenyl, —O-alkynyl, —O-aryl, —O-arylalkyl, —O-cycloalkyl-, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aryl, NH-arylalkyl, NH-cycloalkyl, SH, S-alkyl, S-alkenyl, S-alkynyl, S-aryl, S-arylalkyl, S-acyl, S-cycloalkyl, $CO_2$-alkyl, CONH-alkyl, CON-dialkyl, CONH-alkenyl, CONH-alkynyl, CONH-arylalkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, —$CF_2CF_3$, $CH_2CO_2R$, $(CH_2)_mCOOH$, $(CH_2)_mCOOR$, $(CH_2)_mCONH_2$, $(CH_2)_mCONR_2$, $(CH_2)_mCONHR$, an optionally substituted 3-7 membered carbocyclic, and an optionally substituted 3-7 membered heterocyclic ring having O, S and/or N independently as a heteroatom taken alone or in combination;

m is 0 or 1;

R is H, alkyl or acyl; and Base is a non-natural base selected from the group of:

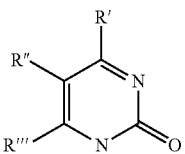

(a)

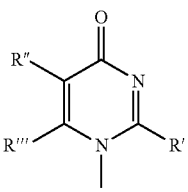

(b)

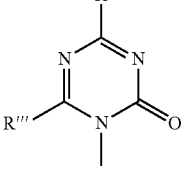

(c)

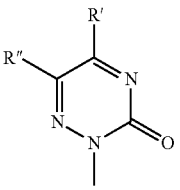

(d)

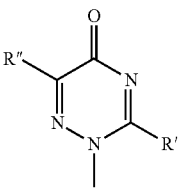

(e)

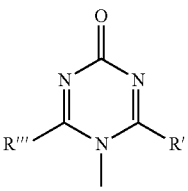

(f)

-continued (g)
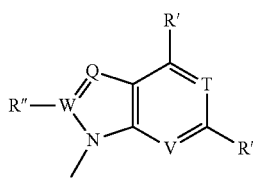

(h)
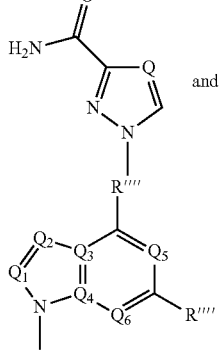
and

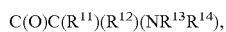

wherein each R', R", R'" and R"" is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-arylalkyl, —O-acyl, O-cycloalkyl, $NH_2$, NH-alkyl, N-dialkyl, NH-acyl, N-aryl, N-arylalkyl, NH-cycloalkyl, SH, S-alkyl, S-acyl, S-aryl, S-cycloalkyl, S-arylalkyl, F, Cl, Br, I, CN, COOH, $CONH_2$, $CO_2$-alkyl, CONH-alkyl, CON-dialkyl, OH, $CF_3$, $CH_2OH$, $(CH_2)_m$OH, $(CH_2)_m NH_2$, $(CH_2)_m COOH$, $(CH_2)_m CN$, $(CH_2)_m NO_2$ and $(CH_2)_m CONH_2$;

m is 0 or 1;

each W is independently C—R" or N;

T and V independently are CH or N;

Q is CH, —CCl, —CBr, —CF, —CI, —CCN, —C—COOH, —C—$CONH_2$, or N;

$Q_1$ and $Q_2$ independently are N or C—R""; and $Q_3$, $Q_4$, $Q_5$ and $Q_6$ Independently are N or CH;

with the proviso that in bases (g) and (i), R', R"" are not H, OH, or $NH_2$; and Q, T, V, $Q_2$, $Q_5$ and $Q_6$ are not N.

In one embodiment, $R^1$ is a 2'-(alkyl or aryl) ester or 3'-(alkyl or aryl) ester of 1', 2', 3' or 4'C-branched-β-D or β-L nucleoside with any natural or non-natural purine or pyrimidine base. In one embodiment, $R^1$ is a 2' or 3'-(D or L)-amino acid ester of 1', 2', 3' or 4' C-branched-β-D or β-L nucleoside, wherein the amino acid is a natural or synthetic amino acid. In another embodiment, $R^1$ is a 3'-D or L-amino acid ester of 1', 2', 3' or 4' C-branched-β-D or β-L nucleoside, wherein the amino acid is a natural or synthetic amino acid. In one embodiment, the amino acid is an L-amino acid.

In one embodiment, the amino acid residue is of the formula

C(O)C($R^{11}$)($R^{12}$)(N$R^{13}R^{14}$), wherein $R^{11}$ is the side chain of an amino acid and wherein, $R^{11}$ can optionally be attached to $R^{13}$ to form a ring structure; or alternatively, $R^{11}$ is an alkyl, aryl, heteroaryl or heterocyclic moiety;

$R^{12}$ is hydrogen, alkyl (including lower alkyl) or aryl; and $R^{13}$ and $R^{14}$ are independently hydrogen, acyl (including an acyl derivative attached to $R^{11}$) or alkyl (including but not limited to methyl, ethyl, propyl, and cyclopropyl).

In another embodiment, at least one of $R^2$ and $R^3$ is an amino acid residue. In one embodiment, at least one of $R^2$ and $R^3$ is L-valinyl.

In one embodiment, $R^1$ is:

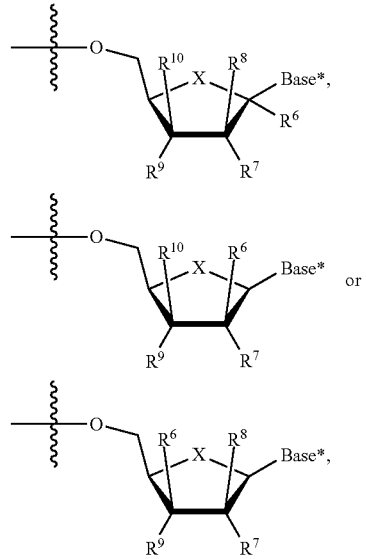

wherein $R^6$, $R^7$, $R^8$, $R^9$, $R^{10}$ and Base* are as defined in Formula XXX, XXXI, XL, XLI or XLII.

In one embodiment, $R^1$ is:

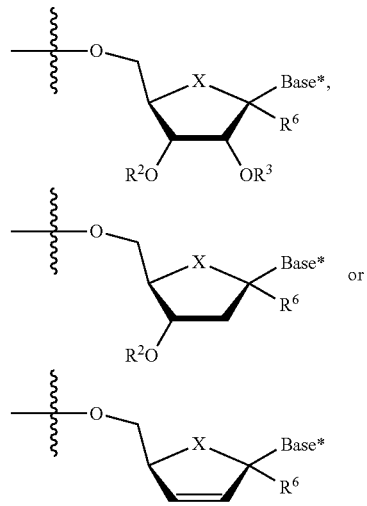

wherein $R^2$, $R^3$, $R^6$ and Base* are as defined in Formula XXX, XXXI, XL, XLI or XLII.

In one embodiment, $R^1$ is:

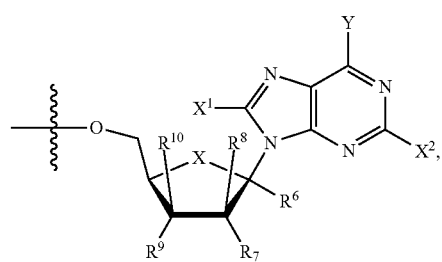

-continued

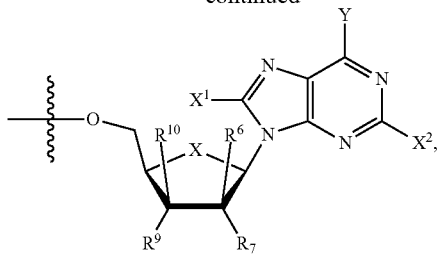

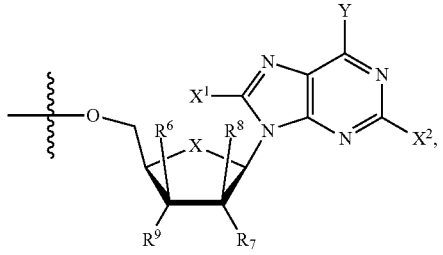

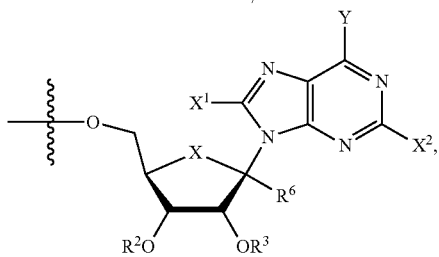

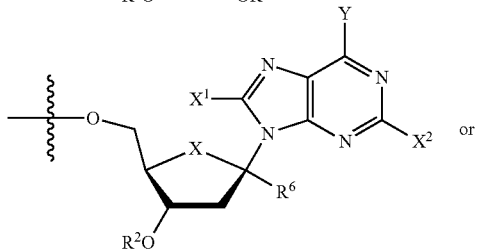

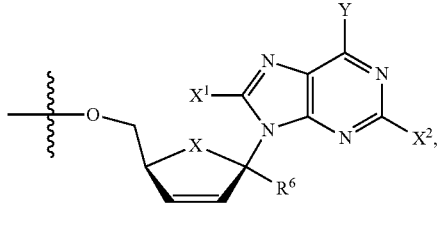

wherein $X^1$ and $X^2$ are each independently hydrogen, alkyl, halo or amino; Y is hydrogen, amino, aminoalkyl, aminocycloalkyl, alkyl, cycloalkyl, hydroxy, alkoxy, cycloalkoxy, SH or thioalkyl; X is O or S; and wherein $R^6$, $R^7$, $R^8$, $R^9$ are as defined in Formula XXX, XXXI, XL, XLI or XLII.

In one embodiment, $R^1$ is:

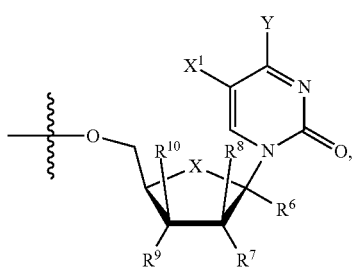

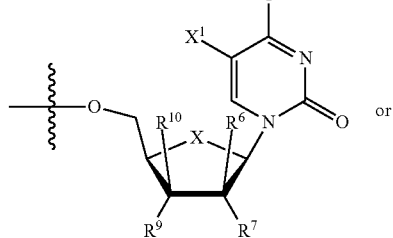

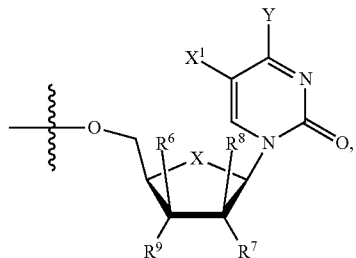

wherein $X^1$ is hydrogen, alkyl, halo or amino; Y is hydrogen, amino, aminoalkyl, aminocycloalkyl, alkyl, cycloalkyl, hydroxy, alkoxy, cycloalkoxy, SH or thioalkyl; X is O or S; and wherein $R^6$, $R^7$, $R^8$, $R^9$ are as defined in Formula XXX, XXXI, XL, XLI or XLII.

In one embodiment, $R^1$ is:

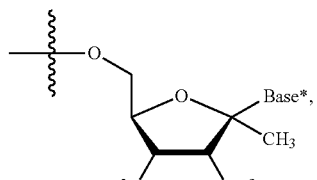

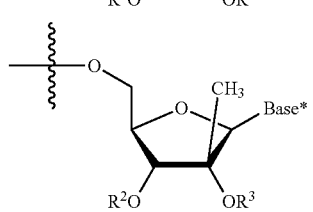

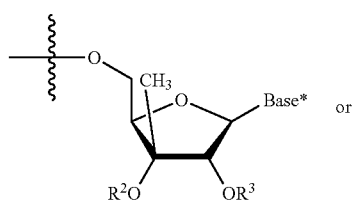

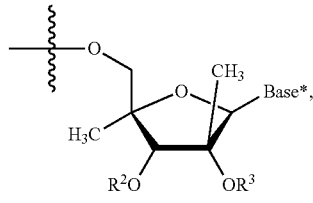

wherein $R^2$, $R^3$, and Base* are as defined in Formula XIII, XXX, XXXI, XL, XLI or XLII.

In one embodiment, $R^1$ is:
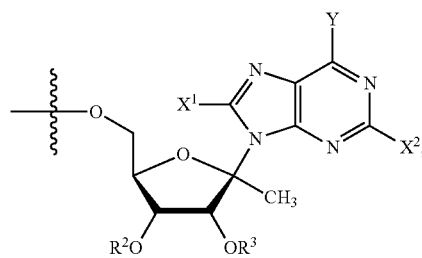
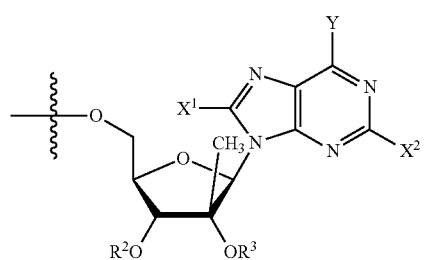
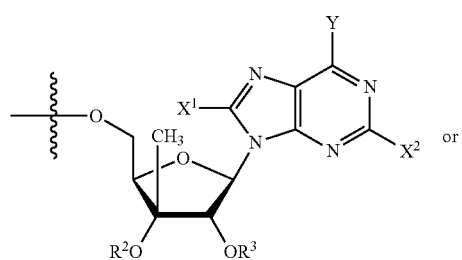
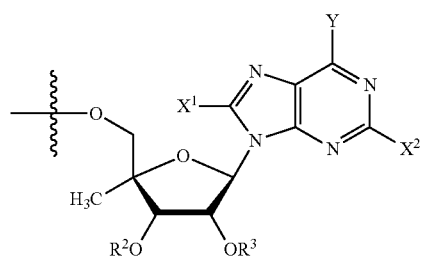
wherein $R^2$, $R^3$, $Y^1$, $Y^3$, $X^1$, and $X^2$ are as defined in Formula XIII.
In one embodiment, $R^1$ is:
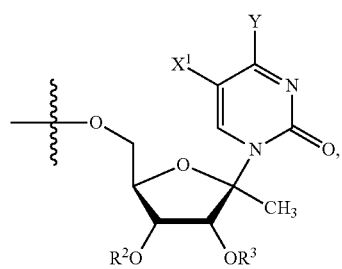
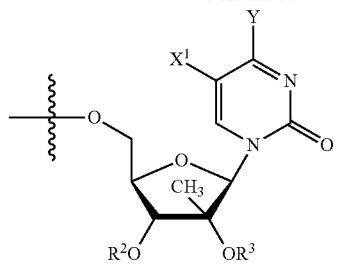
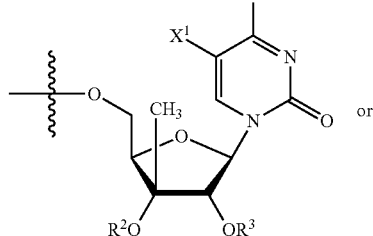
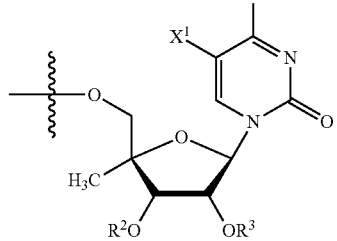
wherein $R^2$, $R^3$, $Y^1$, $Y^3$, $X^1$, and $X^2$ are as defined in Formula XIII.
In one embodiment, $R^1$ is:
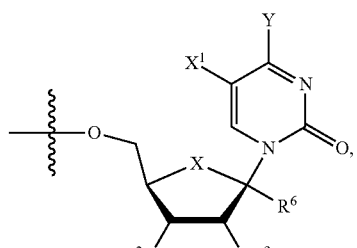
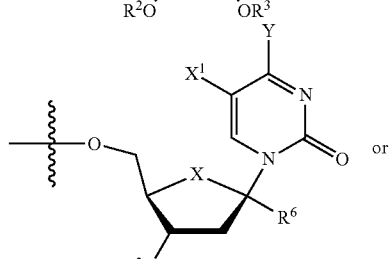
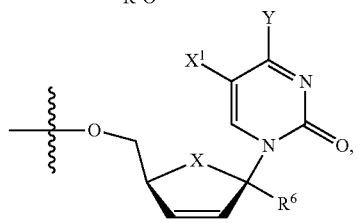

wherein $R^2$, $R^3$, $R^6$, Y, and $X^1$ are as defined in Formula XIII, XX, XXI or XXII.

In one embodiment, $R^1$ is:

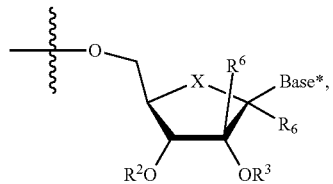

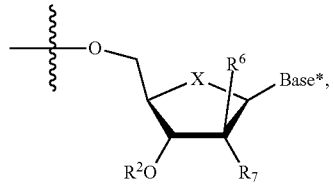

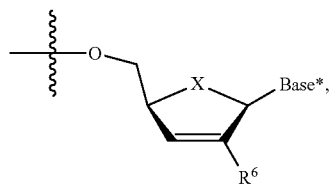

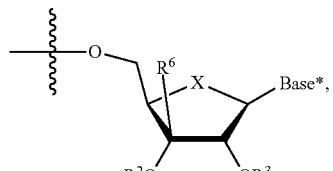

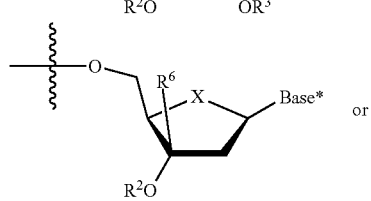 or

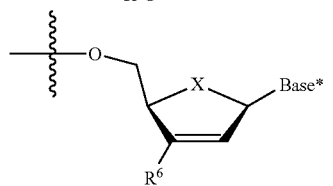

wherein $R^2$, $R^3$, $R^6$, $R^7$, X and Base* are as defined in Formula XIII, XX, XXI, XXII, XL, XLI or XLII.

In one embodiment, $R^1$ is

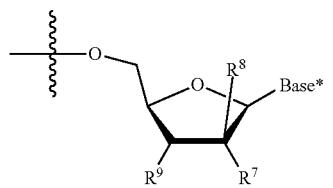

wherein $R^8$ is alkyl, alkenyl or alkynyl; $R^7$ is $OR^{7a}$;

$R^9$ is $OR^{7a}$;

$R^{7a}$ is H or

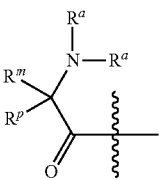

$R^m$ is a side chain of any natural or non-natural amino acid; and $R^p$ is hydrogen, hydroxy, alkyl or alkoxy; and Base* is as defined in Formula XL, XLI or XLII In one embodiment, $R^8$ is methyl, ethyl, vinyl or ethynyl; $R^7$ is hydroxy or fluoro; $R^9$ is hydroxy and other variables are as described herein.

In one embodiment, $R^1$ is

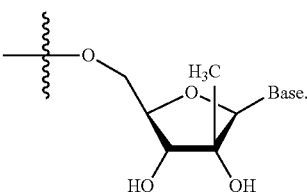

In one embodiment, $R^8$ is methyl or ethyl. In one embodiment, $R^{7a}$ is H or

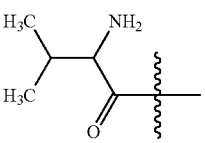

In one embodiment, the phosphoramidate compound provided herein is:

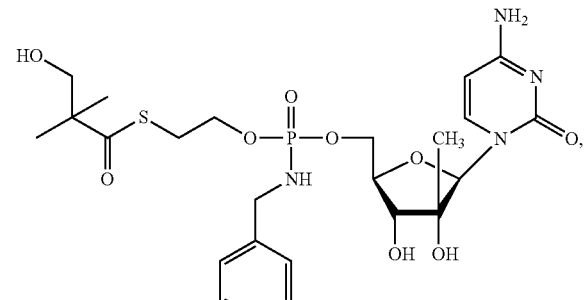

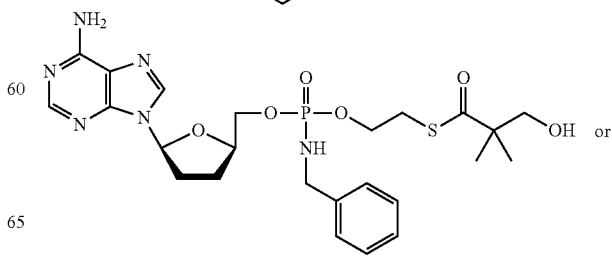

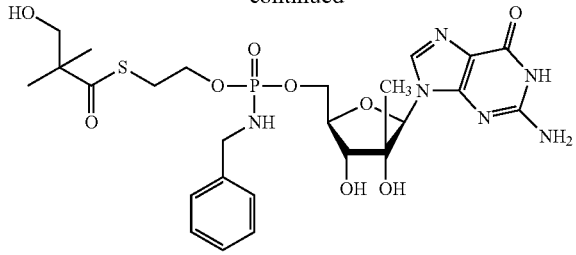

or a pharmaceutically acceptable salt, solvate or hydrate thereof.

In one embodiment, the phosphoramidate compound provided herein is:

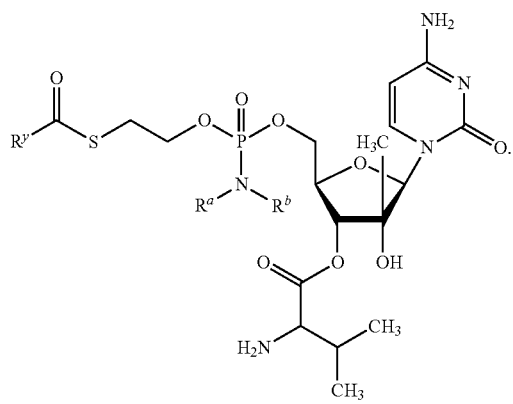

In one embodiment, the phosphoramidate compound provided herein is:

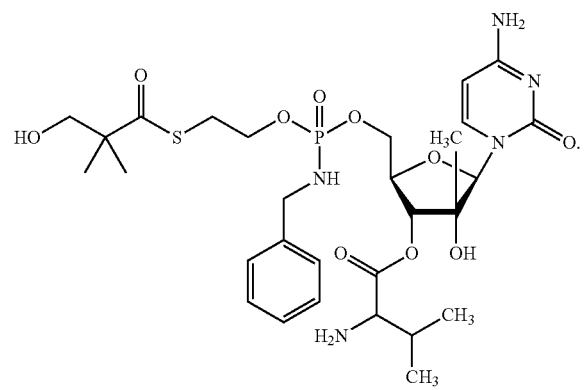

In one embodiment, the phosphoramidate compound provided herein is:

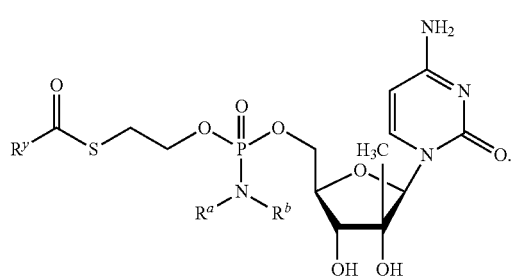

In one embodiment, the phosphoramidate compound provided herein is:

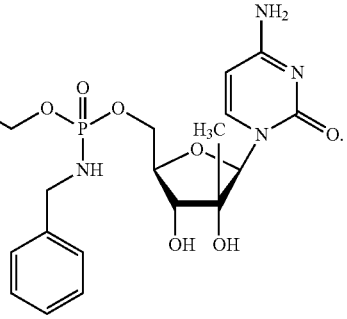

In one embodiment, the phosphoramidate compound provided herein is:

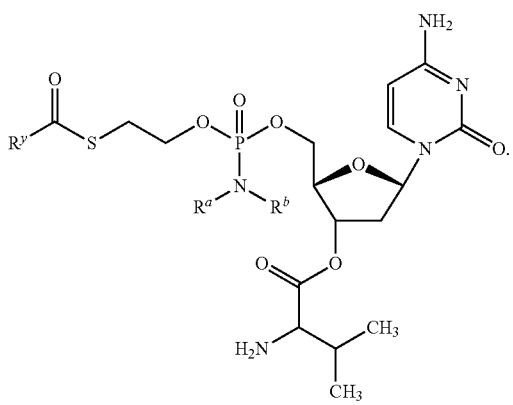

In one embodiment, the phosphoramidate compound provided herein is:

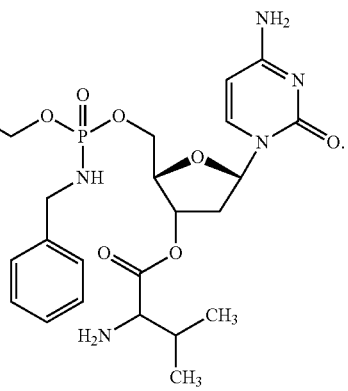

In one embodiment, the phosphoramidate compound provided herein is:

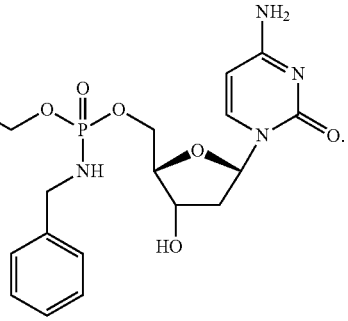

In one embodiment, the phosphoramidate compound provided herein is:

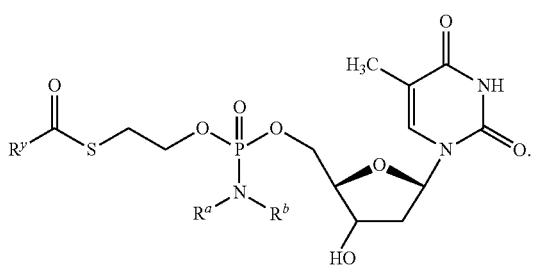

In one embodiment, the phosphoramidate compound provided herein is:

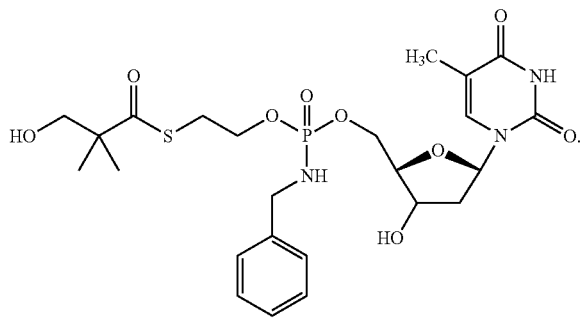

In one embodiment, the phosphoramidate compound provided herein is:

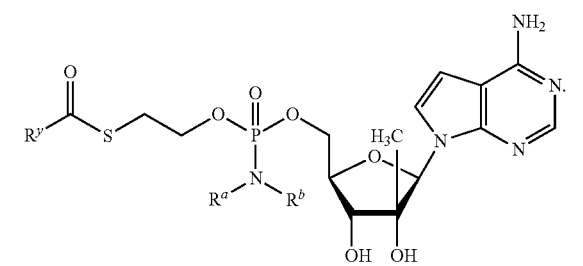

In one embodiment, the phosphoramidate compound provided herein is:

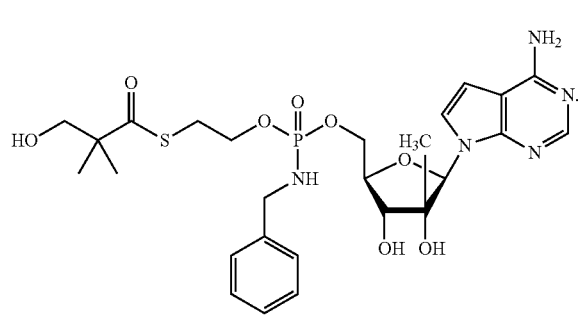

In one embodiment, the phosphoramidate compound provided herein is:

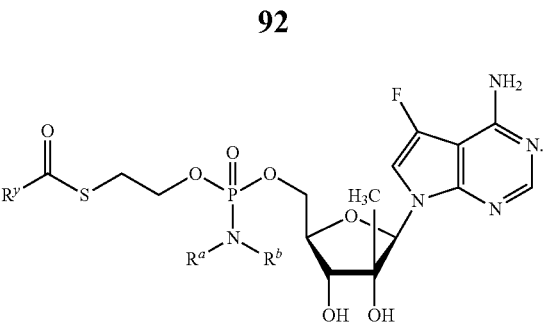

In one embodiment, the phosphoramidate compound provided herein is:

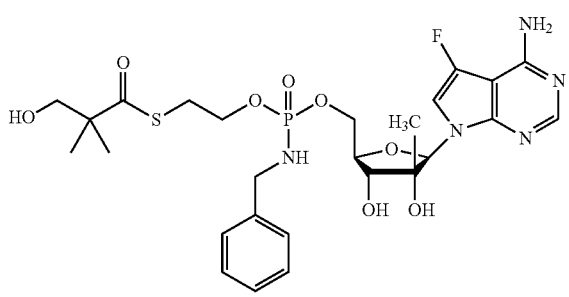

In one embodiment, the phosphoramidate compound provided herein is:

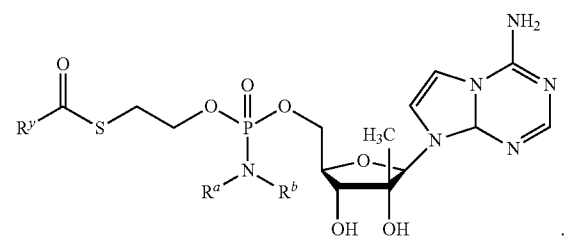

In one embodiment, the phosphonoamidate compound provided herein is a phosphonoamidate form of PMPA or PMEA such as:

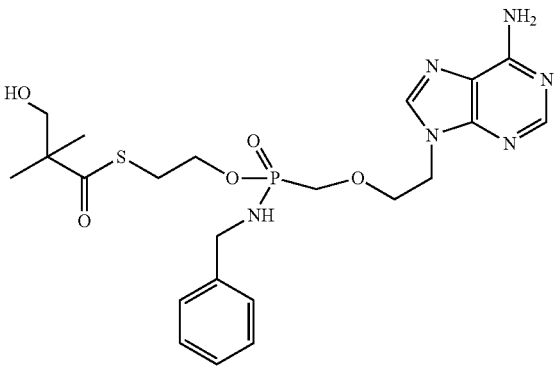 [SMILES: CC(C)(CO)C(=O)SCCOP(=O)(COCCn1cnc2c(N)ncnc21)NCc1ccccc1]

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of a nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a normatively occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, compositions of phosphonoamidate or phosphoramidate compounds are provided that are substantially free of a designated enantiomer of that nucleoside. In a preferred embodiment, in the methods and compounds of this invention, the compounds are substantially free of enantiomers. In some embodiments, the composition includes that includes a compound that is at least 85, 90%, 95%, 98%, 99% to 100% by weight, of the compound, the remainder comprising other chemical species or enantiomers.

Preparation of Compounds

The compounds provided herein can be prepared, isolated or obtained by any method apparent to those of skill in the art. Exemplary methods of preparation are described in detail in the examples below.

In certain embodiments, compounds provided herein can be prepared by coupling alcohols and H-phosphonate monoesters as illustrated in the reaction scheme below:

Scheme A

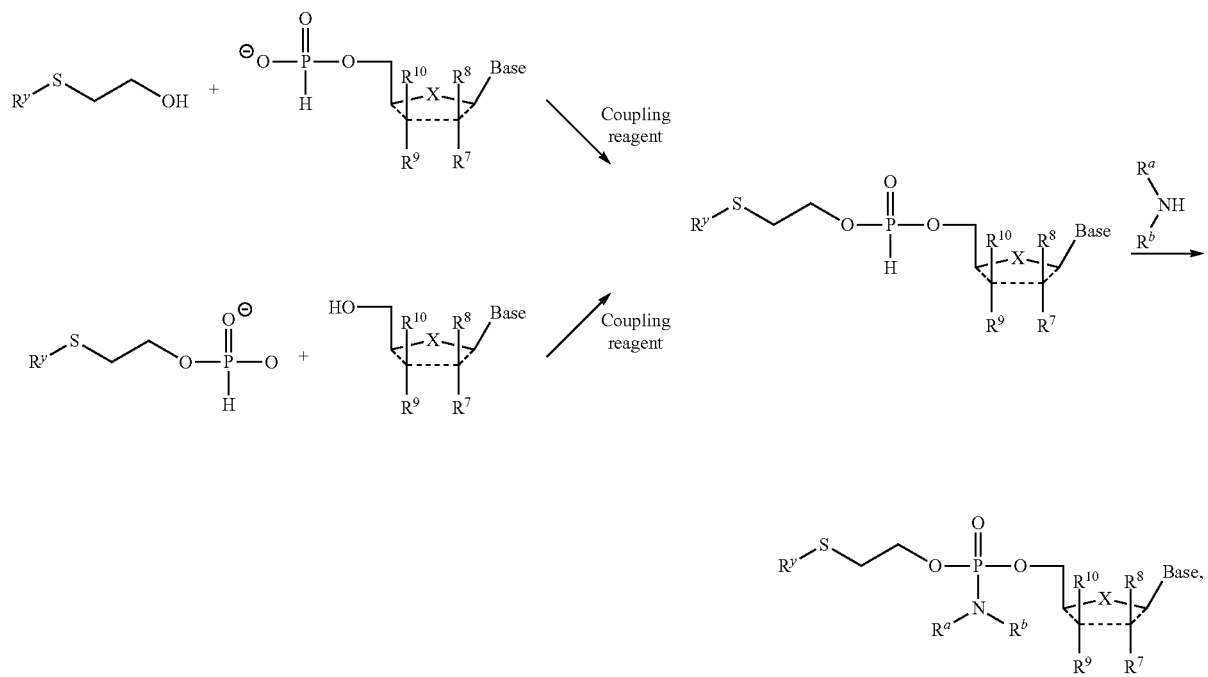

any reactive function on $R^y$, $R^7$, $R^8$, $R^9$, $R^{10}$ or on the base may be protected during the coupling reaction. A variety of coupling agents known to one of skill in the art can be used. Exemplary coupling agents for use in the reaction include, but are not limited to HOBt (N-Hydroxybenzotriazole), HBTU (2-(1H-Benzotriazole-1-yl)-1,1,3,3-tetramethylaminium hexafluorophosphate), DCC(N,N'-dicyclohexylcarbodiimide), BOP (Benzotriazole-1-yl-oxy-tris-(dimethylamino)-phosphoniumhexafluorophosphate), PyBOP (1H-benzotriazol-1-yloxytripyrrolidinophosphonium hexafluorophosphate) and others known to one of skill in the art.

A general scheme for the synthesis of hydroxytBuSATE N-benzylphosphoramidate nucleoside derivatives represented by B is provided in Schemes B1-B3 below.

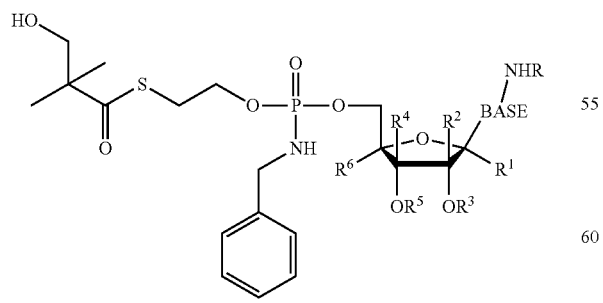

B where R=H, Tr, MMTr or DMTr in case of reactive amine; $R^1$, $R^2$, $R^4$, $R^6$=H, alkyl or halo and $R^3/R^5$ are both H or isopropylidene.

Scheme B1: Synthesis of the H-phosphonate monoester reagent

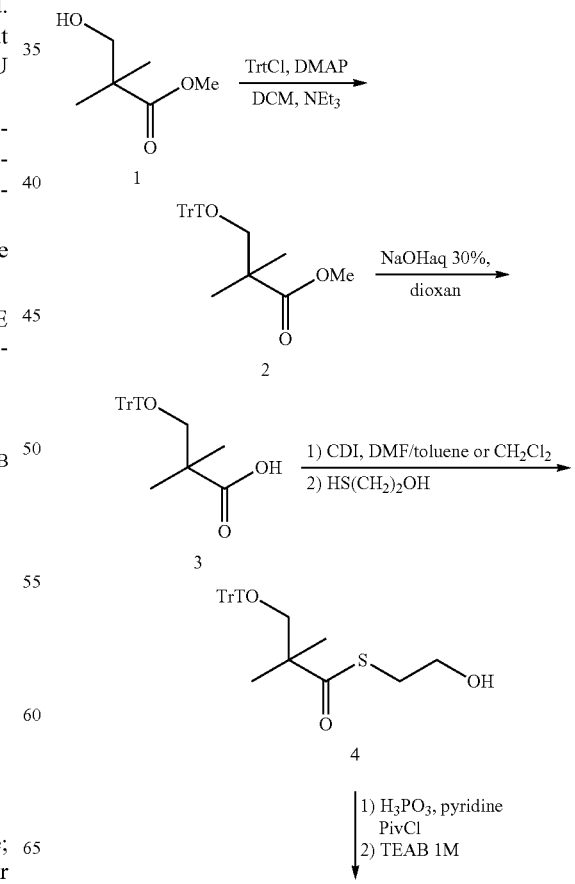

97
-continued
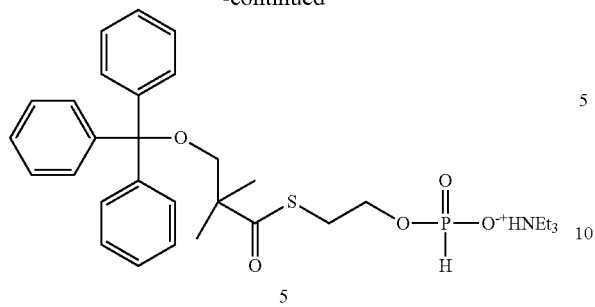
98
-continued
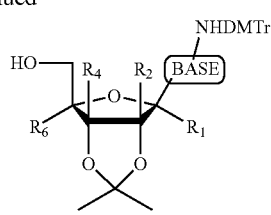
Scheme B2: Synthesis of the protected nucleosides (R = DMTr and/or $R^3/R^5$ = isopropylidene)
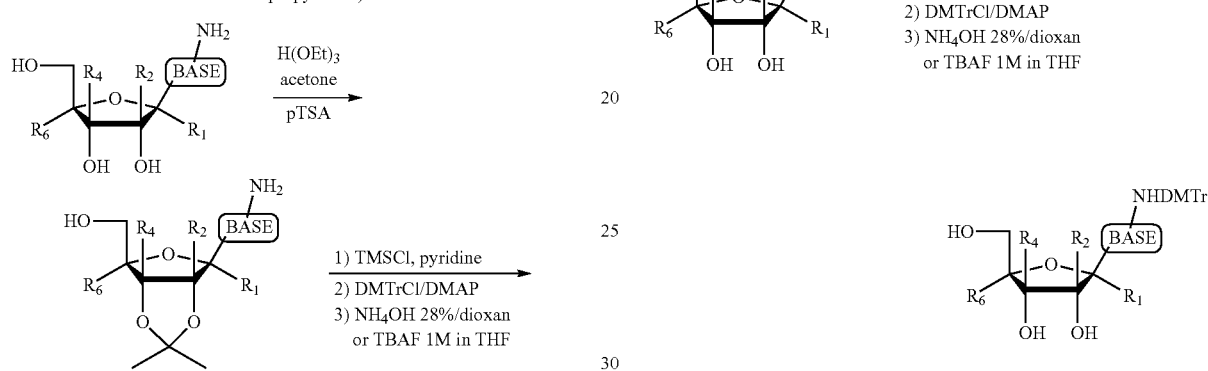
Scheme B3: Coupling of (non)protected nucleosides with reagent 5, oxidative amination and deprotection step
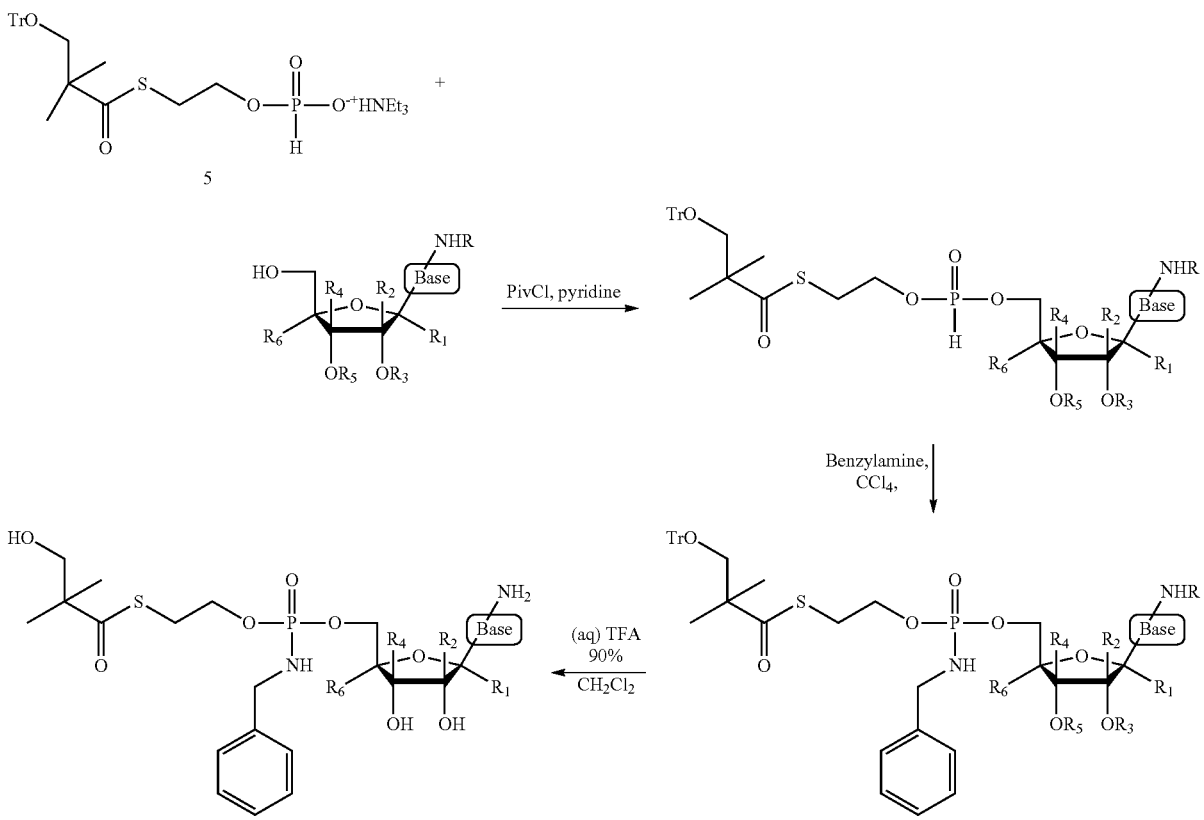

In addition, certain nucleosides and analogs thereof and prodrugs thereof can be prepared according to methods described in U.S. Pat. Nos. 6,812,219; 7,105,493; 7,101,861; 6,914,054; 6,555,676; 7,202,224; 7,105,499; 6,777,395; 6,914,054; 7,192,936; US publication Nos. 2005203243; 2007087960; 2007060541; 2007060505; 2007060504; 2007060503; 2007060498; 2007042991; 2007042990; 2007042940; 2007042939 and 2007037735; International Publication Nos. WO 04/003000; WO 04/022999; WO 04/002422; WO 01/90121 and WO 01/92282. Other patents/ patent applications disclosing nucleoside analogs to treat hepatitis C virus that can be derivatized as described herein include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; 6,846,810; 6,784,166 and 6,660,721 by Roche; PCT Publication Nos. WO 01/79246 (filed Apr. 13, 2001), WO 02/32920 (filed Oct. 18, 2001) and WO 02/48165; US 2005/0009737 and US 2005/0009737; U.S. Pat. Nos. 7,094,770 and 6,927,291 by Pharmasset, Ltd. Contents of these references are hereby incorporated by reference in their entireties.

Assay Methods

Compounds can be assayed for HBV activity according to any assay known to those of skill in the art. Compounds can be assayed for HCV activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In one embodiment, a phosphoramidate or phosphonoamidate nucleoside compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples and assay techniques.

In one embodiment, ddATP concentrations are measured in a sample by comparison to calibration standards made from control samples. The ddATP concentrations in a sample can be measured using an analytical method such as HPLC LC MS. In one embodiment, a test sample is compared to a calibration curve created with known concentrations of ddATP to thereby obtain the concentration of that sample.

In one embodiment, the samples are manipulated to remove impurities such as salts ($Na^+$, $K^+$, etc.) before analysis. In one embodiment, the lower limit of quantitation is about ~0.2 pmol/mL for hepatocyte cellular extracts particularly where reduced salt is present.

In one embodiment, the method allows successfully measuring triphosphate nucleotides formed at levels of 1-10,000 pmol per million cells in e.g. cultured hepatocytes and HepG2 cells.

Methods of Use

The phosphoramidate and phosphonoamidate compounds of a variety of therapeutic agents can be formed using methods available in the art and those disclosed herein. Such compounds can be used in some embodiments to enhance delivery of the drug to the liver.

In one embodiment, the compound comprises a S-acyl-2-thioethyl phosphoramidate or S-acyl-2-thioethyl phosphonoamidate, e.g., a S-pivaloyl-2-thioethyl phosphoramidate or S-hydroxypivaloyl-2-thioethyl phosphonoamidate derivative. Therapeutic agents that can be derivatized to phosphoramidate or phosphonoamidate compound form include any anti-viral agent that includes, or has been derivatized to include a reactive group for attachment of the phosphoramidate or phosphonoamidate moiety, including but not limited to nucleosides and nucleoside analogues including acyclic nucleosides.

Advantageously, such phosphoramidate and phosphonamidate compounds advantageously can have enhanced delivery to the liver. In some embodiments, the compounds permit delivery of an active 5'-monophosphate of a nucleoside to the liver, which can enhance the formation of active triphosphorylated compound.

In one embodiment, provided herein are methods for the treatment and/or prophylaxis of a host infected with Flaviviridae that includes the administration of an effective amount of a compounds provided herein, or a pharmaceutically acceptable salt thereof. In one embodiment, provided herein are methods for treating an HCV infection in a subject. In certain embodiments, the methods encompass the step of administering to the subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described in the sections above.

Flaviviridae that can be treated are discussed generally in *Fields Virology*, Editors: Fields, B. N., Knipe, D. M., and Howley, P. M., Lippincott-Raven Publishers, Philadelphia, Pa., Chapter 31, 1996. In a particular embodiment of the invention, the Flaviviridae is HCV. In an alternate embodiment of the invention, the Flaviviridae is a *flavivirus* or pestivirus. Specific *flaviviruses* include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

*Pestiviruses* that can be treated are discussed generally in *Fields Virology*, Editors: Fields, B. N., Knipe, D. M., and Howley, P. M., Lippincott-Raven Publishers, Philadelphia, Pa., Chapter 33, 1996. Specific *pestiviruses* include, without limitation: bovine viral diarrhea virus ("BVDV"), classical swine fever virus ("CSFV," also called hog cholera virus), and border disease virus ("BDV").

In certain embodiments, provided herein are methods for the treatment and/or prophylaxis of hepatitis B infections that includes administering an effective amount of a compound as described herein, e.g. of Formula I, IIa or IIb, its pharmaceutically acceptable salt or composition. In another embodiment, provided herein are methods of treatment and/prophylaxis of conditions related to hepatitis B infections, such as anti-HBV antibody positive and HBV-positive conditions, chronic liver inflammation caused by HBV, cirrhosis, acute hepatitis, fulminant hepatitis, chronic persistent hepatitis, and fatigue. In certain embodiments, provided herein are prophylactic methods to prevent or retard the progression of clinical illness in individuals who are anti-HBV antibody or HBV-antigen positive or who have been exposed to HBV.

In certain embodiments, the subject can be any subject infected with, or at risk for infection with, HCV and/or HBV. Infection or risk for infection can be determined according to any technique deemed suitable by the practitioner of skill in the art. In one embodiment, subjects are humans infected with HCV and/or HBV.

In certain embodiments, the subject has never received therapy or prophylaxis for an HCV and/or HBV infection. In further embodiments, the subject has previously received therapy or prophylaxis for an HCV and/or HBV infection. For instance, in certain embodiments, the subject has not responded to an HCV and/or HBV therapy. For example, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for an HCV and/or HBV infection but has failed to show, for example, a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding.

In certain embodiments, the subject is a subject that discontinued an HCV and/or HBV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, provided are methods of treating or preventing an HCV infection in subjects where the risk of neuropsychiatric events, such as depression, contraindicates treatment with current HCV therapy. In one embodiment, provided are methods of treating or preventing HCV infection in subjects where a neuropsychiatric event, such as depression, or risk of such indicates discontinuation of treatment with current HCV therapy. Further provided are methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects include bone marrow suppression, neutropenia and thrombocytopenia. Furthermore, ribavirin is toxic to red blood cells and is associated with hemolysis. Accordingly, in one embodiment, provided are methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments, the subject has received an HCV and/or HBV therapy and discontinued that therapy prior to administration of a method provided herein. In further embodiments, the subject has received therapy and continues to receive that therapy along with administration of a method provided herein. The methods can be co-administered with other therapy for HBC and/or HCV according to the judgment of one of skill in the art. In certain embodiments, the methods or compositions provided herein can be co-administered with a reduced dose of the other therapy for HBC and/or HCV.

In certain embodiments, provided are methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin. A pro-drug form of ribavirin, such as taribavirin, may also be used.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8:577-57. The methods provided herein can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J Infect Dis* 179:1254-1258. In one embodiment, compounds provided herein have been shown to suppress HIV in HIV subjects. Thus, in certain embodiments, provided are methods of treating or preventing HIV infection and HCV infection in subjects in need thereof.

In certain embodiments, the compounds or compositions are administered to a subject following liver transplant. Hepatitis C is a leading cause of liver transplantation in the U.S. and many subjects that undergo liver transplantation remain HCV positive following transplantation. In one embodiment, provided are methods of treating such recurrent HCV subjects with a compound or composition provided herein. In certain embodiments, provided are methods of treating a subject before, during or following liver transplant to prevent recurrent HCV infection.

In certain embodiments, provided herein are methods for the treatment and/or prophylaxis of hepatitis B infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue that includes administering an effective amount of a compound or composition provided herein.

In one embodiment, provided herein are methods for treatment and/or prophylaxis of hepatitis B infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue that includes administering an effective amount of a compound or composition provided herein.

Second Therapeutic Agents

In certain embodiments, the compounds and compositions provided herein are useful in methods of treatment of a liver disorder, that comprises further administration of a second agent effective for the treatment of the disorder, such as HCV and/or HBV infection in a subject in need thereof. The second agent can be any agent known to those of skill in the art to be effective for the treatment of the disorder, including those currently approved by the FDA.

In certain embodiments, a compound provided herein is administered in combination with one second agent. In further embodiments, a second agent is administered in combination with two second agents. In still further embodiments, a second agent is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-HCV or hepatitis B agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In certain embodiments, an anti-HCV (or anti-*pestivirus* or anti-*flavivirus*) compound that exhibits an $EC_{50}$ of 10-15 μM, or preferably less than 1-5 μM, is desirable.

It has been recognized that drug-resistant variants of *flaviviruses, pestiviruses* or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Nonlimiting examples of second agents include:

HCV Protease inhibitors: Examples include Medivir HCV Protease Inhibitor (Medivir/Tobotec); ITMN-191 (InterMune), SCH 503034 (Schering) and VX950 (Vertex). Further examples of protease inhibitors include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., *Biochemical and Biophysical Research Communications,* 1997, 238, 643-647; Sudo K. et al. *Antiviral Chemistry and Chemotherapy,* 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., *Tetrahedron Letters* 37:7229-7232, 1996).

SCH 351633, isolated from the fungus *Penicillium griseofulvum,* was identified as a protease inhibitor (Chu M. et al.,

*Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al. which discloses a class of cysteine protease inhibitors for inhibiting HCV endopeptidase 2; U.S. Pat. No. 5,990,276 to Zhang et al. which discloses synthetic inhibitors of hepatitis C virus NS3 protease; U.S. Pat. No. 5,538,865 to Reyes et a; WO 02/008251 to Corvas International, Inc, and U.S. Pat. No. 7,169,760, US2005/176648, WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 and U.S. Pat. No. 6,911,428 to Schering Corporation. Imidazoleidinones as NS3 serine protease inhibitors of HCV are disclosed in WO 02/08198 and U.S. Pat. No. 6,838,475 to Schering Corporation and WO 02/48157 and U.S. Pat. No. 6,727,366 to Bristol Myers Squibb. WO 98/17679 and U.S. Pat. No. 6,265,380 to Vertex Pharmaceuticals and WO 02/48116 and U.S. Pat. No. 6,653,295 to Bristol Myers Squibb also disclose HCV protease inhibitors. Further examples of HCV serine protease inhibitors are provided in U.S. Pat. No. 6,872,805 (Bristol-Myers Squibb); WO 2006000085 (Boehringer Ingelheim); U.S. Pat. No. 7,208,600 (Vertex); US 2006/0046956 (Schering-Plough); WO 2007/001406 (Chiron); US 2005/0153877; WO 2006/119061 (Merck); WO 00/09543 (Boehringer Ingelheim), U.S. Pat. No. 6,323,180 (Boehringer Ingelheim) WO 03/064456 (Boehringer Ingelheim), U.S. Pat. No. 6,642,204 (Boehringer Ingelheim), WO 03/064416 (Boehringer Ingelheim), U.S. Pat. No. 7,091,184 (Boehringer Ingelheim), WO 03/053349 (Bristol-Myers Squibb), U.S. Pat. No. 6,867,185, WO 03/099316 (Bristol-Myers Squibb), U.S. Pat. No. 6,869,964, WO 03/099274 (Bristol-Myers Squibb), U.S. Pat. No. 6,995,174, WO 2004/032827 (Bristol-Myers Squibb), U.S. Pat. No. 7,041,698, WO 2004/043339 and U.S. Pat. No. 6,878,722 (Bristol-Myers Squibb).

Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al. *J. EBS Letters* 421, 217-220; Takeshita N. et al. *Analytical Biochemistry*, 1997, 247, 242-246;

A phenanthrenequinone possessing activity against protease in a SDS-PAGE and autoradiography assay isolated from the fermentation culture broth of *Streptomyces* sp., SCH 68631 (Chu M. et al., *Tetrahedron Letters*, 1996, 37, 7229-7232), and SCH 351633, isolated from the fungus *Penicillium griseofulvum*, which demonstrates activity in a scintillation proximity assay (Chu M. et al., *Bioorganic and Medicinal Chemistry Letters* 9, 1949-1952);

Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

Nucleotide polymerase inhibitors and gliotoxin (Ferrari R. et al. *Journal of Virology*, 1999, 73, 1649-1654), and the natural product cerulenin (Lohmann V. et al., *Virology*, 1998, 249, 108-118);

Interfering RNA (iRNA) based antivirals, including short interfering RNA (siRNA) based antivirals, such as Sirna-034 and others described in International Patent Publication Nos. WO/03/070750 and WO 2005/012525, and US Patent Publication No. US 2004/0209831.

Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

Inhibitors of IRES-dependent translation (Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and Nucleoside analogs have also been developed for the treatment of Flaviviridae infections.

In certain embodiments, the compounds provided herein can be administered in combination with any of the compounds described by Idenix Pharmaceuticals in International Publication Nos. WO 01/90121, WO 01/92282, WO 2004/003000, 2004/002422 and WO 2004/002999.

Other patent applications disclosing the use of certain nucleoside analogs that can be used as second agents to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; U.S. Pat. Nos. 6,846,810; 6,784,166 and 6,660,721 by Roche; PCT Publication Nos. WO 01/79246 (filed Apr. 13, 2001), WO 02/32920 (filed Oct. 18, 2001) and WO 02/48165; US 2005/0009737; US 2005/0009737; U.S. Pat. Nos. 7,094,770 and 6,927,291 by Pharmasset, Ltd.

Further compounds that can be used as second agents to treat hepatitis C virus are disclosed in PCT Publication No. WO 99/43691 to Emory University, entitled "2'-Fluoronucleosides". The use of certain 2'-fluoronucleosides to treat HCV is disclosed.

Other miscellaneous compounds that can be used as second agents include 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidenes (U.S. Pat. No. 5,830,905 to Diana et al.).

Exemplary Second Agents for Treatment of HCV

In one embodiment, one or more compounds provided herein can be administered in combination or alternation with an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b) and Pegasys® (pegylated interferon alfa-2a).

In one embodiment, the anti-hepatitis C virus interferon is infergen, IL-29 (PEG-Interferon lambda), R7025 (Maxy-alpha), Belerofon, Oral Interferon alpha, BLX-883 (Locteron), omega interferon, multiferon, medusa interferon, Albuferon or REBIF®.

In one embodiment, one or more compounds provided herein can be administered in combination or alternation with an anti-hepatitis C virus polymerase inhibitor, such as ribavirin, viramidine, NM 283 (valopicitabine), PSI-6130, R1626, HCV-796 or R7128.

In certain embodiments, the one or more compounds provided herein can be administered in combination with ribavarin and an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b) and Pegasys® (pegylated interferon alfa-2a).

In one embodiment, one or more compounds provided herein can be administered in combination or alternation with an anti-hepatitis C virus protease inhibitor such as ITMN-191, SCH 503034, VX950 (telaprevir) or Medivir HCV Protease Inhibitor.

In one embodiment, one or more compounds provided herein can be administered in combination or alternation with an anti-hepatitis C virus vaccine, such as TG4040, PeviPRO™, CGI-5005, HCV/MF59, GV1001, IC41 or INNO0101 (E1).

In one embodiment, one or more compounds provided herein can be administered in combination or alternation with an anti-hepatitis C virus monoclonal antibody, such as AB68 or XTL-6865 (formerly HepX-C); or an anti-hepatitis C virus polyclonal antibody, such as cicavir.

In one embodiment, one or more compounds provided herein can be administered in combination or alternation with an anti-hepatitis C virus immunomodulator, such as Zadaxin® (thymalfasin), NOV-205 or Oglufanide.

In one embodiment, one or more compounds provided herein can be administered in combination or alternation with Nexavar, doxorubicin, PI-88, amantadine, JBK-122, VGX-410C, MX-3253 (Ceglosivir), Suvus (BIVN-401 or virostat), PF-03491390 (formerly IDN-6556), G126270, UT-231B, DEBIO-025, EMZ702, ACH-0137171, MitoQ, ANA975, AVI-4065, Bavituxinab (Tarvacin), Alinia (nitrazoxanide) or PYN17.

Exemplary Second Agents for Treatment of HBV

It has been recognized that drug-resistant variants of HBV can emerge after prolonged treatment with an antiviral agent. Drug resistance most typically occurs by mutation of a gene that encodes for an enzyme used in the viral life cycle, and most typically in the case of HBV, DNA polymerase. The efficacy of a drug against HBV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The anti-hepatitis B viral activity of compounds provided herein can be enhanced by administering one or more of these further agents in combination or alternation. Alternatively, for example, one or more compounds provided herein can be administered in combination or alternation with any other known anti-hepatitis B virus agent. Such agents include anti-hepatitis B virus interferons, such as Intron A® (interferon alfa-2b) and Pegasys® (Peginterferon alfa-2a); polymerase inhibitors, such as Epivir-HBV (lamivudine), Hepsera (adefovir dipivoxil), baraclude (entecavir), Tyzeka (telbivudine), Emtricitabine (FTC), Clevudine (L-FMAU), Viread (tenofovir), Valtorcitabine, Amdoxovir, ANA 380, Pradefovir (remofovir) and RCV (racivir); vaccines, such as Hi-8 HBV, HepaVaxx B and HBV Core Antigen vaccine; and other agents, such as HepX, SpecifEx-HepB, Zadaxin, EHT899, Bay 41-4109, UT 231-B, HepeX-B and NOV-205 or any other compound that exhibits an $EC_{50}$ of less than 15 micromolar in 2.2.15 cells; or their prodrugs or pharmaceutically acceptable salts. Several other examples of anti-HBV agents are provided in U.S. Application Publication No. 20050080034 and international publication no. WO 2004/096286, which are incorporated by reference in their entireties.

In one embodiment, one or more compounds provided herein can be administered in combination or alternation with anti-hepatitis B virus agent such as interferon α-2b, peginterferon α-2a, lamivudine, hepsera, baraclude, telbivudine, emtricitabine, clevudine, tenofovir, valtorcitabine, amdoxovir, ANA 380, remofovir, racivir, alinia, Hi-8 HBV and HepaVaxx B.

In another embodiment, a compound provided herein is administered in combination or alternation with an immune modulator or other pharmaceutically active modifier of viral replication, including a biological material such as a protein, peptide, oligonucleotide, or gamma globulin, including but not limited to interferon, interleukin, or an antisense oligonucleotides to genes which express or regulate hepatitis B replication.

Any method of alternation can be used that provides treatment to the patient. Nonlimiting examples of alternation patterns include 1-6 weeks of administration of an effective amount of one agent followed by 1-6 weeks of administration of an effective amount of a second anti-HBV agent. The alternation schedule can include periods of no treatment. Combination therapy generally includes the simultaneous administration of an effective ratio of dosages of two or more anti-HBV agents.

In light of the fact that HBV is often found in patients who are also anti-HIV antibody or HIV-antigen positive or who have been exposed to HIV, the active anti-HBV compounds disclosed herein or their derivatives or prodrugs can be administered in the appropriate circumstance in combination or alternation with anti-HIV medications.

The compounds provided herein can also be administered in combination with antibiotics, other antiviral compounds, antifungal agents or other pharmaceutical agents administered for the treatment of secondary infections.

Pharmaceutical Compositions and Methods of Administration

Phosphoramidate and phosphonoamidate compounds of a variety of therapeutic agents can be formulated into pharmaceutical compositions using methods available in the art and those disclosed herein. Such compounds can be used in some embodiments to enhance delivery of the drug to the liver. In one embodiment, the compound comprises a S-acyl-2-thioethyl phosphoramidate or S-acyl-2-thioethyl phosphonoamidate, e.g., a S-pivaloyl-2-thioethyl phosphoramidate or S-hydroxypivaloyl-2-thioethyl phosphonoamidate derivative. Therapeutic agents that can be derivatized to phosphoramidate or phosphonoamidate compound form include any antiviral agent that includes, or has been derivatized to include a reactive group for attachment of the phosphoramidate or phosphonoamidate moiety, including but not limited to nucleosides and nucleoside analogues including acyclic nucleosides. Any of the phosphoramidate or phosphonoamidate compounds disclosed herein can be provided in the appropriate pharmaceutical composition and be administered by a suitable route of administration.

The methods provided herein encompass administering pharmaceutical compositions containing at least one compound as described herein, including a compound of general Formula I, IIa or IIb, if appropriate in the salt form, either used alone or in the form of a combination with one or more compatible and pharmaceutically acceptable carriers, such as diluents or adjuvants, or with another anti-HCV or anti-HBV agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In one embodiment, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379

80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail in the sections above. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompasseed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321: 574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In one embodiment, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, 18th and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, 18th and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing an HCV and/or HBV infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In one embodiment, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat HCV and/or HBV infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In one embodiment, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a liver disorder such as HCV and/or HBV infections. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

The following Examples illustrate the synthesis of representative compounds provided herein. These examples are not intended, nor are they to be construed, as limiting the scope of the claimed subject matter. It will be clear that the scope of claimed subject matter may be practiced otherwise than as particularly described herein. Numerous modifications and variations of the subject matter are possible in view of the teachings herein and, therefore, are within the scope the claimed subject matter.

EXAMPLES

Example 1

Preparation of A550 (NM204), the Hydroxy-tBuSATE N-benzylphosphoramidate derivative of L-2',3'-dideoxyadenosine L-ddA

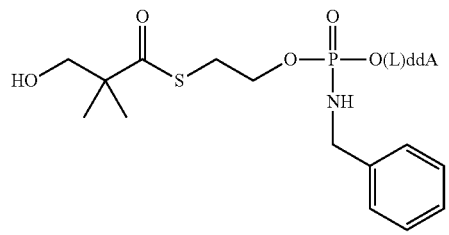

NM204, A550

Synthetic Scheme

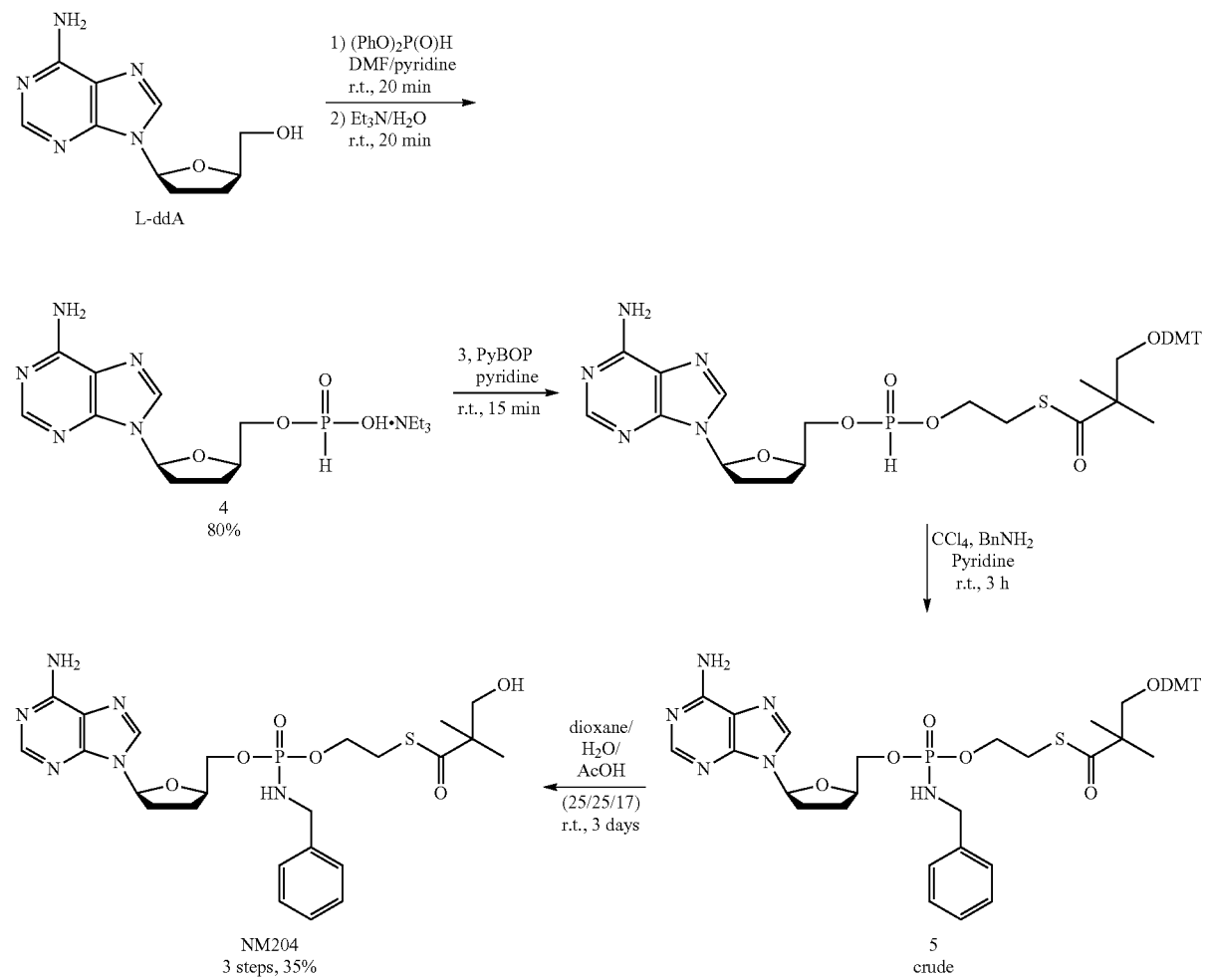

Synthesis of Carboxylic Acid 2

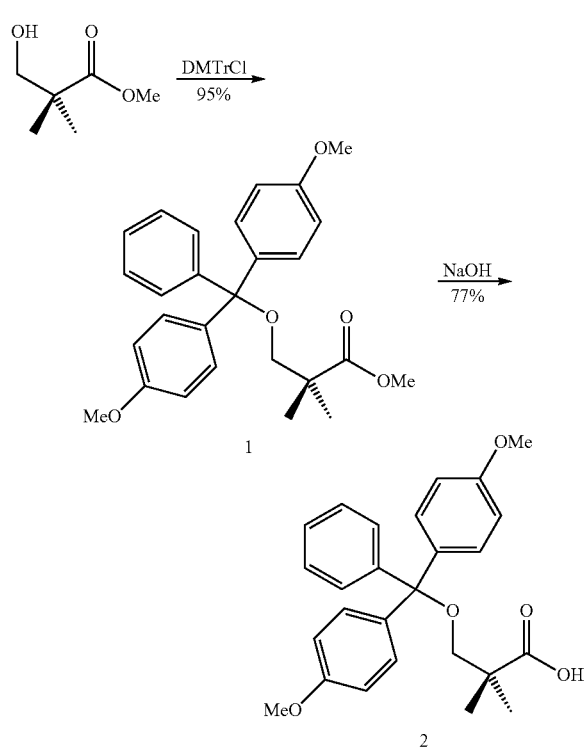

2,2-Dimethyl-3-hydroxypropanoic acid methyl ester (965 µL, 7.57 mmol) was added dropwise to a stirring solution of 4,4'-dimethoxytrityl chloride (2.82 g, 8.33 mmol) in anhydrous pyridine (7.6 mL) at room temperature. The reaction mixture turned to a red solution quickly, then to an orange suspension (ca. 30 min), and this was left stirring overnight. The mixture was poured carefully over saturated aqueous NaHCO$_3$ solution (30 mL) and the product was extracted with Et$_2$O (3×20 mL). The combined organic extracts were washed with brine (20 mL), dried (Na$_2$SO$_4$) and the volatiles were removed under reduced pressure. The resulting oil was co-evaporated with toluene and the residue was quickly purified by flash column chromatography (SiO$_2$, Ø=4 cm, H=20 cm) eluting with 5→10→20→30% Et$_2$O in petroleum ether (40-60). Evaporation of the fractions (R$_f$=0.25, 30% Et$_2$O in petroleum ether (40-60)) afforded ether 1 as a yellow oil (3.11 g, 95%). This compound (3.00 g, 6.91 mmol) was dissolved in THF (35 mL) and an aqueous solution of NaOH (10%, 3.5 g in 35 mL H$_2$O) was then added at room temperature. The solution turned instantly dark orange and this was stirred for 2 days. The medium was then carefully neutralized by dropwise addition of HCl (1M). The product was extracted with Et$_2$O (4×50 mL) and the combined organic extracts were washed with brine (50 mL), dried (Na$_2$SO$_4$) and the volatiles were removed under reduced pressure. The crude yellow oil was quickly purified by flash column chromatography (SiO$_2$, Ø=2 cm, H=10 cm) eluting with 50% Et$_2$O in petroleum ether (40-60). Evaporation of the fractions afforded carboxylic acid 2 as a white foam (2.23 g, 77%). R$_f$=0.50 (50% Et$_2$O in petroleum ether (40-60)); $^1$H-NMR (300 MHz, CDCl$_3$) 1.10 (s, 6H, 2×CH$_3$), 3.06 (s, 2H, CH$_2$O), 3.65 (s, 6H, 2×OCH$_3$), 6.62-6.79 (m, 4H, PhCH), 7.02-7.46 (stack, 8H, PhCH); $^{13}$C-NMR (75 MHz, CDCl$_3$) 22.6 (2×CH$_3$), 43.5 (C(CH$_3$)$_2$), 55.1 (2×OCH$_3$), 85.9 (CPh$_3$), [125.3, 126.7, 127.7, 128.2, 129.1, 130.0, 136.0, 144.9, 158.4 (Ph), some overlap], 182.2 (C=O).

Synthesis of Thioester 3

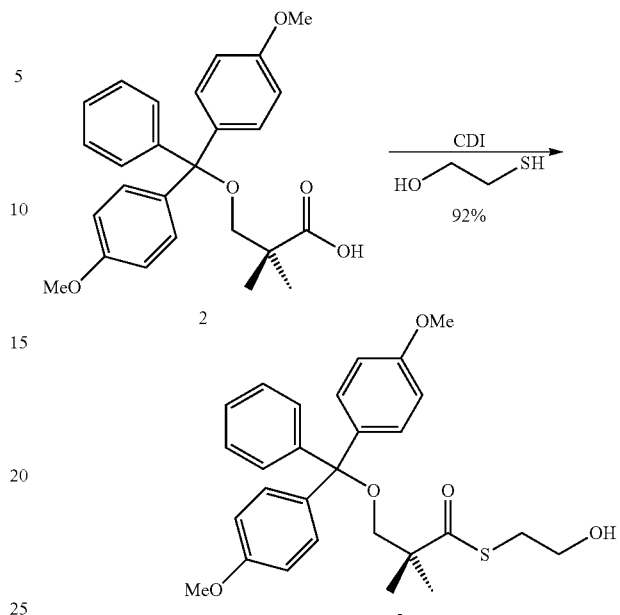

1,1'-carbonyldiimidazole (830 mg, 5.12 mmol) was added to a stirring solution of carboxylic acid 2 in anhydrous PhMe/DMF (2/1, v/v, 2.7 mL) at room temperature and the reaction mixture turned turbid instantly. After 30 min, the medium was diluted by adding anhydrous PhMe/DMF (93/7, v/v, 17 mL) and cooled to −10° C. 2-Mercaptoethanol (359 µL, 5.12 mmol) was then added dropwise and the solution was stirred for 1 h at this temperature. The reaction mixture was diluted with H$_2$O (60 mL) and the product was extracted with Et$_2$O (3×15 mL). The combined organic extracts were washed with brine (15 mL), dried (Na$_2$SO$_4$) and the volatiles were removed under reduced pressure (bath temperature not exceeding 20° C.). The residue was purified by flash column chromatography (SiO$_2$, Ø=4 cm, H=15 cm, 1% Et$_3$N) eluting with 60→70% Et$_2$O in petroleum ether (40-60). Evaporation of the fractions afforded thioester 3 as a white syrup (1.74 g, 92%) that solidified upon storage at 4° C. R$_f$=0.35 (70% Et$_2$O in petroleum ether (40-60)); $^1$H-NMR (300 MHz, CDCl$_3$) 1.16 (s, 6H, 2×CH$_3$), 3.02 (t, J 6.0, 2H, CH$_2$S), 3.09 (s, 2H, CH$_2$O), 3.66 (t, J 6.0, 2H, CH$_2$OH), 3.72 (s, 6H, 2×OCH$_3$), 6.74-6.78 (m, 4H, PhCH), 7.09-7.36 (stack, 8H, PhCH); $^{13}$C-NMR (75 MHz, CDCl$_3$) 22.9 (CH$_3$, 2×CH$_3$), 31.7 (CH$_2$, CH$_2$S), 51.0 (quat. C, C(CH$_3$)$_2$), 55.2 (CH$_3$, 2×OCH$_3$), 61.9 (CH$_2$, CH$_2$OH), 70.0 (CH$_2$, CH$_2$O), 85.8 (quat. C., CPh$_3$), [113.0 (CH, Ph), 126.7 (CH, Ph), 127.7 (CH, Ph), 128.2 (CH, Ph), 130.1 (CH, Ph), some overlap], [135.9 (quat. C, Ph), 144.8 (quat. C, Ph), 158.4 (quat. C, Ph), some overlap], 205.0 (quat. C, C=O).

Synthesis of H-Phosphonate Monoester 4

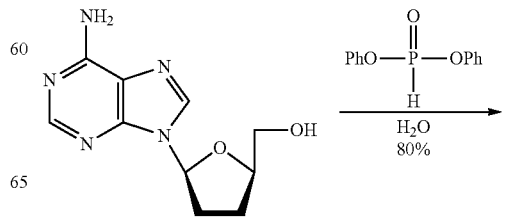

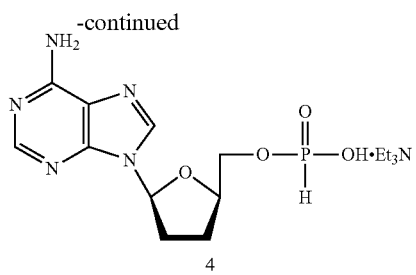

4

β-L-ddA (1.00 g, 4.25 mmol) was co-evaporated with anhydrous pyridine (3×10 mL) and then dissolved in anhydrous pyridine/DMF (1/1, v/v, 21 mL). Diphenyl phosphite (5.76 mL, 29.8 mmol) was then added dropwise to this solution at room temperature. The reaction mixture was stirred for 20 min upon which a mixture of Et$_3$N/H$_2$O (1/1, v/v, 8.5 mL) was added dropwise, and stirring was pursued for an additional 20 min. The reaction mixture was concentrated under reduced pressure to approximately 15-20 mL and this residue was directly purified by flash column chromatography (SiO$_2$, Ø=4 cm, H=15 cm, 1% Et$_3$N) eluting slowly with CH$_2$Cl$_2$ (150 mL) then 5% (200 mL)→10% (200 mL)→15% (300 mL) MeOH in CH$_2$Cl$_2$. Evaporation of the fractions afforded H-phosphonate monoester 4 as a white foam (1.36 g, 80%) that could be kept for several weeks at 4° C. R$_f$=0.10 (Et$_3$N/MeOH/CH$_2$Cl$_2$, Jan. 10, 1989); $^1$H-NMR (300 MHz, CDCl$_3$) 1.21 (t, J 7.4, 9H, 3×NCH$_2$CH$_3$), 1.92-2.50 (stack, 4H, 2×2'-H, 2×3'-H), 3.02 (q, J 7.4, 6H, 3×NCH$_2$CH$_3$), [3.96-4.03 and 4.18-4.30 (stacks, 3H, 4'-H, 2×5'-H), 6.28 (m, 1'-H), 6.91 (d, J 623, 1H, P—H), 7.05 (br s, 2H, NH$_2$), 8.21 (s, 1H), 8.54 (br s, 1H, OH), 8.57 (s, 1H).

Synthesis of Phosphoramidate Diester 5

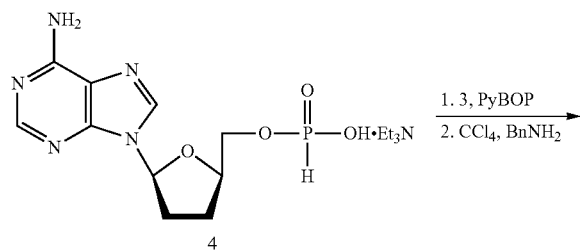

4

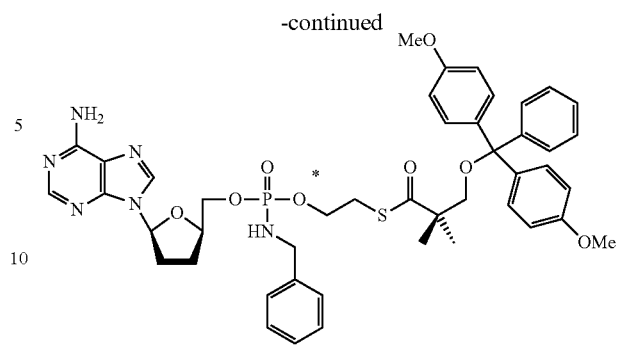

5, used as a crude

H-Phosphonate monoester 4 (1.03 g, 2.57 mmol) and alcohol 3 (1.66 g, 3.45 mmol) were co-evaporated with anhydrous pyridine (3×5 mL) and then dissolved in anhydrous pyridine (5 mL). PyBOP (1H-benzotriazol-1-yloxytripyrrolidinophosphonium hexafluorophosphate, 1.60 g, 3.08 mmol) was then added in one portion and the reaction mixture was stirred for 15 min at room temperature. The solution was poured over saturated aqueous NaHCO$_3$ solution (30 mL) and the product was extracted with CH$_2$Cl$_2$ (4×15 mL). The combined organic extracts were washed with brine (10 mL), dried (Na$_2$SO$_4$) and concentrated under reduced pressure to leave the corresponding H-phosphonate diester as a slightly yellow oil (1.84 g, assuming 2.41 mmol). This was co-evaporated with anhydrous pyridine (3×5 mL; note: do not evaporate to dryness in order to help further solubilization), and the residue was dissolved in anhydrous CCl$_4$ (24 mL). Benzylamine (791 µL, 7.23 mmol) was added dropwise and the reaction mixture turned cloudy instantly (slight heat development was observed). The milky solution was stirred for 1 h at room temperature and poured over saturated aqueous NaHCO$_3$ solution (30 mL) and the product was extracted with CH$_2$Cl$_2$ (4×15 mL). The combined organic extracts were washed with brine (15 mL), dried (Na$_2$SO$_4$) and concentrated under reduced pressure to afford phosphoramidate diester 5 as a yellow oil (2.00 g, assuming 2.31 mmol). This was used in the next step without any further purification. R$_f$=0.29 (4% MeOH in CH$_2$Cl$_2$); $^1$H-NMR (300 MHz, CDCl$_3$) 1.11 (s, 6H, 2×CH$_3$), 1.91-2.05 (m, 2H), 2.31-2.59 (m, 2H), 3.06 (m, 2H, CH$_2$S), 3.08 (s, 2H, CH$_2$ODMTr), 3.69 (s, 6H, 2×OCH$_3$), 3.83-4.28 (stacks, 7H, CH$_2$O, NCH$_2$Ph, 4'-H, 2×5'-H), 5.71 (br s, 1H, NH), 6.18 (m, 1H, 1'-H), 6.69-6.80 (m, 4H, PhCH), 7.02-7.31 (stack, 13H, PhCH), 7.90 (s, 1H), 8.01 (s, 1H), 8.23 (s, 2H, NH$_2$); $^{13}$P-NMR (61 MHz, CDCl$_3$) 8.82, 8.99.

Synthesis of NM204 (A550), the Hydroxy-tBuSATE N-benzylphosphoramidate Derivative of L-ddA

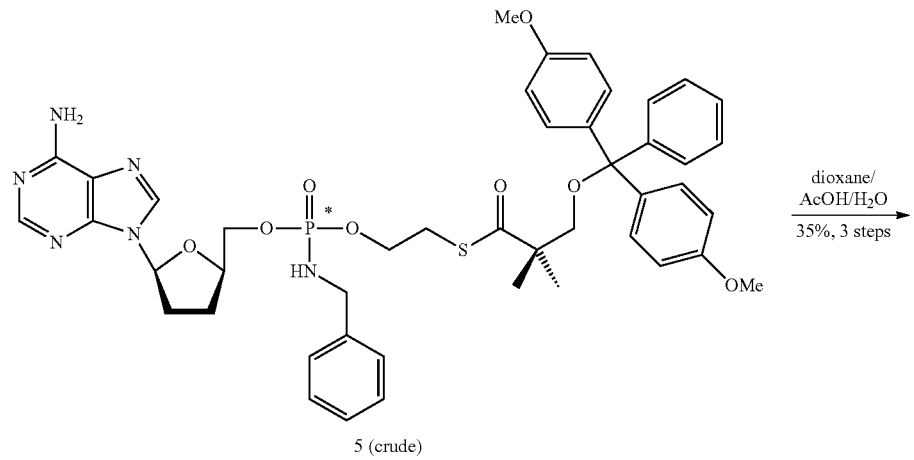

5 (crude)

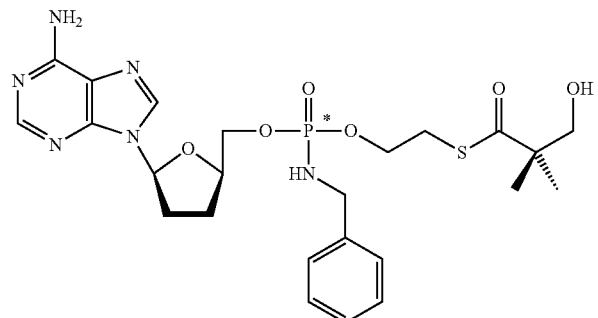

NM 204 (purified and lyophilized)

Crude phosphoramidate diester 5 (2.00 g, assuming 2.31 mmol) was dissolved in dioxane/AcOH/H$_2$O (25/17/25, v/v/v, 462 mL) and the solution was stirred for 3 d at room temperature. Evaporation of the volatiles under reduced pressure left a residue that was purified by flash column chromatography (SiO$_2$, Ø=3 cm, H=15 cm) eluting with CH$_2$Cl$_2$ (100 mL) then 2% (100 mL)→4% (100 mL)→6% (100 mL)→8% (150 mL) MeOH in CH$_2$Cl$_2$. Evaporation of the fractions left NM 204 as a white foam that was dissolved in MeCN (5 mL). Upon addition of H$_2$O (5 mL), the solution turned turbid and required sonication before lyophilization. The resulting white powder was dried at room temperature (using P$_2$O$_5$ as a desiccant) under vacuum for 1d. The title compound was obtained as a highly hygroscopic white powder (1:1 mixture of diastereoisomers as judged by $^{31}$P-NMR; 499 mg, 35% over 3 steps). [α]$^{20}_D$=+4.2° (c 1.0, CHCl$_3$); R$_f$=0.29 (4% MeOH in CH$_2$Cl$_2$);

$^1$H-NMR (300 MHz, DMSO-d6) 1.10 (s, 6H, 2×CH$_3$), 2.02-2.14 (m, 2H, 2×3'-H), 2.41-2.55 (m, 2H, 2×2'-H), 3.01 (t, J 6.4, 2H, CH$_2$S), 3.43 (d, J 5.0, 2H, CH$_2$OH), 3.75-4.07 and 4.18-4.29 (stacks, 7H, CH$_2$O, NCH$_2$Ph, 4'-H, 2×5'-H), 5.02 (t, J 5.0, 1H, OH), 5.62 (m, 1H, NH), 6.25 (t, J 5.1, 1H, 1'-H), 7.16-7.36 (stack, 7H, PhH, NH$_2$), 8.14 (s, 1H), 8.26 (s, 1H);

$^{13}$C-NMR (75 MHz, DMSO-d6) 21.8 (2×CH$_3$), 25.9 and 26.0 (CH$_2$, 3'-C), 28.2 and 28.3 (CH$_2$, CH$_2$S), 30.9 and 31.0 (CH$_2$, 2'-C), 44.2 (CH$_2$, NCH$_2$Ph), 51.7 (quat. C, C(CH$_3$)$_2$), 63.7 and 63.8 (CH$_2$, CH$_2$O), 66.8 (CH$_2$, m, 5'-C), 68.3 (CH$_2$, CH$_2$OH), 78.9 (CH, m, 4'-C), 84.2 (CH, 1'-C), 118.9 (quat. C), [126.5 (CH, Ph), 127.2 (CH, Ph), 128.1 (CH, Ph), some overlap], 138.8 and 138.9 (CH), 140.5 and 140.6 (quat. C), 148.9 (quat. C), 152.3 (CH), 155.0 (quat. C), 204.0 (quat. C, C=O); $^{31}$P-NMR (61 MHz, DMSO-d6) 9.86, 9.95; m/z (FAB$^-$) 563 (2), 306 (76), 153 (100); HRMS 565.2034 ([M+H]$^+$. C$_{24}$H$_{34}$O$_6$N$_6$PS requires 565.1998); HPLC t$_R$=3.52 min (20% TEAC 20 mM in MeCN); UV (EtOH 95%) λ$_{max}$=259 (ε$_{max}$ 15900), λ$_{min}$=224 (ε$_{min}$ 7200).

Example 2

Preparation of B102, the Hydroxy-tBuSATE N-benzylphosphoramidate Derivative of 2'-C-methylcytidine

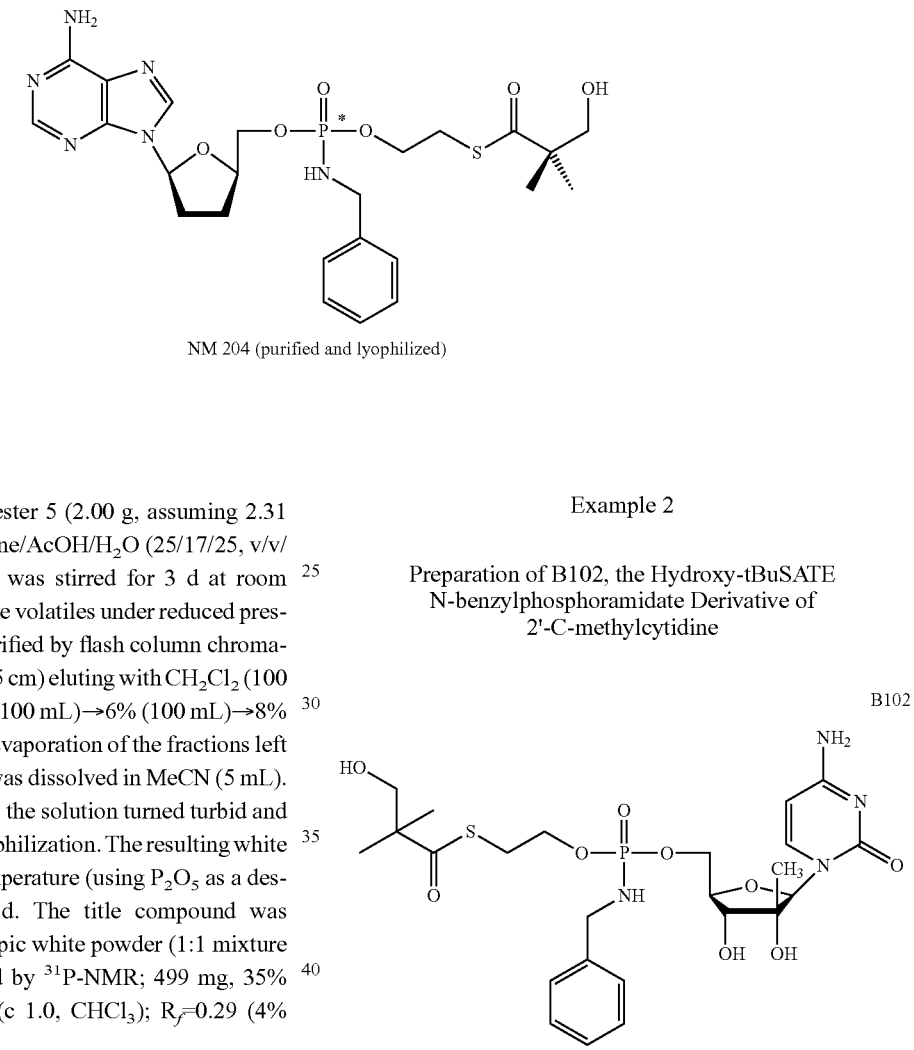

B102

Procedure A

Synthesis of H-Phosphonate Monoester 5

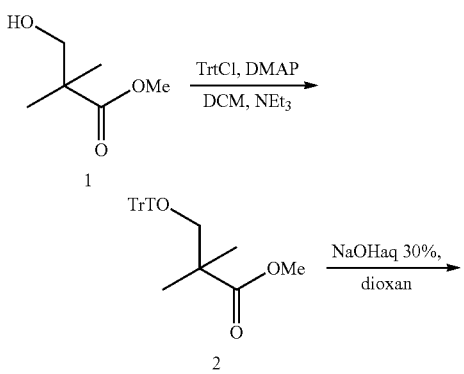

-continued

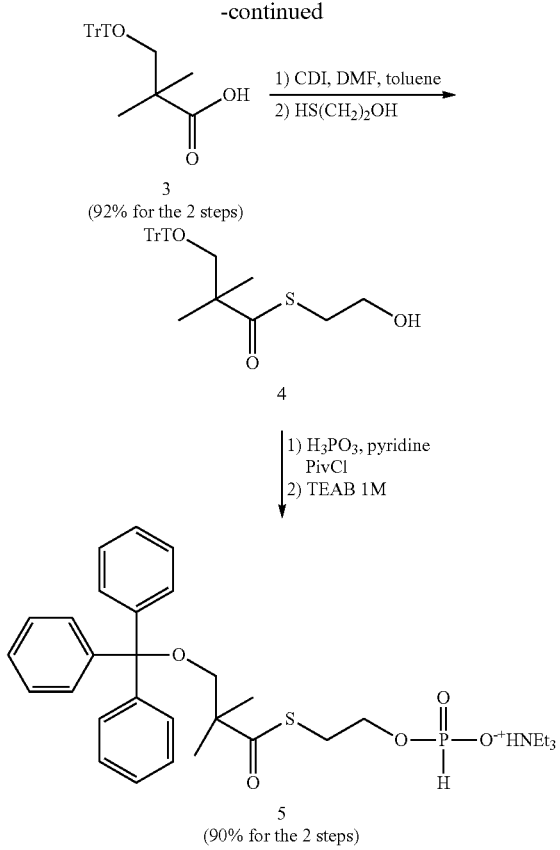

Synthesis of Carboxylic Acid 3

To a stirred solution of 2,2-dimethyl-3-hydroxypropanoic acid methyl ester (1, 15 ml, 117.6 mmol) in a mixture of anhydrous methylene chloride (590 ml) and triethylamine (23 ml), were added triphenylmethylene chloride (1.2 eq, 39.3 g) and 4-dimethylaminopyridine (0.1 eq, 1.44 g). The reaction mixture was left refluxing overnight. The mixture was poured carefully over a saturated aqueous $NaHCO_3$ solution and the product was extracted with methylene chloride and washed with water. The combined organic extracts were evaporated under reduced pressure to give crude compound 2 which will be used for the next step without further purification. The resulting oil was dissolved in a mixture of dioxan (350 ml) and an aqueous solution of NaOH (30%, 350 ml). The heterogene mixture was refluxed for 16 hours. The reaction mixture was allowed to cool down to room temperature, the two phases were separated, and the organic phase carefully neutralized by dropwise addition of HCl (1M). The product was extracted with methylene chloride and the organic phases were evaporated under reduced pressure. The crude orange oil was recrystallized from methylene chloride to afford carboxylic acid 3 as white crystals (92%). $R_f$=0.50 (70% diethyl ether in petroleum ether); $^1$H-NMR (400 MHz, $CDCl_3$) 1.24 (s, 6H, 2×$CH_3$), 3.19 (s, 2H, $CH_2O$), 7.2-7.5 (m, 15H, $C_6H_5$).

Synthesis of H-Phosphonate Monoester 5

1,1'-carbonyldiimidazole (1.3 eq, 1.17 g) was added to a stirring solution of carboxylic acid 3 (2 g, 5.56 mmol) in an anhydrous mixture of toluene and dimethylformamide (2/1, v/v, 4.5 ml) at room temperature, and the reaction mixture turned turbid instantly. After 30 min, the reaction mixture was diluted with a mixture of toluene and dimethylformamide (93/7, v/v, 28 ml), cooled to −10° C., and 2-mercaptoethanol (1.3 eq, 500 μL) was added. The solution was stirred for 3 h at this temperature. The volatiles were removed under reduced pressure (bath temperature not exceeding 25° C.). The residue was dissolved in methylene chloride and washed with water. The organic phases were combined, dried over sodium sulphate ($Na_2SO_4$), filtered and evaporated to dryness to give compound 4 as a yellow oil. This compound will be coevaporated with anhydrous pyridine and used for the next step without further purification. $R_f$=0.71 (70% $Et_2O$ in petroleum ether); $^1$H-NMR (400 MHz, $CDCl_3$) 1.20 (s, 6H, 2×$CH_3$), 3.05 (t, J=6.4 Hz, 2H, $CH_2S$), 3.15 (s, 2H, $CH_2OTr$), 3.69 (t, J=6.4 Hz, 2H, $CH_2OH$), 7.3-7.9 (m, 15H, $C_6H_5$).

Phosphorus acid (10 eq, 4.1 g) was coevaporated two times with anhydrous pyridine, dissolved in that solvent (25 ml) and added to crude 4. The reaction mixture was stirred at room temperature and a white precipitate appeared after few minutes. The reaction mixture was cooled down to 0° C. and pivaloyl chloride (5.5 eq, 3.4 ml) was added. The reaction mixture was allowed to warm to room temperature and stirred for 3 h. The reaction was stopped by addition of a solution of triethylammonium bicarbonate (TEAB 1M, 10 ml) and diluted with ethyl acetate (EtOAc). After extraction with EtOAc and TEAB 0.5M, the organic phases were combined, dried over sodium sulphate, filtered and evaporated to dryness (bath temperature not exceeding 30° C.). The residue was purified by flash column chromatography eluting with 10% of methanol in methylene chloride+1% triethylamine. Evaporation of the fractions afforded the H-phosphonate monoester 5 as a white syrup (90%). $R_f$=0.25 (70% $Et_2O$ in petroleum ether); $^1$H-NMR (400 MHz, $CDCl_3$) 1.17 (m, 2×$CH_3$+excess ($CH_3CH_2$)$_3$N), 2.9 (m, excess ($CH_3CH_2$)$_3$N), 3.12 (t, J=6.8 Hz, 2H, $CH_2S$), 3.37 (s, 2H, $CH_2OTr$), 3.90 (m, 2H, $CH_2OP$), 7.2-7.6 (m, 15H, $C_6H_5$), 9.9 (m, excess ($CH_3CH_2$)$_3$NH); $^{31}$P-NMR (161 MHz, $CDCl_3$) 3.85 (s).

Synthesis of B102, the Hydroxy-tBuSATE N-benzylphosphoramidate Derivative of 2'-C-methylcytidine The following two strategies were used:

Strategy a

Synthesis of the Protected Nucleoside 7

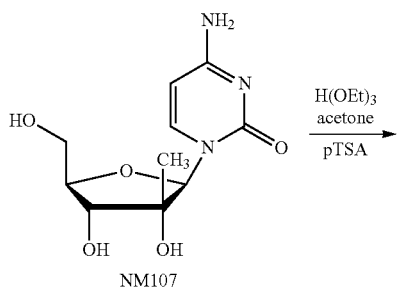

NM107

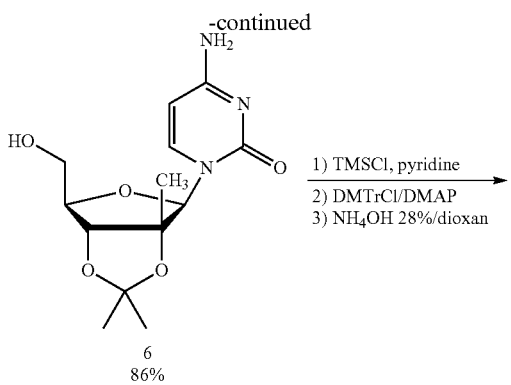

A mixture of 2'C-methylcytidine (NM107) (10 g, 39.0 mmol), triethyl orthoformate (8.3 eq, 54 ml) and p-toluenesulfonic acid monohydrate (1 eq, 7.4 g) in anhydrous acetone (650 ml), was refluxed overnight under nitrogen atmosphere. The reaction mixture was neutralized with an aqueous ammonia solution (26%) and the precipitate filtered. The filtrate was evaporated under reduced pressure and coevaporated with ethanol. Purification of the crude mixture on silica gel column chromatography (eluant: stepwise gradient [0-10%] of methanol in methylene chloride) led to compound 6 as a pale-yellow solid (86%). $R_f$=0.30 (20% MeOH in methylene chloride), $^1$H-NMR (400 MHz, DMSO-$d_6$) 1.06 (s, 3H, CH$_3$), 1.33 (s, 3H, CH$_3$), 1.47 (s, 3H, CH$_3$), 3.6 (m, 2H, H-5', H-5"), 4.1 (m, 1H, H-4'), 4.41 (d, 1H, H-3, J=3.2 Hz), 5.16 (t, 1H, OH-5', J=4.0 Hz, D$_2$O exchangeable), 5.69 (d, 1H, H-5, J=8.0 Hz), 6.04 (s, 1H, H-1'), 7.14-7.19 (bd, 2H, NH$_2$, D$_2$O exchangeable), 7.74 (d, 1H, H-6, J=8.0 Hz); LC/MS Scan ES– 296 (M–H)$^-$, Scan ES+ 298 (M+H)$^+$, $\lambda_{max}$=280.7 nm.

Compound 6 (4.4 g, 14.8 mmol) was dissolved in anhydrous pyridine (74 ml) and chlorotrimethylsilane (3 eq, 5.4 ml) was added. The reaction mixture was stirred at room temperature under nitrogen atmosphere for 2 h, then 4,4'-dimethoxytrityl chloride (1.5 eq, 7.5 g) and 4-dimethylaminopyridine (0.5 eq, 900 mg) were successively added. The reaction mixture was stirred overnight at room temperature, then quenched with a saturated aqueous NaHCO$_3$ solution. The crude product was extracted with methylene chloride, washed with saturated aq NaHCO$_3$ solution, and water. The combined organic phases were concentrated under reduced pressure, then dissolved in a mixture of dioxan (160 ml) and aqueous ammonia (28%, 29 ml). The solution was heated at 70° C. for 3 h and evaporated to dryness. The crude mixture was purified on silica gel column chromatography (eluant: stepwise gradient of methanol [1-5%] in methylene chloride) to give protected nucleoside 7 as a yellow solid (81%). $R_f$=0.16 (30% EtOAc in CH$_2$Cl$_2$) $^1$H-NMR (400 MHz, DMSO-$d_6$) 1.03 (s, 3H, CH$_3$), 1.30 (s, 3H, CH$_3$), 1.42 (s, 3H, CH$_3$), 3.5 (m, 2H, H-5', H-5"), 3.71 (s, 6H, 2×OCH$_3$), 4.0 (d, 1H, H-4', J=3.2 Hz), 4.36 (d, 1H, H-3', J=2.8 Hz), 5.1 (m, 1H, OH-5', D$_2$O exchangeable), 5.90 (s, 1H, H-1'), 6.2 (m, 1H, H-5), 6.8-7.2 (m, 13H, DMTr), 7.6 (m, 1H, H-6), 8.32 (s, 1H, NH, D$_2$O exchangeable); LC/MS Scan ES– 598 (M–H)$^-$, $\pi_{max1}$=231.7 nm, $\lambda_{max2}$ 283.7 nm.

Synthesis B102

Compound 10

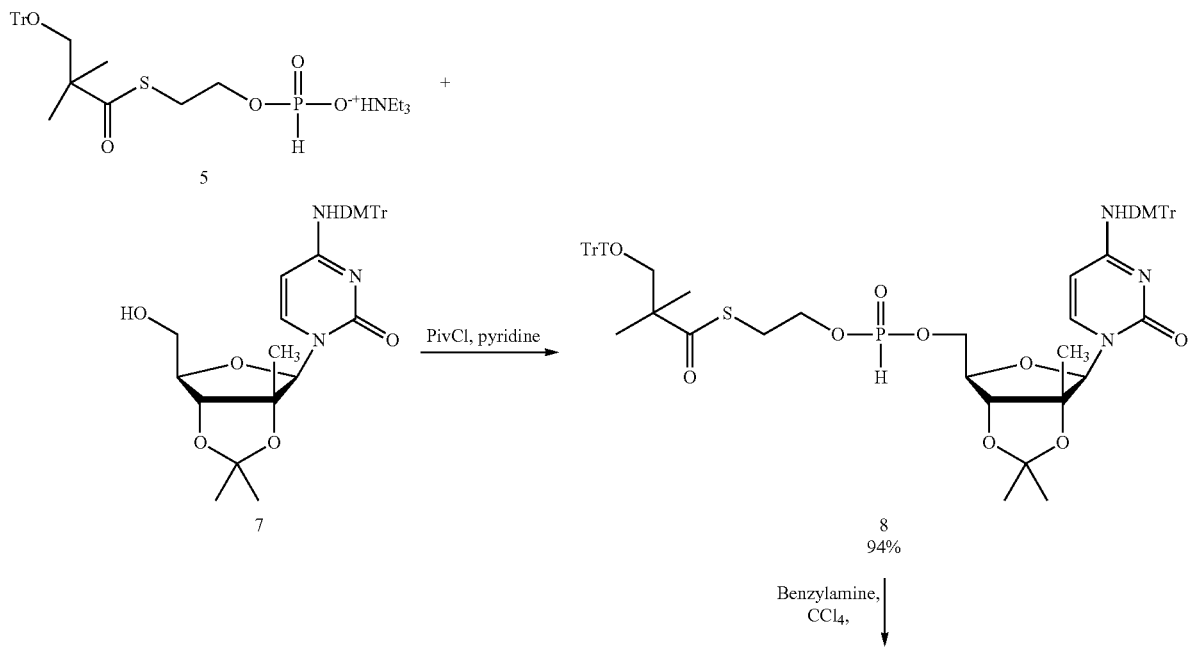

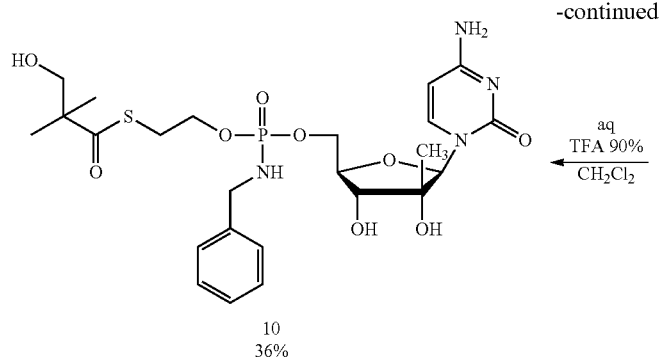 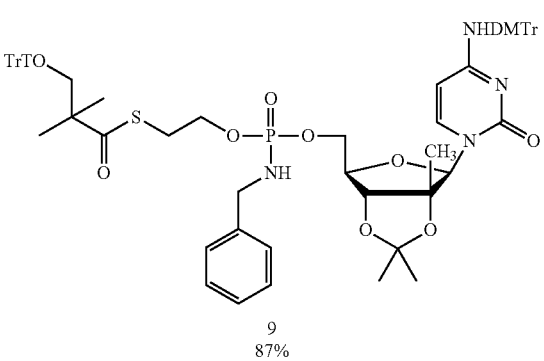

10
36%

9
87%

Compounds 7 (2.0 g, 3.34 mmol) and 5 (2.2 eq, 4.3 g) were coevaporated together with anhydrous pyridine and dissolved in this solvent (50 ml). Pivaloyl chloride (2.5 eq, 1 ml) was added dropwise and the solution stirred at room temperature for 2 h30. The reaction mixture was diluted with methylene chloride and neutralized with an aqueous solution of ammonium chloride (NH$_4$Cl 0.5M). After extraction with methylene chloride/aq NH$_4$Cl 0.5M, the organic phases were combined, evaporated under reduced pressure (bath temperature not exceeding 30° C.) and coevaporated with toluene. The crude mixture was purified on silica gel column chromatography (eluant: stepwise gradient [0-5%] of methanol in methylene chloride+2°/oo acetic acid) to afford the desired product 8 which was coevaporated with toluene to give a beige foam (94%). R$_f$=0.63 (5% MeOH in CH$_2$Cl$_2$); $^1$H-NMR (400 MHz, CDCl$_3$) 1.21 (m, 9H, 3 CH$_3$), 1.42 (s, 3H, CH$_3$), 1.60 (s, 3H, CH$_3$), 3.13 (m, 2H, CH$_2$S), 3.17 (m, 2H, CH$_2$OTr), 3.79 (s, 6H, 2×OCH$_3$), 4.1 (m, 2H, CH$_2$OP), 4.2-4.3 (m, 3H, H-5', H-5", H-4'), 5.09 (d, 1H, H-3', J=7.6 Hz), 5.89 (d, 1H, H-5, J=5.6 Hz), 6.0 (m, 1H, H-1'), 6.8-7.7 (m, 29H, Tr, DMTr, H-6); $^{13}$P-NMR (161 MHz, CDCl$_3$) 7.92, 8.55; LC/MS Scan ES+ 1066 (M+H)$^+$, Scan ES− 1064 (M−H)$^−$.

a solution of compound 8 (3.4 g, 3.15 mmol) in anhydrous carbon tetrachloride (30 ml) was added dropwise benzylamine (10 eq, 3.4 ml). The reaction mixture was stirred at room temperature for 1 h30. A white precipitate appeared. The solution was diluted with methylene chloride and neutralized with an aqueous solution of hydrogen chloride (HCl 1M). After successive extractions with CH$_2$Cl$_2$/HCl 1M and CH$_2$Cl$_2$/aq NaHCO$_3$, the organic phases were combined, dried over Na$_2$SO$_4$, filtered and evaporated to dryness. The crude mixture was purified on silica gel column chromatography (eluant: stepwise gradient [0-5%] of methanol in methylene chloride) to give 9 as a yellow foam (87%). Rf=0.35 (5% MeOH in methylene chloride); $^1$H-NMR (400 MHz, CDCl$_3$) 1.1-1.2 (m, 9H, 3 CH$_3$), 1.40 (s, 3H, CH$_3$), 1.59 (s, 3H, CH$_3$), 2.9-3.2 (m, 4H, CH$_2$OTr, CH$_2$OS), 3.76 (s, 6H, 2×OCH$_3$), 3.9-4.4 (m, 8H, CH$_2$OP, CH$_2$N, H-3', H-4', H-5', H-5"), 5.0 (m, 1H, H-5), 6.0 (2s, 1H, H-1'), 6.7-7.7 (m, 34H, Tr, DMTr, C$_6$H$_5$CH$_2$, H-6); $^{13}$P-NMR (161 MHz, CDCl$_3$) 8.40, 8.8.68; LC/MS Scan ES+ 1171 (M+H)$^+$.

Finally, compound 9 (2.39 g, 2.04 mmol) was dissolved in a mixture of methylene chloride (10 ml) and an aqueous solution of trifluoroacetic acid (90%, 10 ml). The reaction mixture was stirred at 35-40° C. for 2 h, then diluted with ethanol (140 ml). The volatiles were evaporated under reduced pressure and coevaporated with ethanol. The crude mixture was purified by silica gel column chromatography (eluant: stepwise gradient of methanol [0-30%] in methylene chloride), followed by a purification on reverse phase chromatography (eluant: stepwise gradient of acetonitrile [0-50%] in water), to give the desired product 10 (B102) (1:1 mixture of diastereoisomers as judged by $^{31}$P-NMR, 36%) which was lyophilized from a mixture of dioxan/water. Rf=0.34 (15% MeOH in methylene chloride); $^1$H-NMR (400 MHz, DMSO-d6) 0.92 (s, 3H, CH$_3$), 1.10 (s, 6H, 2×CH$_3$), 3.0 (m, 2H, CH$_2$S), 3.33 (m, 1H, H-3'), 3.56 (s, 2H, CH$_2$OH), 3.8-4.0 and 4.05-4.25 (stacks, 7H, CH$_2$OP, NCH$_2$Ph, H-4', H-5' and H-5"), 4.9 (m, 1H, OH-3', J=5.4 Hz, D$_2$O exchangeable), 5.07 (s, 1H, OH-2', D$_2$O exchangeable), 5.3 (m, 1H, CH$_2$OH, D$_2$O exchangeable), 5.6-5.7 (m, 2H, H-5 and NH, D$_2$O exchangeable), 5.91 (s, 1H, H-1'), 7.3-7.4 (stack, 7H, Phil, NH$_2$, D$_2$O exchangeable), 7.6 (m, 1H, H-6); $^{13}$P-NMR (161 MHz, DMSO-d6) 9.71, 9.91; HPLC t$_R$=4.67 min (0-100% acetonitrile over a period of 8 min), $\lambda_{max}$=274.9; LC/MS Scan ES+ 587 (M+H)$^+$.

Strategy b

Synthesis of Protected Nucleoside 11

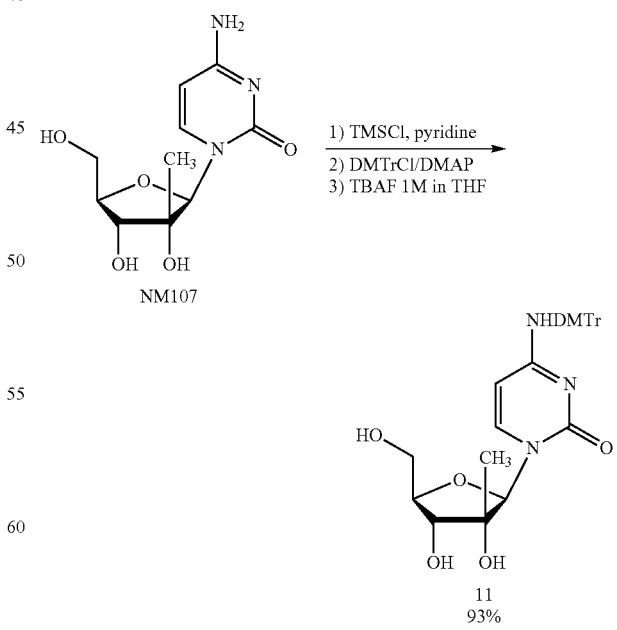

11
93%

NM107 (10 g, 38.87 mmol) was dissolved in anhydrous pyridine (194 ml) and chlorotrimethylsilane (4.5 eq, 21.6 ml)

was added. The reaction mixture was stirred at room temperature under nitrogen atmosphere for 2 h30, then 4,4'-dimethoxytrityl chloride (1.5 eq, 19.8 g) and 4-dimethylaminopyridine (0.5 eq, 2.37 g) were successively added. The reaction mixture was stirred overnight at room temperature, then quenched with a saturated aqueous NaHCO$_3$ solution. The crude product was extracted with methylene chloride, washed with saturated aq NaHCO$_3$ solution, and water. The combined organic phases were concentrated under reduced pressure, then dissolved in tetrahydrofuran (110 ml). To that solution was added tetrabutylammonium fluoride 1M in THF (1 eq, 38.87 ml) and the reaction mixture was stirred for 30 min at room temperature. After extraction with EtOAc and water, the organic phases were collected and evaporated to dryness. The crude mixture was purified on silica gel column chromatography (eluant: stepwise gradient of methanol [0-10%] in methylene chloride) to give protected nucleoside 11 as a yellow solid (93%). R$_f$=0.32 (10% MeOH in CH$_2$Cl$_2$) $^1$H-NMR (400 MHz, DMSO-d$_6$) 0.79 (s, 3H, CH$_3$), 3.56 (m, 2H, H-5', H-5"), 3.71 (s, 7H, 2×OCH$_3$, H-4'), 5.0 (m, 4H, H-3', OH-2', OH-3', OH-5', D$_2$O exchangeable), 5.72 (s, 1H, H-1'), 6.16 (m, 1H, H-5), 6.8-7.2 (m, 13H, DMTr), 7.82 (m, 1H, H-6), 8.24 (m, 1H, NH D$_2$O exchangeable); LC/MS Scan ES− 560 (M+H)$^+$, ES− 558 (M−H)$^-$, λ$_{max}$=284.7 nm.

Synthesis of Protected Phosphoramidate Pronucleotide 13, Precursor of 10

Compound 11 (7 g, 12.5 mmol) and 5 (1.5 eq, 11.0 g) were coevaporated together with anhydrous pyridine and dissolved in this solvent (187 ml). Pivaloyl chloride (2.0 eq, 3.08 ml) was added dropwise at −15° C. and the solution stirred at this temperature for 1 h30. The reaction mixture was diluted with methylene chloride and neutralized with an aqueous solution of ammonium chloride (NH$_4$Cl 0.5M). After extraction with methylene chloride/aq NH$_4$Cl 0.5M, the organic phases were combined, evaporated under reduced pressure (bath temperature not exceeding 30° C.) and coevaporated with toluene. The crude mixture was purified on silica gel column chromatography (eluant: stepwise gradient [0-5%] of methanol in methylene chloride+0.2% acetic acid) to afford the desired product 12 which was coevaporated with toluene to give a white foam (3.5 g, 27%). R$_f$=0.44 (5% MeOH in CH$_2$Cl$_2$); $^1$H-NMR (400 MHz, DMSO) 0.8 (m, 3H, CH$_3$), 1.14 and 1.06 (2s, 6H, 2 CH$_3$), 3.06 (m, 2H, CH$_2$S), 3.16 (m, 2H, CH$_2$OTr), 3.5 (m, 1H, H-3'), 3.70 (m, 6H, 2 OCH$_3$), 3.90 (m, H-4'), 4.03 (m, 2H, CH$_2$OP), 4.24 (m, 2H, H-5', H-5"), 5.30 and 5.04 (2 ms, 2H, OH-2' and OH-3', D$_2$O exchangeable), 5.78 (m, 1H, H-1'), 5.98 (m, 1H, P—H), 6.22 (m, 1H, H-5), 7.0-7.5 (m, 16H, Tr), 8.32 (m, 1H, H-6); $^{13}$P-NMR (161 MHz, DMSO) 9.17, 9.65; LC/MS Scan ES+ 1026 (M+H)$^+$, λ$_{max}$=282.7 nm.

To a solution of compound 12 (500 mg, 0.49 mmol) in anhydrous carbon tetrachloride (4.9 ml) was added dropwise benzylamine (5 eq, 0.266 ml). The reaction mixture was stirred at room temperature for 3 h and the solvent removed

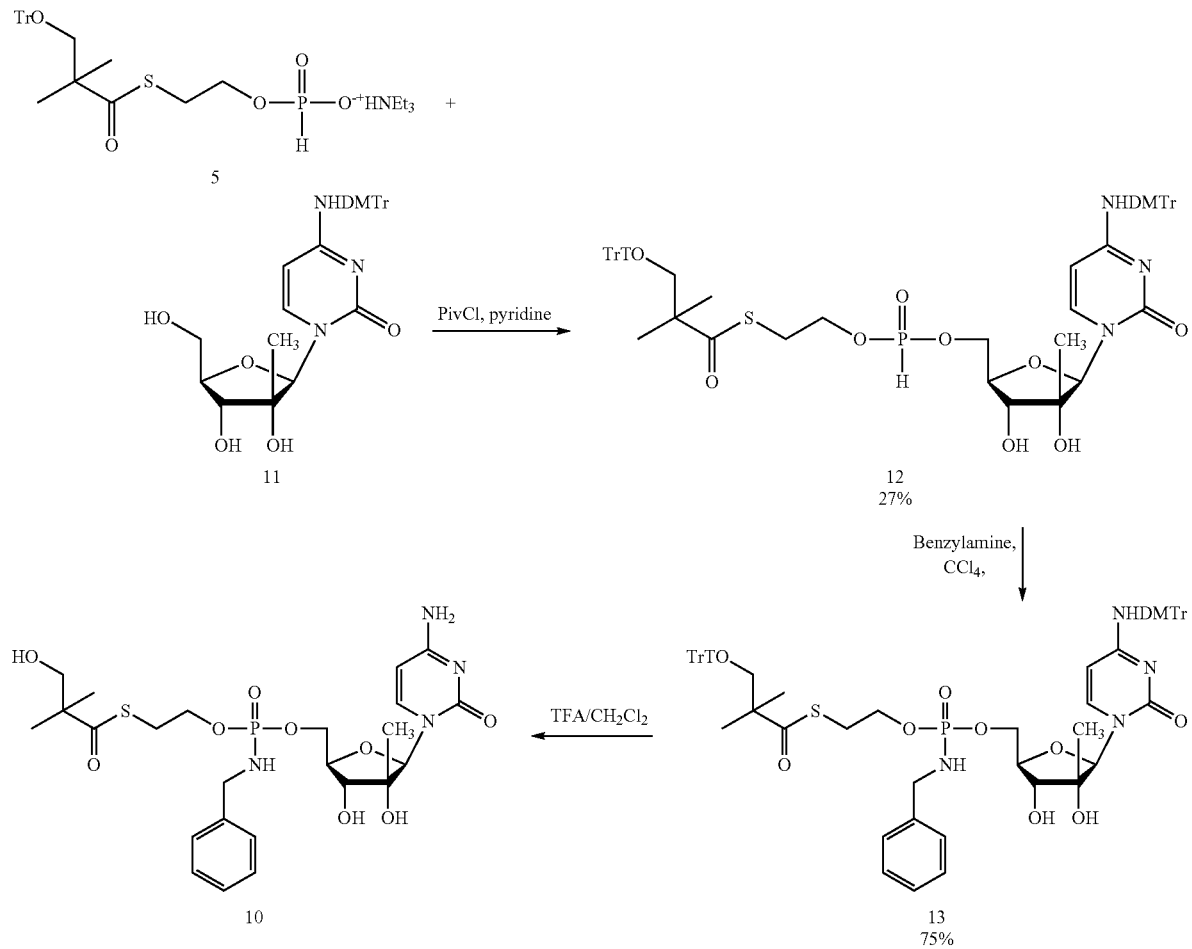

under reduced pressure. The crude mixture was purified on silica gel column chromatography (eluant: stepwise gradient [0-5%] of methanol in methylene chloride) to afford compound 13 as a foam (75%). Rf=0.25 (3% MeOH in methylene chloride); $^1$H-NMR (400 MHz, DMSO) 0.79 (s, 3H, CH$_3$), 1.13 and 1.06 (2s, 6H, 2 CH$_3$), 3.05 (m, 4H, CH$_2$OTr, CH$_2$OS), 3.51 (m, 1H, H-3'), 3.69 (s, 6H, 2×OCH$_3$), 3.87 (m, 3H, CH$_2$OP, CH$_2$N, H-3'), 4.08 (m, 2H, H-5', H-5"), 5.19 and 5.0 (2m, 2H, OH-2' and OH-3', D$_2$O exchangeable), 5.67 (m, 1H, NH, D$_2$O exchangeable), 5.75 (2s, 1H, H-1'), 6.21 (m, 1H, H-5), 6.7-7.5 (m, 34H, Tr, DMTr, C$_6$H$_5$CH$_2$, H-6); $^{13}$P-NMR (161 MHz, DMSO) 9.84, 9.69; LC/MS Scan ES+ 1132 (M+H)$^+$.

Compound 13 can be converted into the phosphoramidate prodrug 10 (B 102) following experimental conditions described for the last step in Examples 3 (Procedure A) and in Example 4.

Synthetic Scheme

B102 is synthesized as a mixture of phosphorous diastereomers in 1:1 ratio. Isolated overall yield from NM107 to B102 was 31%, as not all the coupled material produced was used for deprotection.

Step 1.1:

Procedure B

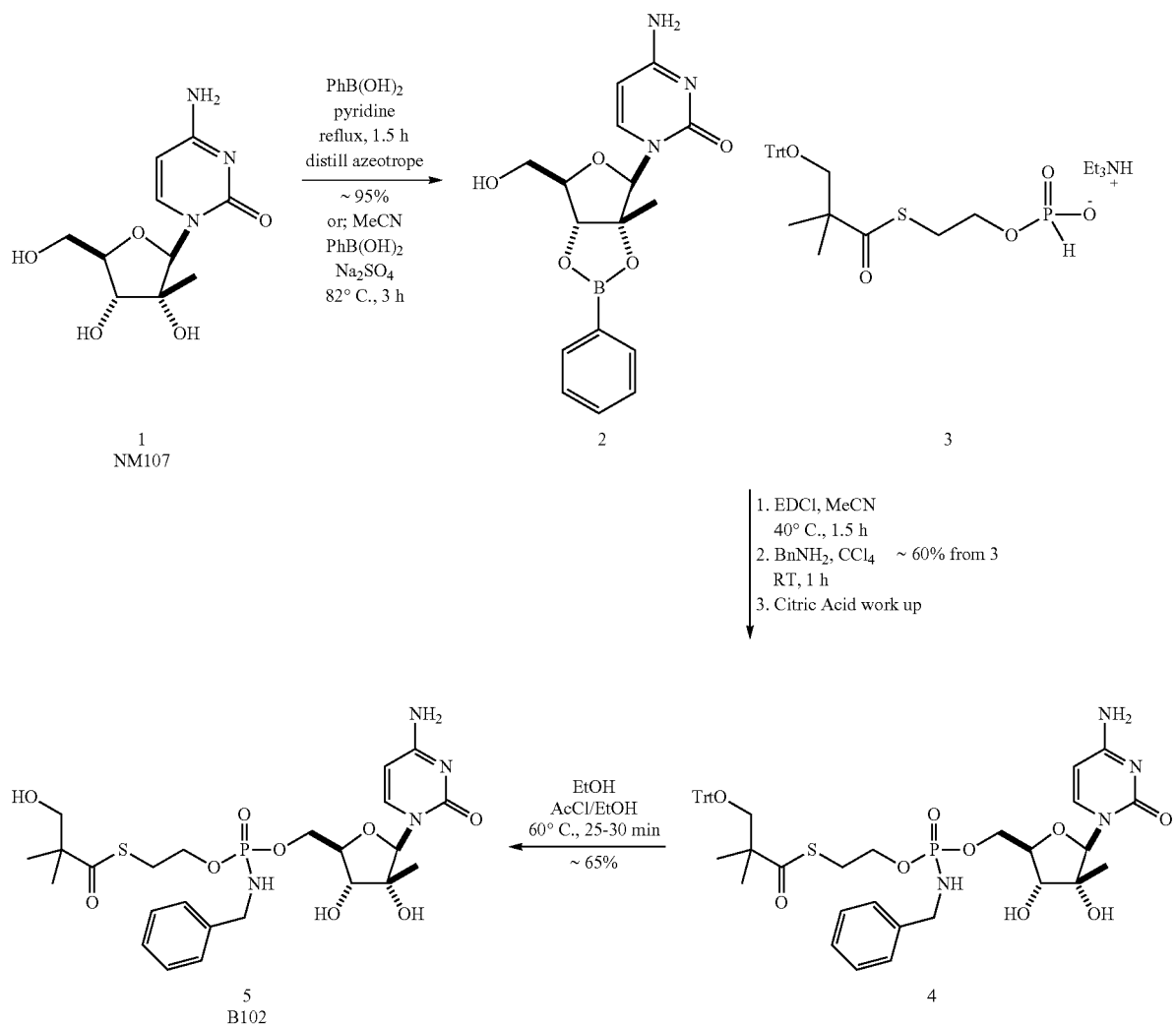

-continued

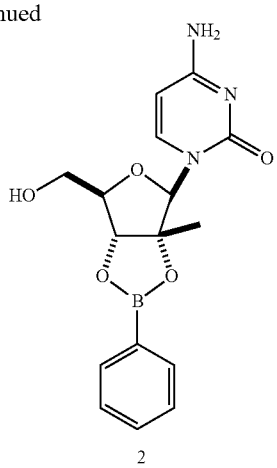

2

| Material | Grade | FW gmol$^{-1}$ | Quantity | Density gml$^{-1}$ | Amount mol | Eq |
|---|---|---|---|---|---|---|
| NM107 | 99% | 257.2 | 150 g | — | 0.583 | 1 |
| PhB(OH)2 | 98% | 122.1 | 78 g | — | 0.639 | 1.10 |
| Pyridine anhydrous | 98% | 79.1 | 2.5 L | 0.978 | — | — |

NM107 was dissolved in pyridine under argon and benzeneboronic acid was added. The stirred mixture was heated at reflux for 3 h under argon. Distillation of the azeotrope was then performed, removing 1.2 L (pyridine/water).
T head: 103° C.→113° C. T mixture: 112° C.→116° C.
The mixture was cooled to room temperature and the pyridine was evaporated under vacuum to get golden oil. The product was stored under vacuum overnight to be used for the next step. A ratio of 97:3 product:starting material was observed by $^1$H-NMR (d6-DMSO). Prior to Step 1.2, the crude was dissolved in 250 mL anhydrous pyridine.
Alternatively the following conditions may be used:
  eq benzeneboronic acid
  5 eq pyridine
  1.5 eq Na$_2$SO$_4$
  5 mL CH$_3$CN for 1 g of NM107
  Heat at reflux for 1 h-1 h30. Cool to RT. Used for next reaction.
98-99% of conversion by proton NMR
Step 1.2:

-continued

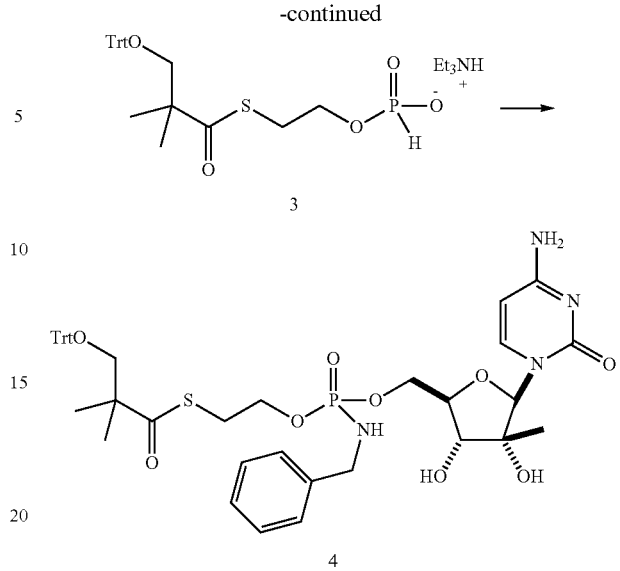

| Material | Grade | FW gmol$^{-1}$ | Quantity | Density gml$^{-1}$ | Amount mol | Eq |
|---|---|---|---|---|---|---|
| 2,3-PhB-NM107 | — | 343.1 | Solution | — | ~0.583 | 1 |
| Phosphonate 3 | — | 585.7 | 615 g | — | 1.049 | 1.8 |
| EDCI•HCl | 98% | 191.7 | 570 g | — | 2.973 | 5.1 |
| Acetonitrile anhydrous | 98% | — | 3 L | — | — | — |
| Benzylamine | 98% | 107.2 | 445 mL | 0.98 | 4.0 | 7* |
| Carbon tetrachloride | 98% | 153.8 | 260 mL | 1.59 | 2.6 | 4* |

*Extra equivalents of these reagents may be added (e.g. 15 eq) if required (if P—OH visible by HPLC)

Phosphonate 3 was dissolved in 3 L of acetonitrile under argon. A solution of 2,3-PhB-NM107 from Step 1.1 was added followed by EDCI.HCl. The mixture was stirred under argon at 41-46° C. for 4 h after which time HPLC analysis indicated ~7:1 ratio of P—H product to NM107. The mixture was cooled to 18° C. and benzylamine was added dropwise followed by carbon tetrachloride. The reaction was slightly exothermic. Analysis by HPLC indicated complete conversion of P—H to phosphoramidate product. Ethyl acetate (1 L) was added to the mixture which was then acidified to pH 4 with 3 L of 20% citric acid. The aqueous phase was extracted with 2.5 L of ethyl acetate. The organic phases were combined and washed with 3 L of 10% citric acid. The organic phase was basified to pH 8 with 5 L of aqueous sodium bicarbonate (saturated) and washed a second time with 2 L of aqueous sodium bicarbonate (saturated). The organic phase was dried over sodium sulfate, filtered under vacuum and evaporated to give a yellow foam, 712 g.

The crude residue was dissolved in dichloromethane (1 L) and purified on silica plug (2.3 Kg of silica). Eluted with: 5 L 4% Methanol/DCM, 2*1 L 4%, 3*1 L 5%, 8*250 mL 6%, 4*250 mL 7%, 9*1 L 7%. Evaporation of the relevant fractions gave 254 g (HPLC purity: 98.5%, yield: 52%) and 73 g (HPLC purity: 87.6%, yield: 13%) of phosphoramidate 4.

Step 2:

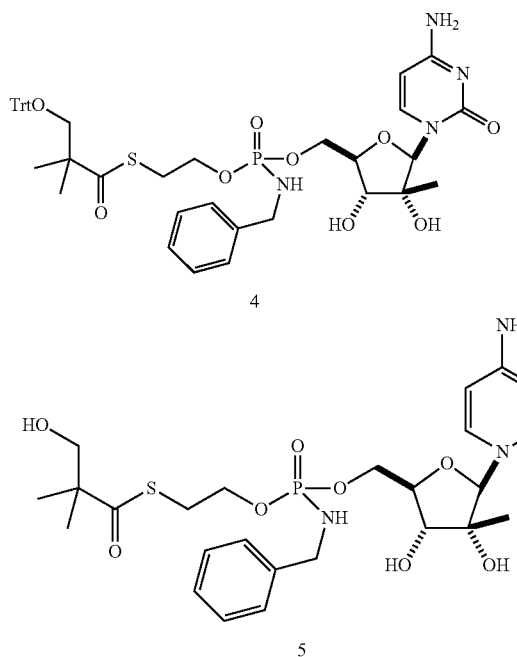

| Material | Grade | FWG mol$^{-1}$ | Quantity | Density gml$^{-1}$ | Amount mol | Eq |
|---|---|---|---|---|---|---|
| Phosphoramidate 4 | — | 828.9 | 246 g | — | 0.291 | 1 |
| AcCl | 99% | 78.5 | 62.6 mL | 1.105 | 1.049 | 3.0* |
| EtOH anhydrous | 98% | — | 3.5 L* | — | — | — |

*Subsequently 2.0 eq AcCl and 1:10 w/v 4:EtOH ratio were used.

Phosphoramidate 4 was dissolved in anhydrous ethanol and acetyl chloride was added (exothermic: 18° C. to 27° C.) to the reaction mixture, under argon. The mixture was stirred at 60° C. under argon. After 30 min, HPLC analysis indicated complete conversion of the phosphoramidate 4 to deprotected product 5. The mixture was cooled to 25° C. and solid sodium bicarbonate (1.04 Kg) was added in several portions (foaming, pH ~5.5-6). The mixture was filtered through Celite and washed with two volumes of ethanol. The filtrate was evaporated under vacuum at 35° C. The residue was triturated with TBME (3 L) for 1 h and then filtered to remove the trityl by-product. The solid obtained was dried under vacuum to give 185 g with 93% purity at 254 nm by HPLC.

If required, any residual benzeneboronic acid may be removed from the product by dissolution in water and treatment with Amberlite IRA-743 resin.

The following alternative reaction conditions (to avoid the possibility of acylating 4) are possible:
  2.0 eq AcCl in EtOH 1:10 v:v to generate HCl and consume all AcCl (exothermic)
  Phosphoramidate 4 in EtOH (to make 1:10 w:v total volume EtOH)
  Add HCl/EtOH solution to reaction mixture at 20° C.
  60° C. under argon, 30-45 min The crude was purified by reverse-phase chromatography (1.5 Kg of prepared Bakerbond 40 μm C-18 RP-silica—washed with 100% acetonitrile gradient to 100% H$_2$O). The crude was dissolved in acetonitrile (58 mL), H$_2$O (164 mL) and saturated aqueous sodium bicarbonate solution (170 mL).

Elution under gentle vacuum with a stepwise gradient of 3% MeCN/H$_2$O, 10%, 15%, 25% (pure product eluted) and evaporation of the relevant fractions gave 106 g B102 (62% yield) with 98.6% purity at 254 nm by HPLC.

Typical Analytical Data is Shown Below:
  B102: C$_{24}$H$_{35}$N$_4$O$_9$PS 586.59 gmol$^{-1}$
  HPLC AUC (Method Test 20): 98.9% @ 254 nm, Rt 3.34 min
  m/z (ESI+): 587.12 [M+H]$^+$100%; 1173.62 [2M+H]$^+$ 80%
  $v_{max}$ (KBr disc) (cm$^{-1}$): 3343.1 br (O—H, N—H); 1647.2 br (C=O base, thioester)
  KF: 2.02% H$_2$O content
  Specific Rotation: $[\alpha]_D^{20}$+55.011 (c. 10.492 mg cm$^{-3}$ in DMSO)
  Elemental analysis: Calculated: C, 49.14%; H, 6.01%; N, 9.55%; S, 5.47%; P, 5.28%.
  Found: C, 48.74%; H, 5.83%; N, 9.41%; S, 5.81%; P, 5.33%.
  NMR: Analyzed using $^1$H, $^{13}$C, $^{31}$P, COSY, DEPT, HSQC and HMBC experiments.
  $^1$H NMR $\delta_H$ (400 MHz, d6-DMSO): 0.94 (3H, d, J 1.8 Hz, CH$_3$), 1.11 (6H, s, (CH$_3$)$_2$C), 3.04 (2H, m, J 6.4 Hz, CH$_2$S), 3.44 (2H, d, J 5.0 Hz, CH$_2$OH), 3.60 (1H, br-m, H-3'), 3.82-4.01 (5H, m, H-4', CH$_2$O, CH$_2$Ph), 4.07-4.12 (1H, m, H-5'), 4.13-4.24 (1H, m, H-5"), 4.94 (1H, t, J 5.0 Hz, CH$_2$OH), 5.07 (1H, d, J 1.8 Hz, OH-2'), 5.26 (1H, t, J 6.8 Hz, OH-3'), 5.64-5.76 (1H, m, P—N—H), 5.69, 5.70 (1H, 2×d, 2×J 7.6 Hz, H-5), 5.93 (1H, br-s, H-1'), 7.13-7.20 (2H, 2×br-s, NH$_2$), 7.20-7.25 (1H, m, Ar—H), 7.28-7.35 (4H, m, 4×Ar—H), 7.53, 7.57 (1H, 2×d, J 7.6 Hz, H-6)
  $^{13}$C NMR $\delta_C$ (100 MHz, d6-DMSO): 19.81 (CH$_3$), 21.79 (C(CH$_3$)$_2$), 28.17, 28.24 (CH$_2$S), 44.18 (PhCH$_2$), 51.62 (C(CH$_3$)$_2$), 63.74, 63.79 (CH$_2$O), 64.21, 64.51 (C-5'), 68.29 (CH$_2$OH), 72.41, 72.57 (C-3'), 77.80, 77.85 (C-2'), 79.47, (C-4'), 91.66, (C-1'), 93.82 (C-5), 126.68, 127.09, 128.08, 128.09 (5×Ar—C), 140.34, 140.38, 140.40 (Ar—C$_{ipso}$, C-6), 155.12, 165.21 (C-2, C-4), 203.85 (C=OS)
  $^{31}$P NMR $\delta_P$ (162 MHz, d6-DMSO): 9.71, 9.91 (1P, 2×s, ratio 1.00:1.07)

Synthetic Procedure A can be used for synthesizing nucleoside prodrugs such as B 102. Protection of the 2' and 3' hydroxyl groups as well as the amino group that may be present on the nucleoside base is preferred. In Strategy A, the 2' and 3' hydroxyl groups are protected, e.g., as the acetonide derivative and the amino group is protected, e.g., as the di-methoxytrityl derivative. Hydrolysis of the acteonide after the coupling of the nucleoside with the SATE intermediate is carried out using an acid such as TFA. This hydrolysis procedure can potentially produce by-products and give low yields, and the di-methoxytrityl chloride is disadvantageously expensive. Synthetic Procedure B, below, can overcome the such difficulties. An acid, such as a boronic acid, such as phenyl boronic acid is used to protect the 2' and 3' hydroxyl groups on the sugar moiety. Coupling the nucleoside phenyl boronate derivative with the SATE intermediate can give good yield, and the phenyl boronate deprotection conveniently takes place during the work-up of the reaction mixture, on washing with an acid such as an aqueous citric acid solution. The final removal of a protecting group such as a trityl group (on the Sate moiety) is mildly carried out using an organic solvent system, such as an acetyl chloride/ethanol mixture. This deprotection reaction can be consistently reproducible, scalable and gave significantly high yield.

Example 3

Preparation of B299, the Hydroxy-tBuSATE N-benzylphosphoramidate Derivative of 2'-C-methylguanosine

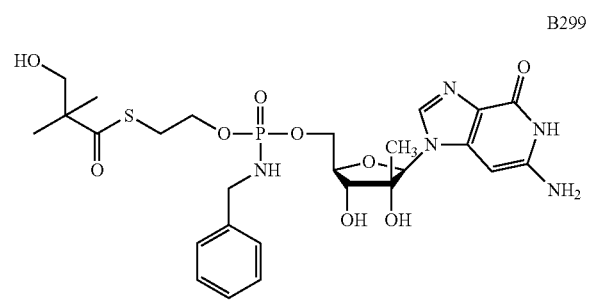

Procedure A

Synthetic Scheme

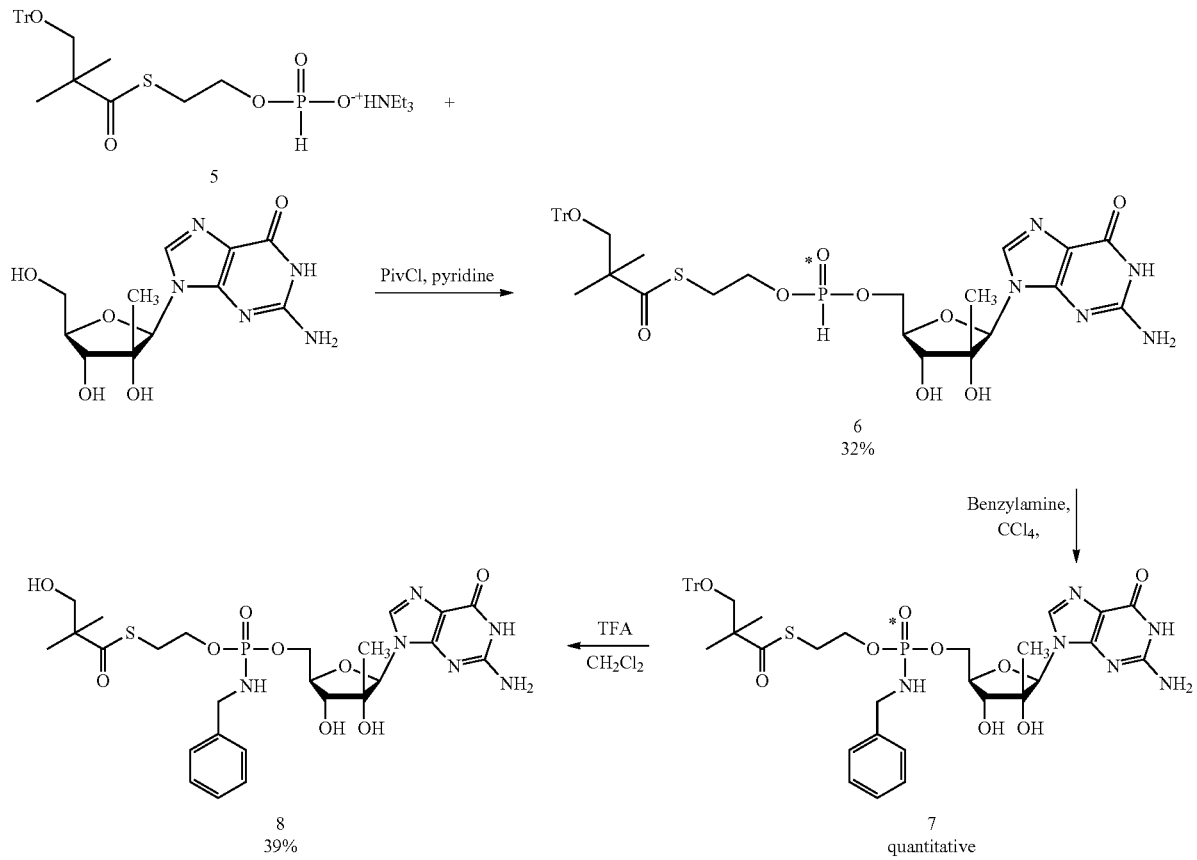

2'-C-methylguanosine (NM108) (3 g, 10.10 mmol) and compound 5 [for the synthesis of 5, See Example 2] (6.48 g, 11.10 mmol) were coevaporated together with anhydrous pyridine and dissolved in this solvent (152 mL). Pivaloyl chloride (2.48 mL, 20.18 mmol) was added dropwise at −15° C. and the solution was stirred at the same temperature for 2 h. The reaction mixture was diluted with methylene chloride and neutralized with an aqueous solution of ammonium chloride ($NH_4Cl$ 0.5M). After extraction with methylene chloride/aq $NH_4Cl$ 0.5M, the organic phases were combined, dried over $Na_2SO_4$ evaporated under reduce pressure (bath temperature not exceeding 30° C.) and coevaporated twice with toluene. The crude mixture was purified on silica gel flash column chromatography (eluant: stepwise gradient [0-10%] of methanol in methylene chloride+0.2% acetic acid) to afford the desired product 6 (2.5 g, 32%). $R_f$=0.34 (15% MeOH in $CH_2Cl_2$); $^1$H-NMR (400 MHz, DMSO-$d_6$ 0.80 (s, 3H, $CH_3$), 1.13 (s, 6H, 2×$CH_3$), 3.04 (m, 2H, $CH_2$OTr), 3.14 (m, 2H, $CH_2$S), 3.97-4.08 (m, 4H, H-3', H-4', $CH_2$OP), 4.28-4.38 (m, 2H, H-5', H-5"), 5.10-5.35 (m, 2H, OH-2', OH-3', $D_2$O exchangeable), 5.77 (s, 1H, H-1'), 6.52 (bs, 2H, $NH_2$, $D_2$O exchangeable), 7.11-7.42 (m, 15H, Tr), 7.75 (s, 1H, H-8), 10.67 (bs, 1H, NH, $D_2$O exchangeable); $^{13}$P-NMR (161 MHz, DMSO-$d_6$) 9.47, 9.20; LC/MS Scan ES+ 764 (M+H)$^+$, Scan ES− 762 (M−H)$^−$.

To a solution of compound 6 (2.5 g, 3.27 mmol) in anhydrous carbon tetrachloride (33 mL) was added dropwise benzylamine (5 eq, 1.79 mL). The reaction mixture was stirred at room temperature for 1 h and evaporated under reduced pressure (bath temperature not exceeding 30° C.). The crude mixture was purified on silica gel flash column chromatography (eluant: stepwise gradient [0-10%] of methanol in methylene chloride) to give compound 7 as a white foam (2.9 g, quantitative yield). Rf=0.27 (10% MeOH in methylene chloride);

$^{1}$H-NMR (400 MHz, DMSO-d$_{6}$) 0.81 (s, 3H, CH$_{3}$), 1.10 (s, 6H, 2×CH$_{3}$), 2.99-3.08 (m, 4H, CH$_{2}$OTr, CH$_{2}$S), 3.87-4.30 (m, 8H, H-3', H-4', H-5', H-5" CH$_{2}$OP, NCH$_{2}$Ph), 5.66 (m, 1H, NH, D$_{2}$O exchangeable), 5.76 (s, 1H, H-1'), 6.60 (bs, 2H, NH$_{2}$, D$_{2}$O exchangeable), 7.17-7.39 (m, 20H, Tr, C$_{6}$H$_{5}$CH$_{2}$), 7.77 (s, 1H, H-8); $^{13}$P-NMR (161 MHz, DMSO-d$_{6}$) 9.93, 9.78; LC/MS Scan ES+ 869 (M+H)$^{+}$, Scan ES− 867 (M−H)$^{−}$.

Compound 7 (2.84 g, 3.27 mmol) was dissolved in a mixture of trifluoroacetic acid (1.1 mL) and methylene chloride (11.4 mL). The reaction mixture was stirred 0.5 h at room temperature. The solution was diluted with ethanol, evaporated under reduce pressure (bath temperature not exceeding 30° C.) and coevaporated twice with toluene. The crude mixture was purified on silica gel flash column chromatography (eluant: stepwise gradient [0-30%] of methanol in methylene chloride) and then, on reverse phase column chromatography (eluant: stepwise gradient [0-100%] of acetonitrile in water) to give the desired product 8 (B299) (1:1 mixture of diastereoisomers according to $^{31}$P-NMR, 800 mg, 39%) which was lyophilized from a mixture of dioxan/water. Rf=0.57 (20% MeOH in methylene chloride); $^{1}$H-NMR (400 MHz, DMSO-d6) 0.82 (s, 3H, CH$_{3}$), 1.09 (s, 6H, 2×CH$_{3}$), 3.01 (m, 2H, CH$_{2}$S), 3.42 (d, 2H, CH$_{2}$OH, J=8.0 Hz), 3.81-4.00 (m, 6H, H-3', H-4' CH$_{2}$OP, NCH$_{2}$Ph), 4.11-4.27 (m, 2H, H-5', H-5"), 4.92 (t, 1H, CH$_{2}$OH, J=8.0 Hz, D$_{2}$O exchangeable), 5.16 (s, 1H, OH-2', D$_{2}$O exchangeable), 5.40 (m, 1H, OH-3', D$_{2}$O exchangeable), 5.64 (m, 1H, NH, D$_{2}$O exchangeable), 5.75 (s, 1H, H-1'), 6.50 (bs, 2H, NH$_{2}$, D$_{2}$O exchangeable), 7.19-7.32 (m, 5H, PhH), 7.77 (s, 1H, H-8), 10.61 (bs, 1H, NH, D$_{2}$O exchangeable); $^{13}$P-NMR (161 MHz, DMSO-d6) 9.91, 9.78;

HPLC t$_{R}$=3.67 min (0-100% acetonitrile over a period of 8 min), λ$_{max}$=251.3; LC/MS Scan ES+ 627 (M+H)$^{+}$, Scan ES− 625 (M−H)$^{−}$.

Example 4

Preparation of B208, the Hydroxy-tBuSATE N-benzylphosphoramidate Derivative of 2'-C-methylthymidine

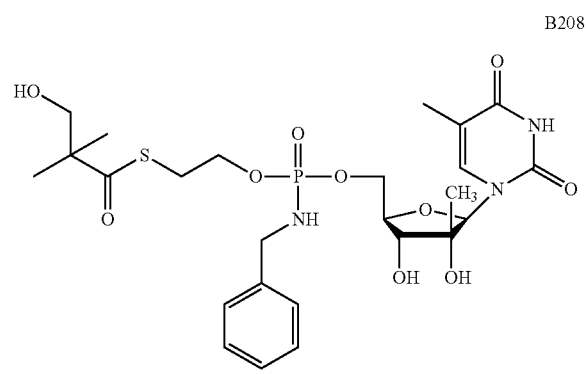

Synthetic Scheme

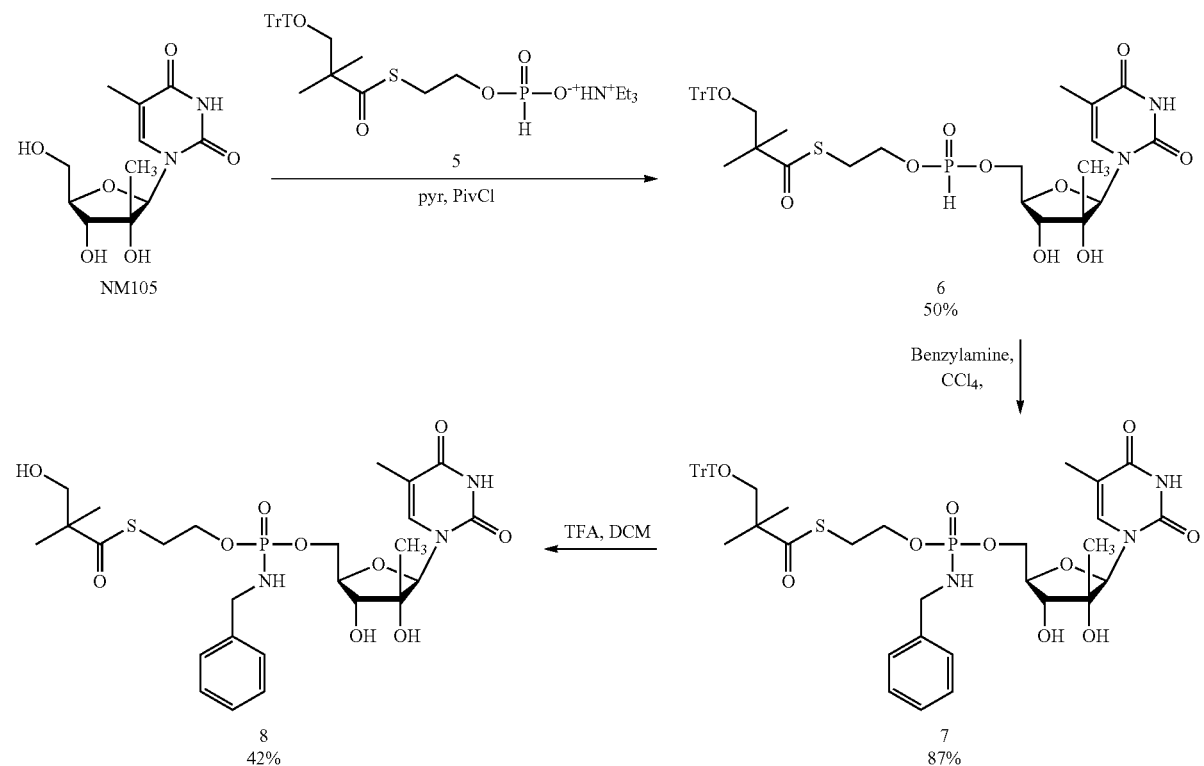

2'-C-Methylthymidine (NM105) (700 mg, 2.57 mmol) and 5 [for the synthesis of 5, See Example 2] (1.1 eq, 1.6 g) were coevaporated together with anhydrous pyridine and dissolved in this solvent (40 ml). Pivaloyl chloride (2.0 eq, 0.633 ml) was added dropwise at −15° C. and the solution stirred at this temperature for 1 h30. The reaction mixture was diluted with methylene chloride and neutralized with an aqueous solution of ammonium chloride (NH$_4$Cl 0.5M). After extraction with methylene chloride/aq NH$_4$Cl 0.5M, the organic phases were combined, evaporated under reduced pressure (bath temperature not exceeding 30° C.) and coevaporated with toluene. The crude mixture was purified on silica gel column chromatography (eluant: stepwise gradient [0-10%] of methanol in methylene chloride+0.2% acetic acid) to afford the desired product 6 which was coevaporated with toluene to give a white foam (942 mg, 50%). R$_f$=0.56 (15% MeOH in CH$_2$Cl$_2$); $^1$H-NMR (400 MHz, DMSO) 1.00 (s, 3H, CH$_3$), 1.13 (s, 6H, 2 CH$_3$), 1.77 (s, 3H, CH$_3$), 3.16 (m, 2H, CH$_2$S), 3.32 (m, 2H, CH$_2$OTr), 3.6 (m, 1H, H-3'), 3.9 (m, 1H, H-4'), 4.0 (m, 2H, CH$_2$OP), 4.2-4.3 (m, 2H, H-5', H-5"), 5.21 (s, 1H, OH-2', D$_2$O exchangeable), 5.40 (t, 1H, OH-3', D$_2$O exchangeable), 5.83 (s, 1H, H-1'), 6.0 (s, 1H, P—H), 7.0-7.5 (m, 16H, Tr, H-6); $^{13}$P-NMR (161 MHz, DMSO) 9.29, 9.68; LC/MS Scan ES+ 761 (M+Na)$^+$.

To a solution of compound 6 (920 mg, 1.25 mmol) in anhydrous carbon tetrachloride (13 ml) was added dropwise benzylamine (10 eq, 1.4 ml). The reaction mixture was stirred at room temperature for 2 h. A white precipitate appeared. The solution was diluted with methylene chloride and neutralized with an aqueous solution of hydrogen chloride (HCl 1M). After successive extractions with CH$_2$Cl$_2$/HCl 1M and CH$_2$Cl$_2$/aq NaHCO$_3$, the organic phases were combined, dried over Na$_2$SO$_4$, filtered and evaporated to dryness. The crude mixture was purified on silica gel column chromatography (eluant: stepwise gradient [0-10%] of methanol in methylene chloride) to give 7 as a white foam (875 mg, 83%). R$_f$=0.56 (15% MeOH in CH$_2$Cl$_2$); $^1$H-NMR (400 MHz, DMSO) 0.99 (s, 3H, CH$_3$), 1.12 (s, 6H, 2 CH$_3$), 1.75 (s, 3H, CH$_3$), 3.04 (m, 4H, CH$_2$OTr, CH$_2$S), 3.69 (m, 1H, H-3'), 3.8-4.0 (m, 5H, CH$_2$OP, CH$_2$N, H-4'), 4.0-4.2 (m, 2H, H-5', H-5"), 5.17 (s, 1H, OH-2', D$_2$O exchangeable), 5.3 (m, 1H, OH-3', D$_2$O exchangeable), 5.7 (m, 1H, NH, D$_2$O exchangeable), 5.82 (s, 1H, H-1'), 7.1-7.5 (m, 21H, Tr, C$_6$H$_5$CH$_2$, H-6); $^{13}$P-NMR (161 MHz, DMSO) 9.95, 9.86; HPLC t$_R$=7.91 min (0-100% acetonitrile over a period of 8 min), λ$_{max}$=266.7 nm; LC/MS Scan ES+ 866 (M+Na)$^+$.

Finally, compound 7 (860 mg, 1.02 mmol) was dissolved in a mixture of methylene chloride (15 ml) and trifluoroacetic acid (0.51 ml). The reaction mixture was stirred at room temperature for 2 h, then diluted with toluene. The volatiles were evaporated under reduced pressure and coevaporated with ethanol. The crude mixture was purified by silica gel column chromatography (eluant: stepwise gradient of methanol [0-10%] in methylene chloride), followed by a purification on reverse phase chromatography (eluant: stepwise gradient of acetonitrile [0-50%] in water), to give the desired product 8 (B208) (257 mg, 42%). Rf=0.31 (10% MeOH in methylene chloride); $^1$H-NMR (400 MHz, DMSO-d6) 0.99 (s, 3H, CH$_3$), 1.10 (s, 6H, 2×CH$_3$), 1.75 (s, 3H, CH$_3$), 3.0 (m, 2H, CH$_2$S), 3.42 (d, 2H, CH$_2$OH), 3.7 (m, 1H, H-3'), 3.8-4.0 (stack, 5H, CH$_2$OP, NCH$_2$Ph, H-4'), 4.0-4.3 (m, 2H, H-5' and H-5"), 4.9 (m, 1H, CH$_2$OH, D$_2$O exchangeable), 5.17 (s, 1H, OH-2', D$_2$O exchangeable), 5.3 (m, 1H, OH-3', D$_2$O exchangeable), 5.7 (m, 1H, NH, D$_2$O exchangeable), 5.81 (s, 1H, H-1'), 7.2-7.4 (stack, 6H, PhH, H-6); $^{13}$P-NMR (161 MHz, DMSO-d6) 9.84, 9.90; HPLC t$_R$=4.98 min (0-100% acetonitrile over a period of 8 min), λ$_{max}$=269.0 nm; LC/MS Scan ES+ 602 (M+H)$^+$.

Example 5

Preparation of B261, the Hydroxy-tBuSATE N-benzylphosphonamidate Derivative of PMEA

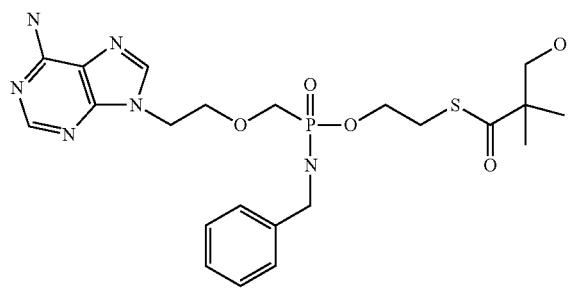

Procedure A

Synthesis of Intermediate 4

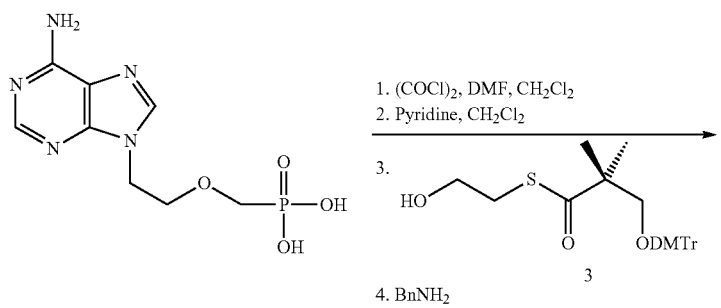

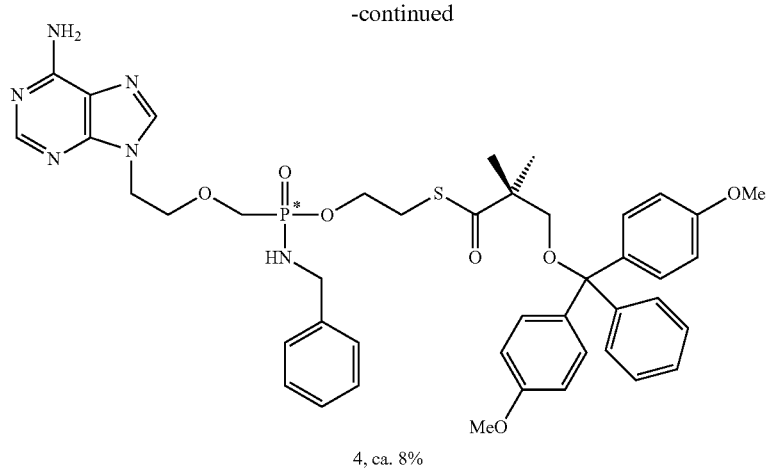

4, ca. 8%

A 500 mL triple-neck flask fitted with a condenser was charged with PMEA (2.00 g, 7.25 mmol), CH2Cl2 (121 mL) and DMF (617 μL, 7.98 mmol). The resulting slurry was vigorously stirred and oxalyl chloride (2.21 mL, 25.4 mmol) was added dropwise at 0° C. over 10 min (gas evolution). The slurry turned to a yellow solution (10 min) before turning turbid (10 min). This was further stirred for 3 h under reflux and turned to a white, thick slurry. The products were schlenk-dried 1 h in situ by evaporation of all volatiles under reduced pressure, at room temperature. The resulting yellow solid could then be partially dissolved in CH2Cl2 (121 mL), and pyridine (1.17 mL, 14.5 mmol) was added dropwise at 0° C. over 10 min. The white suspension turned to a blue solution, which was cooled to −78° C. A solution of alcohol 3 [for the synthesis of 3, See Example 1] (3.480 g, 7.25 mmol) and triethylamine (6.37 mL, 45.7 mmol) in CH2Cl2 (72 mL) was then added slowly (ca. 45 min), dropwise along the internal wall, and the reaction was stirred 10 h at −78° C. Benzylamine (2.37 mL, 21.7 mmol) was then added dropwise at −78° C. and the solution was left stirring warming to r.t. over 1 h. NaHCO3 (aq. sat., 200 mL) was poured over the reaction and the layers separated. The aqueous phase was extracted with CH$_2$Cl$_2$ (2×100 mL) and the combined organic extracts were dried with brine (50 mL) and Na2SO4. The solution was filtered and concentrated to afford ca. 6.5 g of crude yellow syrup. Purification by flash column chromatography (SiO2, Ø=3.5 cm, H=11 cm) eluting with 4→8→12% MeOH in CH$_2$Cl$_2$ (1% Et3N) afforded 3.70 g of a yellow foam (0.15<Rf<0.30, 10% MeOH in CH$_2$Cl$_2$) that were submitted to a second purification by flash column chromatography (SiO2, Ø=3.5 cm, H=12 cm) eluting with 4→6% MeOH in CH$_2$Cl$_2$ (1% Et$_3$N) to afford 2.67 g of a yellow foam (0.16<Rf<0.25, 10% MeOH in CH2Cl2). This was submitted to a third purification by flash column chromatography (SiO2, Ø=3.5 cm, H=12 cm) eluting with 4→6% MeOH in CH$_2$Cl$_2$ (1% Et3N) to produce 165 mg of phosphonamidate 4 (ca. 2.7%) as a white foam and 1.75 g of mixed compounds. These were submitted to a last purification by flash column chromatography (SiO2, Ø=3.5 cm, H=12 cm) eluting with 4→6% MeOH in CH$_2$Cl$_2$ (1% Et3N) afforded 353 mg of phosphonamidate 4 (ca. 5.9%) as a white foam. Total yield: 8.6%. Rf=0.21 (6% MeOH in CH2Cl2); 1H-NMR (300 MHz, CDCl3) 1.13 (s, 6H, 2 CH3), 3.02-3.10 (m, 2H, CH2S), 3.59 (t, J 7.5, 2H, CH2), 3.58 (s, 6H, 2×OCH3), 3.73 (t, J 7.1, 2H, CH2), 3.88-4.09 (stacks, 4H, 2×CH2), 4.21 (t, J 7.0, 2H, CH2O), 5.50 (br s, 2H, NH2), 6.67-6.78 (m, 4H, PhH), 7.04-7.38 (stack, 9H, PhH), 7.72 (s, 1H), 8.22 (s, 1H); 31P-NMR (121 MHz, CDCl$_3$) 25.0; m/z (FAB+) 825 (1), 303 (100); HRMS 825.3171 ([M+H]+. C43H50O7N6PS requires 825.3199).

Synthesis of Compound 5

B261

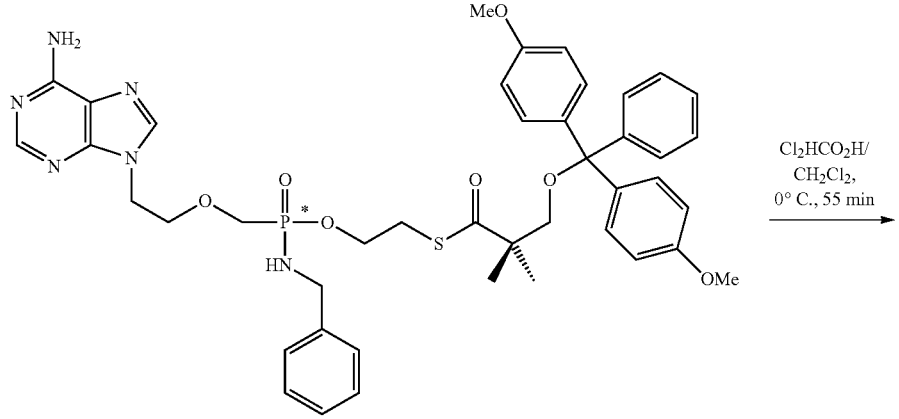

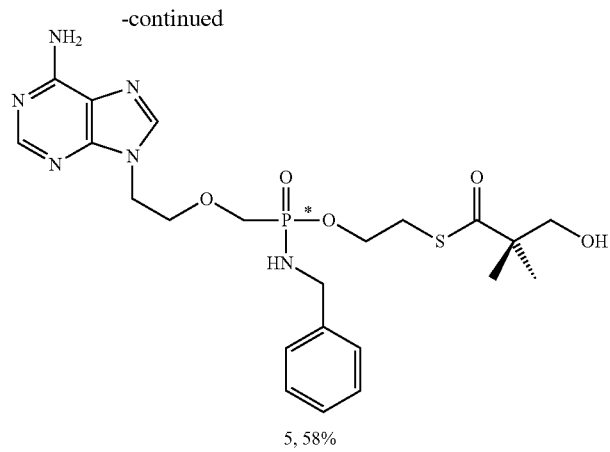

5, 58%

Dichloroacetic acid (20% solution in CH2Cl2, ca. 140 drops) was added dropwise to a solution of ether 4 (353 mg, 0.43 mmol) in CH2Cl2 (4.3 mL) at 0° C. and this was stirred for 55 min. Solid NaHCO3 (ca. 1.5 g) was then added and the slurry was stirred for 10 min before filtration and evaporation. Purification by flash column chromatography (SiO2, Ø=1.5 cm, H=10 cm) eluting with 4%→10% MeOH in CH2Cl2 afforded pure phosphonamidate 5 (130 mg after lyophilization in THF/H$_2$O and 3 day-stay in P2O5 desiccator, 58%). This reaction was also performed on 165 mg of ether 4 to produce 51 mg of phosphonamidate 5 (B261, 49%). Rf=0.20 (10% MeOH in CH$_2$Cl$_2$); $^1$H-NMR (300 MHz, DMSO-d6) 1.10 (s, 6H, 2×CH3), 2.80 (t, J 7.0, 2H, CH2S), 3.43 (d, J 5.5, 2H, CH2OH), 3.69 (A of AB, J 4.8, 1H, 1×CH2P), 3.71 (B of AB, J 4.8, 1H, 1×CH2P), 3.75-3.88 (stacks, 4H, CH2O, NCH2), 3.88-4.07 (m, 2H, NCH2Ph), 4.30 (t, J 7.0, 2H, CH2O), 4.97 (t, J 6.1, 1H, OH), 5.31-5.42 (m, 1H, NH), 7.16-7.32 (stack, 7H, PhH, NH2), 8.09 (s, 1H), 8.13 (s, 1H); 13C-NMR (75 MHz, DMSO-d6) 21.8 (2×CH3), 28.4 and 28.5 (CH2, CH2S), 42.4 (CH2, NCH2), 43.3 (CH2, NCH2), 51.7 (quat. C, C(CH3)2), 61.7 and 61.8 (CH2, CH2O), 64.6 (CH2, CH2O), 68.4 (CH2, CH2O), 118.5 (quat. C), [126.5 (CH, Ph), 127.0 (CH, Ph), 128.0 (CH, Ph), some overlap], 140.5 and 140.6 (quat. C), 141.0 (CH), 149.4 (quat. C), 152.3 (CH), 155.9 (quat. C), 203.9 (quat. C, C=O); 31P-NMR (121 MHz, DMSO-d6) 25.9; m/z (FAB+) 161 (32), 256 (42), 523 (100); HRMS 523.1899 ([M+H]+. C22H32O5N6PS requires 523.1892); HPLC(C18, flow: 0.5 mL/min, solution A=TEAC 20 mM, solution B=20% TEAC 20 mM): tR=5.04 min (60% A in B), tR=27.24 min (t=0→10 min: 100% A; t=10→30 min: 0→50% B in A; t=30→35 min: 50→100% B in A); UV (EtOH 95%) λmax=205 (εmax 23900), λmin=228 (εmin 5400).

Procedure B

Improved Preparation of the Hydroxy-tBuSATE N-benzylphosphoramidate Derivative (B261, Compound) of PMEA Synthetic Scheme

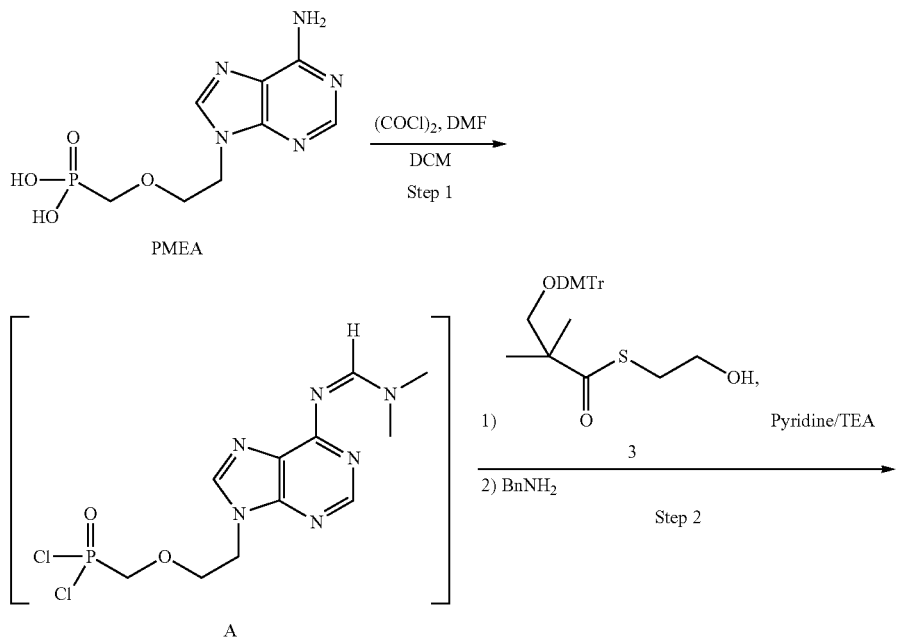

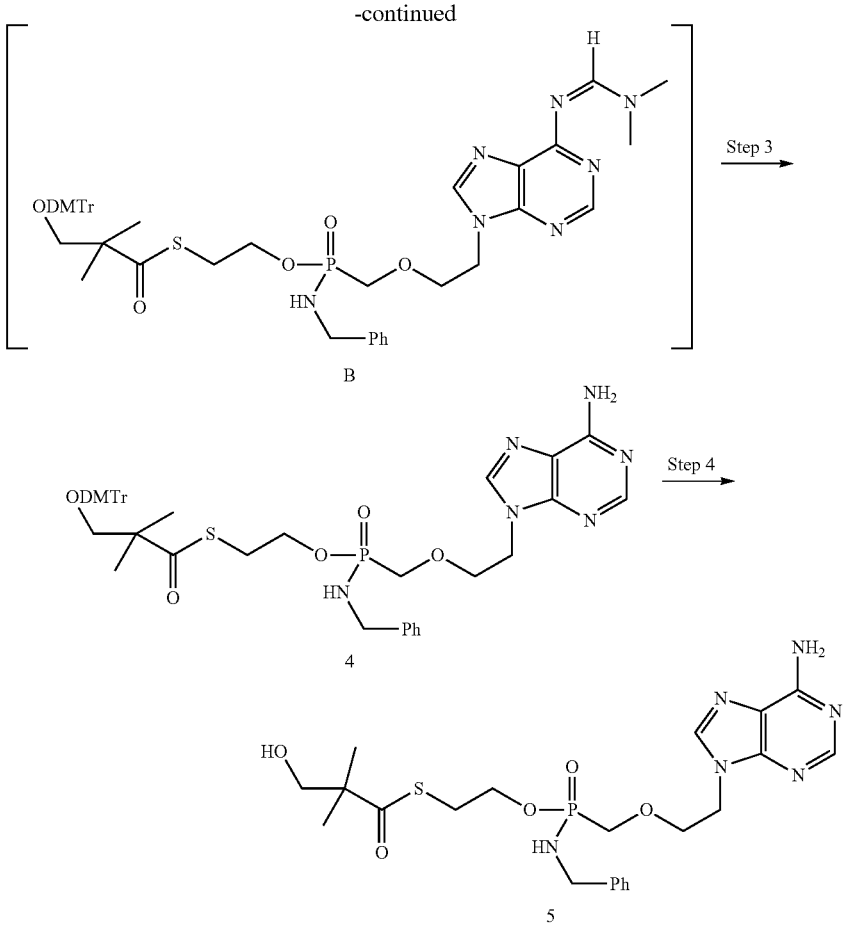

Step 1: Synthesis of Intermediate A

To the suspension of PMEA (2 g, 7.3 mmol) in 120 mL of DCM (anhydrous) was added DMF (640 mg, 1.2 eq), followed with oxalyl chloride (2.3 mL, 3.5 eq) at room temperature. The mixture was heated to reflux for 1.5 hrs to give a thick yellow suspension. The mixture was concentrated to dryness through rotarvap to give the crude intermediate 2 as pale yellow solid. LCMS analysis of the aliquot of intermediate 2 in methanolic solution confirmed the structure of the product in good purity.

Step 2: Synthesis of Intermediate B

The crude intermediate A (7.33 mmol) was suspended into 100 mL of anhydrous DCM. The suspension was cooled to 0° C. To this was added pyridine (1.2 mL, 14.6 mmol, 2 eq) at 0° C. After the addition, the pale yellow suspension turned to a golden colored clear solution. This solution was cooled to −32° C. with ACN/dry ice bath. To this was added a solution of 2 (3.52 g, 7.33 mmol, 1 eq) in 70 mL of anhydrous DCM that contained triethylamine (6.3 mL, 44 mmol, 6 eq) dropwise. The internal reaction temperature was maintained between −35° C.~−30° C. during the addition. The bright golden colored solution turned to a green colored solution with some precipitate crashing out from the solution during the addition. The precipitate was presumably the triethylamine HCl salt. It took 20 minutes to complete the addition. After the addition, the mixture was stirred at −30° C.~−10° C. for 1 hr. The reaction mixture was cooled back to −20° C. To this was added benzylamine (2.4 mL, 22 mmol, 3 eq). The mixture was stirred at −20° C. for 10 minutes. To the reaction mixture was added saturated NaHCO$_3$/H$_2$O and the mixture was stirred for 2 minutes. The DCM layer was separated, dried with Na$_2$SO$_4$ and concentrated to dryness to give the crude intermediate B as yellow viscous oil. HPLC analysis of the crude intermediate gave 62% purity at 272 nm.

Step 3: Synthesis of Intermediate 4

The crude intermediate B (7.33 mmol) as viscous pale yellow oil was dissolved into 200 mL of MeOH. The reaction mixture was refluxed overnight. HPLC analysis of the reaction mixture indicated the complete conversion of the amidine to amine. [The retention time of amidine (RT=5.92 min) is very close to the amine (RT=5.98 min) by the current in-house HPLC method!] The mixture was cooled to RT and filtered. The filtrate was concentrated to dryness by rotar-vap. The obtained crude product was purified through silica gel column chromatography (120 g silica gel combiflash column was used, 3-8% of MeOH in DCM as the eluent) to give 3.1 g pure product 4 as white foam in 51% isolated yield from 2 g of PMEA. $^1$H-NMR of the obtained 4 was consistent with the desired structure. HPLC analysis of the obtained 4 gave 96% purity (AUC).

Step 4: Synthesis of B261 (Compound 5)

Intermediate 4 (300 mg, 0.36 mmol) was dissolved into EtOH (anhydrous, 5 mL). To this was added acetyl chloride (43 mg, 1.5 eq) in one portion at room temperature. The reaction should be operated in a closed reaction flask to avoid the loss of HCl gas. The reaction mixture was stirred at RT for 30 min. To this was added solid $NaHCO_3$ and the mixture was stirred for 15 min. pH of the reaction mixture was found to be around 7-8. The mixture was filtered and the filtrate was concentrated to dryness. The crude product was purified through silica gel column chromatography (5-10% MeOH in DCM as the eluent) to give 163 mg of a as clear viscous oil in 86% yield. $^1$H-NMR of the obtained product was consistent with the desired structure. HPLC analysis of the obtained product gave 97.4% purity (AUC).

Example 6

Preparation of B263, the Hydroxy-tBuSATE N-benzylphosphoramidate Derivative of 2'-C-methyladenosine

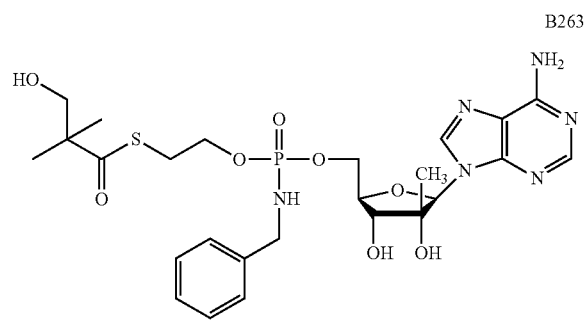

B263

Synthetic Scheme

The pronucleotide B263 (94 mg, 6% overall yield) has been synthesized from its parent nucleoside 2'-C-methyl-6-NH-dimethoxytrityl-adenosine (1.59 g, 2.73 mmol) following a similar procedure than the one described for the synthesis of the pronucleotide prepared in the Example 2 (Procedure A, Strategy b), and isolated as a white lyophilized powder. $^1$H NMR (DMSO-$d_6$, 400 MHz) δ (ppm) 0.80 (s, 3H), 0.97-0.98 (d, J=4.26 Hz, 6H), 3.02 (m, 2H), 3.34-3.35 (m, 2H), 3.76-3.96 (m, 4H), 4.03-4.05 (m, 2H), 4.15-4.17 (m, 2H), 4.76-4.79 (m, 1H), 5.32 (s, 1H), 5.34-5.36 (m, 1H), 5.45-5.55 (m, 1H), 5.93 (s, 1H), 7.1-7.4 (m, 7H), 8.14 (s, 1H), 8.21 (1H); $^{31}$P NMR (DMSO-$d_6$, 162 MHz) δ (ppm) 9.75 and 9.86 (2s); Scan ES$^+$ 611 (M+H)$^+$, $\lambda_{max}$=258 nm; HPLC (0-100% ACN over a period of 8 min) $t_R$=4.79 min $\lambda_{max}$=260.8 nm.

Example 7

Preparation of B229, the Hydroxy-tBuSATE N-benzylphosphoramidate Derivative of [2'-C-methyluridine

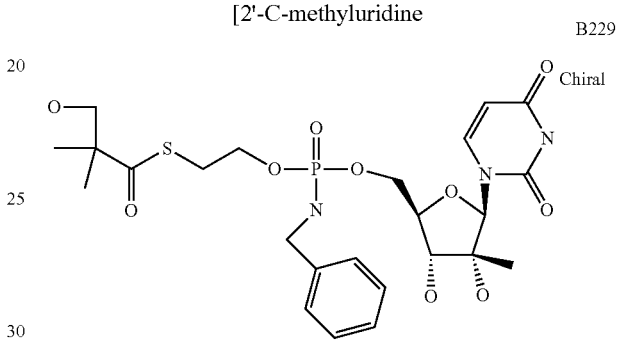

B229

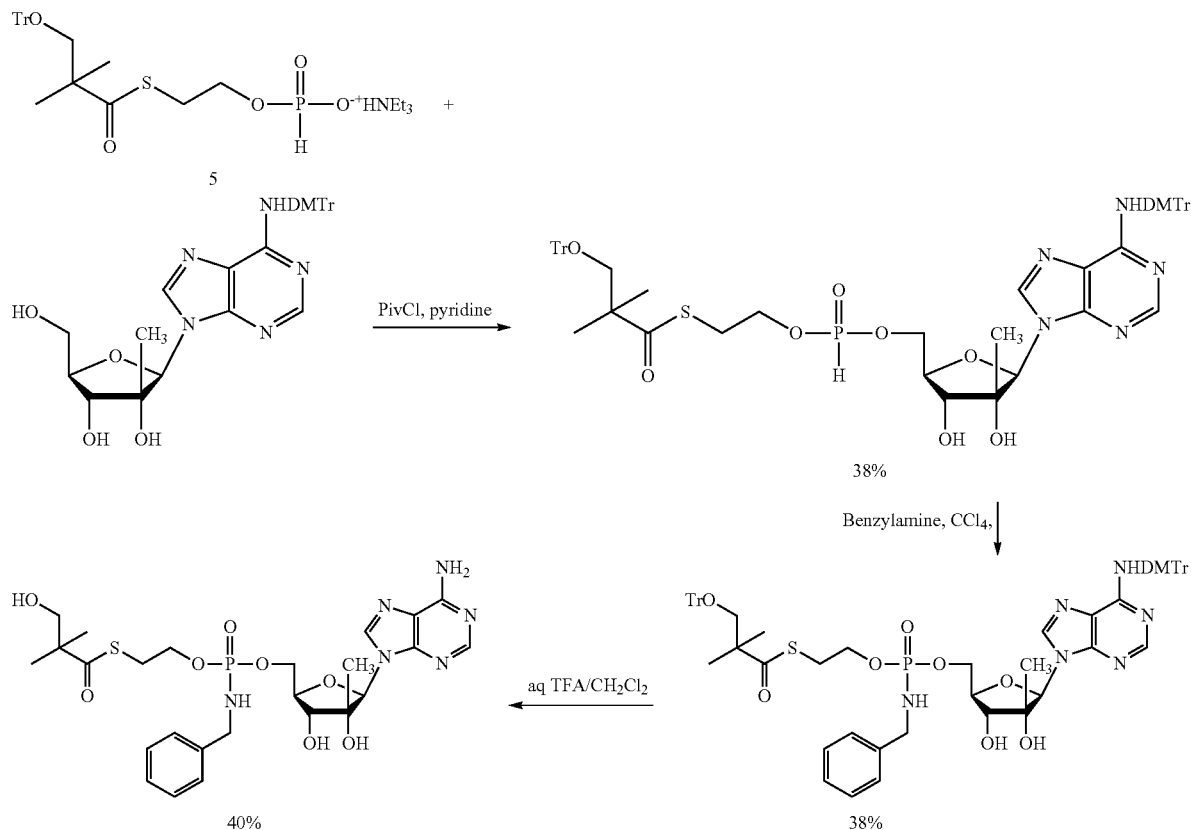

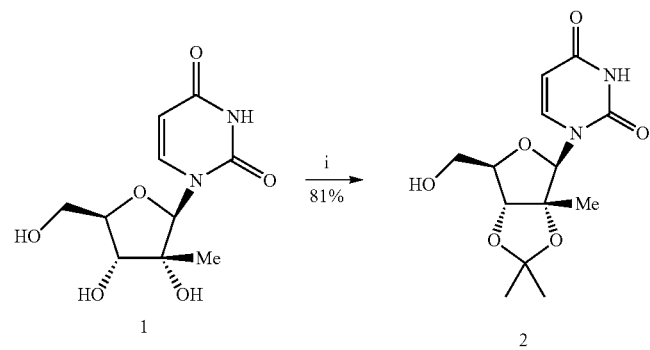
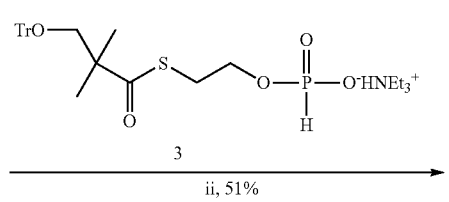
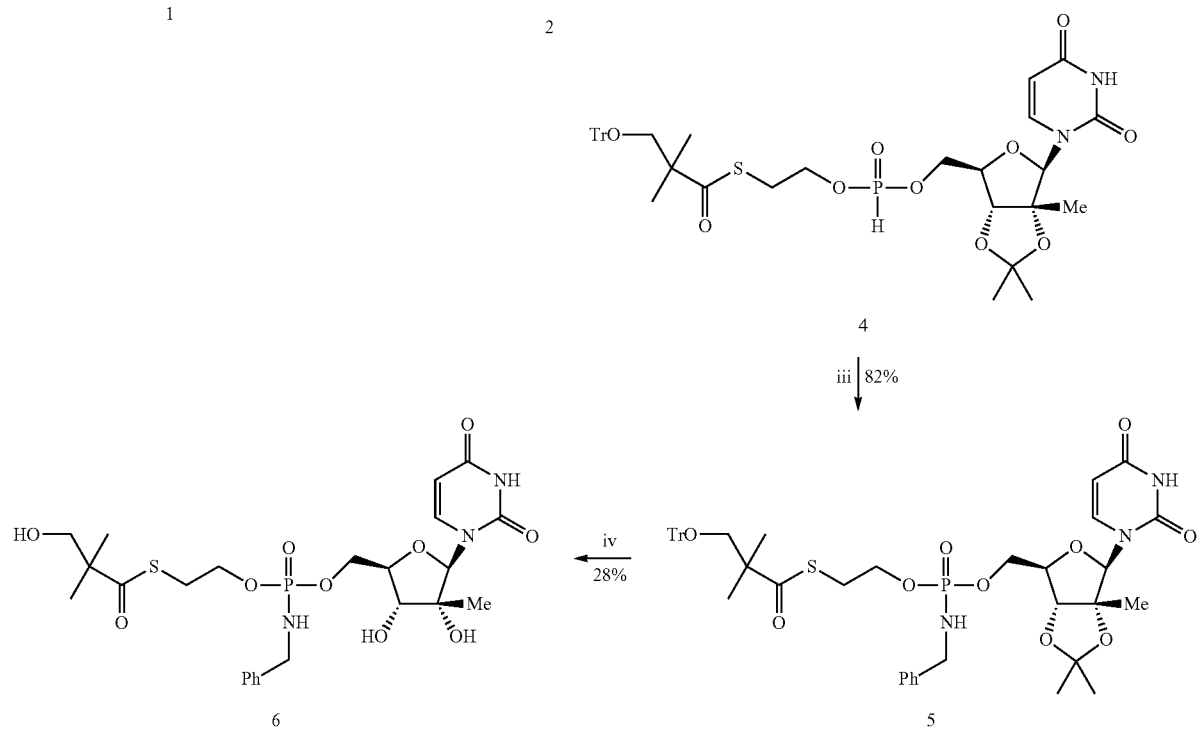

Reagents and Conditions: (i) pTsOH·H₂O, CH(OEt)₃, acetone, r.t.; (ii) PivCl, pyr, r.t; (iii) Benzylamine, CCl₄, rt; (iv) aq. 90% TFA, DCM, r.t.

The pronucleotide 6 (446 mg, 0.76 mmol, overall yield 9% over 4 steps) has been synthesized from its nucleoside parent 1 following a similar procedure described for the synthesis of the pronucleotide prepared in Example 2, Strategy A. B229 6.

$^1$H NMR (400 MHz, DMSO-$d_6$): δ 0.98 (s, 3H, CH$_3$); 1.10 (s, 6H, 2×CH$_3$); 3.03 (m, 2H, CH$_2$S); 3.41 (m, 2H, C$\underline{H}_2$OH, J 5.6 Hz); 3.61 (m, 1H, H-3'); 3.8-4.0 and 4.05-4.25 (stacks, 5H, NC$\underline{H}_2$Ph, H-4', H-5' and H-5"); 4.05-4.25 (2×1H, 2×m, C$\underline{H}_2$OP); 4.91 (t, 1H, 3'-O$\underline{H}$, D$_2$O exchangeable, J=5.62 Hz); 5.20 (br-s, 1H, 2'-O$\underline{H}$, D$_2$O exchangeable); 5.39 (a-t, 1H, CH$_2$O$\underline{H}$, D$_2$O exchangeable, J=7.32 Hz); 5.52 (m, 1H, H-5); 5.65 (m, 1H, PhN$\underline{H}$, D$_2$O exchangeable); 5.8 (br-s, 1H, H-1'); 7.2-7.32 (m, 5H, ArH); 7.55 (a-dd, 1H, H-6); 11.37 (br-s, 1H, NH, D$_2$O exchangeable).

$^{31}$P NMR (161.8 MHz, DMSO-$d_6$): δ 9.73 and 9.98 (ratio of signals by integration of 52:48) m/z (ES+) 588.11 (M+H)$^+$.

HPLC (Method 20): chemical purity 99.2%, 3.48 mins.

CHN analysis:—Found: C, 49.29, H, 5.95; N, 6.88, P, 5.16; C$_{24}$H$_{34}$N$_3$O$_{10}$PS requires C, 49.06, H, 5.83; N, 7.15, P, 5.46.

[α]$_D^{23}$+26.3 (c, 0.571 in H$_2$O).

ν$_{max}$ (KBr): 3373 (br, NH and OH), 1682 (C=O).

Example 8

Preparation of B186, the Hydroxy-tBuSATE N-benzylphosphoramidate Derivative of 2'-C-methylinosine

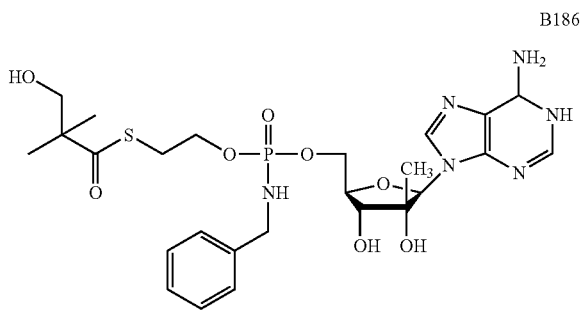

B186

Synthetic Scheme

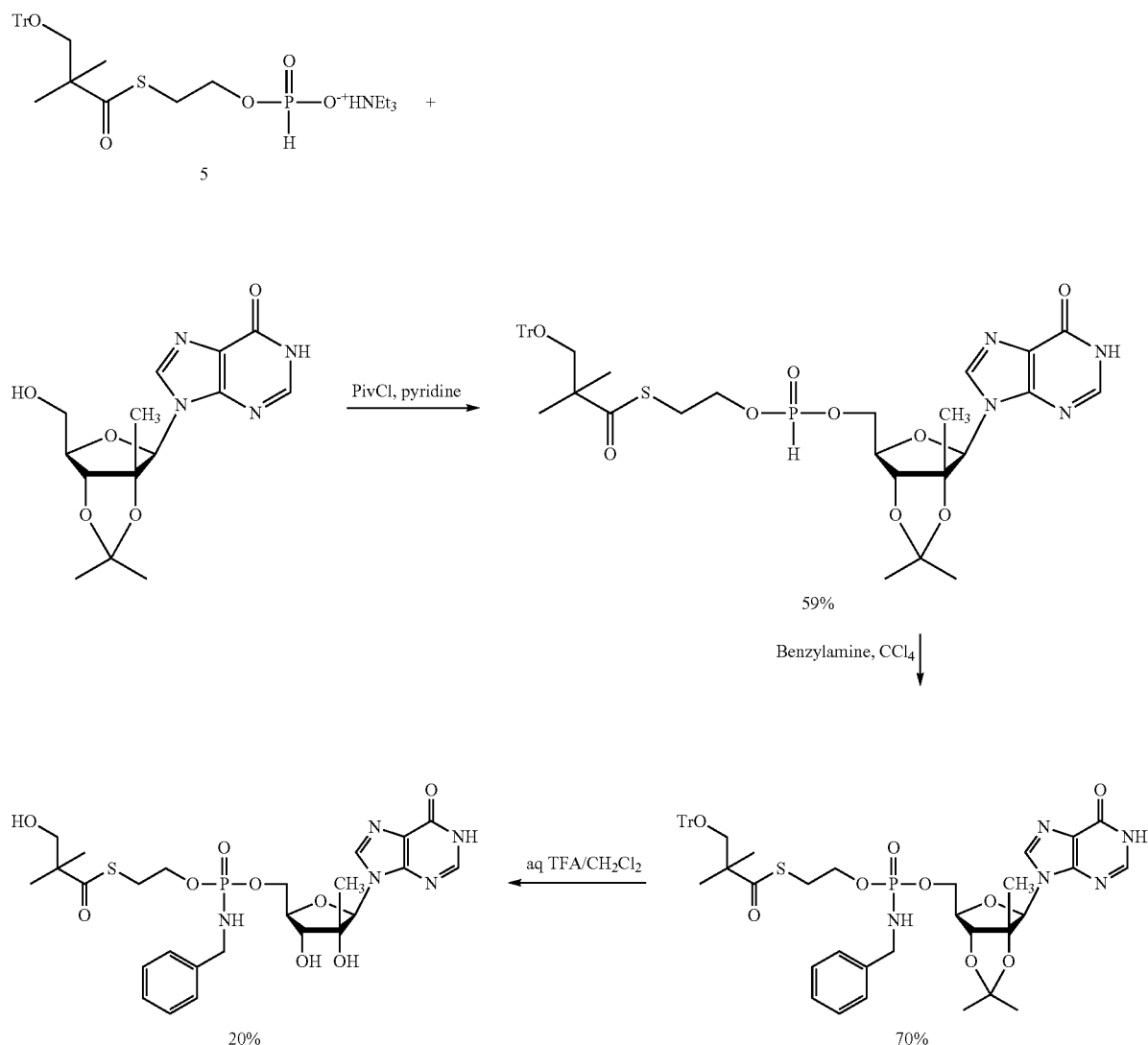

The pronucleotide B186 (314 mg, 8% overall yield) has been synthesized from its parent nucleoside 2',3'-O-isopropylidene-2'-C-methyl-inosine (2.0 g, 6.26 mmol) following a similar procedure than the one described for the synthesis of the pronucleotide prepared in the Example 2 (Procedure A, Strategy a), and isolated as a white lyophilized powder. $^1$H NMR (DMSO-$d_6$, 400 MHz) δ (ppm) 0.79 (s, 3H), 1.09 (s, 6H), 3.01-3.04 (t, J=6.53 Hz, 2H), 3.42 (s, 2H), 3.84-3.91 (m, 2H), 3.94-4.03 (m, 3H), 4.05-4.09 (m, 1H), 4.15-4.26 (m, 2H), 4.92 (s, 1H), 5.36 (s, 1H), 5.43 (t, J=6.54 Hz, 1H), 5.62-5.71 (m, 1H), 5.94 (s, 1H), 7.18-7.22 (m, 1H), 7.25-7.30 (m, 4H), 8.08 (s, 1H), 8.10 (s, 1H), 12.15 (brs, 1H); $^{31}$P NMR (DMSO-$d_6$, 162 MHz) δ (ppm) 9.76-9.90 (2s); Scan ES$^+$ 612 (M+H)$^+$, $\lambda_{max}$=240.7 nm; HPLC (0-100% ACN over a period of 8 min) $t_R$=4.72 min $\lambda_{max}$=243.1 nm.

Example 9

Preparation of B396, the Hydroxy-tBuSATE N-benzylphosphoramidate Derivative of 9-[2-C-methyl-β-ribofuranosyl]-6-chloropurine

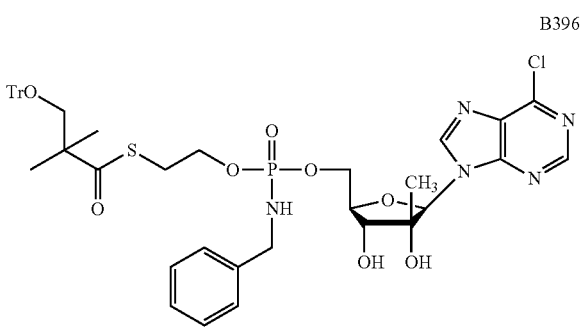

B396

Synthetic Scheme

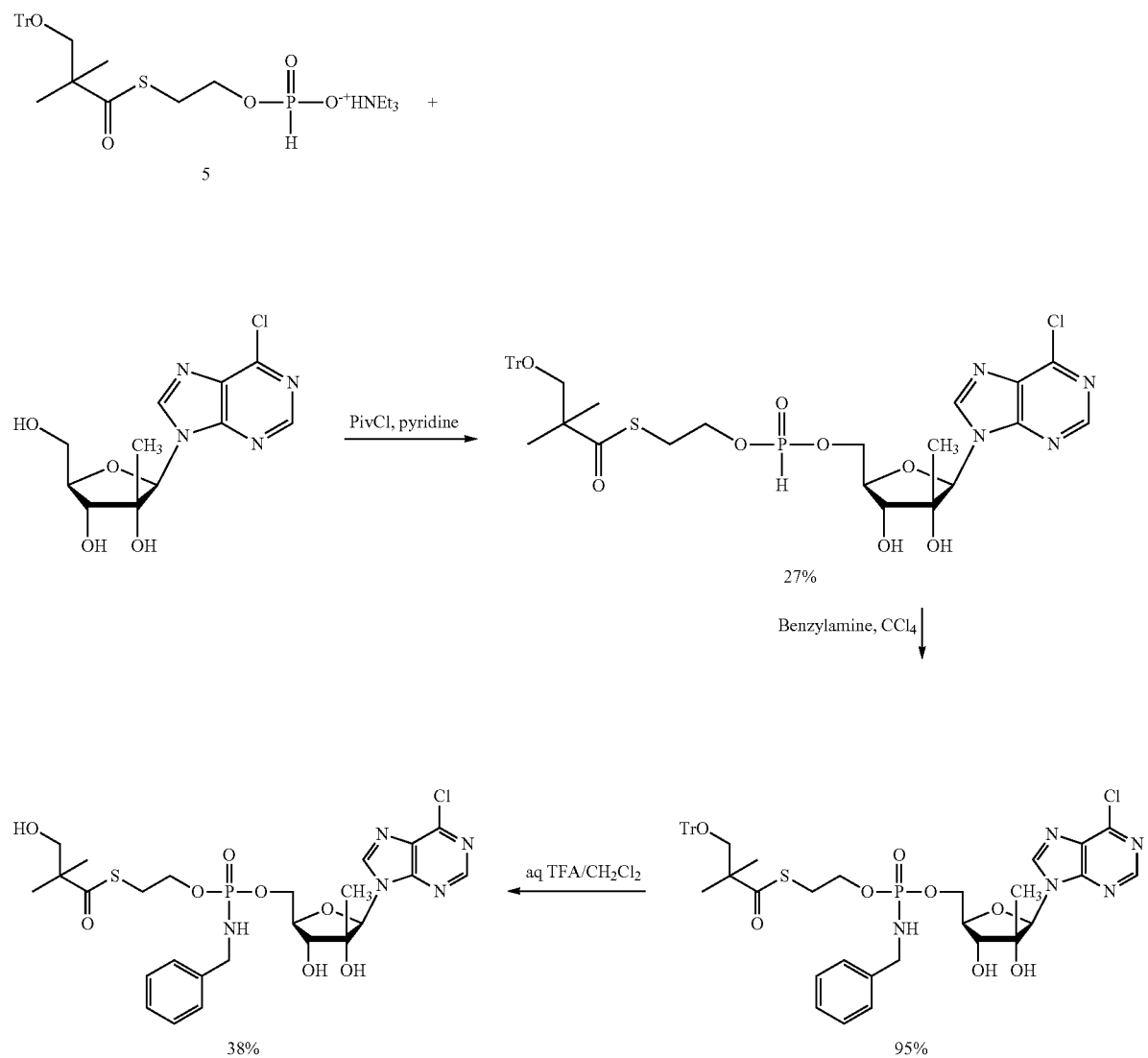

The pronucleotide B396 (75 mg, 10% overall yield) has been synthesized from its parent nucleoside 9-[2-C-methyl-β-ribofuranosyl]-6-chloropurine (571 mg, 1.90 mmol) following a similar procedure than the one described for the synthesis of the pronucleotide prepared in the Example 4 and isolated as a white lyophilized powder. $^1$H NMR (DMSO-$d_6$, 400 MHz) δ (ppm) 0.82 (d, J=2.63 Hz, 3H), 1.07 (s, 6H), 3.02 (m, 2H), 3.40-3.41 (q, J=3.36 Hz and J=1.89 Hz, 2H), 3.85-3.98 (m, 4H), 4.12 (s, 2H), 4.25 (m, 2H), 4.89-4.90 (m, 1H), 5.47 (s, 1H), 5.50 (s, 1H), 5.62-5.70 (m, 1H), 6.10 (d, J=1.23 Hz, 1H), 7.17-7.29 (m, 5H), 8.76 (s, 1H), 8.82 (s, 1H); $^{31}$P NMR (DMSO-$d_6$, 162 MHz) δ (ppm) 9.91 and 9.79 (2s); Scan ES$^+$ 630 (M+H)$^+$, $\lambda_{max}$=260 nm; HPLC (0-100% ACN over a period of 8 min) $t_R$=4.42 min $\lambda_{max}$=265 nm.

Example 10

Preparation of B307, the Hydroxy-tBuSATE N-benzylphosphoramidate Derivative of 2',3'-O-carbonate-2'-C-methylguanosine

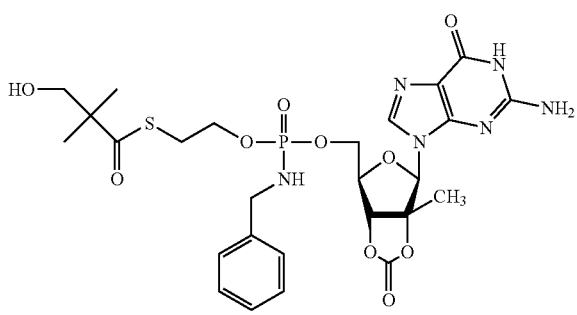

B307

Synthetic Scheme

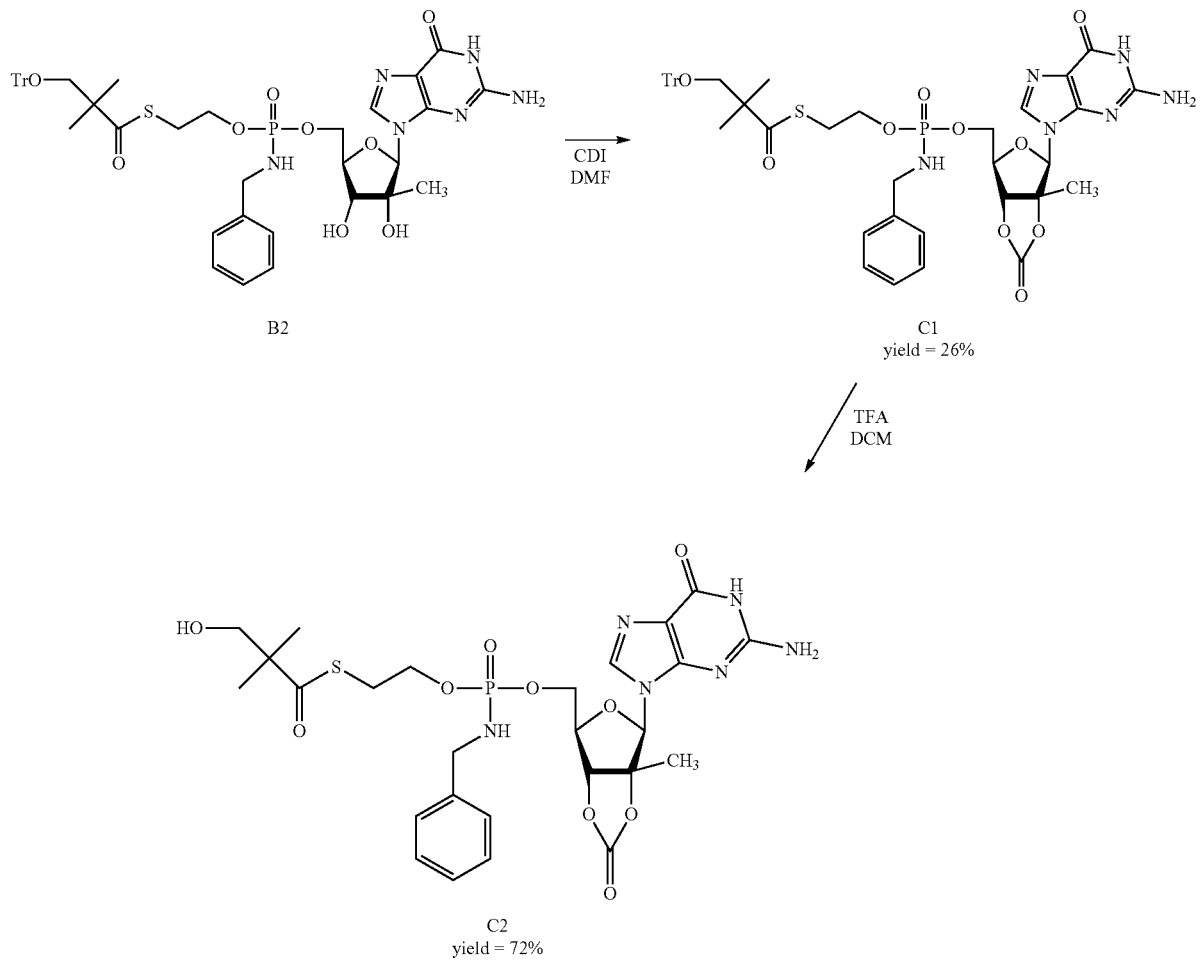

N-Benzylaminyl-2',3'-O-carbonate-2'-C-methylguanosin-5'-yl-O-(triphenylmethyloxy-tert-butyl-5-acyl-2-thioethyl)phosphate (C1)

Compound B2 [See, Compound 7, Example 3, Procedure A] (250 mg, 0.288 mmol) was dissolved in dimethylformamide (3.5 mL) and treated with 1,1-carbonyldiimidazole (186.60 mg, 1.15 mmol). The mixture was stirred at room temperature for 4 h 30 and concentrated under reduced pressure (bath temperature not exceeding 30° C.). The crude residue was subjected to silica gel chromatography, eluting with a gradient 0-10% methanol in dichloromethane, to give C1 as a colorless oil. (68 mg, 26%). Compound C1: $^1$H NMR (400 MHz, DMSO-d$_6$) δ 10.80 (1s, 1H, NH), 7.80 (s, 1H, H-8), 7.33-7.18 (m, 20H, 4C$_6$H$_5$), 6.66 (s1, 2H, NH$_2$), 6.30 (s, 1H, H-1'), 5.78 (m, 1H, PNH), 5.22 (m, 1H, H-3'), 4.47-4.30 (m, 2H, H-4' and H-5' a), 4.20-4.05 (m, 1H, H-5' b), 3.99-3.87 (m, 4H, CH$_2$O and CH$_2$N), 3.10-3.03 (m, 4H, CH$_2$S and CH$_2$OTr), 1.27 (s, 3H, CH$_3$), 1.11 (s, 6H, 2 CH$_3$). $^{31}$P NMR (162 MHz, DMSO-d$_6$) δ 10.42 (s), 10.18 (s). LR LC/MS (M+H$^+$) 895.4 (5.57 min). UV: λ$_{max}$=253 nm.

N-Benzylaminyl-O-(hydroxy-tert-butyl-5-acyl-2-thioethyl)-2',3'-O-carbonate-2'-C-meth-ylguanosin-5'-yl phosphate B307 (Compound C2)

Compound C1 (65 mg, 0.073 mmol) was dissolved in dichloromethane (260 μL) and treated with TFA (26 μL). The mixture was stirred at room temperature for 15 min, then diluted with ethanol, evaporated to dryness (bath temperature not exceeding 30° C.) and coevaporated with toluene. The resulting residue was purified by reverse phase (C18) silica gel column chromatography eluting with a gradient 0-100% acetonitrile in water and lyophilised from a mixture of water/dioxane to give B307 (Compound C2) (34 mg, 72%, white lyophilised powder). B307 (Compound C2): $^1$H NMR (400 MHz, DMSO-d$_6$) δ10.84 (1s, 1H, NH), 7.80 (s, 1H, H-8), 7.32-7.20 (m, 5H, C$_6$H$_5$), 6.69 (1s, 2H, NH$_2$), 6.30 (s, 1H, H-1'), 5.77 (m, 1H, PNH), 5.25 (d, 1H, H-3', J$_{3'-4'}$=20.0 Hz), 4.92 (1s, 1H, OH), 4.50-4.41 (s, 2H, CH$_2$OH), 3.03 (t, 2H, CH$_2$S, J$_{CH2S-CH2O}$=8.0 Hz), 1.30 (s, 3H, CH$_3$), 1.10 (s, 3H, CH$_3$), 1.08 (s, 3H, CH$_3$). $^{13}$C NMR (100 MHz, DMSO-d$_6$): δ 204.4 (C=O), 154.5 (C-4), 153.1 (C-2), 150.7 (C-6), 140.9 (C$_6$H$_5$), 135.6 (C-8), 128.7-127.3 (5C, C$_6$H$_5$), 117.0 (C-5), 89.7 (C-1'), 83.7 and 83.6 (2C, C-2' and C-3'), 81.8 (C-4'), 68.8 (CH$_2$OH), 65.1 (CH$_2$O), 64.5 (C-5'), 52.2 (C(CH$_3$)$_2$ CH$_2$OH), 44.7 (CH$_2$N), 28.7 (CH$_2$S), 22.3 (2C, 2 CH$_3$), 18.3 (CH$_3$). $^{31}$P NMR (162 MHz, DMSO-d$_6$) δ 10.39 (s), 10.15 (s). LR LC/MS (2M+H$^+$) 1305.4 (M+H$^+$) 653.2 (2M−H$^−$) 1303.8 (M−H$^−$) 651.4 (5.57 min). HRFAB-MS C$_{26}$H$_{34}$O$_{10}$N$_6$PS (M+H$^+$) calculated 653.1795. found 653.1819. UV: λ$_{max}$=251 nm. R$_f$ 0.67 (MeOH/CH$_2$Cl, 20/80, v/v).

Example 11

Preparation of B242, the Hydroxy-tBuSATE N-(4-trifluoromethyl)benzylphosphoramidate Derivative of 2'-C-methylguanosine

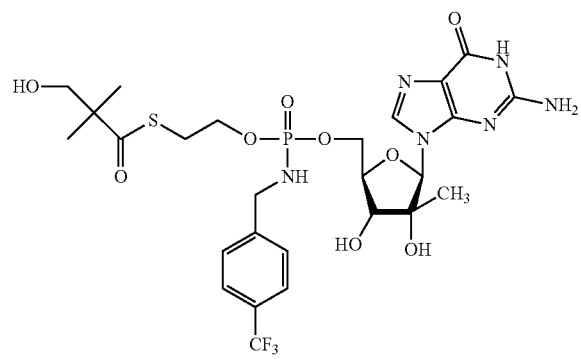

B242

Synthetic Scheme

2'-C-Methylguanosin-5'-yl-N-(4-trifluoromethyl)-benzylaminyl-O-(triphenylmethyloxy-tert-butyl-5-acyl-2-thioethyl)phosphate (D1)

To a solution of compound B1 [See, Compound 7, Example 3, Procedure A] (355 mg, 0.465 mmol) in anhydrous carbon tetrachloride (4.65 mL) 4-trifluoromethylbenzylamine (331 µL, 2.324 mmol) was added. The reaction mixture was stirred at room temperature for 1 h 30 and concentrated under reduced pressure (bath temperature not exceeding 30° C.). The resulting residue was subjected to silica gel chromatography, eluting with a gradient 0-10% methanol in dichloromethane, to give D1 as a white solid. (420 mg, 96%). Compound D1: $^1$H NMR (400 MHz, DMSO-$d_6$) δ 7.77-7.20 (m, 20H, 3 $C_6H_5$, $C_6H_4CF_3$ and H-8), 6.57 (1s, 2H, $NH_2$), 5.84-5.75 (m, 2H, H-1' and PNH), 5.50 (m, 1H, OH-3'), 4.26-3.86 (m, 8H, H-3', H-4', H-5', $CH_2O$ and $CH_2N$), 3.10 (t, 2H, $CH_2S$, $J_{CH2S—CH2O}$=4.0 Hz), 3.03 (m, 2H, $CH_2OTr$), 1.11 (s, 6H, 2 $CH_3$), 0.82 (s, 3H, $CH_3$). $^{13}$C NMR (100 MHz, DMSO-$d_6$): δ 204.0 (C=O), 157.2 (C-4), 154.2 (C-2), 151.3 (C-6), 145.8-143.9 (4C, 3 $C_6H_5$ and $C_6H_4CF_3$), 135.6 (C-8), 129.0-120.0 (20C, 3 $C_6H_5$ and $C_6H_4CF_3$), 117.0 (C-5), 91.0 (C-1'), 86.1 (C($C_6H_5$)), 80.7 (C-3'), 78.7 (C-2'), 73.3 (C-4'), 70.0 ($CH_2OTr$), 65.9 ($CH_2O$), 64.4 (C-5'), 50.8 (C($CH_3$)$_2CH_2OTr$), 44.2 ($CH_2N$), 28.8 ($CH_2S$), 22.7 (2C, 2 $CH_3$), 20.4 ($CH_3$). $^{31}$P NMR (162 MHz, DMSO-$d_6$): δ9.80 (s), 9.64 (s). $^{19}$F NMR (376 MHz, DMSO-

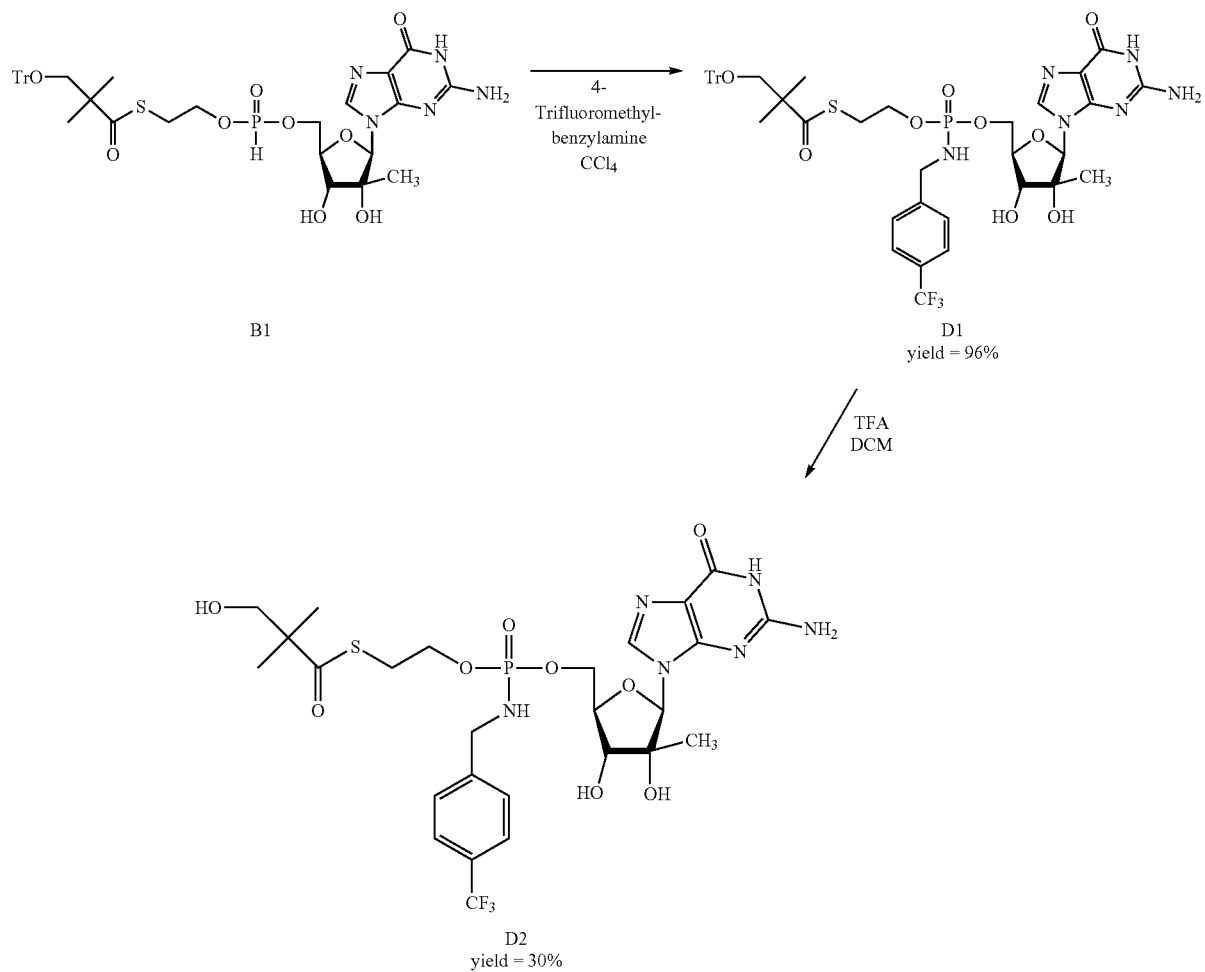

$d_6$): δ −60.8 (s). LR LC/MS (M+H$^+$) 937.3 (M−H$^-$) 935.4 (5.47 min). UV: $\lambda_{max}$=254 nm. $R_f$ 0.61 (MeOH/CH$_2$Cl, 15/85, v/v).

O-(Hydroxy-tert-butyl-5-acyl-2-thioethyl)-2'-C-methylguanosin-5'-yl-N-(4-trifluoromethyl)-benzylaminyl phosphate B242 (Compound D2)

Compound D1 (400 mg, 0.427 mmol) was dissolved in dichloromethane (1.6 mL) and treated with TFA (160 µL). The mixture was stirred at room temperature for 15 min, then diluted with ethanol, evaporated to dryness (bath temperature not exceeding 30° C.) and coevaporated with toluene. The resulting residue was subjected to silica gel chromatography, eluting with a gradient 0-15% methanol in dichloromethane and then purified by reverse phase (C18) silica gel column chromatography eluting with a gradient 0-100% acetonitrile in water and lyophilised from a mixture of water/dioxan to give compound B2742 (Compound D2) (90 mg, 30%, white lyophilised powder). B242 (Compound D2): $^1$H NMR (400 MHz, DMSO-$d_6$) δ 10.54 (1s, 1H, NH), 7.75 (s, 1H, H-8), 7.75-7.52 (m, 4H, C$_6$H$_4$CF$_3$), 6.50 (s1, 2H, NH$_2$), 5.82-5.74 (m, 2H, H-1' and PNH), 5.40 (m, 1H, OH-3'), 5.17 (s, 1H, OH-2'), 4.92 (t, 1H, OH, J$_{OH-CH2}$=4.0 Hz), 4.26-3.84 (m, 8H, H-3', H-4', H-5', CH$_2$O and CH$_2$N), 3.41 (d, 2H, CH$_2$OH, J$_{CH2-OH}$=4.0 Hz), 3.03 (t, 2H, CH$_2$S, J$_{CH2S-CH2O}$=8.0 Hz), 1.07 (s, 6H, 2 CH$_3$), 0.82 (s, 3H, CH$_3$). $^{13}$C NMR (100 MHz, DMSO-$d_6$): δ 204.4 (C=O), 157.2 (C-4), 154.1 (C-2), 151.2 (C-6), 145.9 (C$_6$H$_4$CF$_3$), 135.8 (C-8), 128.3-125.4 (6C, C$_6$H$_4$CF$_3$), 117.0 (C-5), 90.9 (C-1'), 80.5 (C-3'), 78.7 (C-2'), 73.2 (C-4'), 68.8 (CH$_2$OH), 66.0 (CH$_2$O), 64.4 (C-5'), 52.2 (C(CH$_3$)$_2$CH$_2$OH), 44.3 (CH$_2$N), 28.7 (CH$_2$S), 22.3 (2C, 2 CH$_3$), 20.4 (CH$_3$). $^{31}$P NMR (162 MHz, DMSO-$d_6$): δ 9.62 (s), 9.77 (s). $^{19}$F NMR (376 MHz, DMSO-$d_6$): δ−60.8 (s). LR LC/MS (M+H$^+$) 695.2 (M−H$^-$) 693.4 (4.25 min). HRFAB-MS C$_{26}$H$_{35}$O$_9$N$_6$F$_3$PS (M+H$^+$) calculated 695.1876. found 695.1874. UV: $\lambda_{max}$=253 nm. $R_f$ 0.43 (MeOH/CH$_2$Cl, 20/80, v/v).

Example 12

Preparation of B503, the Hydroxy-tBuSATE N-benzylphosphoramidate Derivative of 9-[(2R)-2-deoxy-2-fluoro-2-C-ethynyl-β-D-erythro-furanosyl]-guanine

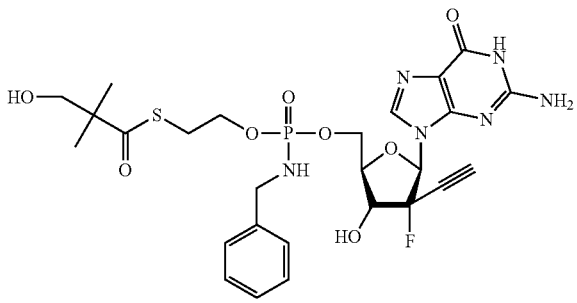

B503

Synthetic Scheme

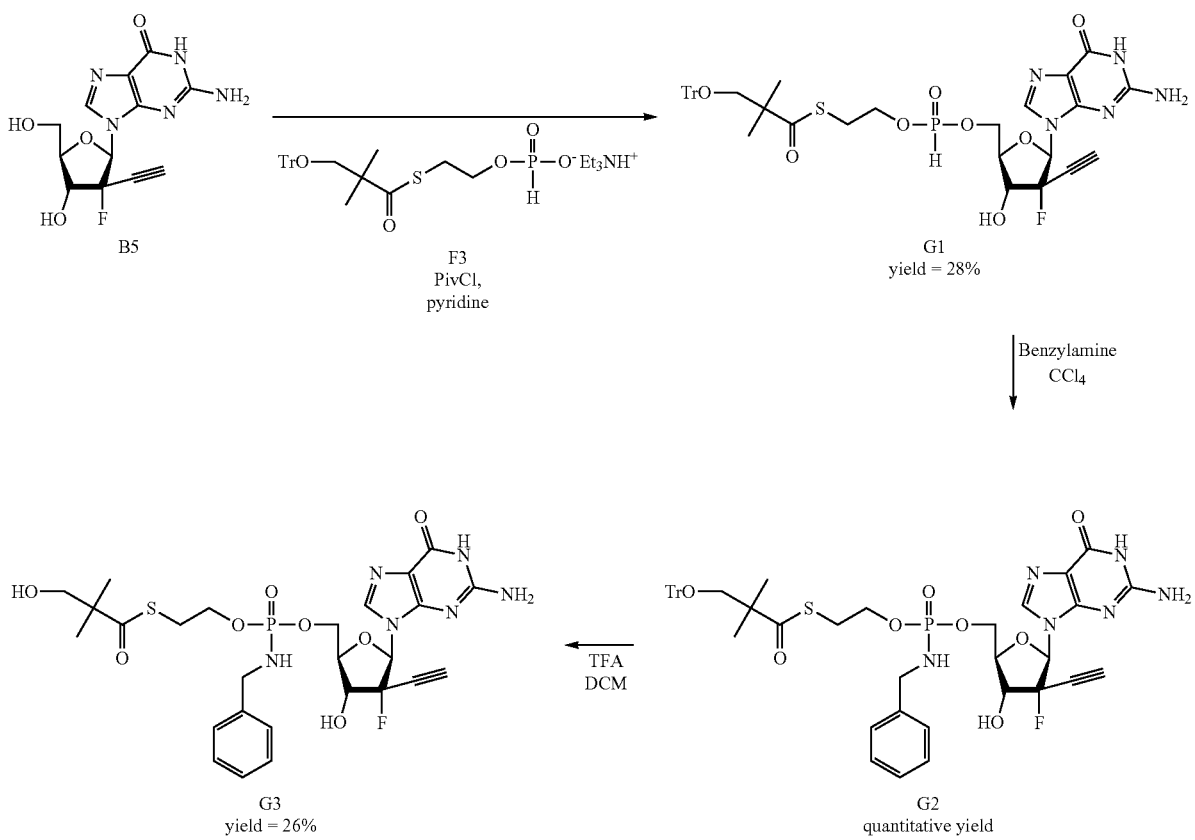

{9-[(2R)-2-Deoxy-2-fluoro-2-C-ethynyl-β-D-erythro-furanosyl]-guanin}-5'-yl-O-(triphenylmethyloxy-tert-butyl-5-acyl-2-thioethyl) H-phosphonate (G1)

Compound B5 [Unpublished results] (100 mg, 0.32 mmol) and compound F3 [See Compound 5 of Example 2] (246 mg, 0.42 mmol) were coevaporated together with anhydrous pyridine and dissolved in this solvent (4.8 mL). Pivaloyl chloride (80 µL, 0.64 mmol) was added dropwise at −15° C. and the solution was stirred at the same temperature for 2 h. The reaction mixture was diluted with dichloromethane and neutralised with an aqueous solution of $NH_4Cl$ 0.5M. The mixture was partitioned between dichloromethane and aqueous $NH_4Cl$ 0.5M, the organic phases were combined, dried over $Na_2SO_4$ evaporated under reduced pressure (bath temperature not exceeding 30° C.) and coevaporated twice with toluene. The crude mixture was purified by flash column chromatography eluting with a gradient 0-10% methanol in dichloromethane+0.2% acetic acid) to afford the desired product G1 as a colorless oil (68 mg, 28%). Compound G1: $^1$H NMR (400 MHz, DMSO-$d_6$): δ 10.72 (1s, 1H, NH), 7.83 (s, 1H, H-8), 7.35-7.11 (m 15H, 3 $C_6H_5$), 6.59 (m, 2H, $NH_2$), 6.36 (d, 1H, OH-3', $J_{OH-3'}$=7.6 Hz), 6.14 (d, 1H, H-1', $J_{1'-F}$=18.0 Hz), 4.65 (m, 1H, H-3'), 4.40-4.33 (m, 2H, H-5'), 4.10-4.01 (m, 3H, H-4' and $CH_2O$), 3.93 (d, 1H, CCH, $^4J_{H-F}$=5.6 Hz), 3.15-3.12 (m, 2H, $CH_2S$), 3.04 (s, 2H, $CH_2OTr$). $^{31}$P NMR (162 MHz, DMSO-$d_6$): δ 9.50 (s), 9.22 (s). $^{19}$F NMR (376 MHz, DMSO-$d_6$): δ −156.5 (m). LR LC/MS (B) (M+Na$^+$) 798.2 (M−H$^-$) 774.2 (4.93 min). UV: $\lambda_{max}$=254 nm. $R_f$ 0.48 (MeOH/$CH_2Cl$, 15/85, v/v).

N-Benzylaminyl-{9-[(2R)-2-deoxy-2-fluoro-2-C-ethynyl-β-D-erythro-furanosyl]-guanin}-5'-yl-O-(triphenylmethyloxy-tert-butyl-5-acyl-2-thioethyl) phosphate (G2)

To a solution of compound G1 (68 mg, 0.088 mmol) in anhydrous carbon tetrachloride (880 µL), benzylamine (48 µL, 0.44 mmol) was added dropwise. The reaction mixture was stirred at room temperature for 2 h and evaporated to dryness (bath temperature not exceeding 30° C.). The crude mixture was filtered on a silica gel plug, eluting with a gradient 0-10% methanol in dichloromethane to give compound G2 as a white solid (80 mg, quantitative yield). Compound G2: $^{31}$P NMR (162 MHz, DMSO-$d_6$): δ 9.95 (s) 9.80 (s). $^{19}$F NMR (376 MHz, DMSO-$d_6$): δ −157.5 (m). LR LC/MS (B) (M+H$^+$) 881.3 (M−H$^-$) 879.4 (5.18 min). UV: $\lambda_{max}$=254 nm. $R_f$ 0.31 (MeOH/$CH_2Cl$, 15/85, v/v).

N-Benzylaminyl-{9-[(2R)-2-deoxy-2-fluoro-2-C-ethynyl-β-D-erythro-furanosyl]-guanin}-5'-yl-O-(hydroxy-tert-butyl-5-acyl-2-thioethyl)phosphate B503 (Compound G3)

Compound G2 (80 mg, 0.09 mmol) was dissolved in dichloromethane (320 µL) and treated with TFA (32 µL). The mixture was stirred at room temperature for 10 min, filtered through a solid phase extraction column eluting with a gradient 0-30% methanol in dichloromethane, then purified by reverse phase (C18) silica gel column chromatography eluting with a gradient 0-100% acetonitrile in water and lyophilised from a mixture of water/dioxan to give compound B503 (Compound G3) (15 mg, 26%, white lyophilised powder). B503 (Compound G3): $^1$H NMR (400 MHz, DMSO-$d_6$): δ 10.61 (1s, 1H, NH), 7.83 (s, 1H, H-8), 7.30-7.18 (m, 5H, $C_6H_5$), 6.60 (1s, 2H, $NH_2$), 6.32 (m, 1H, OH-3'), 6.11 and 6.12 (2 d, 2×1H, 2H-1', $J_{1'-F}$=18.0 Hz), 5.68 (m, 1H, PNH), 4.93 (t, 1H, OH, $J_{OH-CH2}$=5.5 Hz), 4.61 (m, 1H, H-3'), 4.26-4.18 (m, 2H, H-5'), 4.08 (m, 1H, H-4'), 3.98-3.82 (m, 5H, $CH_2O$, $CH_2N$ and CCH), 3.42 (d, 2H, $CH_2OH$, $J_{CH2-OH}$=5.0 Hz), 3.01 (m, 2H, $CH_2S$), 1.09 (s, 6H, 2 $CH_3$). $^{31}$P NMR (162 MHz, DMSO-$d_6$): δ 9.92 (s), 9.79 (s). $^{19}$F NMR (376 MHz, DMSO-$d_6$): δ −156.8 (m). LR LC/MS (B) (M+H$^+$) 639.2 (M−H$^-$) 637.3 (3.85 min). HRFAB-MS $C_{26}H_{33}O_8N_6FPS$ (M+H$^+$) calculated 639.1802. found 639.1816. UV: $\lambda_{max}$=253 nm. $R_f$ 0.46 (MeOH/$CH_2Cl$, 20/80, v/v).

The starting nucleoside was synthesized as follows:

Synthesis of 9-[(2R)-2-deoxy-2-C-ethynyl-2-fluoro-β-D-erythro-furanosyl]-guanine (D961, Starting Nucleoside of EXAMPLE 12), and Synthesis of its Triphosphate Derivative B427)

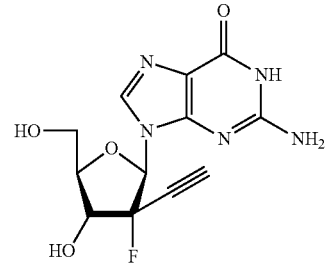

D961

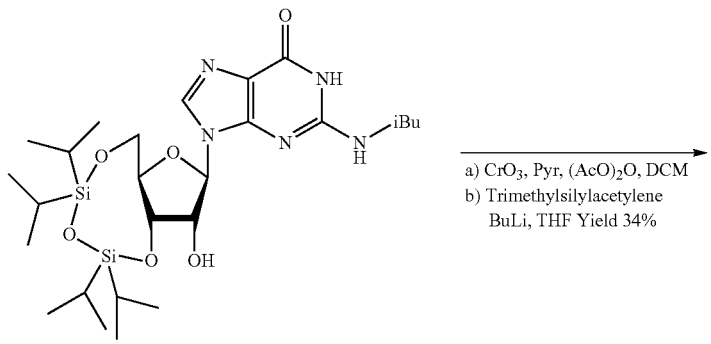

a) $CrO_3$, Pyr, $(AcO)_2O$, DCM
b) Trimethylsilylacetylene
BuLi, THF Yield 34%

Synthetic Scheme

B1

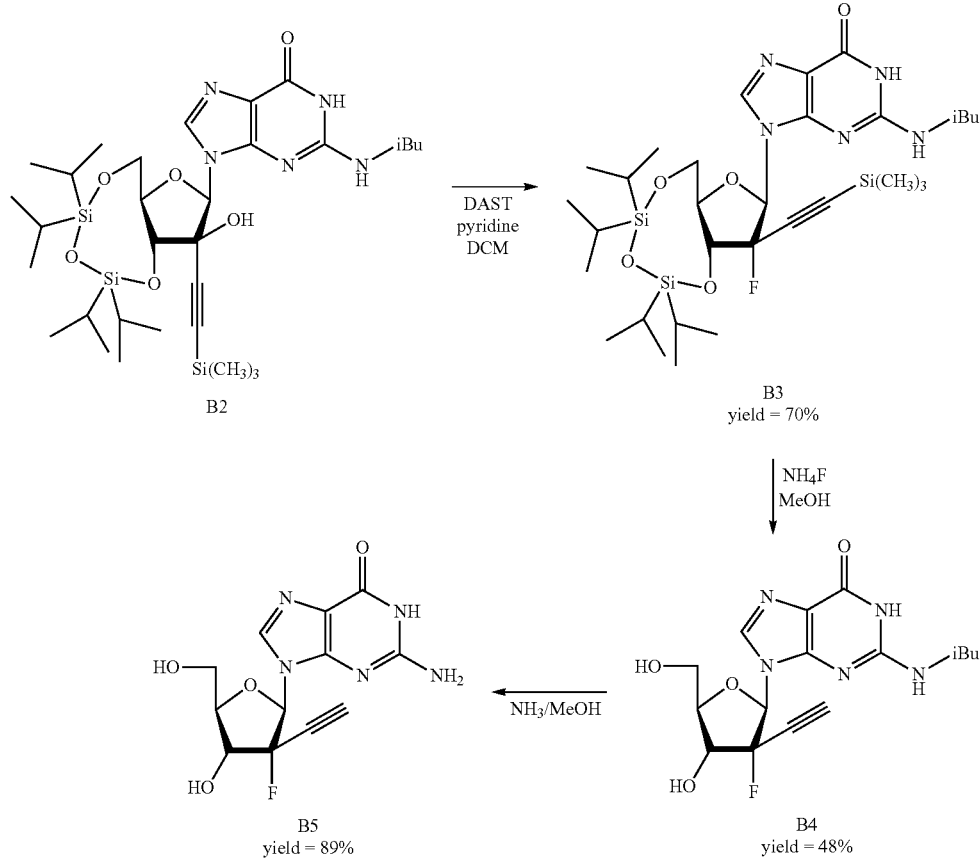

B2

B3
yield = 70%

B5
yield = 89%

B4
yield = 48%

9-[3,5-O-(1,3-Diyl-1,1,3,3-tetraisopropyldisiloxane)-ribo-furanosyl]-N²-isobutyryl-guanine (1)

Hirao, I.; Ishikawa, M.; Miura, K. *Chem. Lett.* 1986, 11, 1929-1932.

9-[3,5-O-(1,3-diyl-1,1,3,3-tetraisopropyldisiloxane)-2-C-trimethylsilylethynyl-β-D-arabino-furanosyl]-N²-isobutyryl-guanine (B2): To a suspension of $CrO_3$ (11.07 g, 110.76 mmol) in dichloromethane (220 mL) at 0° C., acetic anhydride (10.4 mL, 110.76 mmol) and anhydrous pyridine (17.82 mL, 221.52 mmol) were added. Compound B1 (22 g, 36.92 mmol) in solution in dichloromethane (110 mL) was added dropwise. The cooling bath was removed and the resulting solution stirred at room temperature for 5 h. The reaction mixture was poured into cold ethyl acetate, filtered through a silica and celite gel plug, concentrated to dryness and coevaporated twice with toluene. The residue obtained was dissolved in dichloromethane and stirred with an excess of $MgSO_4$ overnight, filtered and evaporated to get the ketone. The trimethylsilylacetylene (12.5 mL, 88.60 mmol) was dissolved in anhydrous THF (98 mL) under argon. Butyllithium (55.4 mL, 1.6 M in hexanes) was added dropwise at −78° C. The reaction mixture was stirred for 30 min at −78° C. and then allowed to warm up to −55° C. The ketone in solution in THF (49 mL) was added dropwise at −78° C. The reaction mixture was stirred for 1 h at −78° C. and then allowed to warm up to −30° C. and stirred for 3 h. The reaction was quenched by careful addition of aqueous saturated $NH_4Cl$ (72 mL) at −78° C. After warming to room temperature, the mixture was diluted with ethyl acetate, washed twice with saturated brine, dried ($Na_2SO_4$) and concentrated to dryness. The crude material was purified using column chromatography eluting with 1.5% MeOH in dichloromethane to give compound B2 (8.59 g, 34%, 2 steps) as a pale yellow foam.

Compound B2: NMR $^1$H (250 MHz, DMSO-$d_6$): δ 12.10 (1s, 1H, NH), 11.69 (1s, 1H, NH), 7.91 (s, 1H, H-8), 6.69 (s, 1H, OH), 5.94 (s, 1H, H-1'), 4.29 (d, 1H, H-3', $J_{3'-4'}$=5.5 Hz), 3.85-3.95 (m, 3H, H-4', H-5' and H-5"), 2.46 (m, 1H, $CH(CH_3)_2$), 0.90-1.08 (m, 30H, iPr and $CH(CH_3)_3$), 0.00 (s, 9H, $Si(CH_3)_3$). LC/MS (A): (M+H⁺) 692.4 (24.96 min). UV: $\lambda_{max1}$=254 nm, $\lambda_{max2}$=281 nm. $R_f$ 0.34 (MeOH/$CH_2Cl$, 15/85, v/v).

9-[(2R)-2-Deoxy-2-fluoro-3,5-O(1,3-diyl-1,1,3,3-tetraisopropyldisiloxane)-2-C-trimethyl-silylethynyl-β-D-erythro-furanosyl]-N²-isobutyryl-guanine (B3)

Compound B2 (2.00 g, 2.89 mmol) was dissolved in dried DCM (60 mL) under argon and pyridine (1.45 mL, 18.06 mmol) was added. The reaction mixture was cooled to −20° C. and DAST (4.11 mL, 31.35 mmol) was added dropwise. The cooling bath was removed after completion of the addition. Stirring was continued for 1 h 15 and the mixture was dissolved with ethyl acetate and poured into saturated $NaHCO_3$ and stirred for 5 min. The organic layer was washed with saturated brine, dried ($Na_2SO_4$), concentrated, and purified by silica gel chromatography eluting with ethyl acetate in DCM (2%) to give the desired compound B3 (1.41 g, 70%) as a yellow oil. Compound B3: NMR $^1$H (250 MHz, DMSO-$d_6$) δ 12.22 (s, 1H, NH), 8.09 (s, 1H, H-8), 6.21 (d, 1H, H-1', $J_{1'-F}$=15.6 Hz), 4.54 (dd, 1H, H-3', $J_{3'-F}$=23.6 Hz, $J_{3'-4'}$=9.8 Hz), 4.33 (m, 1H, H-5', $^2J_{5'-5''}$=13.1 Hz), 4.16 (m, 1H, H-5"), 2.81 (m, 1H, $CH(CH_3)_2$), 1.13-1.03 (m, 34H, iPr and $CH(CH_3)_2$), 0.08 (s, 9H, $Si(CH_3)_3$, $^3J_{H-H}$=6.9 Hz). NMR $^{19}$F (235 MHz, DMSO-$d_6$) δ −160.26 (dd, $J_{F-1'}$=16.1 Hz, $J_{F\text{-}3'}$=23.3 Hz). LC/MS (A): (M+H$^+$) 694.7 (24.02 min). LRFAB-MS (GT): 694 (M+H)$^+$, 692 (M–H)$^-$. UV: $\lambda_{max}$=256 nm. R$_f$ 0.46 (MeOH/CH$_2$Cl, 05/95, v/v).

9-[(2R)-2-Deoxy-2-C-ethynyl-2-fluoro-β-D-erythro-furanosyl]-N$^2$-isobutyryl-guanine (B4)

Compound B3 (1.31 g, 1.89 mmol) was dissolved in methanol (13.8 mL) and ammonium fluoride (908.9 mg, 24.54 mmol) was added. The resulting solution was stirred at reflux for 1 h and evaporated to dryness. The crude material was purified on silica gel chromatography eluting with a stepwise gradient 6-10% of methanol in dichloromethane to yield compound B4 (344 mg, 48%) as a pale yellow oil. Compound B4: NMR $^1$H (400 MHz, DMSO-d$_6$) δ 12.18 (1s, 1H, NH), 11.77 (1s, 1H, NH), 8.34 (s, 1H, H-8), 6.29 (d, 1H, OH-3', $J_{OH\text{-}3'}$=7.5 Hz), 6.20 (d, 1H, H-1', $J_{1'\text{-}F}$=16.2 Hz), 5.39 (t, 1H, OH-5', $J_{OH\text{-}5'}$=5.1 Hz), 4.52 (dt, 1H, H-3', $J_{3'\text{-}F}$=22.9 Hz), 3.98 (m, 1H, H-4'), 3.90-3.85 (m, 2H, H-5' and ethynyl), 3.72 (m, 1H, H-5"), 2.52 (m, 1H, CH(CH$_3$)$_2$), 1.14 (d, 6H, CH(CH$_3$)$_2$, $^3J_{H\text{-}H}$=6.9 Hz). NMR $^{13}$C (100 MHz, DMSO-d$_6$): δ 180.7 (C-6), 155.3 (C-2), 148.9 (C-4), 137.3 (C-8), 120.4 (C-5), 95.8 (d, C-2', $^1J_{2'\text{-}F}$=182.1 Hz), 87.7 (d, C-1', $^2J_{1'\text{-}F}$=39.2 Hz), 83.4 (d, CCH, $^3J_{C\text{-}F}$=9.1 Hz), 82.6 (C-4'), 75.9 (d, CCH, $^2J_{C\text{-}F}$=31.2 Hz), 72.9 (d, C-3', $^2J_{3'\text{-}F}$=19.1 Hz), 59.3 (C-5'). NMR $^{19}$F 2.35 MHz, DMSO$_6$) δ –158.9 (m). LC/MS (A): (M+H$^+$) 380.3 (8.34 min). UV: $\lambda_{max1}$=260 nm, $\lambda_{max2}$=277 nm. R$_f$ 0.40 (MeOH/CH$_2$Cl, 15/85, v/v).

9-[(2R)-2-Deoxy-2-C-ethynyl-2-fluoro-β-D-erythro-furanosyl]-guanine D961 (Compound B5)

Compound B4 (0.78 g, 1.33 mmol) was dissolved in saturated methanolic ammonia (62 mL) and stirred at room temperature for 20 h. The reaction mixture was then evaporated to dryness under reduced pressure. The residue was dissolved in water and washed twice with ethyl acetate. The aqueous layer was evaporated and purified on reverse phase column chromatography (C18) eluting with a gradient 2-15% of acetonitrile in water. The residue obtained was then dissolved in hot ethyl acetate, filtered and dried to give D961 (Compound B5) (134 mg, 33%) as a yellow solid. NMR $^1$H (400 MHz, DMSO-d$_6$): δ 10.70 (1s, 1H, NH), 7.98 (s, 1H, H-8), 6.60 (1s, 2H, NH$_2$), 6.21 (d, 1H, OH-3', $J_{OH\text{-}3'}$=7.6 Hz), 5.83 (d, 1H, H-1', $J_{1'\text{-}F}$=16.9 Hz), 5.29 (t, 1H, OH-5', $J_{OH\text{-}5'}$=5.2 Hz), 4.50 (td, 1H, H-3', $J_{3'\text{-}F}$=22.8 Hz, $J_{3'\text{-}4'}$=9.2 Hz), 3.93-3.81 (m, 3H, H-4', H-5' and ethynyl), 3.70 (m, 1H, H-5").

NMR $^{13}$C (100 MHz, DMSO-d$_6$): δ 157.2 (C-6), 154.3 (C-2), 151.05 (C-4), 135.1 (C-8), 116.7 (C-5), 96.4 (d, C-2', $^1J_{C\text{-}F}$=182.1 Hz), 87.4 (d, C-1', $^2J_{C\text{-}F}$=39.2 Hz), 83.1 (d, CCH, $J_{C\text{-}F}$=9.1 Hz), 82.4 (C-4'), 76.2 (d, CCH, $^2J_{C\text{-}F}$=31.2 Hz), 73.2 (d, C-3', $^2J_{C\text{-}F}$=20.1 Hz), 59.5 (C-5'). NMR $^{19}$F (235 MHz, DMSO$_6$: δ –158.5 (m). LC/MS (A): (M+H$^+$) 310.1 (5.55 min). LRFAB-MS (GT): 619 (2M+H)$^+$, 310 (M+H)$^+$, 152 (B+H)$^+$, 617 (2M–H)$^-$, 308 (M–H)$^-$. UV: $\lambda_{max}$=254 nm.

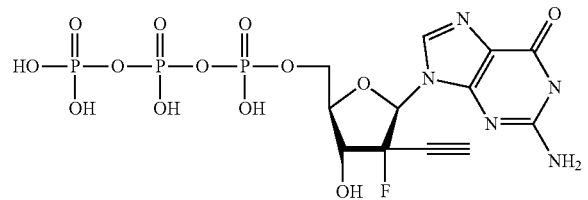

B427

Synthetic Scheme

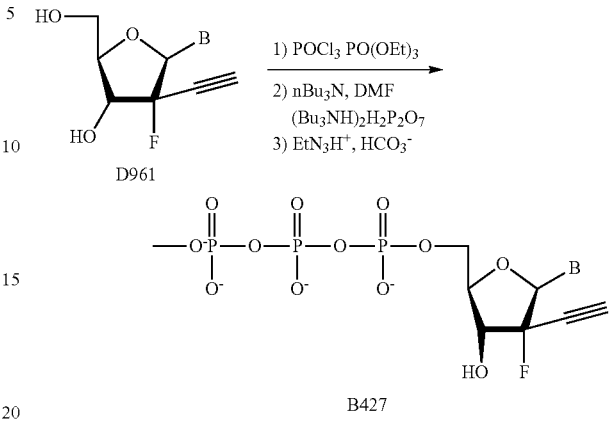

Standard Procedure for Preparation of nucleoside 5'-triphosphate (Ludwig, J. *Acta Biochim. Biophys. Acad. Sci. Hung.* 1981, 16, 131-133.)

To a solution of nucleoside (0.286 mmol) in triethylphosphate (750 μL), phosphoryle chloride (75 μL, 0.807 mmol) was added at 0° C. This reaction mixture A was stirred overnight at 5° C. Tributylammonium pyrophosphate (PPi/Bu$_3$N 1/1.5, 1 g, 2.19 mmol) was dissolved in anhydrous DMF (2 mL). Tributylamine (420 μL, 1.76 mmol) was added to the PPi and the resulting mixture was stirred for 15 min at 0° C. 2.4 mL of this solution were added to the reaction mixture A. The reaction mixture was stirred at 0° C. for 1 min. The reaction was carefully quenched with TEAB 1M (pH=7.5, 10 mL), stirred 20 min at 0° C., then diluted with water and ethyl acetate. The aqueous phase was concentrated under reduced pressure. The crude material was subjected to DEAE-Sephadex chromatography eluting with a gradient 10$^{-3}$-1 M of TEAB). The desired fractions were combined, concentrated under reduced pressure and coevaporated with a mixture of water/methanol, and finally coevaporated with water. The resulting residue was purified on semipreparative HPLC. Fractions containing the expected product were concentrated under reduced pressure, coevaporated with a mixture of water/methanol and lyophilised from water. The triethylammonium salt triphosphate was eluted three times with water on a Dowex Na$^+$ resin column to yield after lyophilisation from water to the sodium salt.

9-[(2R)-2-deoxy-2-C-ethynyl-2-fluoro-β-D-erythro-furanosyl]-guanine 5'-triphosphate sodium salt (B427)

$^1$H NMR (400 MHz, D$_2$): δ 7.97 (s, 1H, H-8), 6.19 (d, 1H, H-1', $^3J_{1'\text{-}F}$=16.0 Hz), 4.70 (m, 1H under H$_2$O, H-3'), 4.39 (m, 1H, H-5'), 4.29-4.22 (m, 2H, H-4' and H-5"), 2.98 (d, 1H, ethynyl, $^4J_{H\text{-}F}$=5.0 Hz). $^{31}$P NMR (162 MHz, D$_2$O): –10.50 (d, 1P, P$_γ$, $J_{Pγ\text{-}Pβ}$=19.4 Hz), –11.03 (d, 1P, P$_α$, $J_{Pα\text{-}Pβ}$=19.4 Hz), –22.38 (t, 1P, P$_β$, $J_{Pβ\text{-}Pγ}$=$J_{Pβ\text{-}Pα}$=19.4 Hz). NMR $^{19}$F (376 MHz, DMSO-d$_6$): δ –159.1 (m). LRFAB-MS (GT): 638

$(M+Na)^+$, 616 $(M+H)^+$, 594 $(M-Na+2H)^+$, 572 $(M-2Na+3H)^+$, 550 $(M-3Na+4H)^+$, 592 $(M-Na)^-$, 570 $(M-2Na+H)^-$, 548 $(M-3Na+2H)^-$.

Example 13

Preparation of B306, the Hydroxy-tBuSATE N-benzylphosphoramidate Derivative of 2'-C-methyl-5-aza-7-deaza-guanosine The pronucleotide B306 (25 mg, 6% overall yield) has been synthesized from its parent nucleoside 2'-C-methyl-5-aza-7-deaza-guanosine (200 mg, 0.67 mmol) following a similar procedure than the one described for the synthesis of the pronucleotide prepared in the Example 4 and isolated as a white lyophilized powder. $^1$H NMR (DMSO-$d_6$, 400 MHz) δ (ppm) 0.90-0.91 (d, J=2.56 Hz, 3H), 1.09 (d, J=4.26 Hz, 6H), 3.07-3.10 (t, J=6.66 Hz, 2H), 3.42 (d, J=5.64 Hz, 2H), 3.86-3.99 (m, 6H), 4.10-4.15 (m, 1H), 4.15-4.20 (m, 1H), 4.90-4.93 (t, J=5.64 Hz, 1H), 5.28 (s, 1H), 5.46-5.50 (m, 1H) 5.62-5.69 (m, 1H), 5.80 (s, 1H), 7.00 (s, 2H), 7.18-7.21 (m, 2H), 7.26-7.33 (m, 5H); $^{31}$P NMR (DMSO-$d_6$, 162 MHz) δ (ppm) 9.80-9.95 (2s); Scan ES$^+$ 627 $(M+H)^+$, $\lambda_{max}$=261.7 nm; HPLC (0-100% ACN over a period of 8 min) $t_R$=3.18 min $\lambda_{max}$=258.4 nm.

Example 14

Preparation of B389, the Hydroxy-tBuSATE N-benzylphosphoramidate derivative of 2'-C-methyl-7-deaza-guanosine

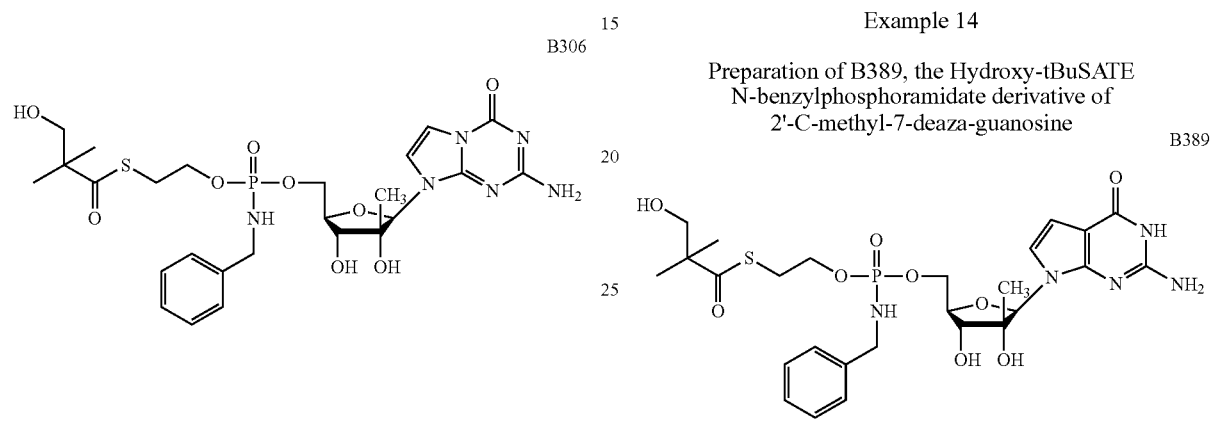

Synthetic Scheme

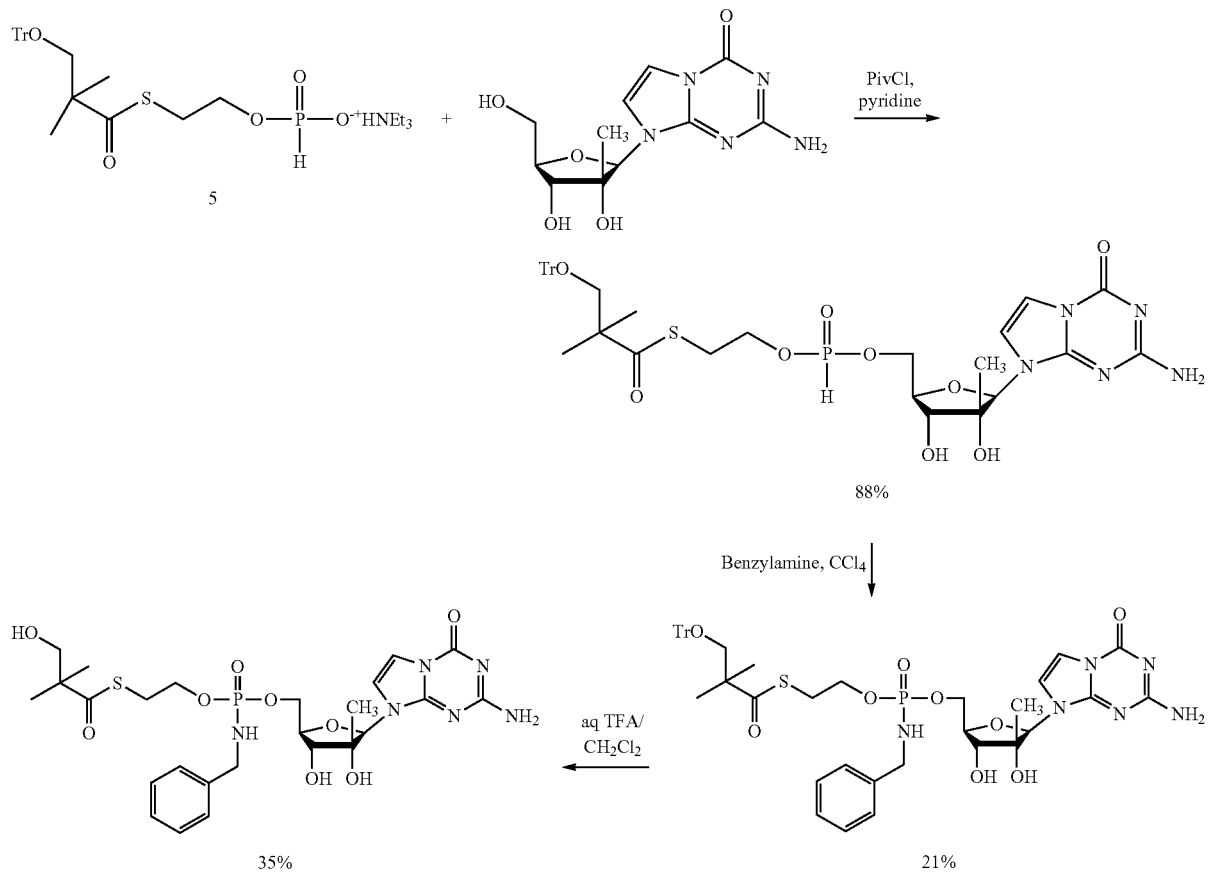

Synthetic Scheme

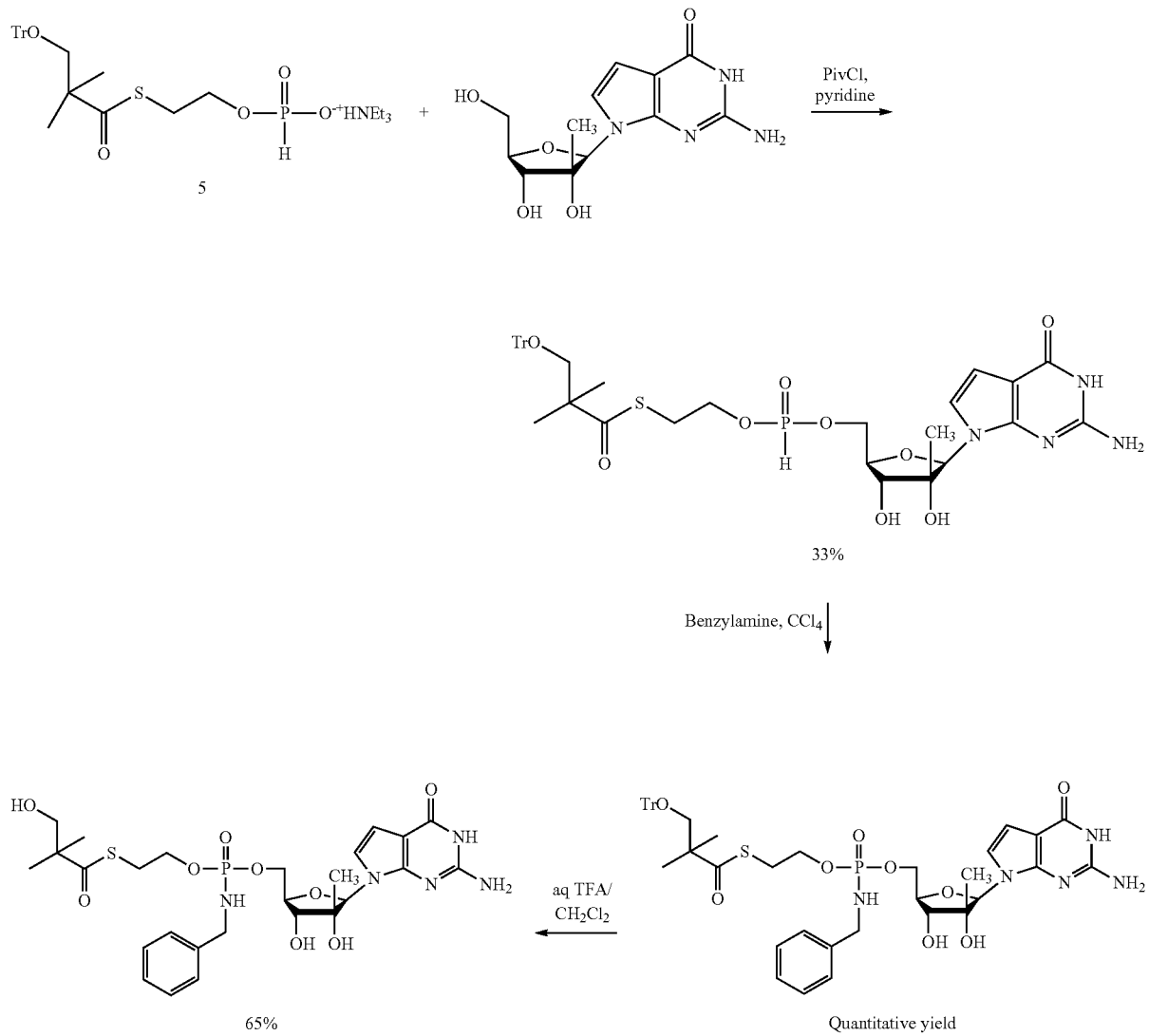

The pronucleotide B389 (80 mg, 21% overall yield) has been synthesized from its parent nucleoside 2'-C-methyl-7-deaza-guanosine (200 mg, 0.67 mmol) following a similar procedure than the one described for the synthesis of the pronucleotide prepared in the Example 4 and isolated as a white lyophilized powder. $^1$H NMR (DMSO-d$_6$, 400 MHz) δ (ppm) 0.74 (s, 3H), 1.09 (s, 6H), 3.0 (t, J=6.10 Hz, 2H), 3.42 (d, J=5.49 Hz, 2H), 3.8-4.0 (2m, 6H), 4.04-4.11 (m, 1H), 4.24-4.17 (m, 1H), 4.90-4.93 (t, J=5.36 Hz 1H), 4.96-4.98 (d, J=4.76 Hz, 1H), 5.31-5.36 (m, 1H), 5.57-5.67 (m, 1H), 5.93 (s, 1H), 6.21-6.26 (m, 3H), 6.76 (d, J=22 Hz, 1H), 7.19-7.23 (m, 1H), 7.27-7.32 (m, 4H), 10.34 (brs, 1H); $^{31}$P NMR (DMSO-d$_6$, 162 MHz) δ (ppm) 9.77 and 9.90 (2s); Scan ES$^+$ 626 (M+H)$^+$, $\lambda_{max}$=258.7 nm; HPLC (0-100% ACN over a period of 8 min) t$_R$=3.84 min $\lambda_{max}$=259.6 nm.

Example 15

Preparation of B288, the Hydroxy-tBuSATE N-benzylphosphoramidate Derivative of 3'-C-methyluridine

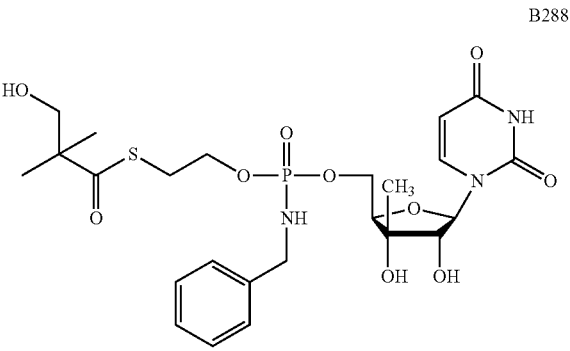

B288

Synthetic Scheme

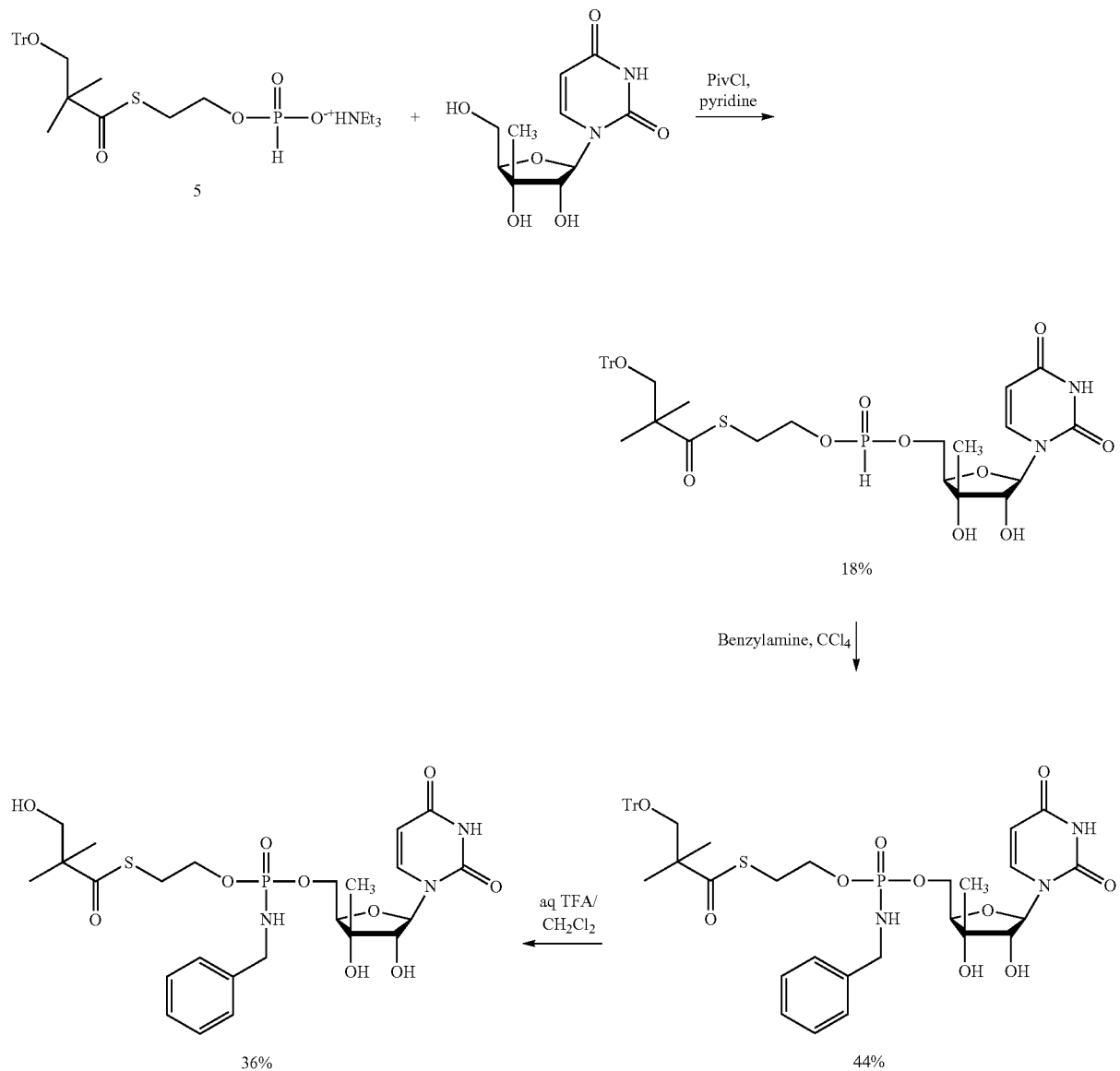

The pronucleotide B288 (34 mg, 3% overall yield) was synthesized from its parent nucleoside 3'-C-methyl-uridine (513 mg, 1.99 mmol) following a similar procedure than the one described for the synthesis of the pronucleotide prepared in the Example 4 and isolated as a white lyophilized powder. $^1$H NMR (DMSO-$d_6$, 400 MHz) δ (ppm) 1.09 (s, 6H), 1.15 (s, 3H), 3.00-3.05 (m, 2H), 3.30 (s, 1H), 3.42 (d, J=6.13 Hz, 2H), 3.76-3.79 (m, 1H), 3.86-3.99 (m, 6H), 4.92-4.94 (t, J=5.40 Hz, 1H), 4.97 (s, 1H), 5.47 (m, 1H), 5.59-5.62 (m, 1H), 5.67-5.78 (m, 1H), 5.83-5.87 (m, 1H), 7.20-7.24 (m, 1H), 7.30 (m, 4H), 7.66-7.71 (m, 1H), 11.32 (brs, 1H); $^{31}$P NMR (DMSO-$d_6$, 162 MHz) δ (ppm) 9.66 and 9.95 (2s); Scan ES$^+$ 588 (M+H)$^+$, $\lambda_{max}$=261.7 nm.

Example 16

Preparation of B350, the Hydroxy-tBuSATE N-benzylphosphoramidate Derivative of 3'-C-methylguanosine

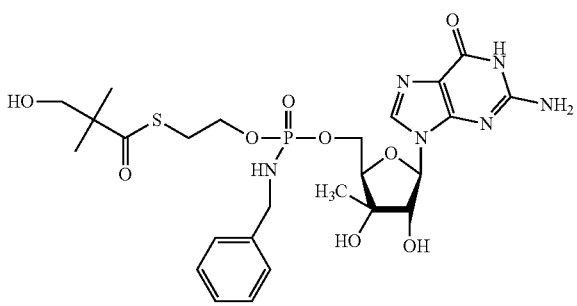

B350

Synthetic Scheme

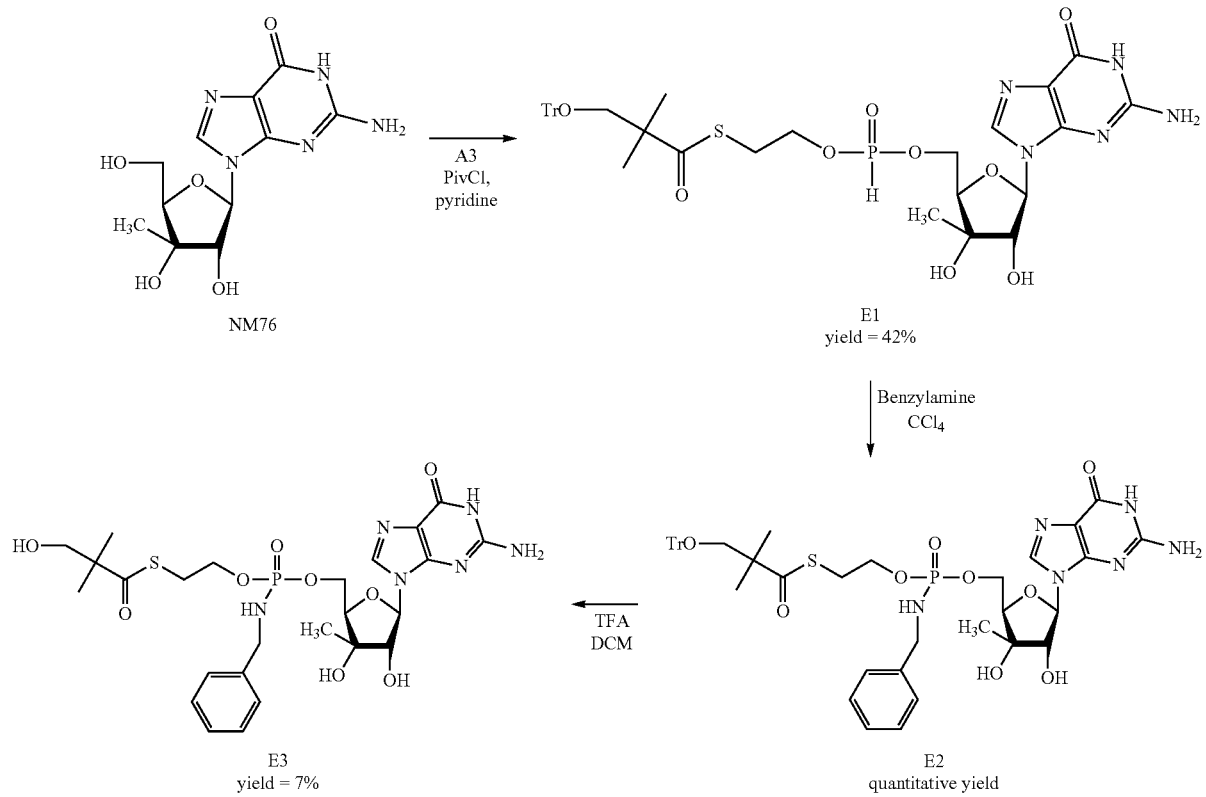

3'-C-Methylguanosin-5'-yl-O-(triphenylmethyloxy-tert-butyl-5-acyl-2-thioethyl) H-phos-phonate (E1)

3'-C-Methylguanosine (NM76) (233.7 mg, 0.79 mmol) and compound A3 [See Compound 5 of Example 2] (504.9 mg, 0.87 mmol) were coevaporated together with anhydrous pyridine and dissolved in this solvent (11.8 mL). Pivaloyl chloride (193.7 μL, 1.57 mmol) was added dropwise at −15° C. and the solution was stirred at the same temperature for 2 h. The reaction mixture was diluted with dichloromethane and neutralized with an aqueous solution of $NH_4Cl$ 0.5M. The mixture was partitioned between dichloromethane and aqueous $NH_4Cl$ 0.5M, the organic phases were combined, dried over $Na_2SO_4$ evaporated under reduced pressure (bath temperature not exceeding 30° C.) and coevaporated twice with toluene. The crude mixture was filtered on a silica gel plug eluting with a gradient 0-10% methanol in dichloromethane+ 0.2% acetic acid) to afford the desired product E1 (250 mg, 42%). Compound E1: $^{31}P$ NMR (162 MHz, DMSO-$d_6$): δ 9.93 (s), 9.13 (s). LR LC/MS (M+H$^+$) 521.1 (5.88 min). UV: $\lambda_{max}$=262 nm. $R_f$ 0.21 (MeOH/CH$_2$Cl, 15/85, v/v).

N-Benzylaminyl-3'-C-methylguanosin-5'-yl-O-(triphenylmethyloxy-tert-butyl-5-acyl-2-thioethyl) phosphate (E2)

To a solution of compound E1 (250 mg, 0.33 mmol) in anhydrous carbon tetrachloride (3.3 mL), benzylamine (178 μL, 1.637 mmol) was added dropwise. The reaction mixture was stirred at room temperature for 1 h 30 and evaporated to dryness (bath temperature not exceeding 30° C.). The crude mixture was filtered on a silica gel plug eluting with a gradient 0-30% methanol in dichloromethane) to give compound E2 as a white solid (290 mg, quantitative yield). Compound E2: $^{31}P$ NMR (162 MHz, DMSO-$d_6$) δ 9.91 (s), 9.74 (s). LR LC/MS (M+H$^+$) 869.3 (M−H$^-$) 867.7 (5.20 min). UV: $\lambda_{max}$=253 nm. $R_f$ 0.13 (MeOH/CH$_2$Cl, 10/90, v/v).

N-Benzylaminyl-O-(hydroxyl-tert-butyl-5-acyl-2-thioethyl)-3'-C-methylguanosin-5'-yl phosphate B350 (Compound E3)

Compound E2 (290 mg, 0.33 mmol) was dissolved in dichloromethane (1.16 mL) and treated with TFA (113 μL). The mixture was stirred at room temperature for 10 min, then diluted with ethanol, evaporated to dryness (bath temperature not exceeding 30° C.) and coevaporated with toluene. The resulting residue was subjected to silica gel chromatography, eluting with a gradient 0-30% methanol in dichloromethane, then purified by reverse phase (C18) silica gel column chromatography eluting with a gradient 0-100% acetonitrile in water and lyophilised from a mixture of water/dioxan to give B350 (Compound E3) (15 mg, 7%, white lyophilised powder). B350 (Compound): $^1H$ NMR (400 MHz, DMSO-$d_6$) δ 10.60 (m, 1H, NH), 7.90 (s, 1H, H-8), 7.30-7.19 (m, 5H, C$_6$H$_5$), 6.47 (1s, 2H, NH$_2$), 5.72-5.59 (m, 2H, H-1' and PNH), 5.51 (d, 1H, OH-2', $J_{OH2'-1'}$=8.0 Hz), 4.94-4.92 (2H, OH-3' and OH), 4.28 (m, 1H, H-2'), 4.01-3.83 (m, 7H, H-4', H-5', CH$_2$O and CH$_2$N), 3.41 (m, 2H, CH$_2$OH), 3.02 (t, 2H, CH$_2$S, $J_{CH2S-CH2O}$=6.0 Hz), 1.20 (s, 3H, CH$_3$), 1.09 (s, 6H, 2 CH$_3$). $^{31}P$ NMR (162 MHz, DMSO-$d_6$) δ 9.86 (s), 9.72 (s). LR LC/MS (M+H$^+$) 627.2 (M−H$^-$) 625.5 (3.87 min). HRFAB-MS C$_{25}$H$_{36}$O$_9$N$_6$PS (M+H$^+$) calculated 627.2002. found 627.2014. UV: $\lambda_{max}$=251 nm.

Example 17

Preparation of B305, the Hydroxy-tBuSATE N-benzylphosphoramidate Derivative of 1-[2-C-methyl-β-ribofuranosyl]-3-carboxamido-4-fluoro-pyrazole

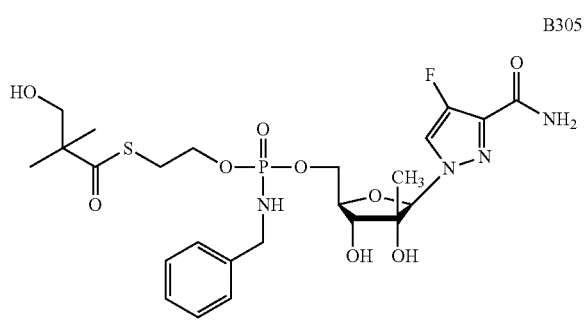

Synthetic Scheme

The pronucleotide B305 (28.3 mg, 8% overall yield) has been synthesized from its parent nucleoside 1-[2-C-methyl-β-ribofuranosyl]-pyrazolo-3-carboxamide-4-fluoro (180 mg, 0.65 mmol) following a similar procedure than the one described for the synthesis of the pronucleotide prepared in the Example 4 and isolated as a white lyophilized powder. $^1$H NMR (DMSO-$d_6$, 400 MHz) δ (ppm) 0.75 (s, 3H), 1.08-1.09 (d, J=3.35 Hz, 6H), 2.98-3.02 (m, 2H), 3.40-3.42 (m, 2H), 3.85-4.03 (m, 5H), 4.16-4.19 (m, 2H), 4.89-4.92 (m, 1H), 5.25-5.29 (m, 2H), 5.55 (s, 1H), 5.56-5.64 (m, 1H), 7.19-7.22 (m, 1H), 7.26-7.50 (m, 7H), 8.05 (d, J=4.32 Hz, 1H); $^{31}$P NMR (DMSO-$d_6$, 162 MHz) δ (ppm) 9.75 and 9.90 (2s); $^{19}$F NMR ($d_6$-DMSO, 235 MHz) δ (ppm) −170.70 (d, J=61.74 Hz, 1F); Scan ES$^+$ 605 (M+H)$^+$, $\lambda_{max}$=233.7 nm; HPLC (0-100% ACN over a period of 10 min) $t_R$=4.56 min $\lambda_{max}$=235.2 nm.

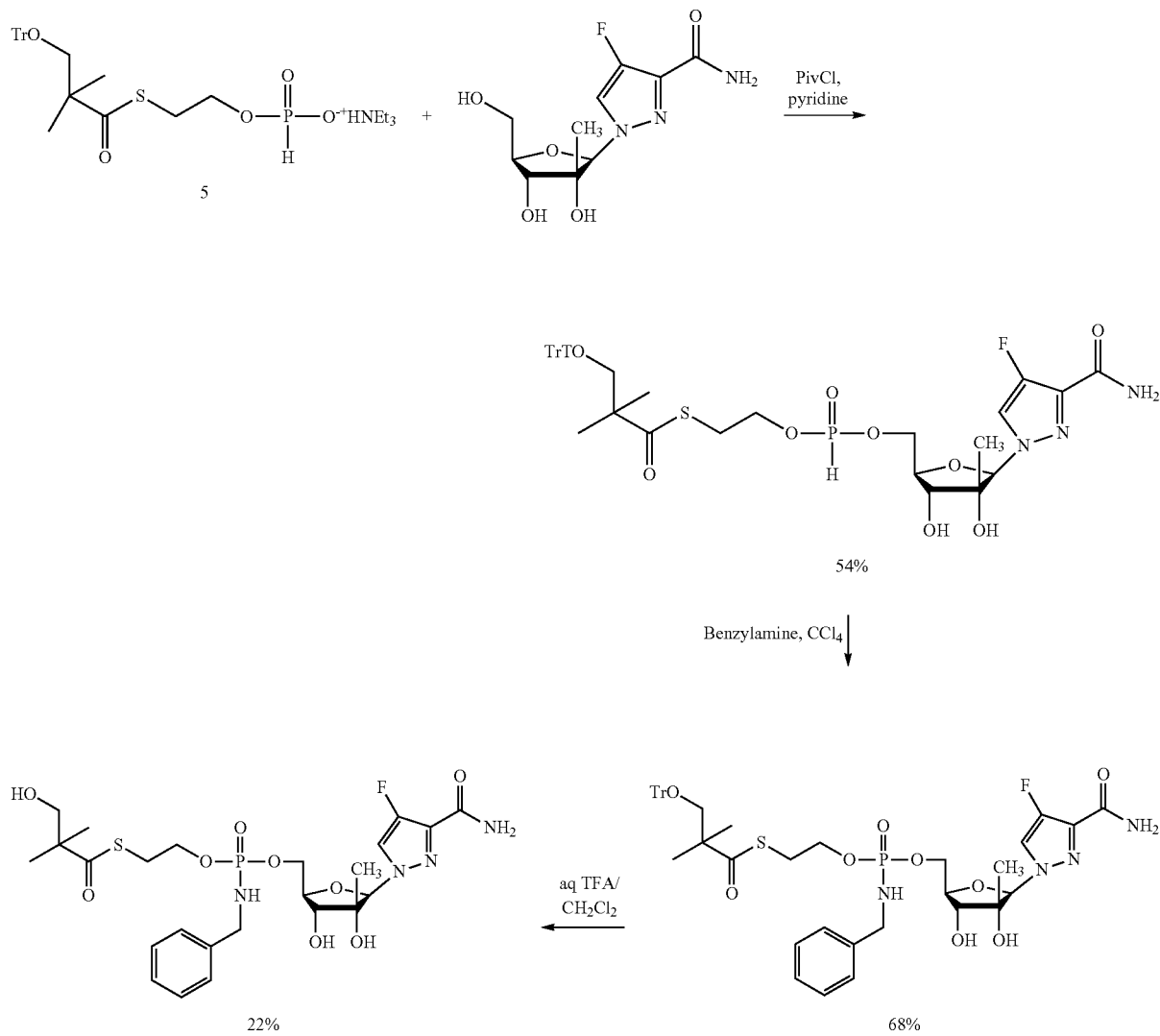

Example 18

Preparation of B436, the Hydroxy-tBuSATE N-benzylphosphoramidate derivative of 2'-C-methyl-7-deaza-7-fluoro-adenosine

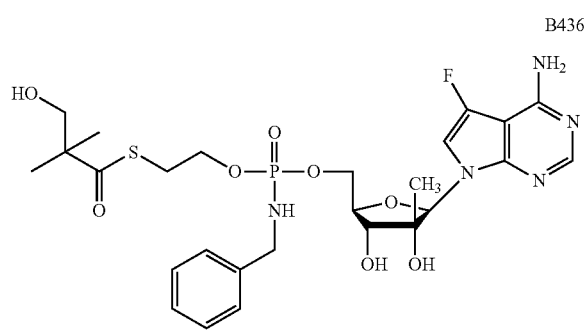

Synthetic Scheme

The pronucleotide B436 (30 mg, 9% overall yield) has been synthesized from its parent nucleoside 2'-C-methyl-7-deaza-6-NH-dimethoxytrityl-adenosine (320 mg, 0.53 mmol) following a similar procedure than the one described for the synthesis of the pronucleotide prepared in the Example 2 (Procedure A, Strategy b), and isolated as a white lyophilized powder. $^1$H NMR (DMSO-d$_6$, 400 MHz) δ (ppm) 0.66 (s, 3H), 1.02 (s, 6H), 2.95-2.98 (t, J=6.10 Hz, 2H), 3.35 (d, J=5.49 Hz, 2H), 3.77-3.85 (m, 3H), 3.88-3.95 (m, 3H), 4.03-4.18 (m, 2H), 4.83-4.86 (t, J=5.44 Hz, 1H), 5.14 (s, 1H), 5.21-5.25 (t, J=7.40 Hz, 1H), 5.55-5.66 (m, 1H), 6.14 (s, 1H), 6.9-7.3 (m, 8H), 8.01 (s, 1H); $^{31}$P NMR (DMSO-d$_6$, 162 MHz) δ (ppm) 9.77 and 9.89 (2s); $^{19}$F NMR (d$_6$-DMSO, 235 MHz) δ (ppm) −166.85 (d, J=14.16 Hz, 1F); Scan ES$^+$ 628 (M+H)$^+$, λ$_{max}$=280.7 nm; HPLC (0-100% ACN over a period of 10 min) t$_R$=4.78 min λ$_{max}$=280.8 nm.

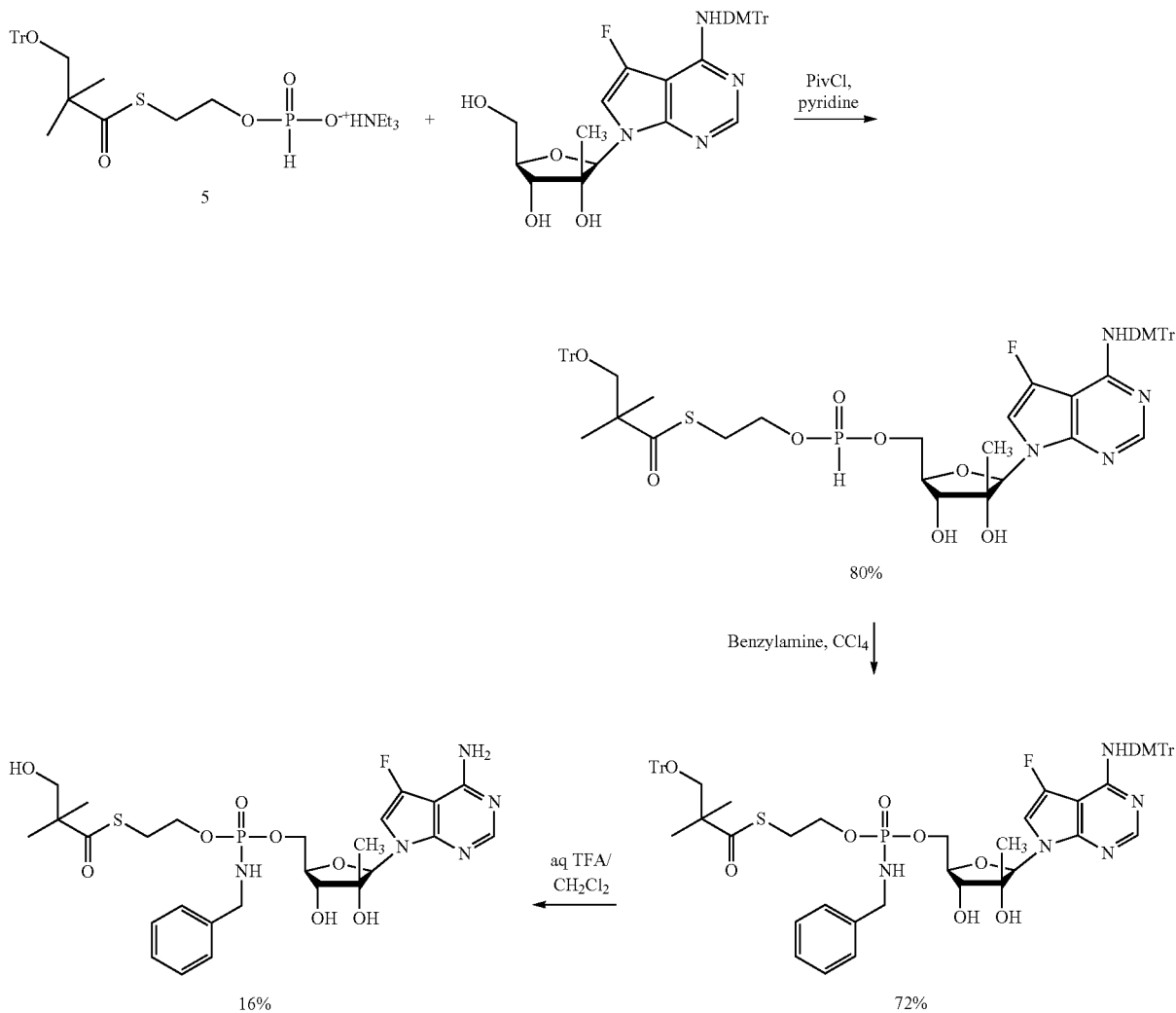

Example 19

Preparation of B589, the Hydroxy-tBuSATE N-benzylphosphoramidate Derivative of 4'-C-methyluridine

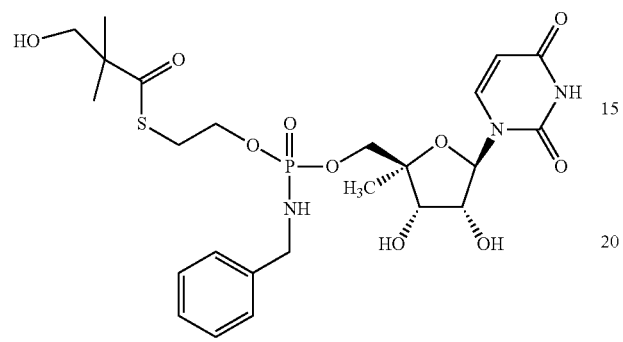

B589

Synthetic Scheme

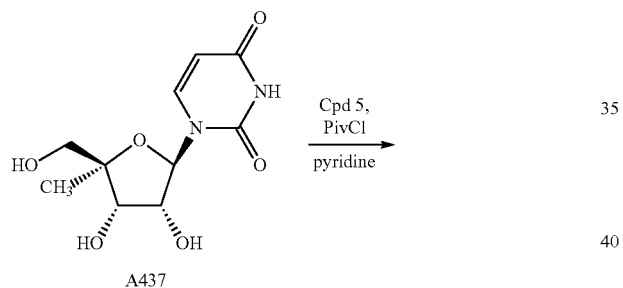

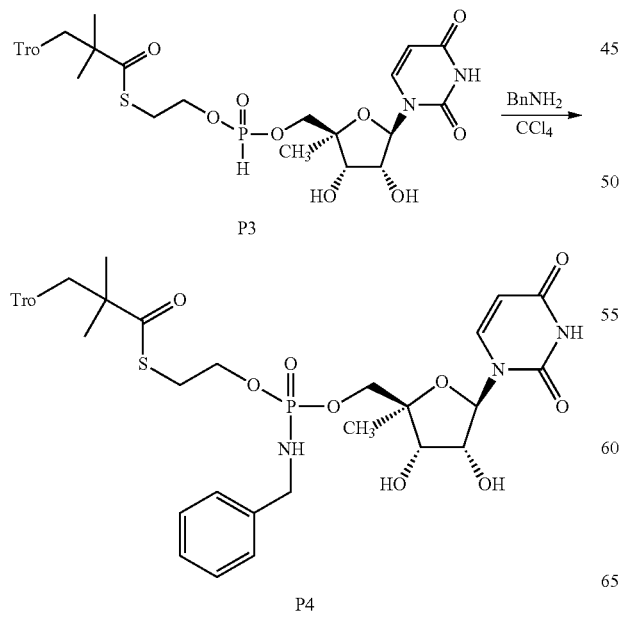

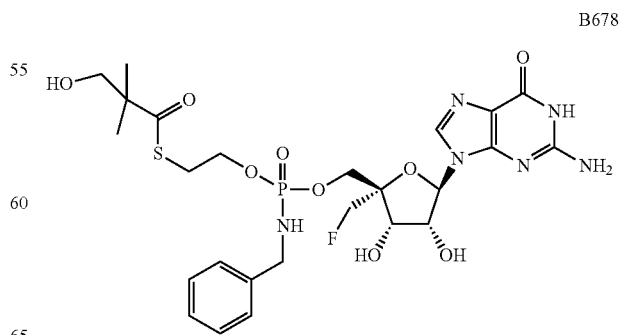

B589

Following the procedures described for Example 4, and starting from 4'-C-methyluridine (A437) (200 mg, 0.77 mmol), intermediate P3 was first produced (62 mg, 11%. $^{31}$P NMR (DMSO-$d_6$, 162 MHz) δ (ppm) 9.15, 9.56 (2s); Scan ES$^+$ 747 (M+Na)$^+$, $\lambda_{max}$=259.7 nm), then compound P4 during the second step (28 mg, 39%. Scan ES$^+$ 852 (M+Na)), and finally the desired prodrug B589 was obtained as a white powder after lyophilization from dioxane (21 mg, 58%). $^1$H NMR (DMSO-$d_6$, 400 MHz) δ (ppm) 1.10 (s, 6H), 1.13 (s, 3H), 3.03 (t, J=6.42 Hz, 2H), 3.15 (d, J=5.29 Hz, 1H), 3.42 (d, J=5.67 Hz, 2H), 3.72-4.16 (m, 7H), 4.06-4.15 (m, 1H), 4.92 (t, J=5.29 Hz, 1H), 5.22 (d, J=5.29 Hz, 1H), 5.36-5.38 (2d, 1H), 5.57-5.60 (2d, 1H), 5.64-5.70 (m, 1H), 5.78-5.80 (2d, 1H), 7.20-7.31 (m, 5H), 7.60-7.64 (2d, 1H); $^{31}$P NMR (DMSO-$d_6$, 162 MHz) δ (ppm) 9.58, 9.77 (2s); Scan ES$^+$ 610 (M+Na)$^+$, $\lambda_{max}$=260.7 nm.

Example 20

Preparation of B678, the Hydroxy-tBuSATE N-benzylphosphoramidate Derivative of 4'-C-fluoromethylguanosine

B678

Synthetic Scheme

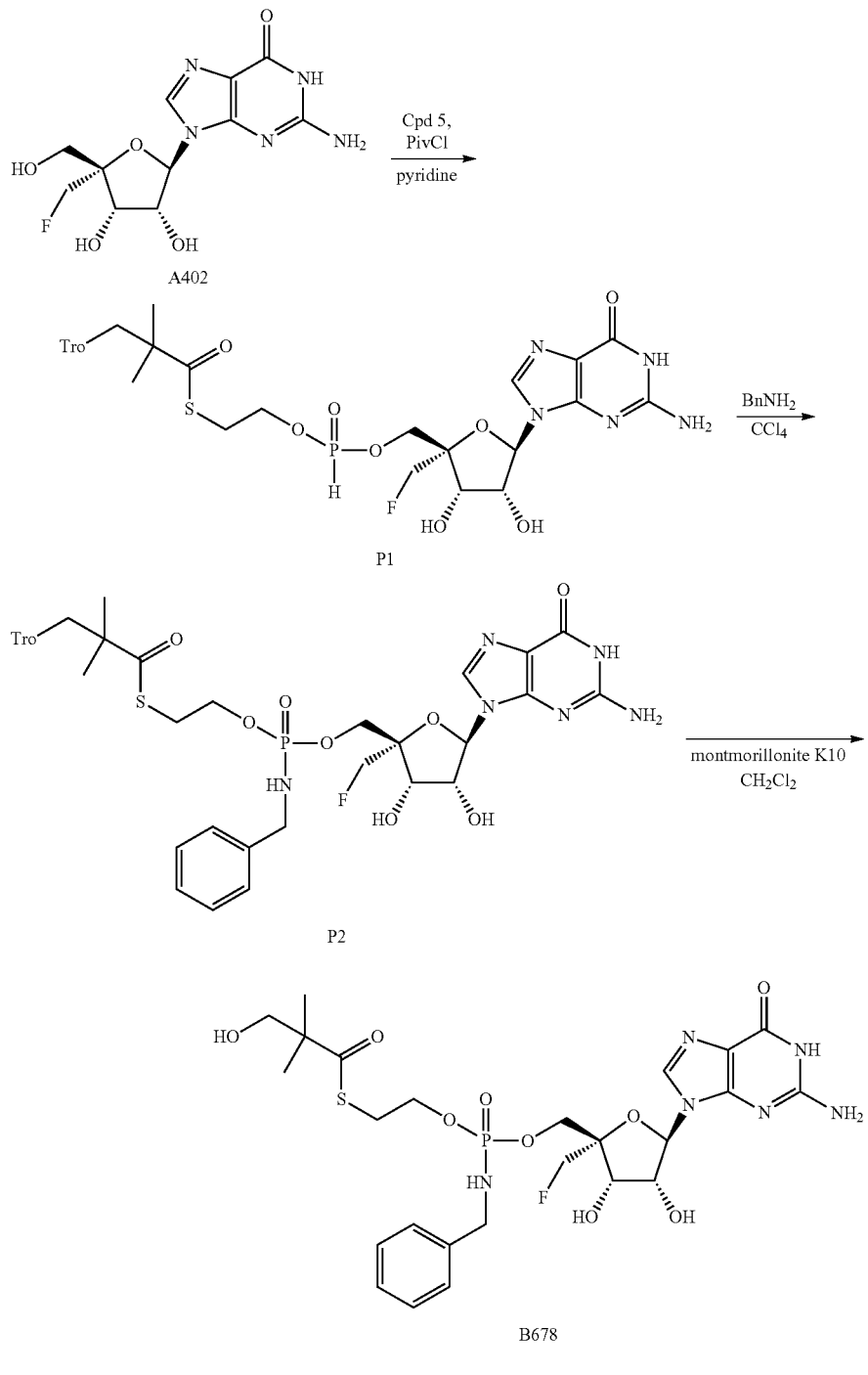

Following the procedures of the Procedure A described in Example 3, and starting from 4'-C-fluoromethylguanosine (A402) (69.4 mg, 0.22 mmol), compound P1 (67.5 mg, 39%) was obtained as intermediate after the first step. Scan ES⁻ 780 (M−H)⁻. Second step led to the formation of intermediate P2 (57.5 mg; 76%). Compound P2 (26.3 mg, 0.03 mmol) was dissolved in dichloromethane (1 ml) and treated with montmorillonite K10 (150 mg) and stirred at room temperature for 1 h. The reaction mixture was directly deposited on silica SPE tube and extracted with a gradient 0-100% MeOH in dichloromethane to give after lyophilization from dioxane/water B678 as a white powder (7.7 mg, 40%). $^1$H NMR (DMSO-$d_6$, 400 MHz) δ (ppm) 1.09 (21s, 6H), 3.03-3.05 (m, 2H), 3.42 (m, 2H), 3.87-4.00 (m, 6H), 4.15-4.24 (m, 2H), 4.43-4.66 (m, 2H), 4.74 (m, 1H), 4.93 (m, 1H), 5.52 (d, J=4.36 Hz, 1H), 5.58 (m, 1H), 5.70-5.73 (m, 1H), 5.75-5.77 (d, J=8.05 Hz, 1H), 6.52 (1s, 2H), 7.24-7.35 (m, 5H), 7.92 (2s, 1H); $^{31}$P NMR (DMSO-$d_6$, 162 MHz) δ (ppm) 9.70, 9.83 (2s); $^{19}$F NMR ($d_6$-DMSO, 235 MHz) δ (ppm) −235.92, −236.25 (2s); Scan ES⁺ 645 (M+H)⁺, $\lambda_{max}$=250.7 nm HPLC (0-100% ACN over a period of 8 min) $t_R$=3.91 min $\lambda_{max}$=251.1 nm.

Example 21

Preparation of B704, the Hydroxy-tBuSATE N-benzylphosphoramidate Derivative of acyclovir

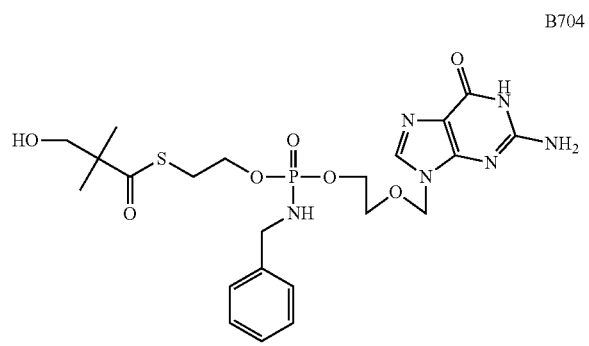 [SMILES: CC(C)(CO)C(=O)SCCOP(=O)(NCc1ccccc1)OCCOCn1cnc2c(=O)[nH]c(N)nc21]

Synthetic Scheme

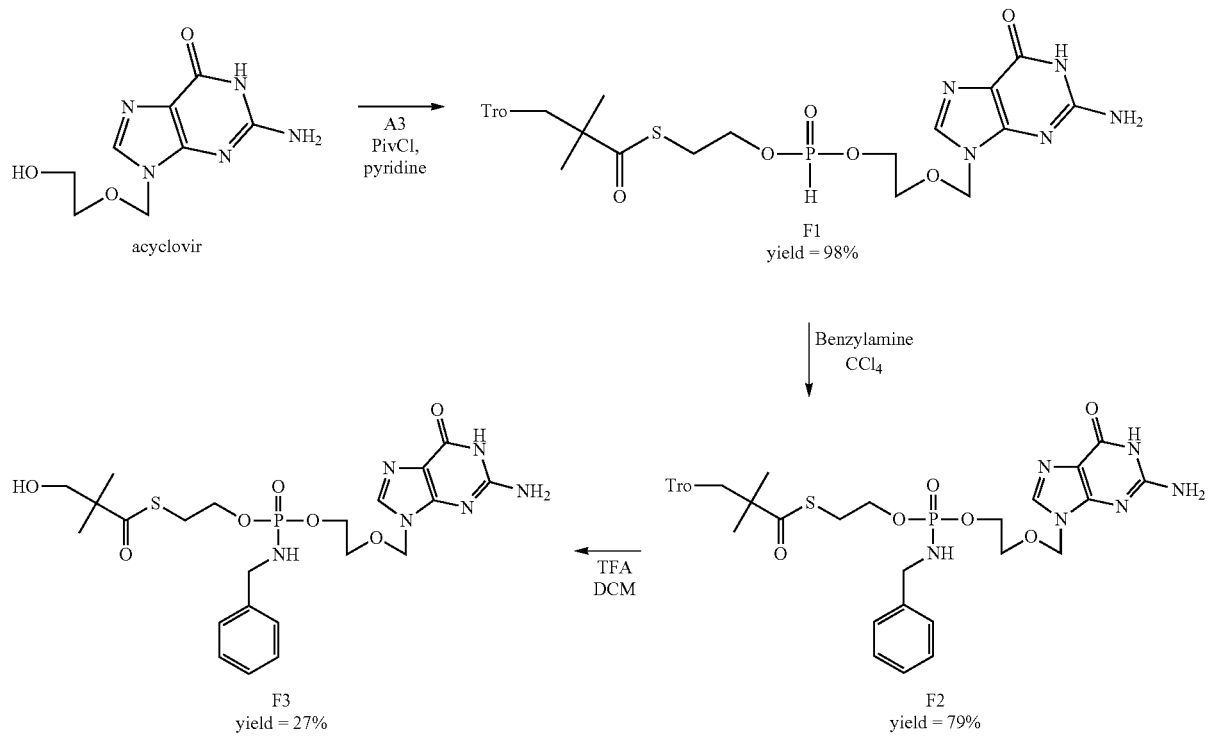

9-(2-Hydroxy-ethoxymethyl)-guanin-5'-yl-O-(triphenylmethyloxy-tert-butyl-5-acyl-2-thioethyl) H-phosphonate (F1)

Acyclovir (200 mg, 0.89 mmol) and compound A3 [See Compound 5 of Example 2] (674.2 mg, 1.15 mmol) were coevaporated together with anhydrous pyridine and dissolved in this solvent (13.3 mL). Pivaloyl chloride (162 μL, 1.15 mmol) was added dropwise at −15° C. and the solution was stirred at room temperature for 2 h. The reaction mixture was diluted with dichloromethane and neutralized with an aqueous solution of $NH_4Cl$ 0.5M. The mixture was partitioned between dichloromethane and aqueous $NH_4Cl$ 0.5M, the organic phases were combined, dried over $Na_2SO_4$ evaporated under reduced pressure (bath temperature not exceeding 30° C.) and coevaporated twice with toluene. The crude mixture was filtered on a silica gel plug eluting with a gradient 0-15% methanol in dichloromethane+0.2% acetic acid) to afford the desired product F1 (602 mg, 98%). Compound F1:LR LC/MS (M+H$^+$) 691.9 (M−H$^-$) 690.0 (4.82 min). UV: $\lambda_{max}$=254 nm.

N-Benzylaminyl-9-(2-hydroxy-ethoxymethyl)-guanin-5'-yl-O-(triphenylmethyloxy-tert-butyl-5-acyl-2-thioethyl)phosphate (F2)

To a solution of compound F1 (602 mg, 0.87 mmol) in anhydrous carbon tetrachloride (8.7 mL), benzylamine (475 μL, 4.35 mmol) was added dropwise. The reaction mixture was stirred at room temperature for 1 h 30 and evaporated to dryness (bath temperature not exceeding 30° C.). The crude mixture was subjected to silica gel chromatography, eluting with a gradient 0-10% methanol in dichloromethane to give compound F2 as a white solid (550 mg, 79%). Compound F2:

$^1$H NMR (400 MHz, DMSO-d$_6$) δ 7.77 (s, 1H, H-8), 7.58-7.17 (m, 20H, 4 $C_6H_5$), 6.68 (1s, 2H, $NH_2$), 5.59 (m, 1H, PNH), 5.32 (s, 2H, $OCH_2N$), 3.92-3.78 (m, 6H, $CH_2SCH_2O$, $CH_2N$, $POCH_2CH_2O$), 3.51 (t, 2H, $POCH_2CH_2O$, $J_{CH2-CH2}$=5.2 Hz), 3.16 (s, 2H, $CH_2OTr$), 3.00 (t, 2H, $CH_2S$, $J_{CH2S-CH2O}$=5.6 Hz), 1.12 (s, 6H, 2 $CH_3$). $^{13}$C NMR (100 MHz, DMSO-d$_6$): δ 204.0 (C═O), 157.2 (C-4), 154.6 (C-2), 151.8 (C-6), 143.9 (4C, 4 $C_6H_5$), 136.9 (C-8), 128.9-127.2 (20C, 4 $C_6H_5$), 117.0 (C-5), 86.3 (1C, $C(C_6H_5)_3$), 72.3 ($OCH_2N$), 70.0 ($CH_2OTr$), 68.2 ($POCH_2CH_2O$), 64.8

(POCH$_2$CH$_2$O), 64.2 (CH$_2$SCH$_2$O), 50.8 (C(CH$_3$)$_2$), 44.7 (CH$_2$N), 28.8 (CH$_2$S), 22.8 (2C, C(CH$_3$)$_2$). $^{31}$P NMR (162 MHz, DMSO-d$_6$) δ 9.79 (s). LR LC/MS (M+H$^+$) 797.2 (5.15 min). UV: λ$_{max}$=254 nm. R$_f$ 0.57 (MeOH/CH$_2$Cl$_2$ 15/85, v/v).

N-Benzylaminyl-9-(2-hydroxy-ethoxymethyl)-guanin-5'-yl-O-(hydroxy-tert-butyl-5-acyl-2-thioethyl) phosphate B704 (Compound F3)

Compound F2 (550 mg, 0.69 mmol) was dissolved in dichloromethane (2.2 mL) and treated with TFA (220 μL). The mixture was stirred at room temperature for 15 min, filtered through a solid phase extraction column eluting with a gradient 0-15% methanol in dichloromethane, then purified by reverse phase (C18) silica gel column chromatography eluting with a gradient 0-100% acetonitrile in water and lyophilised from a mixture of water/dioxan to give B704 (Compound F3), (103 mg, 27%, white lyophilised powder). B704 (Compound F3): $^1$H NMR (400 MHz, DMSO-d$_6$): δ 10.57 (1s, 1H, NH), 7.79 (s, 1H, H-8), 7.29-7.18 (m, 5H, C$_6$H$_5$), 6.49 (1s, 2H, NH$_2$), 5.55 (m, 1H, PNH), 5.33 (s, 2H, OCH$_2$N), 4.92 (t, 1H, OH, J$_{OH-CH2}$=5.2 Hz), 3.94-3.73 (m, 6H, CH$_2$SCH$_2$O, CH$_2$N, POCH$_2$CH$_2$O), 3.60 (t, 2H, POCH$_2$CH$_2$O, J$_{CH2-CH2}$=4.2 Hz), 3.42 (d, 2H, CH$_2$OH, J$_{CH2-OH}$=4.4 Hz), 3.00 (t, 2H, CH$_2$S, J$_{CH2S-CH2O}$=6.4 Hz), 1.10 (s, 6H, 2 CH$_3$). $^{13}$C NMR (100 MHz, DMSO-d$_6$): δ 204.4 (C=O), 157.2 (C-4), 154.4 (C-2), 151.9 (C-6), 141.0 (1C, C$_6$H$_5$), 138.1 (C-8), 128.6-127.2 (5C, C$_6$H$_5$), 117.0 (C-5), 72.3 (OCH$_2$N), 68.8 (CH$_2$OH), 68.2 (POCH$_2$CH$_2$O), 64.7 (POCH$_2$CH$_2$O), 64.2 (CH$_2$SCH$_2$O), 52.2 (C(CH$_3$)$_2$), 44.7 (CH$_2$N), 28.7 (CH$_2$S), 22.3 (2C, C(CH$_3$)$_2$). $^{31}$P NMR (162 MHz, DMSO-d$_6$): δ 9.76 (s). LR LC/MS (M+H$^+$) 555.9 (M−H$^−$) 553.9 (3.77 min). HRFAB-MS C$_{22}$H$_{32}$O$_7$N$_6$PS (M+H$^+$) calculated 555.1791. found 555.1795. UV: λ$_{max}$=250 nm.

Example 22

Preparation of B390, the Hydroxy-tBuSATE N-benzylphosphoramidate Derivative of 2'-C-methyl-2',3'-di-O-acetyl-cytidine

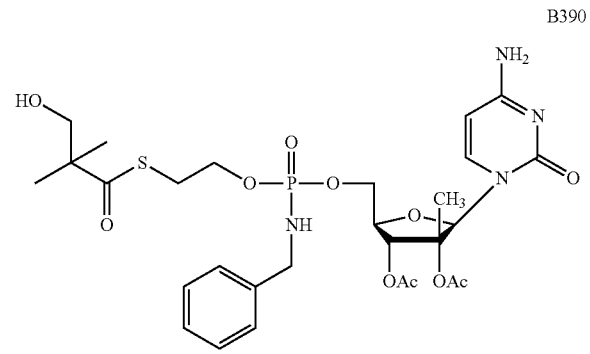

B390

Synthetic Scheme

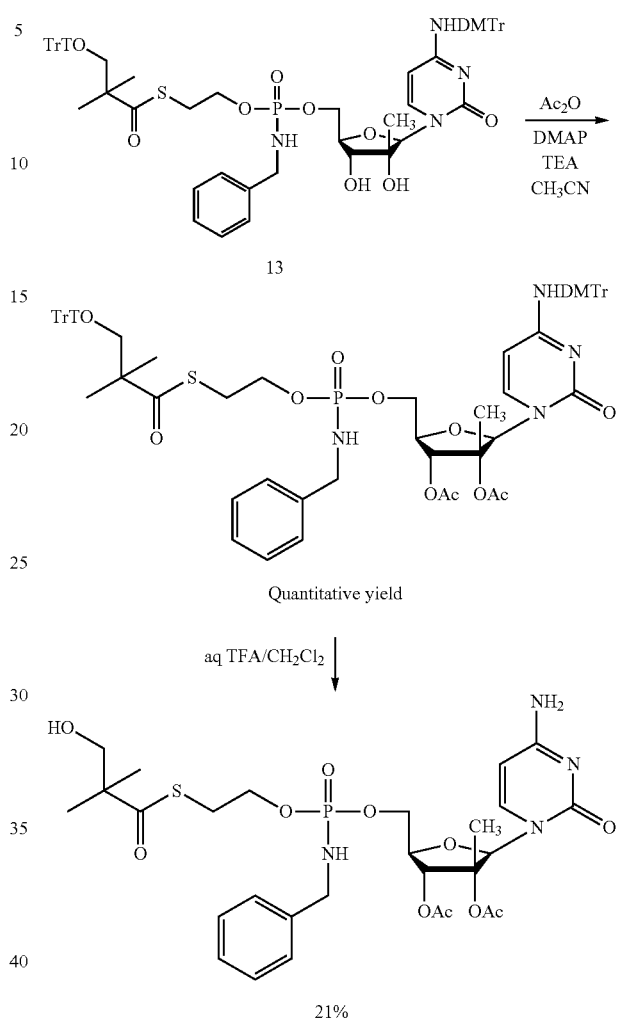

To a solution of pronucleotide 13 (See Example 2, Procedure A, Strategy b) (300 mg, 0.27 mmol) in anhydrous acetonitrile were successively added triethylamine (92 μl), acetic anhydride (2.2 eq, 54 μl) and 4-dimethylaminopyridine (0.1 eq, 4 mg). The reaction mixture was stirred at room temperature for 2 h and triethylamine (92 μl), acetic anhydride (2.2 eq, 54 μl) and 4-dimethylaminopyridine (0.1 eq, 4 mg) were added again. After removal of the solvents under reduced pressure, the crude mixture was purified on silica gel column chromatography (eluant: stepwise gradient of methanol [0-5%] in methylene chloride) to give the fully protected pronucleotide (329 mg, quantitative yield). This compound was finally treated with a mixture of trifluoroacetic acid (132 μl) and methylene chloride (3.9 ml). After 1 h30 stirring at room temperature trifluoroacetic acid (132 μl) were added again and the mixture stirred 1 h more. The solvents were evaporated under reduced pressure and coevaporated with toluene. The crude mixture was purified on silica gel column chromatography (eluant: stepwise gradient of methanol [0-10%] in methylene chloride) to give B390 (36.4 mg, 21%) lyophilized as a white powder. $^1$H NMR (DMSO-d$_6$, 400 MHz) δ (ppm) 1.10 (s, 6H), 1.33 (d, J=2.60 Hz, 3H), 2.05 (s, 6H), 3.01-3.04 (t, J=6.54 Hz, 2H), 3.31 (d, J=5.45H, 2H), 3.85-3.90 (m, 2H), 3.94-3.99 (m, 2H), 4.09-4.11 (m, 2H), 4.21-4.23 (m, 1H), 4.90-4.93 (t, J=5.71 Hz, 1H), 5.22 (m, 1H), 5.67-5.73 (m, 2H), 6.20 (m, 1H), 7.21-7.27 (m, 7H), 7.54 (m, 1H); $^{31}$P NMR (DMSO-$d_6$, 162 MHz) δ (ppm) 9.69 and 9.86 (2s); Scan ES$^+$ 671 (M+H)$^+$, $\lambda_{max}$=273.7 nm; HPLC (0-100% ACN over a period of 10 min) $t_R$=5.04 min $\lambda_{max}$=233.7 nm and 271.4 nm.

Example 23

Preparation of B302

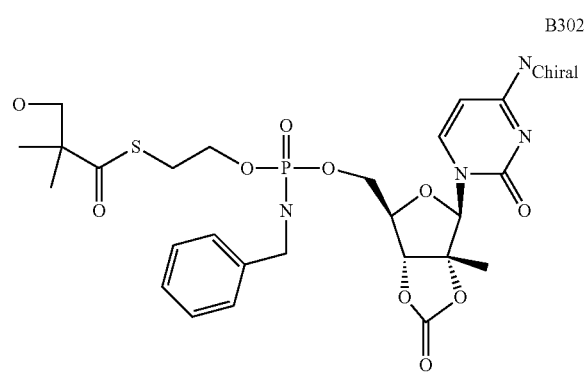 [SMILES: CC(C)(CO)C(=O)SCCOP(=O)(NCc1ccccc1)OC[C@H]1O[C@@H](n2ccc(N)nc2=O)[C@]2(C)OC(=O)O[C@H]12]

Synthesis of Hydroxy-tBuSATE
N-benzylphosphoramidate 2',3'-cyclic carbonate
Derivative of 2'-C-methylcytidine B302

The following strategy was used for the synthesis:

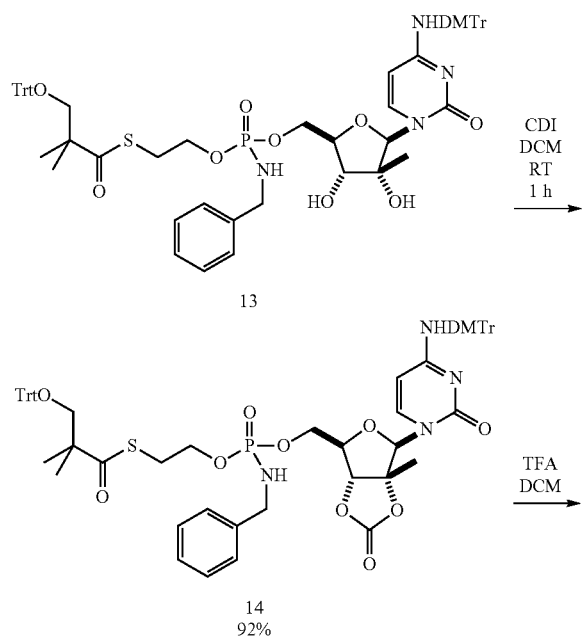

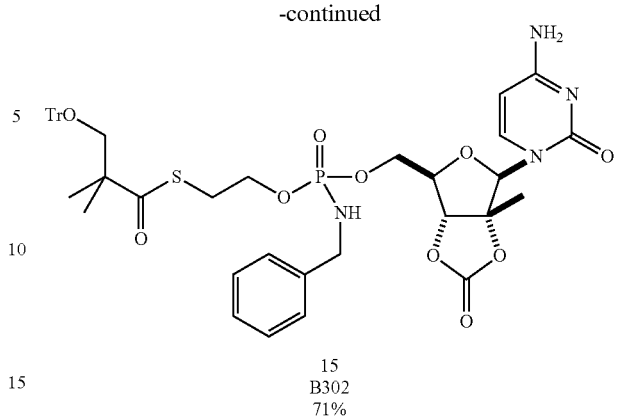

Protected phosphoramidate 13 (1.72 g, 1.52 mmol) was dissolved in anhydrous dichloromethane (17 ml) under argon. 1,1'-Carbonyldiimidazole (251 mg, 1.55 mmol) was added and the reaction mixture was stirred at room temperature under argon for 1 h.

Analysis by TLC (8% MeOH in DCM) indicated incomplete conversion of starting material (Rf 0.35) to product (Rf 0.56). HPLC analysis (method Test20, 272 nm) confirmed the profile: 9% starting material (Rt 7.30 min) and 91% product (Rt 7.97 min).

Further portions of CDI (final total 299 mg, 1.84 mmol) were added and the reaction mixture was left to stir for an additional 24 h at room temperature after which time analysis by HPLC indicated 1.5% SM and 97.5% P.

The reaction mixture was evaporated in vacuo to give an off-white foam (1.97 g). Purification by silica gel plug column, eluting with ethyl acetate, and evaporation of the appropriate fractions gave the protected cyclic carbonate 14 ($C_{65}H_{65}N_4O_{12}PS$ 1157.27 gmol$^{-1}$) as a white foam (1.62 g, 92% yield). TLC (8% MeOH in DCM): Rf 0.56; HPLC Test20 AUC: 99.5% @ 254 nm, Rt 7.97 min; m/z (ESI-): 1155.9 [M-H]$^-$ 100%; m/z (ESI+): 1157.5 [M+H]$^+$ 100%, 1179.5 [M+Na]$^+$ 20%.

Protected cyclic carbonate 14 (1.50 g, 1.30 mmol) was dissolved in anhydrous dichloromethane (15 ml) at room temperature under argon. Neat trifluoroacetic acid (1.77 g, 15.5 mmol) was added dropwise to the reaction mixture which was then stirred for 45 min at room temperature. Analysis by HPLC (method Test20, 272 nm) indicated disappearance of starting material (Rt 7.97 min) and formation of product (Rt 3.80 min).

Anhydrous methanol (5 ml) was added to the reaction mixture and solvents (10 ml) were partially removed in vacuo at 25° C. Further methanol (7 ml) was added to the mixture which was then evaporated to give an orange residue. Trituration with hexane/TBME 3:2 (12 ml) for 20 min yielded a sticky residue plus an opaque supernatant which was decanted. Retrituration with hexane/TBME 3:2 (5 ml) for 1 h and removal of the second supernatant gave, after coevaporation with methanol (3 ml), a pale foam (1.18 g).

The crude foam was purified by reverse phase chromatography (loaded in 1 ml acetonitrile and eluted with 0%, 10%, 15%, 20%, 25%, 30% acetonitrile in water). Combination of the relevant fractions, evaporation of the solvents at 25° C. and chasing with ethanol (1 ml) gave cyclic carbonate 15, B302, as a white foamy solid (560 mg, 71% yield).

B302: $C_{25}H_{33}N_4O_{10}PS$ 612.59 gmol$^{-1}$
HPLC AUC (Method Test20): 99% @ 254 nm, Rt 3.83 min m/z (ESI+): 613.1 [M+H]⁺ 100%; 1225.5 [2M+H]⁺ 100%; 453.1 [N+H]⁺ 95% m/z (ESI−): 611.4 [M−H]⁻ 80%; 1223.9 [2M−H]⁻ 50%; 451.3 [N−H]⁻ 100%

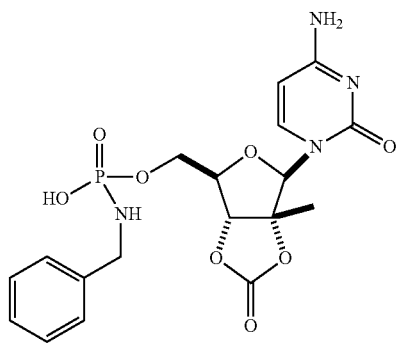

Fragment N =

Chemical Formula: $C_{18}H_{21}N_4O_8P$
Exact Mass: 452.1097

Exactly similar fragmentation is observed for B102 and B234.

$\nu_{max}$ (KBr disc) (cm$^{-1}$): 3346.4, 3206.5 O—H, intermolecular H-bond; 1815.3 C=O cyclic 5-ring carbonate; 1650.9 br C=O base, thioester KF: 1.54% H₂O content Specific Rotation: $[\alpha]_D^{20}$ +9.289 (c 10.104 mg cm$^{-3}$ in DMSO)

m.p.: 100-102° C. contracts and softens, 104-106° C. phase transition I, 127-135° C. phase transition II to a sticky glass, 140-150° C. partial melting to sticky residue, 200-210° C. decomposes to a brown sticky material Elemental Analysis: Calculated: C, 49.02%; H, 5.43%; N, 9.15%.

Found: C, 49.30%; H, 5.26%; N, 9.30%-passed with 0.26% F present (from TFA).

NMR: Assigned using ¹H, ¹³C, ³¹P, COSY, TOCSY, DEPT, HSQC and HMBC

H NMR $\delta_H$ (400 MHz, d6-DMSO): 1.11 (6H, s, (CH₃)₂C), 1.30 (3H, br-s, CH₃), 3.04 (2H, m, CH₂S), 3.44 (2H, d, J 4 Hz, CH₂OH), 3.87-3.92 (2H, m, CH₂O), 3.94-4.01 (2H, m, CH₂Ph), 4.15-4.25 (2H, m, H-5', H-5''), 4.37 (1H, br-s, H-4'), 4.95 (2H, br-s, H-3', CH₂OH), 5.75-5.77 (2H, 2xd, J 7 Hz, H-5, P—N—H), 6.07 (1H, br-s, H-1'), 7.22-7.25 (1H, m, Ar—H), 7.29-7.33 (4H, m, 4×Ar—H), 7.39, 7.44 (2H, 2×br-s, NH₂), 7.62 (1H, br-d, J=7 Hz, H-6)

¹³C NMR $\delta_C$ (100 MHz, d6-DMSO): 17.72 (CH₃), 21.78 (C(CH₃)₂), 28.13, 28.21 (CH₂S), 44.17 (PhCH₂), 51.62 (C(CH₃)₂), 63.84, 63.89 (CH₂O), 64.55 (C-5'), 68.29 (CH₂OH), 94.23 (C-5), 126.70 (Ar—C$_{para}$), 127.08, 128.11 (2×Ar—C$_{meta}$, 2×Ar—C$_{ortho}$), 140.35, 140.38 (Ar—C$_{ipso}$), 152.73, 154.45 (C-2, C-4), 165.69 (C-6), 203.87 (C=OS). C-1', C-2', C-3', C-4' and C=O broadened into baseline and were not observed.

³¹P NMR $\delta_P$ (162 MHz, d6-DMSO): 9.80, 9.94 (1P, 2xs, ratio 1.15:1.00)

Example 24

Preparation of B234, the Hydroxy-tBuSATE N-benzylphosphoramidate derivative of 3'-O-L-valinyl-2'-C-methylcytidine

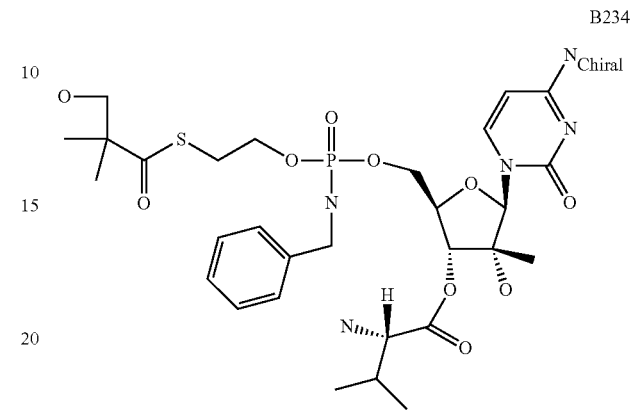

B234

The following strategy was used for the synthesis:

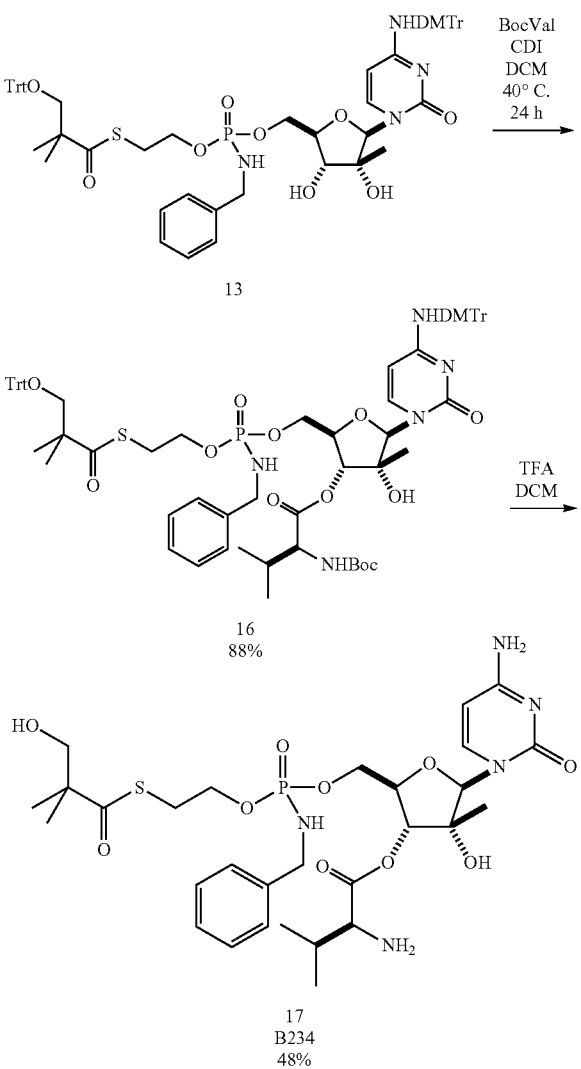

Boc protected valine (6.72 g, 30.94 mmol) was dissolved in anhydrous DCM (50 ml) and 1,1'-carbonyldiimidazole (4.87 g, 30.01 mmol) was added at room temperature under argon. Vigorous evolution of gas was observed initially during the activation step and the mixture was stirred at room temperature for 30 min.

Protected phosphoramidate 13 (10.0 g, 8.84 mmol) was dissolved in anhydrous dichloromethane (50 ml) in a separate vessel under argon. The activated Boc-Val solution was added dropwise to the phosphoramidate solution and the resulting mixture was heated to 40° C. under argon for 24 h.

Analysis by TLC (8% MeOH in DCM) indicated complete conversion of starting material 13 (Rf 0.35) to product (Rf 0.50). HPLC analysis (method Test20, 272 nm) confirmed the profile: starting material (Rt 7.30 min) and product (Rt 9.46 min).

The reaction mixture was evaporated in vacuo to give an off-white foam. Purification by silica gel column chromatography, loaded from DCM, eluting with ethyl acetate/hexane 1:1 then 100% ethyl acetate, and evaporation of the appropriate fractions gave the protected valine ester 16 ($C_{74}H_{84}N_5O_{14}PS$ 1330.52 gmol$^{-1}$) as a white foam (10.3 g, 88% yield). TLC (ethyl acetate): Rf 0.24; HPLC Test20 AUC: 97% @ 272 nm, Rt 9.46 min; m/z (ESI−): 1329.29 [M−H]$^-$ 100%; m/z (ESI+): 1331.68 [M+H]$^+$ 25%, 303.16 [DMTr]$^+$ 100%.

Protected valine ester 16 (3.0 g, 2.25 mmol) was dissolved in anhydrous dichloromethane (22.5 ml) at room temperature under argon. Neat trifluoroacetic acid (4.5 ml, 58.4 mmol) was added dropwise to the reaction mixture over 3 min which was then stirred for 1 h at room temperature. Analysis by HPLC (method Test20, 272 nm) indicated disappearance of starting material (Rt 9.46 min) and formation of product (Rt 3.33 min) along with significant Boc intermediate (Rt 4.60 min).

Additional neat trifluoroacetic acid (1.0 ml, 13.0 mmol) was added dropwise to the reaction mixture which was then stirred for a further 1 h at room temperature. Analysis by HPLC (method Test20, 272 nm) indicated disappearance of Boc intermediate (Rt 4.60 min) and formation of product (Rt 3.33 min).

The reaction mixture was cooled to 5° C. and anhydrous methanol (50 ml) was added, stirring for 30 min. Solvents were removed in vacuo at 25° C. The residue was treated with TBME (50 ml×3) and triturated, decanting the three TBME liquors.

The residual material was dissolved in anhydrous methanol (5 ml) and anhydrous DCM (10 ml) and solid sodium bicarbonate (5 g) was added, stirring for 30 min, to give pH 6. The clear liquid was passed through a syringe filter. The residual solid bicarbonate was washed with 25% methanol in DCM (anhydrous, 10 ml) and the solution was again filtered. The combined filtrates were concentrated in vacuo to give crude 17 (2.15 g).

The crude material was purified by reverse phase chromatography (loaded in 15 ml water and 3 ml acetonitrile and eluted with 0%, 5%, 20%, 30% acetonitrile in water). Combination of the relevant fractions and evaporation of the solvents at 25° C. gave valine ester 17, B234, as a white foamy solid (737 mg, 48% yield).

B234: $C_{29}H_{44}N_5O_{10}PS$ 685.73 gmol$^{-1}$
HPLC AUC (Method Test20): 99% @ 254 nm, Rt 3.33 min
m/z (ESI+): 686.3 [M+H]$^+$ 100%; 1371.6 [2M+H]$^+$ 20%; 526.1 [N+H]$^+$ 20%
m/z (ESI−): 744.4 [M+OAc]$^-$ 35%; 1369.8 [2M−H]$^-$ 35%; 1430.2 [2M+OAc]$^-$ 15%; 524.5 [N−H]$^+$ 100%

Fragment N =

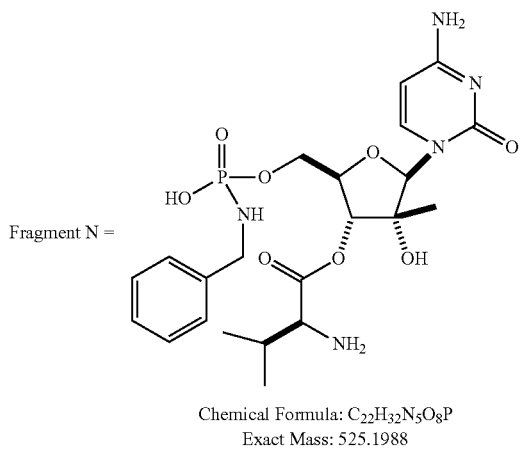

Chemical Formula: $C_{22}H_{32}N_5O_8P$
Exact Mass: 525.1988

Exactly similar fragmentation is observed for B102 and B302.

$v_{max}$ (KBr disc) (cm$^{-1}$): 3350.7, 3211.9 O—H, N—H, 1757.8 C=O ester; 1673.9, 1652.0 C=O thioester, base KF: 1.94% $H_2O$ content Specific Rotation: $[\alpha]_D^{20}$ +44.37° (c 10.033 mg cm$^{-3}$ in DMSO)

H NMR: Assigned using $^1$H, $^{13}$C, $^{31}$P, COSY, TOCSY, DEPT, HSQC and HMBC H NMR $\delta_H$ (400 MHz, d6-DMSO): 0.96, 0.98 (2×3H, 2×s, $(CH_3)_2CH$), 1.03 (3H, br-s, $CH_3$), 1.11 (6H, s, $(CH_3)_2C$), 2.15 (1H, m, $(CH_3)_2CH$), 3.03 (2H, m, $CH_2S$), 3.44 (2H, a-s, $CH_2OH$), 3.85 (1H, a-d, J 4.8 Hz, CHNH$_2$), 3.85-3.92 (2H, m, $CH_2O$), 3.92-4.00 (2H, m, $CH_2Ph$), 4.06-4.11 (1H, br-m, H-5'), 4.17-4.20 (1H, br-m, H-5"), 4.27-4.29 (1H, br-m, H-4'), 5.08 (1H, br-s, H-3'), 5.73 (1H, a-t, J 7.3 Hz, H-5), 5.74-5.82 (1H, m, P—N—H), 5.92 (1H, br-s, H-1'), 7.22-7.25 (1H, m, Ar—H), 7.28-7.32 (4H, m, 4×Ar—H), 7.60, 7.63 (2×0.5H, 2×d, J=7.3 Hz, H-6). 2×O—H and 2×NH$_2$ not observed.

$^{13}$C NMR $\delta_C$ (100 MHz, d6-DMSO): 17.84, 17.96 (CH $(CH_3)_2$), 20.42, 20.48 ($CH_3$), 21.78, ($C(CH_3)_2$), 28.09, 28.16 ($CH_2S$), 29.72 ($CH(CH_3)_2$), 44.16 ($PhCH_2$), 51.62 ($C(CH_3)_2$), 57.84 ($CHNH_2$), 63.77, 63.81 ($CH_2O$, C-5'), 68.26 ($CH_2OH$), 74.67 (C-3'), 77.28 (C-4'), 78.09 (C-2'), 91.32 (C-1'), 94.22 (C-5), 126.71 (Ar—$C_{para}$), 127.04, 127.08, 128.11 (2×Ar—$C_{meta}$, 2×Ar—$C_{ortho}$), 140.23, 140.27, 140.32 (Ar—$C_{ipso}$, C-6), 155.06 (C-2), 165.32 (C-4), 169.65, 169.72 ($CO_2R$), 203.84 (C=OS). C-1', C-3', C-4' broadened into baseline but observable.

$^{31}$P NMR $\delta_P$ (162 MHz, d6-DMSO): 9.63, 9.96 (1P, 2×s, ratio 1.02:1.00)

Example 25

Preparation of B183, the Hydroxy-tBuSATE N-benzylphosphoramidate Derivative of 2'-C-methyl-NH-4-acetyl-cytidine

B183

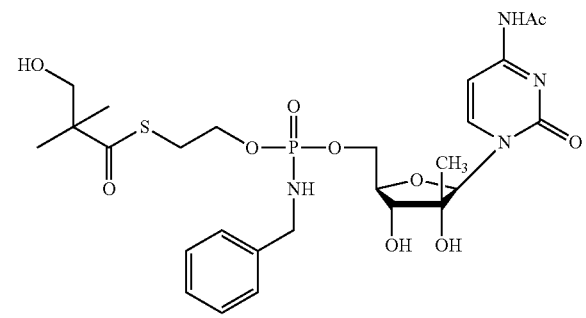

Synthetic Scheme

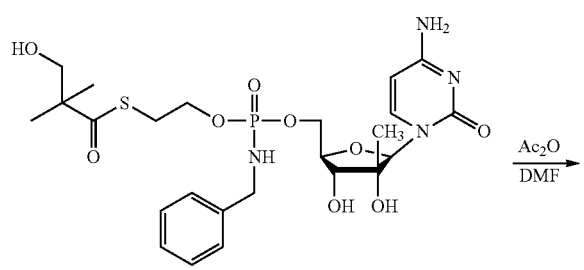

10

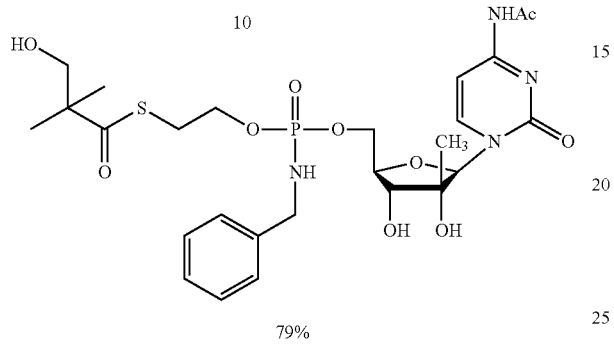

79%

To a solution of B102 (See Example 2) (compound 10, 200 mg, 0.34 mmol) in anhydrous dimethylformamide (3.4 ml) was added dropwise acetic anhydride (1.1 eq, 34 μl). The reaction mixture was stirred at room temperature for 4 h and 10 μl of acetic anhydride were added again. The reaction mixture was stirred overnight and the solvent evaporated under reduced pressure. The crude mixture was purified on silica gel column chromatography (eluant: stepwise gradient of methanol [0-10%] in methylene chloride) to give the desired acetylated pronucleotide B183 (169 mg, 79%) isolated as a white lyophilized powder. $^1$H NMR (DMSO-d$_6$, 400 MHz) δ (ppm) 0.93 (s, 3H), 1.09 (s, 6H), 2.09 (s, 3H), 3.01-3.04 (t, J=6.54 Hz, 2H), 3.40-3.42 (d, J=5.10 Hz, 1H), 3.53-3.62 (m, 2H), 3.83-3.91 (m, 1H), 3.94-4.01 (m, 4H), 4.10-4.15 (m, 1H), 4.20-4.25 (m, 1H), 4.88-4.91 (t, J=5.20 Hz, 1H), 5.23 (s, 1H), 5.33-5.37 (t, J=7.19 Hz, 1H), 5.67-5.78 (m, 1H), 5.93 (s, 1H), 7.18-7.21 (m, 1H), 7.27-7.32 (m, 5H), 7.96 and 8.03 (2d, J=7.59 Hz, 1H), 10.87 (s, 1H); $^{31}$P NMR (DMSO-d$_6$, 162 MHz) δ (ppm) 9.74 and 9.98 (2s); Scan ES$^+$ 629 (M+H)$^+$, λ$_{max}$=300.7 nm; HPLC (0-100% ACN over a period of 8 min) t$_R$=4.89 min λ$_{max}$=302.1 nm Example 26

Preparation of B187, the Hydroxy-tBuSATE N-(2-(trifluoromethyl)benzyl)phosphoramidate derivative of 2'-C-methylcytidine

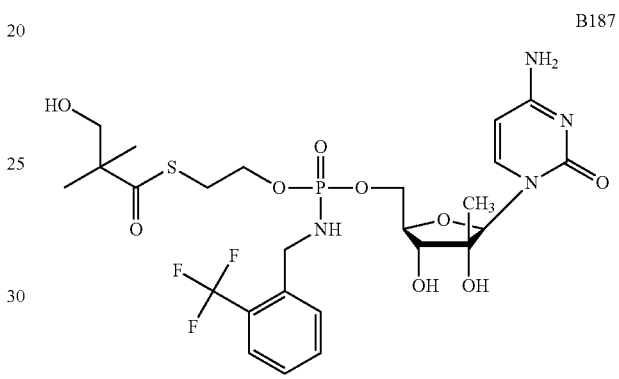

Synthetic Scheme

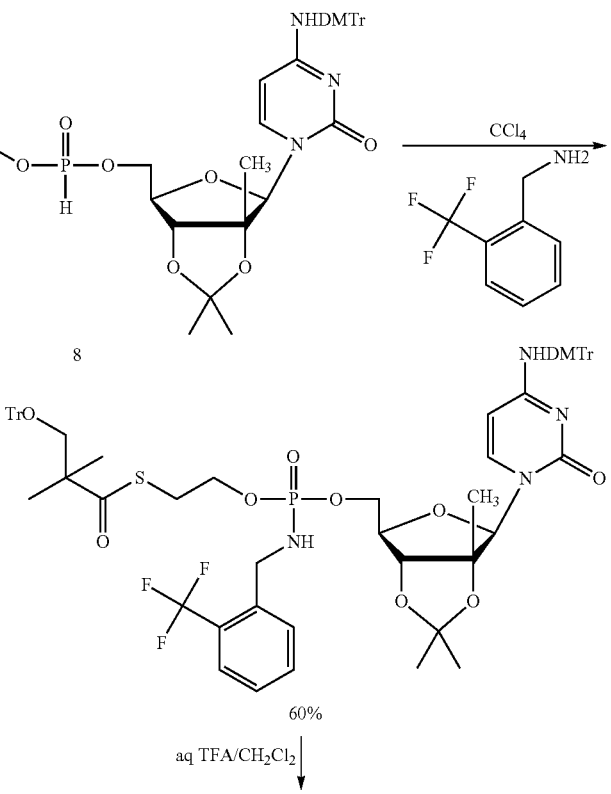

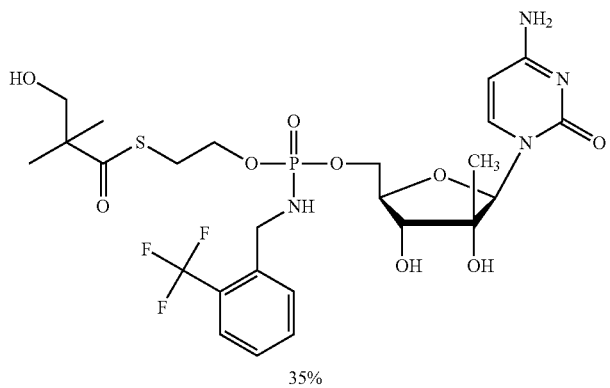

35%

To a solution of compound 8 (See Example 2, Procedure A, Strategy a) (1.4 g, 1.3 mmol) in anhydrous carbon tetrachloride (13 ml) was added dropwise N-2-(trifluoromethyl)benzylamine (10 eq, 2.3 g). The reaction mixture was stirred at room temperature for 3 h and the solvent removed under reduced pressure. The crude mixture was purified on silica gel column chromatography (eluant: stepwise gradient [0-3%] of methanol in methylene chloride) to afford the desired protected nucleoside as a foam (60%). This compound was converted into the phosphoramidate prodrug B187 (245 mg, 35%) following experimental conditions described in the Example 2 Strategy A and isolated as a white lyophilized powder. $^1$H NMR (DMSO-d$_6$, 400 MHz) δ (ppm) 0.92 (s, 3H), 1.09 (s, 6H), 3.05 (t, J=6.45 Hz, 2H), 3.29 (s, 1H), 3.41 (d, J=5.60 Hz, 2H), 3.91-3.93 (m, 3H), 4.17-4.21 (m, 4H), 4.91 (t, J=5.59 Hz, 1H), 5.06 (d, J=4.25 Hz, 1H), 5.23 (t, J=7.50 Hz, 1H), 5.65-5.67 (m, 1H), 5.76-5.83 (m, 1H), 5.91 (s, 1H), 7.08 and 7.16 (2s, 2H), 7.45-7.79 (m, 5H); $^{31}$P NMR (DMSO-d$_6$, 162 MHz) δ (ppm) 9.57-9.78 (2s, 1P); $^{19}$F NMR (d$_6$-DMSO, 235 MHz) δ (ppm) −60.79 (s, 3F); Scan ES$^+$ 655 (M+H)$^+$, λ$_{max}$=280.73 nm; HPLC (0-100% ACN over a period of 10 min) t$_R$=5.08 min λ$_{max}$=271.4 nm.

Example 27

Preparation of B399, the Hydroxy-tBuSATE N-(4-(trifluoromethyl)benzyl)phosphoramidate Derivative of 2'-C-methylcytidine

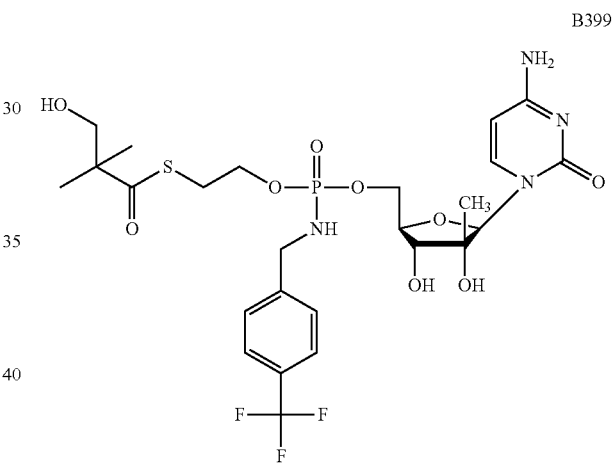

B399

Synthetic Scheme

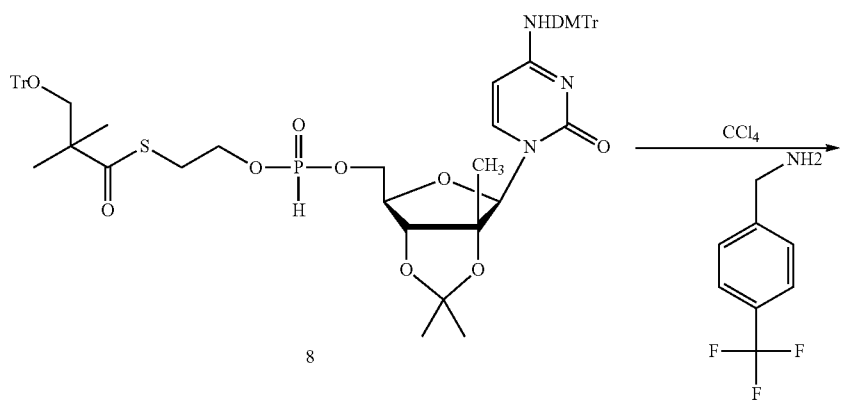

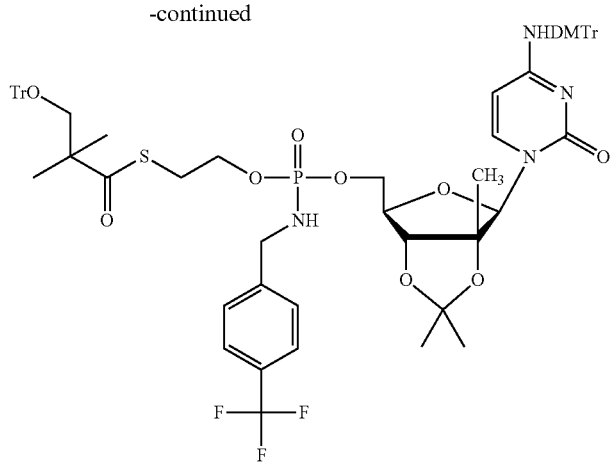

84% aq TFA/CH₂Cl₂ ↓

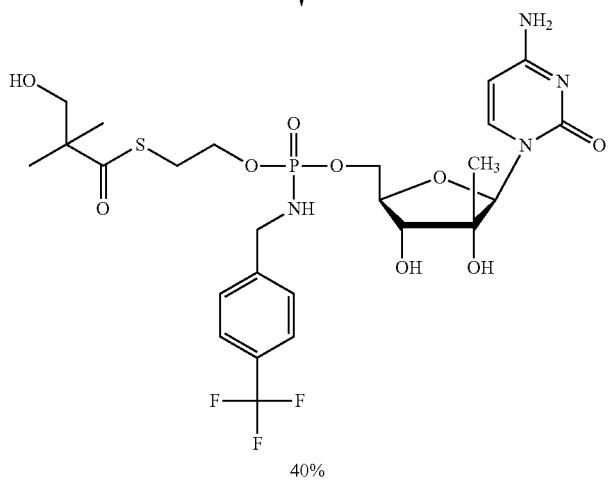

40%

To a solution of compound 8 (See Example 2, Procedure A, Strategy a) (1.0 g, 0.94 mmol) in anhydrous carbon tetrachloride (10 ml) was added dropwise N-4-trifluoromethylbenzylamine (5 eq, 670 µl). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (84%). This compound was converted into the phosphoramidate prodrug B399 (204 mg, 40%) following experimental conditions described in the Example 2 Strategy A and isolated as a white lyophilized powder. $^1$H NMR (DMSO-d$_6$, 400 MHz) δ (ppm) 0.91-0.92 (d, J=2.09 Hz, 3H), 1.09 (s, 6H), 3.02-3.06 (m, 2H), 3.41 (d, J=6.17 Hz, 2H), 3.53-3.57 (m, 1H), 3.84-3.94 (m, 3H), 4.03-4.13 (m, 3H), 4.18-4.23 (m, 1H), 4.91-4.94 (t, J=5.48 Hz, 1H), 5.06 (s, 1H), 5.23-5.27 (t, J=6.82 Hz, 1H), 5.65-5.67 (m, 1H), 5.79-5.87 (m, 1H), 5.90 (s, 1H), 7.09 and 7.16 (2s, 2H), 7.48-7.55 (m, 3H), 7.64-7.67 (m, 2H); $^{19}$F NMR (d$_6$-DMSO, 235 MHz) δ (ppm) −60.79 (s, 3F); $^{31}$P NMR (DMSO-d$_6$, 162 MHz) δ (ppm) 9.55 and 9.76 (2s); Scan ES$^+$ 655 (M+H)$^+$, λ$_{max}$=270 nm; HPLC (0-100% ACN over a period of 10 min) t$_R$=5.03 min λ$_{max}$=271 nm.

Example 28

Preparation of B204, the Hydroxy-tBuSATE N-(n-methyl-n-octyl-amine)phosphoramidate derivative of 2'-C-methylcytidine

B204

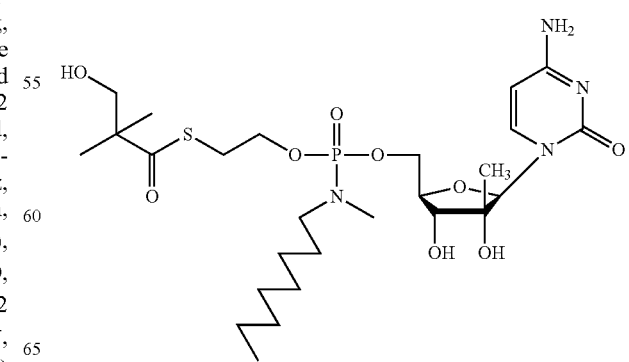

Synthetic Scheme

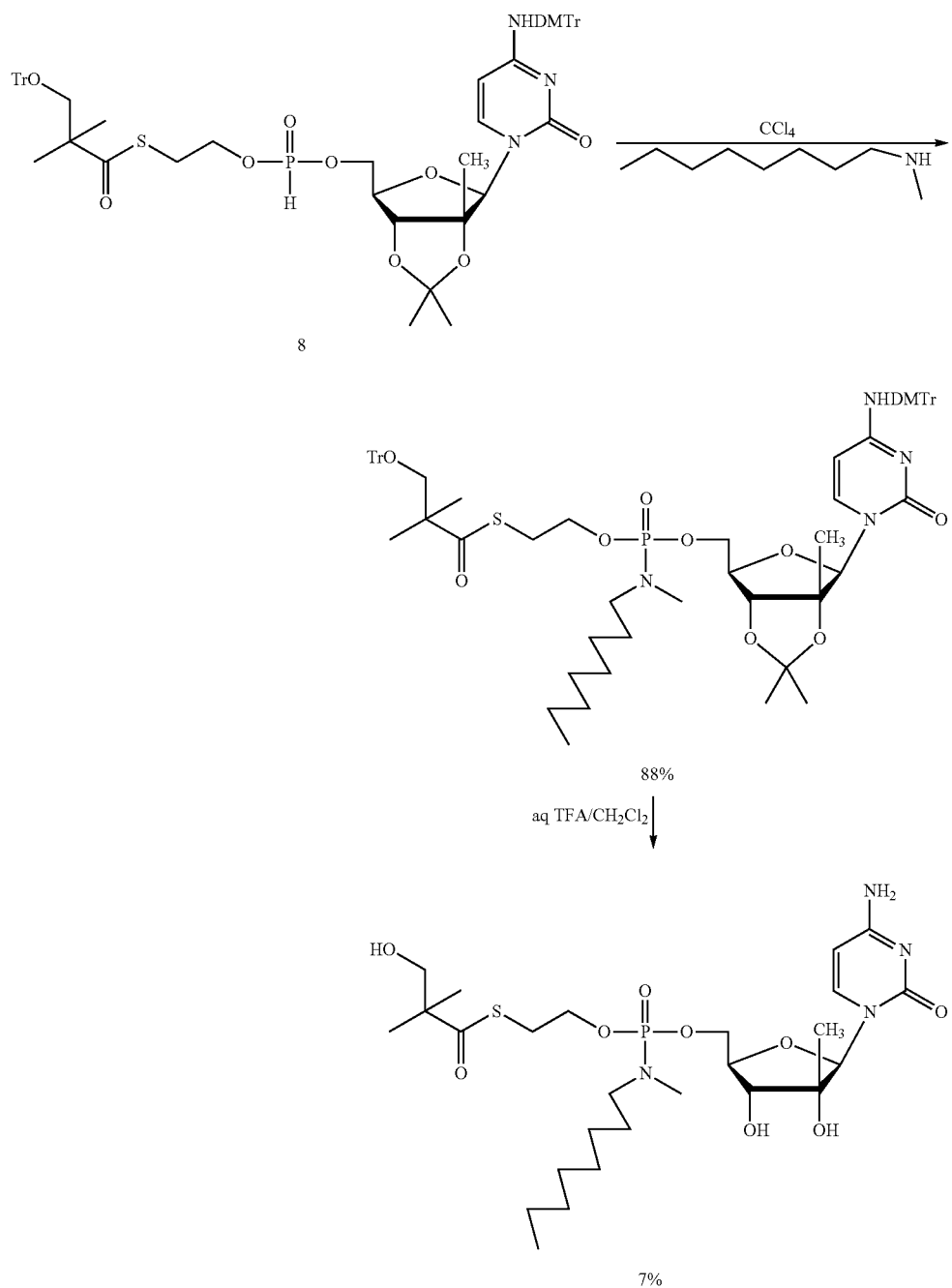

To a solution of compound 8 (See Example 2, Procedure A, Strategy a) (950 mg, 0.89 mmol) in anhydrous carbon tetrachloride (9 ml) was added dropwise n-methyl-n-octylamine (10 eq, 1.28 g). The reaction mixture was stirred at room temperature for 3 h and the solvent removed under reduced pressure. The crude mixture was purified on silica gel column chromatography (eluant: stepwise gradient [0-3%] of methanol in methylene chloride) to afford the desired protected nucleoside as a foam (88%). This compound was converted into the phosphoramidate prodrug B204 (52 mg, 7%) following experimental conditions described in the Example 2 Strategy A and isolated as a white lyophilized powder.

$^1$H NMR (DMSO-d$_6$, 400 MHz) δ (ppm) 0.83 (m, 3H), 0.93-0.94 (d, J=3.75 Hz, 3H), 1.10 (s, 6H), 1.22 (s, 10H), 1.44 (m, 2H), 2.56 (d, J=8.2 Hz, 3H), 2.88-2.93 (m, 2H), 3.31 (m, 2H), 3.43 (d, J=5.60 Hz, 2H), 3.50-3.53 (m, 1H), 3.91-3.93 (m, 3H), 4.04-4.07 (m, 1H), 4.13-4.16 (m, 1H), 4.91 (t, J=5.59 Hz, 1H), 5.06 (s, 1H), 5.23 (m, 1H), 5.65-5.67 (m, 1H), 5.91 (s, 1H), 7.08-7.16 (m, 2H), 7.50-7.57 (m, 1H); $^{31}$P NMR (DMSO-d$_6$, 162 MHz) δ (ppm) 10.52 and 10.66 (2s); Scan ES$^+$ 623 (M+H)$^+$, λ$_{max}$=280.73 nm; HPLC (0-100% ACN over a period of 8 min) t$_R$=6.07 min λ$_{max}$=274.9 nm.

Example 29

Preparation of B244, the Hydroxy-tBuSATE N,N-(dibutylamine)phosphoramidate Derivative of 2'-C-methylcytidine

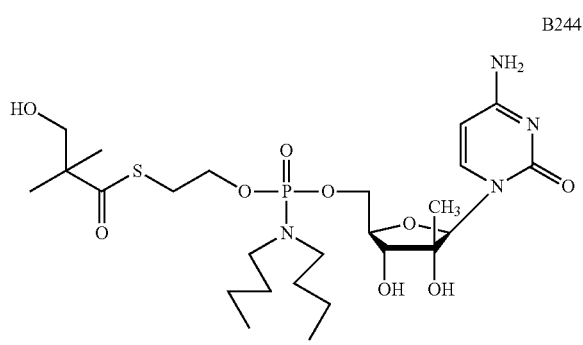

Synthetic Scheme

To a solution of compound 12 (See Example 2, Procedure A, Strategy b) (1.5 g, 1.46 mmol) in anhydrous carbon tetrachloride (15 ml) was added dropwise dibutylamine (10 eq, 2.5 ml). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (61%). This compound was converted into the phosphoramidate prodrug B244 (21 mg, 4%) following experimental conditions described in the Example 2 Strategy B and isolated as a white lyophilized powder. $^1$H NMR (DMSO-$d_6$, 400 MHz) δ (ppm) 0.76-0.81 (td, J=2.40 Hz and J=7.43 Hz, 6H), 0.86-0.87 (d, J=5.51 Hz, 3H), 1.05 (s, 6H), 1.11-1.19 (m, 4H), 1.33-1.39 (m, 4H), 2.80-2.87 (q, J=9.50 Hz, J=8.67 Hz, 4H), 3.01-3.04 (t, J=6.23 Hz, 2H), 3.42-3.43 (m, 2H), 3.50-3.60 (m, 1H), 3.81-3.88 (m, 3H), 3.97-4.01 (m, 1H), 4.07-4.10 (m, 1H), 4.84-4.87 (m, 1H), 5.06 (s, 1H), 5.23 and 5.29 (2d, J=8.0 Hz, 1H), 5.70 (s, 1H), 5.91 (brs, 1H), 7.10 and 7.17 (2s, 2H), 7.49 and 7.55 (2d, J=8.0 Hz, 1H); $^{31}$P NMR (DMSO-$d_6$, 162 MHz) δ (ppm) 10.44 and 10.56 (2s); Scan ES$^+$ 609 (M+H)$^+$, $\lambda_{max}$=279.7 nm; HPLC (0-100% ACN over a period of 8 min) $t_R$=5.59 min $\lambda_{max}$=274.9 nm.

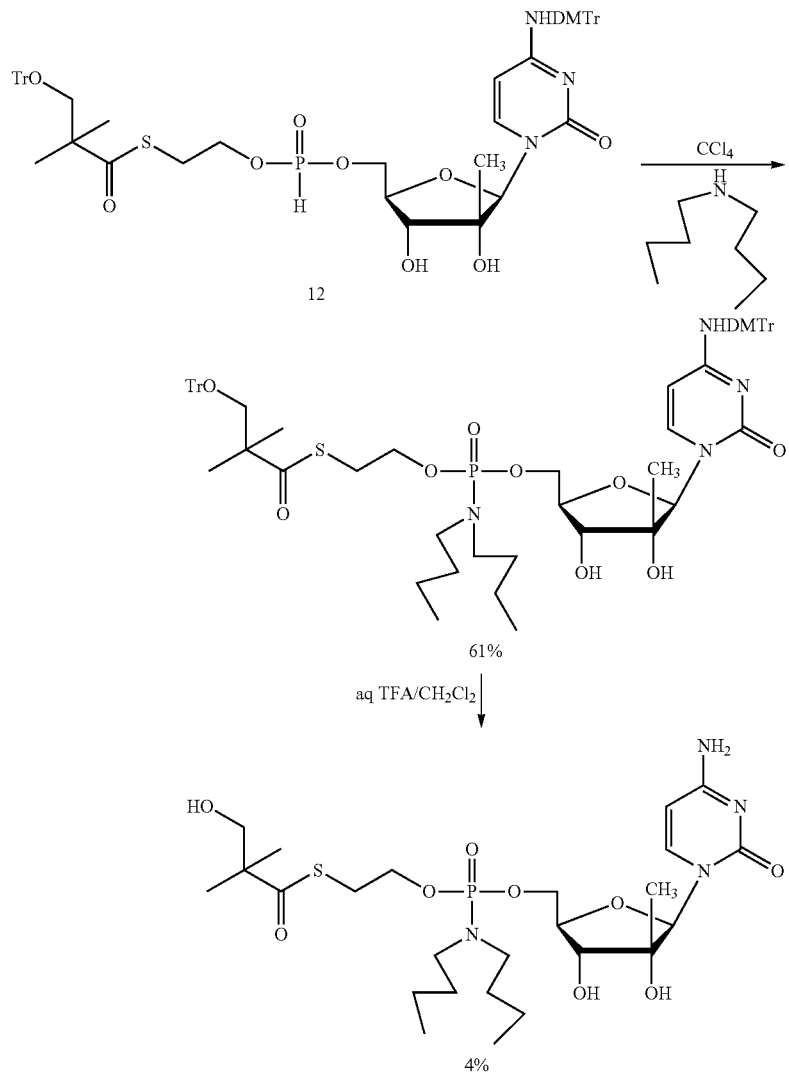

Example 30

Preparation of B308, the Hydroxy-tBuSATE N-methylbenzylphosphoramidate derivative of 2'-C-methyl-cytidine

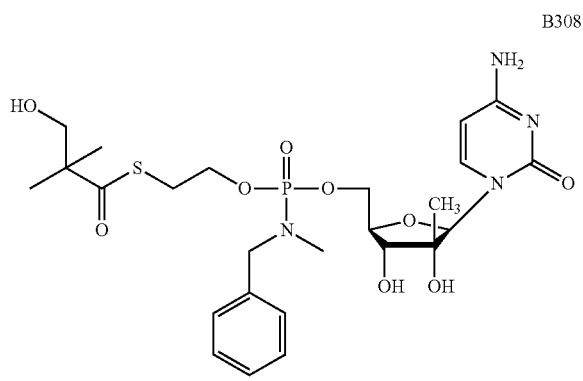

Synthetic Scheme

To a solution of compound 12 (See Example 2, Procedure A, Strategy b) (2.7 g, 2.6 mmol) in anhydrous carbon tetrachloride (26 ml) was added dropwise N-benzylmethylamine (5 eq, 1.67 ml). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (44%). This compound was converted into the phosphoramidate prodrug B308 (43 mg, 2%) following experimental conditions described in the Example 2 Strategy B and isolated as a white lyophilized powder.

$^1$H NMR (DMSO-$d_6$, 400 MHz) δ (ppm) 0.93-0.94 (s, 3H), 1.10 (s, 6H), 2.43-2.45 (d, J=4.26 Hz, 3H), 3.13 (t, J=6.23 Hz, 2H), 3.36-3.37 (d, J=5.24 Hz, 2H), 3.56-3.60 (m, 2H), 3.97-4.01 (m, 3H), 4.07-4.21 (m, 3H), 4.92-4.94 (m, 1H), 5.08 (s, 1H), 5.30-5.32 (m, 1H), 5.59-5.67 (2d J=8.0 Hz, 1H), 5.91 (s, 1H), 7.13 (m, 2H), 7.42-7.50 (m, 5H), 7.45-7.54 (2d J=8.0 Hz, 1H); $^{31}$P NMR (DMSO-$d_6$, 162 MHz) δ (ppm) 10.53 and 10.34 (2s); Scan ES$^+$ 601 (M+H)$^+$, $\lambda_{max}$=268.7; HPLC (0-100% ACN over a period of 8 min) $t_R$=3.37 min $\lambda_{max}$=274.9 nm.

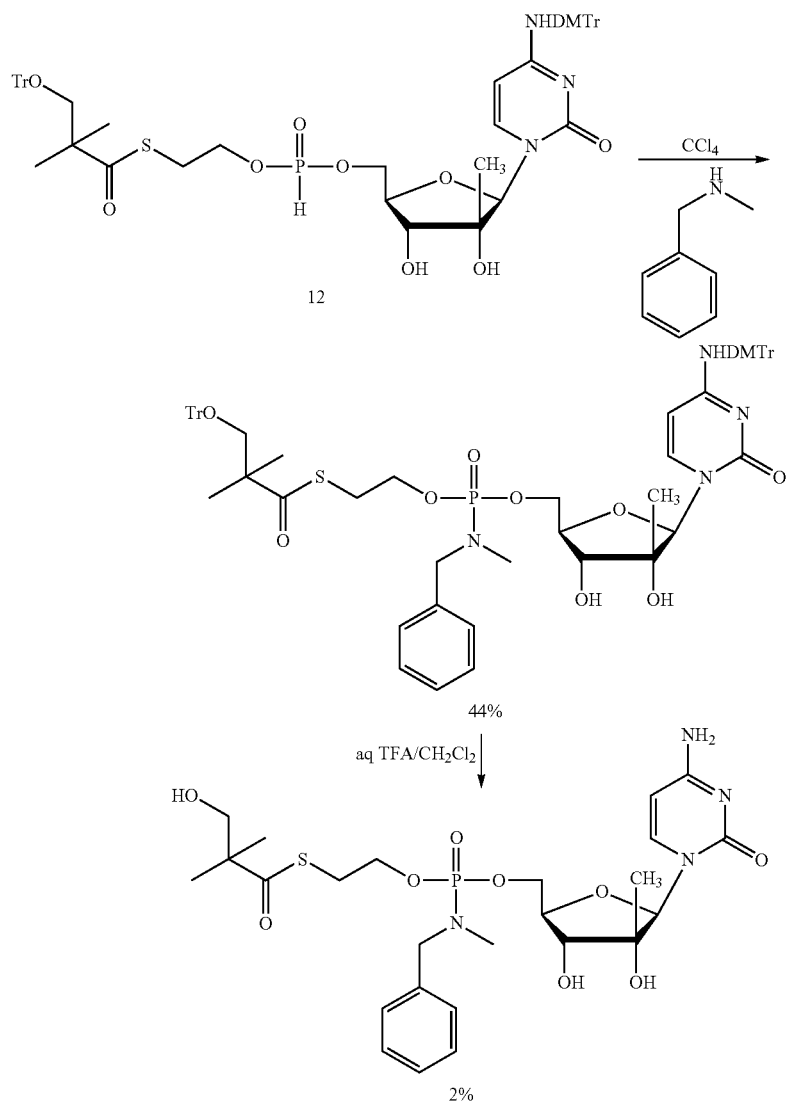

Example 31

Preparation of B353, the Hydroxy-tBuSATE N-piperidinephosphoramidate Derivative of 2'-C-methyl-cytidine

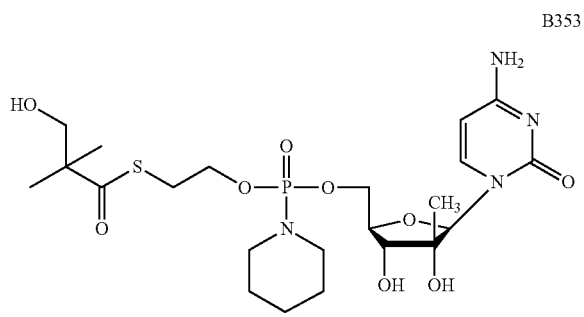

B353

Synthetic Scheme

To a solution of compound 12 (See Example 2, Procedure A, Strategy b) (300 mg, 0.29 mmol) in anhydrous carbon tetrachloride (3 ml) was added dropwise piperidine (5 eq, 145 µl). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (55%). This compound was converted into the phosphoramidate prodrug B353 (19 mg, 22%) following experimental conditions described in the Example 2 Strategy B and isolated as a white lyophilized powder. $^1$H NMR (DMSO-$d_6$, 400 MHz) δ (ppm) 0.92 (d, J=2.56, 3H), 1.10 (s, 6H), 1.44-1.43 (m, 4H), 1.50-1.53 (m, 2H), 2.97-3.02 (m, 4H), 3.07-3.10 (t, J=6.66 Hz, 2H), 3.42 (d, J=5.64 Hz, 2H), 3.56-3.60 (m, 1H), 3.89-3.94 (m, 3H), 4.04-4.10 (m, 1H), 4.13-4.20 (m, 1H), 4.91-4.93 (t, J=5.64 Hz, 1H), 5.06 (s, 1H), 5.25-5.31 (2d, J=9.31 Hz, 1H), 5.68 (m, 1H), 5.90 (s, 1H), 7.17 and 7.10 (2s, 2H), 7.50-7.55 (2d, J=9.01 Hz, 1H); $^{31}$P NMR (DMSO-$d_6$, 162 MHz) δ (ppm) 8.75 and 8.59 (2s); Scan ES$^+$ 565 (M+H)$^+$, $\lambda_{max}$=275.7 nm; HPLC (0-100% ACN over a period of 6 min) $t_R$=3.08 min $\lambda_{max}$=273.7 nm.

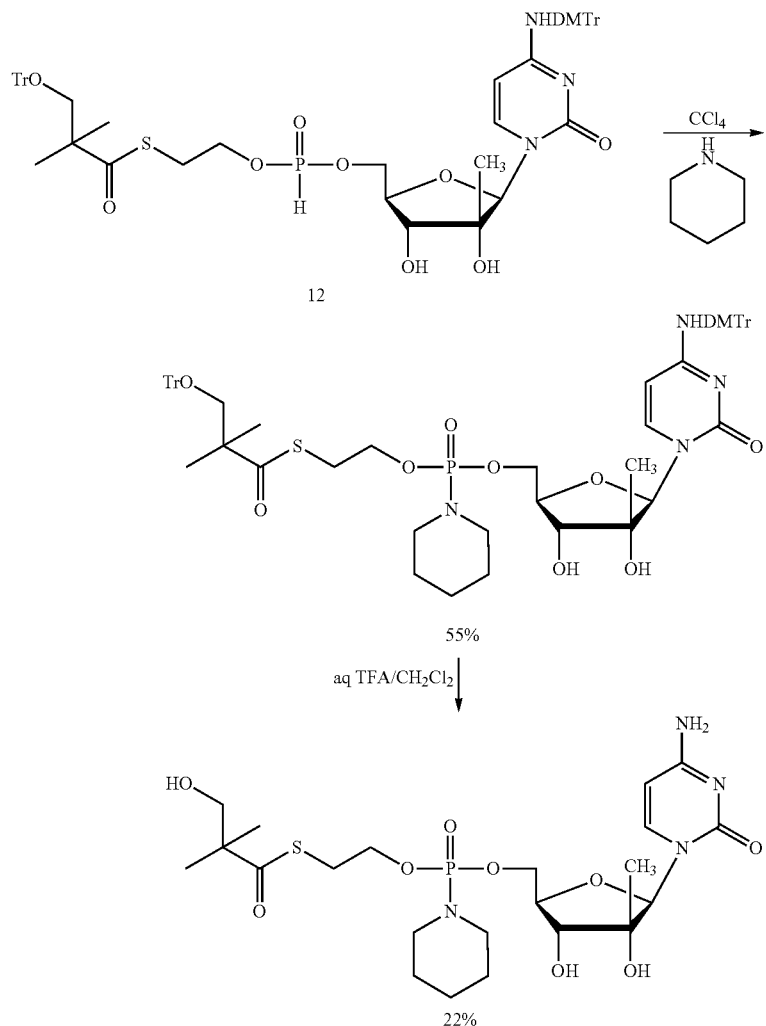

Example 32

Preparation of B354, the Hydroxy-tBuSATE N-cyclohexylaminephosphosphoramidate Derivative of 2'-C-methyl-cytidine

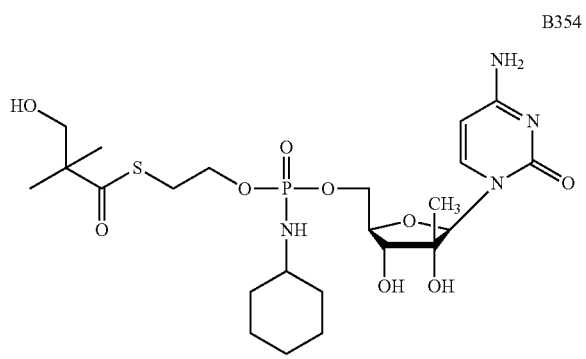

Synthetic Scheme

To a solution of compound 12 (See Example 2, Procedure A, Strategy b) (300 mg, 0.29 mmol) in anhydrous carbon tetrachloride (3 ml) was added dropwise cyclohexylamine (5 eq, 170 µl). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (55%). This compound was converted into the phosphoramidate prodrug B354 (44 mg, 50%) following experimental conditions described in the Example 2 Strategy B and isolated as a white lyophilized powder. $^1$H NMR (DMSO-$d_6$, 400 MHz) δ (ppm) 0.92 (d, J=2.56, 3H), 1.10 (s, 6H), 1.13 (m, 5H), 1.46-1.47 (m, 1H), 1.62 (m, 2H), 1.76-1.78 (m, 2H), 2.80 (m, 1H), 3.07-3.10 (t, J=6.66 Hz, 2H), 3.42 (d, J=5.64 Hz, 2H), 3.56-3.60 (m, 1H), 3.89-3.94 (m, 3H), 4.04-4.10 (m, 1H), 4.13-4.20 (m, 1H), 4.91-4.93 (t, J=5.64 Hz, 1H), 5.06 (m, 2H), 5.25 and 5.31 (2d, J=7.2 Hz, 1H), 5.68-5.71 (m, 1H), 5.90 (s, 1H), 7.19 and 7.09 (2s, 2H), 7.50 and 7.55 (2d, J=7.2 Hz, 1H); $^{31}$P NMR (DMSO-$d_6$, 162 MHz) δ (ppm) 9.05 and 8.91 (2s) Scan ES$^+$ 579 (M+H)$^+$, $\lambda_{max}$=280.7 nm; HPLC (0-100% ACN over a period of 6 min) $t_R$=3.23 min $\lambda_{max}$=274.9 nm.

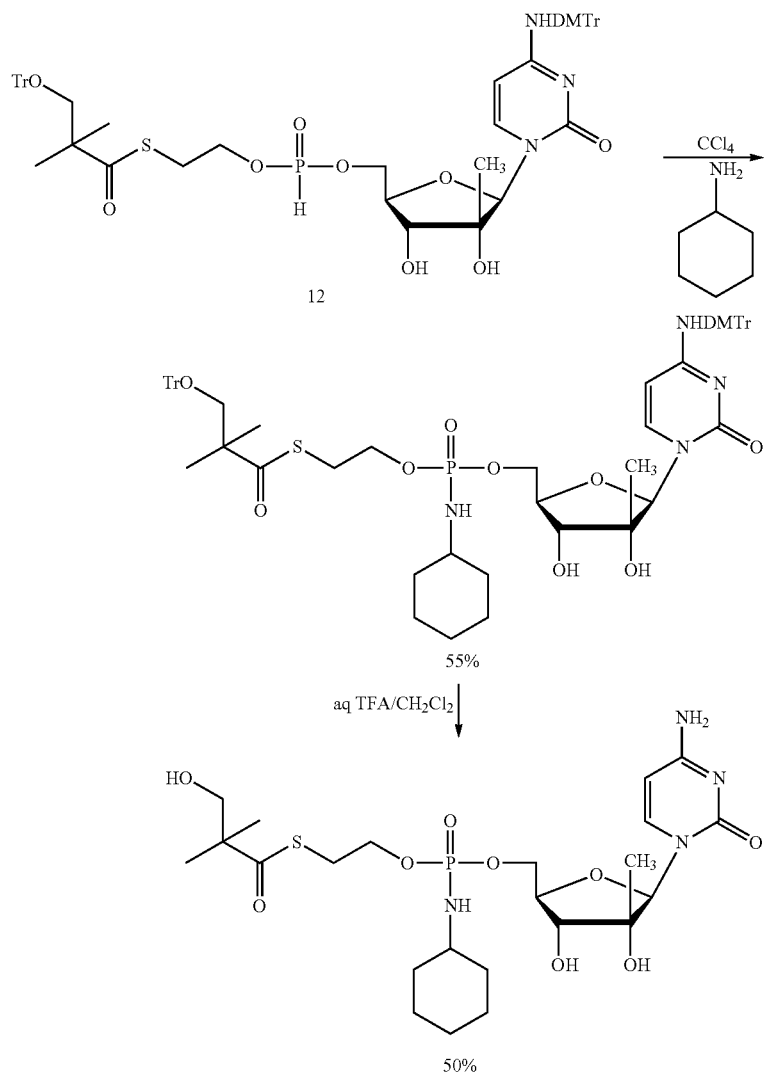

Example 33

Preparation of B391, the Hydroxy-tBuSATE N-morpholinophosphoramidate Derivative of 2'-C-methylcytidine

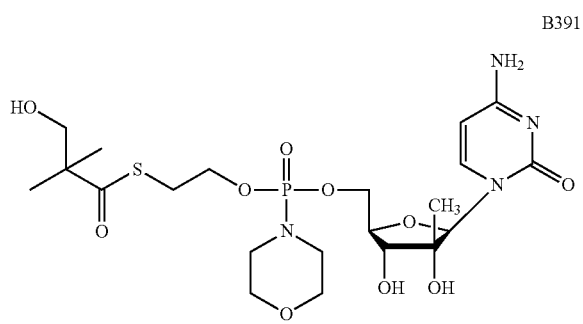

Synthetic Scheme

To a solution of compound 12 (See Example 2, Procedure A, Strategy b) (350 mg, 0.34 mmol) in anhydrous carbon tetrachloride (3.4 ml) was added dropwise morpholine (10 eq, 300 μl). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (70%). This compound was converted into the phosphoramidate prodrug B391 (53 mg, 49%) following experimental conditions described in the Example 2 Strategy B and isolated as a white lyophilized powder. $^1$H NMR (DMSO-d$_6$, 400 MHz) δ (ppm) 0.92 (d, J=2.56, 3H), 1.10 (s, 6H), 3.0 (m, 4H), 3.07-3.10 (t, J=6.66 Hz, 2H), 3.31 (s, 2H), 3.42 (d, J=5.64 Hz, 2H), 3.56-3.60 (m, 3H), 3.89-3.94 (m, 3H), 4.04-4.10 (m, 1H), 4.13-4.20 (m, 1H), 4.91-4.93 (t, J=5.64 Hz, 1H), 5.08 (s, 1H), 5.25-5.31 (m, 1H), 5.68-5.71 (d, J=7.2 Hz, 1H), 5.90 (s, 1H), 7.18 and 7.12 (2s, 2H), 7.52 and 7.50 (2d, J=7.6 Hz, 1H); $^{31}$P NMR (DMSO-d$_6$, 162 MHz) δ (ppm) 7.76 and 7.61 (2s); Scan ES$^+$ 567 (M+H)$^+$, $\lambda_{max}$=279.7 nm; HPLC (0-100% ACN over a period of 10 min) $t_R$=3.42 min $\lambda_{max}$=273.7 nm.

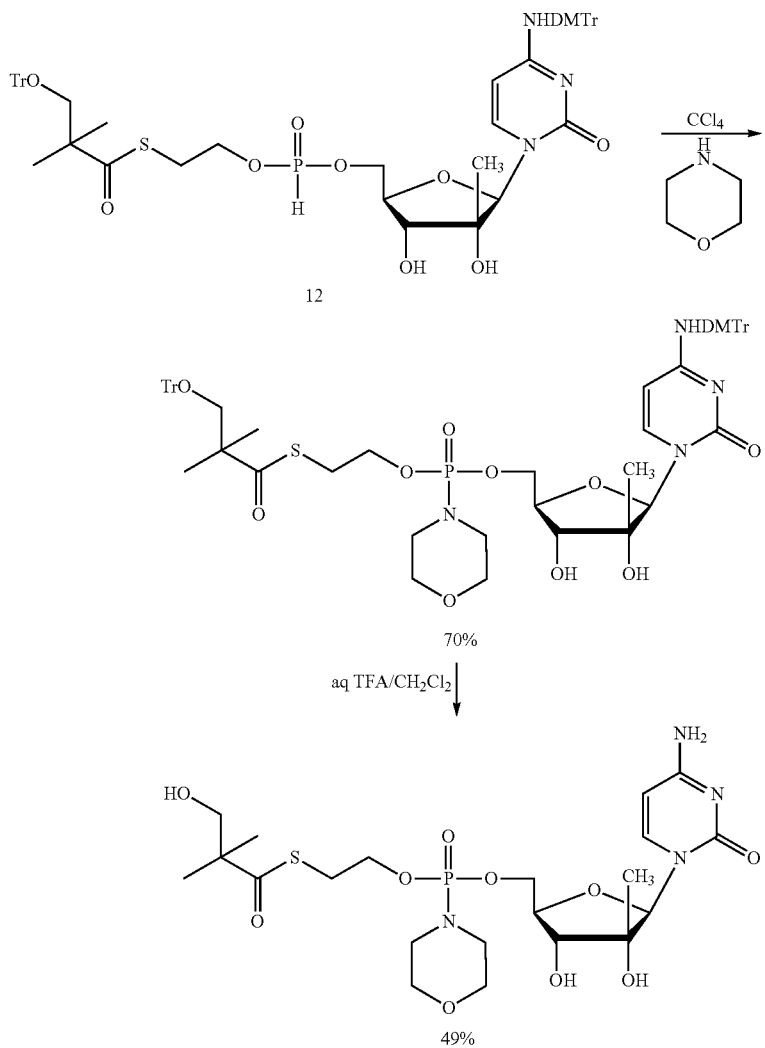

Example 34

Preparation of B395, the Hydroxy-tBuSATE N-pyrrolidinephosphoramidate derivative of 2'-C-methylcytidine

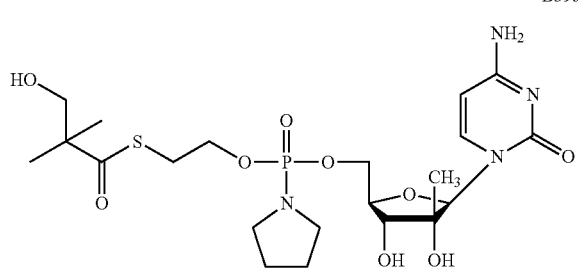

B395

Synthetic Scheme

To a solution of compound 12 (See Example 2, Procedure A, Strategy b) (500 mg, 0.49 mmol) in anhydrous carbon tetrachloride (5 ml) was added dropwise pyrrolidine (5 eq, 200 μl). The reaction mixture was stirred at room temperature for 3 h and the solvent removed under reduced pressure. The crude mixture was purified on silica gel column chromatography (eluant: stepwise gradient [0-5%] of methanol in methylene chloride) to afford the desired protected nucleoside as a foam (87%). This compound was converted into the phosphoramidate prodrug B395 (48 mg, 21%) following experimental conditions described in the Example 2 Strategy B and isolated as a white lyophilized powder. $^1$H NMR (DMSO-$d_6$, 400 MHz) δ (ppm) 0.93-0.94 (d, J=3.75 Hz, 3H), 1.10 (s, 6H), 1.78-1.79 (q, J=5.80 Hz, 4H), 3.09-3.09 (m, 6H), 3.42 (s, 2H), 3.57-3.59 (m, 1H), 3.92-3.93 (m, 3H), 4.09-4.11 (m, 1H), 4.16-4.18 (m, 1H), 4.93 (brs, 1H), 5.10 (s, 1H), 5.28-5.32 (t, J=8.00 Hz, 1H), 5.70 (d, J=8.0 Hz, 1H), 5.89 (s, 1H), 7.27 and 7.40 (2s, 2H), 7.55 and 7.61 (2d, J=8.0 Hz, 1H); $^{31}$P NMR (DMSO-$d_6$, 162 MHz) δ (ppm) 7.56 and 7.69 (2s); Scan ES$^+$ 551 (M+H)$^+$, $\lambda_{max}$=275.7 nm; HPLC (0-100% ACN over a period of 10 min) $t_R$=3.88 min $\lambda_{max}$=273.7 nm.

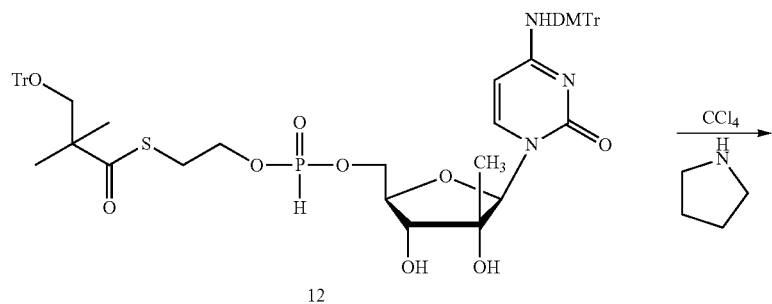

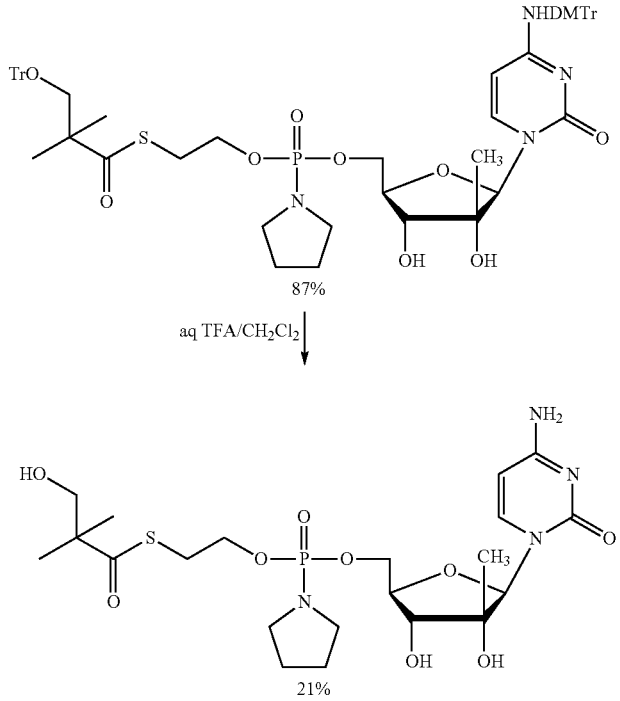

Example 35

Anti-HBV Activity

The compound of Example 1 (NM 204) (Hydroxy-tBu-SATE N-benzylphosphoramidate derivative of L-ddA) (A550) was contacted with HBV-infected HepG2 cells. $EC_{50}$ values were measured according to standard techniques. As shown in the table below, the compound of Example 1 showed significant activity compared to parent molecule LddA.

| Drug | N | HBV wt (HepG2) $EC_{50}$ (μM) |
|---|---|---|
| LddA | 3 | >10 |
| Ex 1 (A550) | 3 | 0.062 ± 0.018 |
| LdT | 3 | 0.26 ± 0.048 |
| Lamivudine | 3 | 0.022 ± 0.007 |

Example 36

Preparation of Calibration Curve for Measurement of ddATP

Measurements of the concentration of 2'-3'-dideoxyadenosine-5'-triphosphate (ddATP) (the triphosphate nucleotide of 2'-3'-dideoxyadenosine (ddA) are performed by liquid chromatography tandem mass spectrometry (LC/MS/MS), e.g., of methanolic extracts of hepatocytes.

The concentration of ddATP is measured by comparison to a standard curve.

Working stock solutions of TP-ddA are prepared from a 100 pmol/μl stock solution in de-ionized water of ddATP (tetrasodium salt of >91% purity) purchased from Sigma Chemical Co as follows:

| ddATP working stock solutions and Preparation of Standard Curve for ddATP. | | | | | | |
|---|---|---|---|---|---|---|
| 1. Working stock#1 | | | | | | |
| Test compound | Stock conc pmol/μL | Vol taken μL | DIH₂O vol μL | Total vol μL | Conc pmol/μl | mol per 10 μL |
| TP-ddA | 100 | 2000 | 2000 | 4000 | 50.0 | 500 |
| Test article | Stock conc pmol/μl | Vol taken μL | DIH2O vol μL | Total vol μL | Conc pmol/μl | |
| 2. Working stock#2 | | | | | | |
| TP-ddA | 100 | 1000 | 3000 | 4000 | 25.0 | 250 |
| 3. Working stock#4 (prepared from stock#1) | | | | | | |
| TP-ddA | 100 | 500 | 3500 | 4000 | 12.5 | 125 |
| 4. Working stock#5 (prepared from stock#1) | | | | | | |
| TP-ddA | 100 | 200 | 3800 | 4000 | 5.0 | 50 |
| 5. Working stock#6 (prepared from stock#1) | | | | | | |
| TP-ddA | 100 | 100 | 3900 | 4000 | 2.5 | 25 |
| 6. Working stock#7 (prepared from stock#1) | | | | | | |
| TP-ddA | 100 | 40 | 3960 | 4000 | 1.0 | 10 |

Internal standard (ISTD) working stock are prepared from a 0.50 mg/mL stock solution of 2-deoxyadenosine 5-triphosphate purchased from Sigma Chemical Co.

| ISTD | Stock conc μg/mL | Vol taken μl | MeOH vol μl | Total vol μl | Conc μg/mL | Conc pmol/mL |
|---|---|---|---|---|---|---|
| dATP | 500 | 200 | 9800 | 10000 | 10 | 500 |

In some embodiments, calibration standards are prepared as follows using liver samples:

| Preparation of cal stds: | | | | | | | | |
|---|---|---|---|---|---|---|---|---|
| cal std# | std conc pmol/ml | liver wt G | working stock# | working stock con pmol/μL | working stock vol μL | ISTD vol μL | MeOH vol μL | total vol μL |
| Blk | 0 | 0.1 | | | 0 | 50 | 940 | 990 |
| #1 | 50 | 0.1 | #5 | 5.0 | 10 | 50 | 940 | 1000 |
| #2 | 125 | 0.1 | #4 | 12.5 | 10 | 50 | 940 | 1000 |
| #3 | 250 | 0.1 | #3 | 25.0 | 10 | 50 | 940 | 1000 |
| #4 | 500 | 0.1 | #2 | 50.0 | 10 | 50 | 940 | 1000 |
| #5 | 1000 | 0.1 | #1 | 100.0 | 10 | 50 | 940 | 1000 |

In some embodiments the following HPLC conditions are used for the HPLC MS, e.g. HPLC Tandem MS analysis instrument method:

HPLC is conducted on Phenomenex Luna Amino 3 μm 100A, 30×2 mm column, with a mobile phase: A: 70% 10 mM NH4OAc 30% ACN pH 6.0; and B: 70% 1 mM NH4OAc 30% ACN pH 10.5 as follows:

| Gradient elution program: | | | | |
|---|---|---|---|---|
| Step | Time(min) | Flow (μl/min) | A (%) | B (%) |
| 0 | 0 | 400 | 60 | 40 |
| 1 | 1.1 | 400 | 60 | 40 |
| 2 | 1.11 | 400 | 40 | 60 |
| 3 | 2.11 | 400 | 30 | 70 |
| 4 | 2.6 | 400 | 20 | 80 |
| 5 | 3.1 | 400 | 0 | 100 |
| 6 | 5.5 | 400 | 0 | 100 |
| 7 | 5.51 | 400 | 60 | 40 |
| 8 | 10 | 400 | 60 | 40 |

-continued

| Gradient elution program: | |
|---|---|
| Injection volume: | 50 ul |
| Flow rate to MS: | 0.400 mL/min, no splitting of flow |

| Multiple Reaction Monitoring (MRM) conditions: (API3000) | |
|---|---|
| Ionization Mode: | Positive Ion Electrospray (ESI+) |
| IonSpray Voltage (IS): | 5000 V |
| Temperature (TEM): | 550° C. |
| Turbo IS gas | 8 L/min |
| Nebulizer (NEB): | 14 |
| CAD Gas Setting (CAD): | 6 |
| Declustering potential (DP) | 68 V |
| Collision energy (CE) | 27 eV |
| Entrance/Exit potentials (EP/CXP) | 10 V/11 V |

| Compound | Precursor ion | => | Product Ion |
|---|---|---|---|
| ddA triphosphate | 476.2 | => | 135.9 |
| ddA diphosphate | 396.2 | => | 135.9 |
| dA triphosphate (ISTD) | 460.2 | => | 135.9 |

*Luna Amino column is directly connected on the inlet end to a "Security Guard" cartridge holder suitable for 2.1 mm Phenomenex columns, containing a C18 cartridge.

Example 37

In Vitro Phosphorylation in Hepatocytes

Primary hepatocytes (Rat, Cynomolgus Monkey or human) were seeded at $0.8 \times 10^6$ in a collagen-coated 12-well plate and allowed to attach 4-6 hours after which time the seeding medium was replaced with serum-free culture medium and cells allowed to acclimatize to the new medium overnight. On the next day, cells were exposed for 1, 4, 8 and 24 hours to test article (NM204) (A550) at 10 and 50 μM prepared in fresh culture medium from stock solution in DMSO (final DMSO concentration was 0.1%). At each time point, an aliquot (500 μl) was collected and immediately added to 500 μl of acetonitrile and stored at −20° C. until analysis. The remaining exposure medium was removed and the cell monolayer (stuck to dish) washed 2 times with ice-cold PBS. Any remaining PBS was carefully removed by aspiration and cells were harvested by scraping in 1 mL 70% ice-cold methanol. Cell samples were placed overnight at −20° C. and cellular debris removed by centrifugation on the next day. The supernatants were removed and filtered prior to analysis by LC/MS. A standard curve was prepared by using untreated cells processed similarly except that prior to harvesting in 70% methanol, 10 μl of LddATP standard solutions prepared in methanol were added to the washed monolayers. These control samples were then processed and analyzed as described for test samples.

The results are shown below:

| LddA-TP formation in hepatocytes | | | |
|---|---|---|---|
| | LddA TP Levels (pmol/million cells) | | |
| Time (hour) | Rat | Monkey | Human |
| Ex 1 (A550) 10 μM | | | |
| 1 | 159.5 | 287.5 | 161.5 |
| 4 | 388.0 | 978.0 | 312.5 |
| 8 | 468.5 | 1230.0 | 352.5 |
| 24 | 422.0 | 344.0 | 366.0 |

| LddA-TP formation in hepatocytes | | | |
|---|---|---|---|
| | LddA TP Levels (pmol/million cells) | | |
| Time (hour) | Rat | Monkey | Human |
| Ex 1 (A550) 50 μM | | | |
| 1 | 393.0 | 2085.0 | 682.5 |
| 4 | 1212.0 | 5690.0 | 1480.0 |
| 8 | 1590.0 | 6030.0 | 1930.0 |
| 24 | 1505.0 | 3030.0 | 2062.5 |

As indicated from the data, significant levels of L-ddATP were detected in the hepatocytes. In monkey hepatocytes, the levels appear to reach a maximum level at 8 hours followed by a rapid decline. In contrast, levels in both rat and human hepatocyte appear to level off after 8 hours.

Example 38

In Vivo Studies in Rat

Distribution of NM-204 (the compound of Example 1 (Hydroxy-tBuSATE N-benzylphosphoramidate derivative of L-ddA) (A550) in the rat liver was evaluated following a single intravenous (I.V.) or oral administration of A550 (NM-204) at a dose of 20 (oral) or 10 (I.V.) mg/Kg body weight. The dose solutions were prepared on the same day prior to dose administration.

At the specified time point (1 and 3 hours for IV animals or 1, 3 and 8 hours for oral animals), each animal was euthanized by $CO_2$ gas followed by exsanguination via the abdominal vein. Livers were collected immediately after sacrifice, flash frozen in liquid nitrogen, placed on dry ice, and later stored at −70° C., before being analyzed.

Preparation of Calibration Standards from Control Liver Extracts:

Control rat liver samples were taken from whole frozen livers (Bioreclamation, Inc. Hicksville, N.Y.) with the aid of a tissue coring utensil (Harris Unicore, 8.0 mm, VWR). Each ~0.1 g sample was placed in individual 2 mL poly vials with 0.940 mL of 80% MeOH/20% $DIH_2O$ and homogenates were prepared using a mechanical tissue disruptor (Tissue Master, Omni-International, Inc, Marietta Ga.). The vials received a 10 μl aliquot of a working stock solution and a 50 μl aliquot of the ISTD before vortexing for ~30 sec. The mixtures were stored overnight at −20° C. and the next day were removed for 10 min of centrifugation in a benchtop centrifuge. Each supernatant was transferred to individual centrifugation filtration units (0.45 μm) and the resulting filtrates were transferred to HPLC vials for the LC/MS/MS analysis. The final concentrations of ddATP in the calibration standards was 1000, 500, 250, 125, 50, and 0 pmol/ml. Each calibration standard was directly injected in a 50 μL volume onto the ion-exchange column for analysis. Standard curve analysis of calibration standards from control liver extracts was conducted.

Analysis of ddATP was done by an ion-exchange chromatography method with on-line positive ionization ESI-MS/MS detection in multiple reaction monitoring (MRM) detection mode. The peak areas obtained for 4 of the 5 calibrants allowed for construction of a standard curve that demonstrated good linearity ($R^2$=0.9996) over a 50-1000 pmol/ml concentration range. This is equivalent to a range of 5-100 pmol per gram liver by the sample preparation employed. The HPLC MS MS conditions described in Example 5 were utilized. The lower limit of quantitation demonstrated by the LC/MS/MS method is e.g., ~0.2 pmol/mL for hepatocyte cellular extracts which contain much less salt.

The results showing intracellular levels of A550 (NM204) (showing the compound entered the liver cells) and LddATP (showing cleaving of the phosphoramidate moiety and triphosphorylation of the ddA to the active triphosphate in the liver) are shown below:

| A550 (Ex 1) and LddATP measured in livers of male rats dosed IV or O with A550 (Ex 1) | | | | |
|---|---|---|---|---|
| | Concentration Compound (A550) (Ex 1) | Timepoint | Concentration. ddA-TP | |
| Animal Number | (pmol/g liver) | (hrs) | (pmol/g liver) | (pmol/$10^6$ cells)* |
| IV dose (10 mg/kg) | | | | |
| 1M1 | 65.8 | 1 | 2025 | 17.8 |
| 1M2 | 89.1 | 1 | 1930 | 16.9 |
| 1M3 | 85.1 | 1 | 1355 | 11.9 |
| Mean | 80.0 | | 1770 | 15.5 |
| 2M1 | 28.3 | 3 | 1345 | 11.8 |
| 2M2 | 26.0 | 3 | 1940 | 17.0 |
| 2M3 | 29.3 | 3 | 2990 | 26.2 |
| Mean | 27.9 | | 2092 | 18.3 |
| Oral dose (20 mg/kg) | | | | |
| 3M1 | 411 | 1 | 210 | 1.8 |
| 3M2 | 272 | 1 | 575 | 5.0 |
| 3M3 | 70.2 | 1 | 400 | 3.5 |
| Mean | 251 | | 395 | 3.5 |
| 4M1 | 360 | 3 | 200 | 1.8 |
| 4M2 | 92.1 | 3 | 330 | 2.9 |
| 4M3 | 161 | 3 | 405 | 3.6 |
| Mean | 204 | | 312 | 2.7 |
| 5M1 | 16.4 | 8 | 280 | 2.5 |
| 5M2 | 28 | 8 | 805 | 5.2 |
| 5M3 | 16.2 | 8 | 275 | 2.4 |
| Mean | 20.1 | | 382 | 3.3 |

*Hepatocellularity number for rat was 114 × 106 cells per gram liver (*Toxicology in Vitro* 20 (2005) 1582-1586.

Thus, these results show that the compound can be used to enhance concentration of the drug in the liver. These results also show the enhanced concentration of the active triphosphate which is formed in the liver cells.

Example 39

HCV Replicon Assay

Huh-7 cells containing HCV Con1 subgenomic replicon (GS4.1 cells), (C. Seeger; Fox Chase University, Philadelphia, Pa., USA), are grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin and 0.5 mg/mL G418 (Invitrogen). For dose-response testing, the cells are seeded in 96-well plates at 7.5×$10^3$ cells/well in a volume of 50 µL and incubated at 37° C./5% $CO_2$. Three hours after plating, 50 µL of ten 2-fold serial dilutions of compounds (highest concentration, 75 µM) are added and cell cultures were incubated at 37° C./5% $CO_2$ in the presence of 0.5% DMSO. Alternatively, compounds are tested at a single concentration of 15 µM. In all cases, Huh-7 cells lacking the HCV replicon served as negative control. The cells are incubated in the presence of compounds for 72 hours after which they were monitored for expression of the NS4A protein by enzyme-linked immunosorbent assay (ELISA). For this, the plates were then fixed for 1 min with 1:1 acetone:methanol, washed twice with phosphate-buffered saline (PBS), 0.1% Tween 20, blocked for 1 hour at room temperature with TNE buffer containing 10% FBS and then incubated for 2 h at 37° C. with the anti-NS4A mouse monoclonal antibody A-236 (ViroGen) diluted in the same buffer. After washing three times with PBS, 0.1% Tween 20, the cells are incubated 1 hour at 37° C. with anti-mouse immunoglobulin G-peroxidase conjugate in TNE, 10% FBS. After washing as described above, the reaction is developed with O-phenylenediamine (Zymed). The reaction is stopped after 30 minutes with 2 N $H_2SO_4$ and the absorbance is read at 492 nm using a Sunrise Tecan spectrophotometer. $EC_{50}$ values are determined from the % inhibition versus concentration data using a sigmoidal non-linear regression analysis based on four parameters with Tecan Magellan software. When screening at a single concentration, the results are expressed as % inhibition at 15 µM. For cytotoxicity evaluation, GS4.1 cells are treated with compounds as described above and cellular viability was monitored using a Cell Titer 96 $AQ_{ueous}$ One Solution Cell Proliferation Assay (Promega). $CC_{50}$ values are determined from the % cytotoxicity versus concentration data with Tecan Magellan software as described above.

Results

Compounds presented in the table below were assayed according to the replicon assay described above.

| Compound Reference | Structure | HCV ELISA 2 | |
|---|---|---|---|
| | | EC$_{50}$ (µM) | CC$_{50}$ (µM) |
| NUCLEOSIDE PARENT: A634 (NM107) | 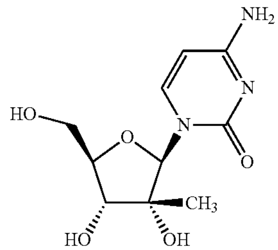 [SMILES: C[C@@]1(O)[C@H](O)[C@@H](CO)O[C@H]1n1ccc(N)nc1=O] | ++ | + |
| EXAMPLE 2: B102 | 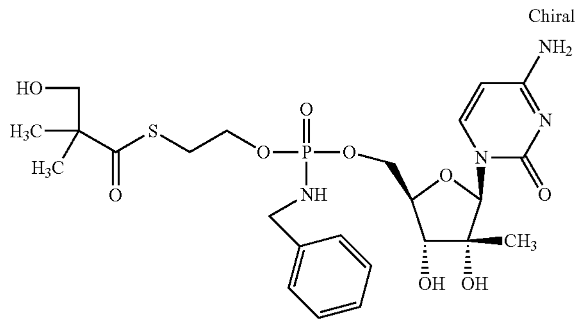 [SMILES: CC(C)(CO)C(=O)SCCOP(=O)(NCc1ccccc1)OC[C@H]1O[C@@H](n2ccc(N)nc2=O)[C@](C)(O)[C@@H]1O] | ++ | + |
| EXAMPLE 26: B187 | 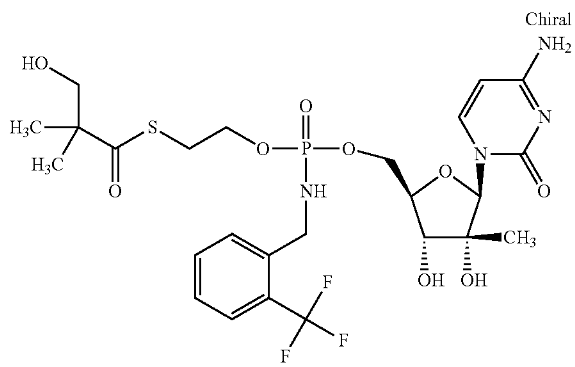 [SMILES: CC(C)(CO)C(=O)SCCOP(=O)(NCc1ccccc1C(F)(F)F)OC[C@H]1O[C@@H](n2ccc(N)nc2=O)[C@](C)(O)[C@@H]1O] | ++ | + |
| EXAMPLE 27: B399 | 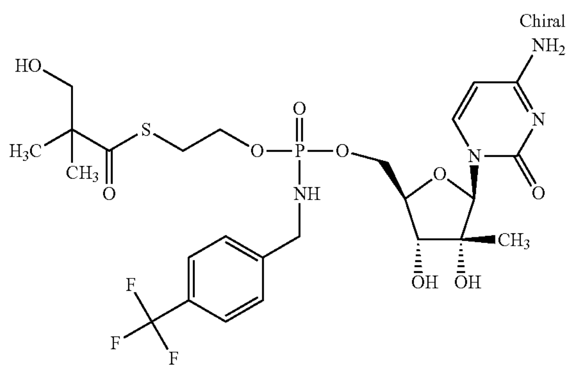 [SMILES: CC(C)(CO)C(=O)SCCOP(=O)(NCc1ccc(C(F)(F)F)cc1)OC[C@H]1O[C@@H](n2ccc(N)nc2=O)[C@](C)(O)[C@@H]1O] | ++ | + |

-continued

| Compound Reference | Structure | HCV ELISA 2 EC$_{50}$ (µM) | CC$_{50}$ (µM) |
|---|---|---|---|
| EXAMPLE 28: B204 | 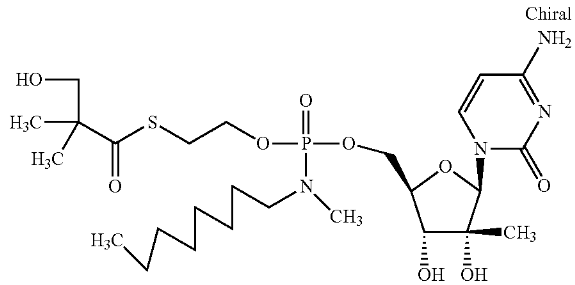 [SMILES: CCCCCCCCN(C)P(=O)(OCCSC(=O)C(C)(C)CO)OC[C@H]1O[C@@H](n2ccc(N)nc2=O)[C@](C)(O)[C@@H]1O] | ++ | + |
| EXAMPLE 29: B244 | 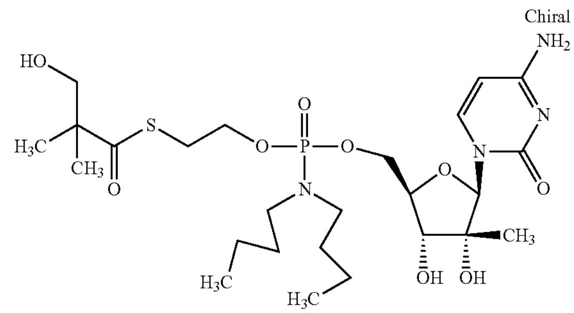 [SMILES: CCCCN(CCCC)P(=O)(OCCSC(=O)C(C)(C)CO)OC[C@H]1O[C@@H](n2ccc(N)nc2=O)[C@](C)(O)[C@@H]1O] | + | + |
| EXAMPLE 30: B308 | 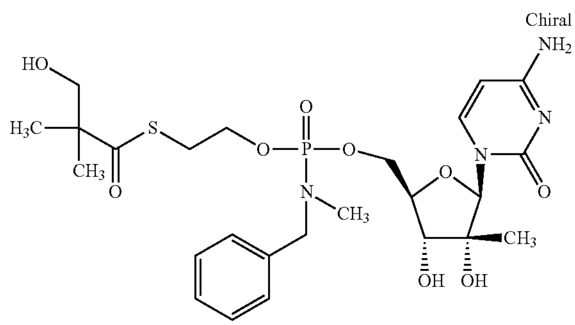 [SMILES: CN(Cc1ccccc1)P(=O)(OCCSC(=O)C(C)(C)CO)OC[C@H]1O[C@@H](n2ccc(N)nc2=O)[C@](C)(O)[C@@H]1O] | ++ | + |
| EXAMPLE 31: B353 | 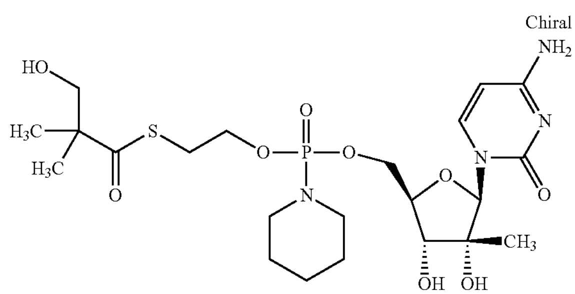 [SMILES: CC(C)(CO)C(=O)SCCOP(=O)(OC[C@H]1O[C@@H](n2ccc(N)nc2=O)[C@](C)(O)[C@@H]1O)N1CCCCC1] | + | + |
| EXAMPLE 32: B354 | 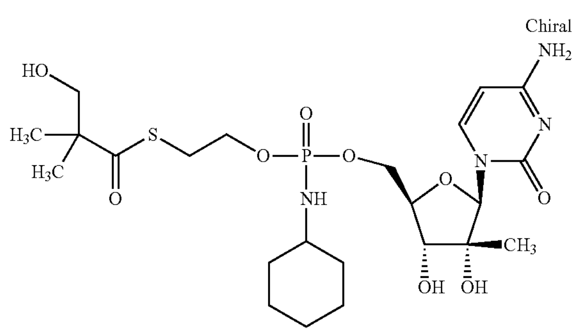 [SMILES: CC(C)(CO)C(=O)SCCOP(=O)(NC1CCCCC1)OC[C@H]1O[C@@H](n2ccc(N)nc2=O)[C@](C)(O)[C@@H]1O] | ++ | + |

-continued

| Compound Reference | Structure | HCV ELISA 2 EC$_{50}$ (μM) | CC$_{50}$ (μM) |
|---|---|---|---|
| EXAMPLE 33: B391 | 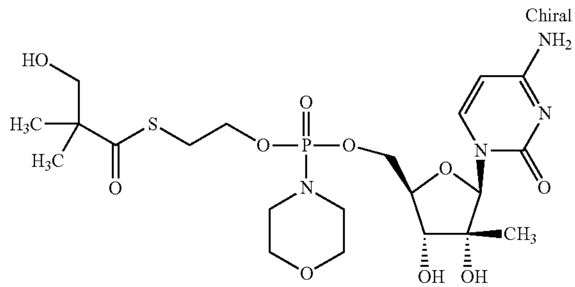 [SMILES: CC(C)(CO)C(=O)SCCOP(=O)(OC[C@H]1O[C@@H](n2ccc(N)nc2=O)[C@](C)(O)[C@@H]1O)N1CCOCC1] | + | + |
| EXAMPLE 34: B395 | 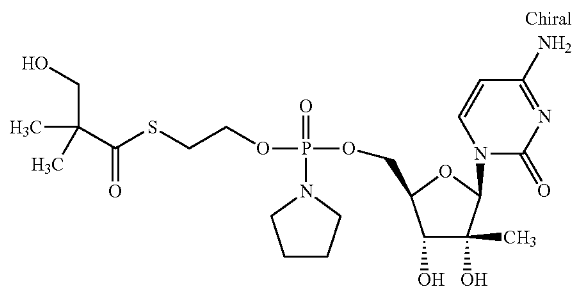 [SMILES: CC(C)(CO)C(=O)SCCOP(=O)(OC[C@H]1O[C@@H](n2ccc(N)nc2=O)[C@](C)(O)[C@@H]1O)N1CCCC1] | ++ | + |
| EXAMPLE 24: B234 | 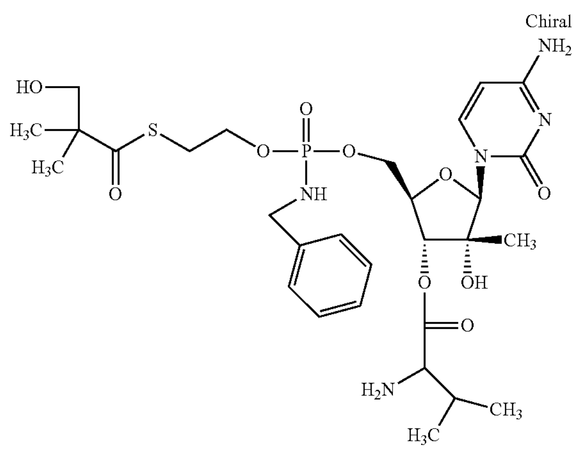 [SMILES: CC(C)C(N)C(=O)O[C@@H]1[C@@H](COP(=O)(NCc2ccccc2)OCCSC(=O)C(C)(C)CO)O[C@@H](n2ccc(N)nc2=O)[C@]1(C)O] | ++ | + |
| EXAMPLE 23: B302 | 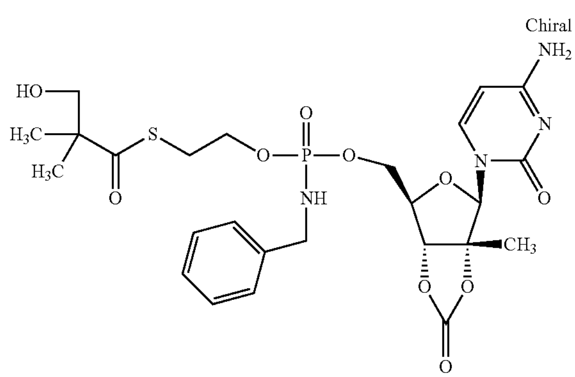 [SMILES: CC(C)(CO)C(=O)SCCOP(=O)(NCc1ccccc1)OC[C@H]1O[C@@H](n2ccc(N)nc2=O)[C@]2(C)OC(=O)O[C@H]12] | ++ | + |

-continued

| Compound Reference | Structure | HCV ELISA 2 | |
|---|---|---|---|
| | | EC$_{50}$ (µM) | CC$_{50}$ (µM) |
| EXAMPLE 22: B390 | 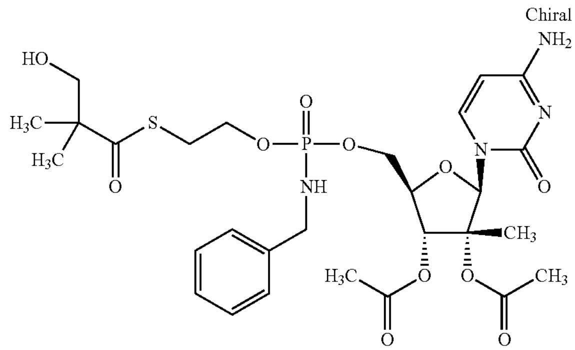 [SMILES: CC(=O)O[C@@H]1[C@@H](COP(=O)(NCc2ccccc2)OCCSC(=O)C(C)(C)CO)O[C@@H](n2ccc(N)nc2=O)[C@]1(C)OC(C)=O] | + | + |
| EXAMPLE 25: B183 | 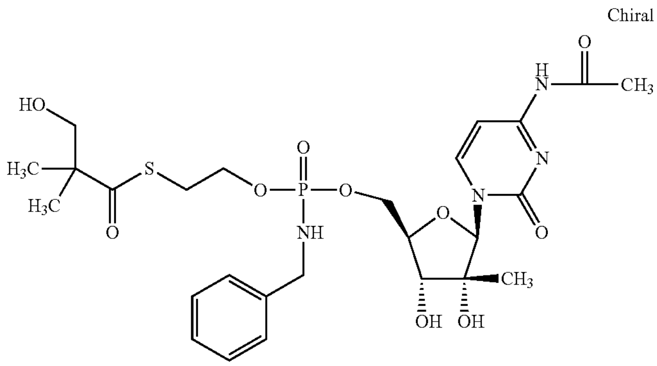 [SMILES: CC(=O)Nc1ccn([C@@H]2O[C@H](COP(=O)(NCc3ccccc3)OCCSC(=O)C(C)(C)CO)[C@@H](O)[C@@]2(C)O)c(=O)n1] | + | + |
| NUCLEOSIDE PARENT: A844 (NM108) | 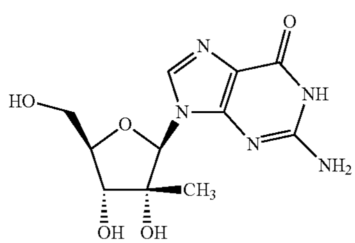 [SMILES: C[C@@]1(O)[C@H](O)[C@@H](CO)O[C@H]1n1cnc2c(=O)[nH]c(N)nc21] | ++ | + |
| EXAMPLE 3: B299 | 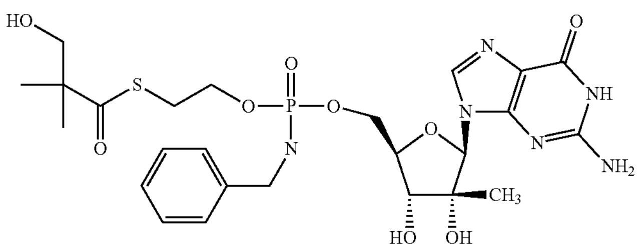 [SMILES: CC(C)(CO)C(=O)SCCOP(=O)(NCc1ccccc1)OC[C@H]1O[C@@H](n2cnc3c(=O)[nH]c(N)nc32)[C@](C)(O)[C@@H]1O] | +++ | + |
| EXAMPLE 11: B242 | 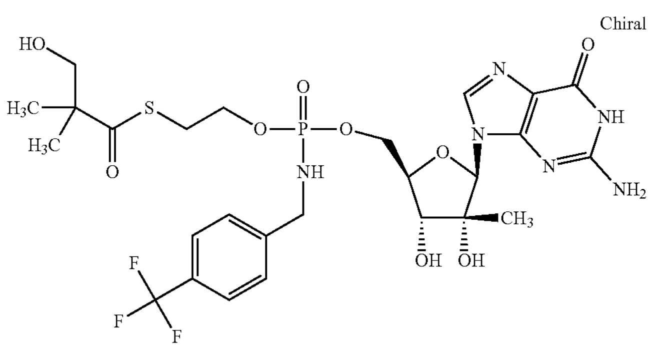 [SMILES: CC(C)(CO)C(=O)SCCOP(=O)(NCc1ccc(C(F)(F)F)cc1)OC[C@H]1O[C@@H](n2cnc3c(=O)[nH]c(N)nc32)[C@](C)(O)[C@@H]1O] | +++ | + |

-continued

| Compound Reference | Structure | HCV ELISA 2 EC$_{50}$ (μM) | CC$_{50}$ (μM) |
|---|---|---|---|
| EXAMPLE 10: B307 | 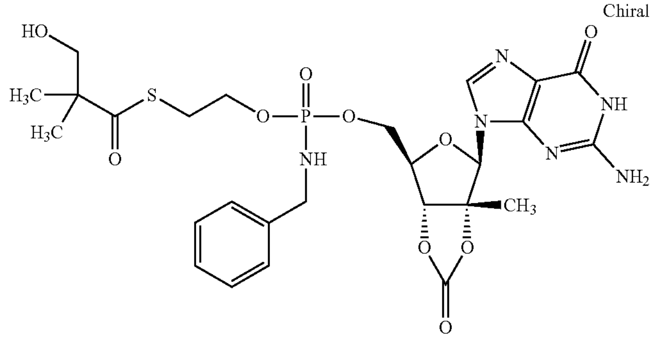 [SMILES: CC(C)(CO)C(=O)SCCOP(=O)(NCc1ccccc1)OC[C@H]1O[C@@H](n2cnc3c(=O)[nH]c(N)nc32)[C@]2(C)OC(=O)O[C@H]12] | +++ | + |
| NUCLEOSIDE PARENT: A374 (NM80) | 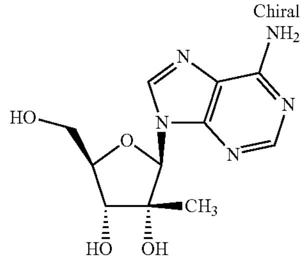 [SMILES: C[C@@]1(O)[C@H](O)[C@@H](CO)O[C@H]1n1cnc2c(N)ncnc21] | +++ | ++ |
| EXAMPLE 6: B263 | 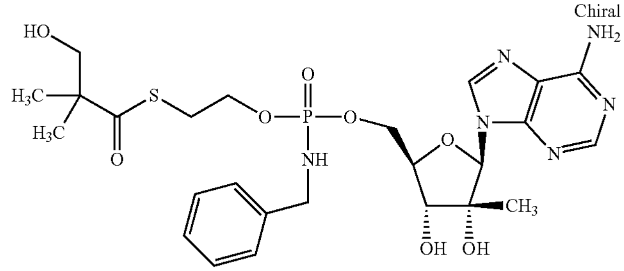 [SMILES: CC(C)(CO)C(=O)SCCOP(=O)(NCc1ccccc1)OC[C@H]1O[C@@H](n2cnc3c(N)ncnc32)[C@](C)(O)[C@@H]1O] | ++ | + |
| NUCLEOSIDE PARENT: C809 (NM106) | 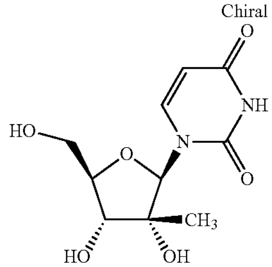 [SMILES: C[C@@]1(O)[C@H](O)[C@@H](CO)O[C@H]1n1ccc(=O)[nH]c1=O] | + | + |
| EXAMPLE 7: B229 | 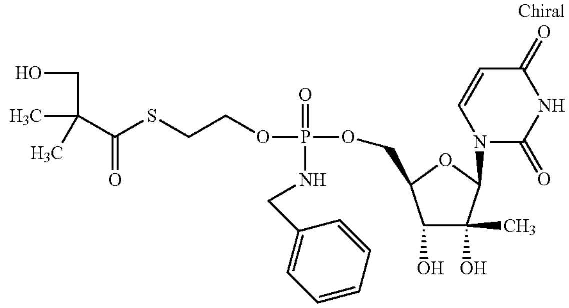 [SMILES: CC(C)(CO)C(=O)SCCOP(=O)(NCc1ccccc1)OC[C@H]1O[C@@H](n2ccc(=O)[nH]c2=O)[C@](C)(O)[C@@H]1O] | ++ | + |

-continued

| Compound Reference | Structure | HCV ELISA 2 | |
|---|---|---|---|
| | | EC$_{50}$ (μM) | CC$_{50}$ (μM) |
| NUCLEOSIDE PARENT: A608 | 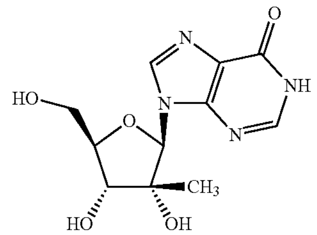 | + | + |
| EXAMPLE 8: B186 | 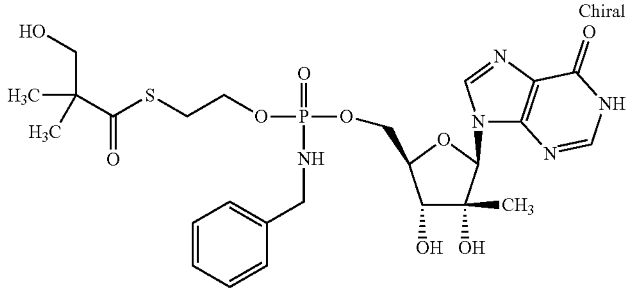 [SMILES: CC(C)(CO)C(=O)SCCOP(=O)(NCc1ccccc1)OC[C@H]1O[C@@H](n2cnc3c(=O)[nH]cnc32)[C@](C)(O)[C@@H]1O] | ++ | + |
| NUCLEOSIDE PARENT: A849 | 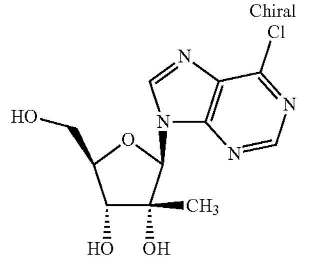 [SMILES: C[C@@]1(O)[C@H](O)[C@@H](CO)O[C@H]1n1cnc2c(Cl)ncnc21] | +++ | + |
| EXAMPLE 9: B396 | 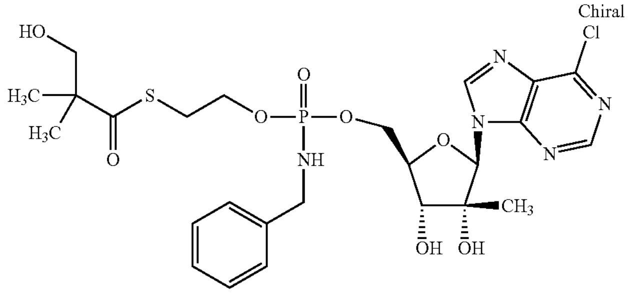 [SMILES: CC(C)(CO)C(=O)SCCOP(=O)(NCc1ccccc1)OC[C@H]1O[C@@H](n2cnc3c(Cl)ncnc32)[C@](C)(O)[C@@H]1O] | +++ | ++ |
| NUCLEOSIDE PARENT: D961 | 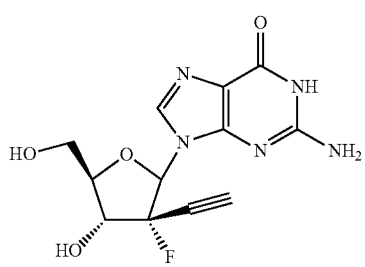 [SMILES: C#C[C@]1(F)C(n2cnc3c(=O)[nH]c(N)nc32)O[C@H](CO)[C@H]1O] | + | + |

| Compound Reference | Structure | HCV ELISA 2 EC$_{50}$ (μM) | CC$_{50}$ (μM) |
|---|---|---|---|
| EXAMPLE 12: B503 | 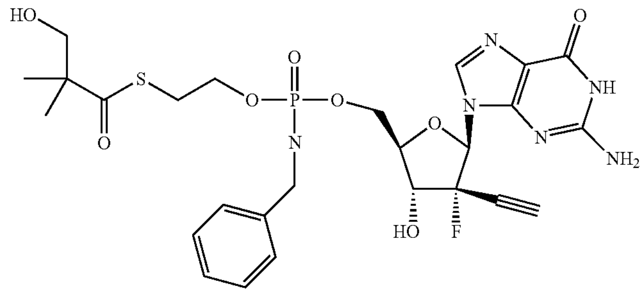 [SMILES: C#C[C@@]1(F)[C@H](O)[C@@H](COP(=O)(NCc2ccccc2)OCCSC(=O)C(C)(C)CO)O[C@H]1n1cnc2c(=O)[nH]c(N)nc21] | ++ | + |
| NUCLEOSIDE PARENT: E810 | 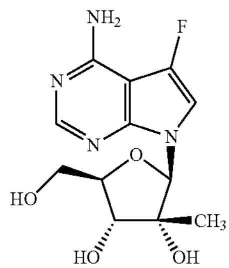 [SMILES: C[C@@]1(O)[C@H](O)[C@@H](CO)O[C@H]1n1cc(F)c2c(N)ncnc21] | +++ | + |
| EXAMPLE 18: B436 | 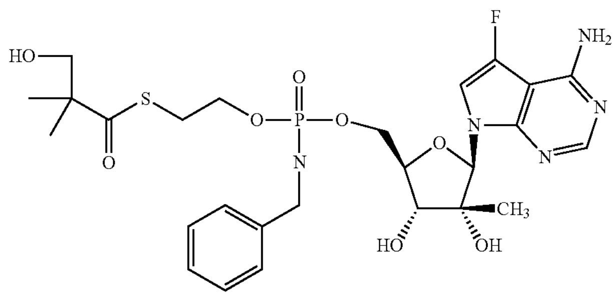 [SMILES: CC(C)(CO)C(=O)SCCOP(=O)(NCc1ccccc1)OC[C@H]1O[C@@H](n2cc(F)c3c(N)ncnc32)[C@](C)(O)[C@@H]1O] | ++ | + |

EC$_{50}$ in ELISA 2 assay is provided as follows:
+++ ≤ 1 μm, ++ > 1-10 μm and + > 10 μm
CC$_{50}$ is provided as follows:
++ ≤ 75 μm, + > 75 μm Example 40

HBV Drug Susceptibility Assay a) Collagen-I coated cell culture plates were seeded with cells at a density of 0.25–0.5×10$^6$ cells per well in 2 ml of growth/selection media.
b) Drug stock solutions were made up freshly in 100% DMSO as 200× stocks. Seven 4-fold dilutions of test compound were prepared ranging from 2.5 μM to 0.0006 μM (final). Master drug dilutions were divided into 4 aliquots, and then stored at −20° C. until used.
c) One day after cells were seeded, drug treatments were initiated by adding 10 μl of drug dilution along with 2 ml of fresh growth/selection media. Thus, the final DMSO concentration did not exceed 0.5%. The no-drug control wells received 10 μl of DMSO in fresh media.
d) Cells were treated every-other-day with 2 ml of fresh drug combinations/medium for a total of 8 days. Cell lysates were then collected on day 10 as described below and endogenous polymerase assay were performed.

Preparation of Nucleocapsid-Containing Lysates for EPA Analysis
a) Two days after the final drug treatment, cells were harvested.
b) Media was carefully aspirated and the cell monolayers were rinsed once with 1 ml of PBS.
c) 1 ml of lysis buffer (50 mM Tris-HCl pH 7.5/150 mM NaCl/5 mM MgCl$_2$/0.2% NP-40) was added to each well. The detergent is required to strip the outer envelope from virions and to allow capture of the inner nucleocapsids. Plates were kept on ice for >30 min.
d) Lysed cells were transferred to 1.5 ml-microfuge tubes.
e) Lysates were clarified by spinning at room temperature for 5 min at 14,000 rpm.
f) Clarified lysates were transferred to fresh tubes and immediately frozen on dry-ice, then stored at −80° C. until endogenous polymerase assays can be performed as described below.

Endogenous Polymerase Assay (EPA) of Cell Lysates
a) EPAs were performed essentially as described in Seifer, et al (1998). *J. Virol.* 72: 2765-2776. Clarified lysates were thawed at room temperature.
b) Intracellular HBV nucleocapsids were immunoprecipitated from the cytoplasmic lysates overnight at 4° C.

with a polyclonal rabbit anti-HBcAg antibody and immobilized on protein A sepharose CL-4B beads.

c) After 2 washes of the immobilized capsids with 1 ml of EPA wash buffer (75 mM $NH_4Cl$, 50 mM Tris-HCl pH 7.4, 1 mM EDTA), endogenous polymerase reactions were initiated by adding 50 µl of detergent-containing EPA cocktail (50 mM Tris-HCl pH7.4, 75 mM $NH_4Cl$, 1 mM EDTA, 20 mM $MgCl_2$, 0.1 mM (3-ME, 0.5% NP-40, 100 µM cold dGTP, TTP, dCTP, and 50 nM $^{33}$P-dATP) and incubated overnight at 37° C. The detergent is required to enhance permeability of the nucleocapsids.

d) Following digestion with 1 mg/ml of Proteinase K for 1 hour at 37° C., endogenously $^{33}$P-labeled HBV DNA was liberated via phenol/chloroform extraction.

e) The nucleic acids were then precipitated with one volume of 5 M $NH_4$-acetate and 2.5 volumes 100% EtOH, and separated on a 1% native agarose gel in Tris-borate buffer.

f) Gels were blotted onto positively charged nylon membrane overnight at room temperature via capillary transfer in 0.4 N NaOH.

g) Dried membranes were exposed to a phoshoimager screen (GE Healthcare) overnight at room temperature, then scanned (Storm 860, GE Healthcare) and quantitated with ImageQuant software (GE Healthcare).

h) Dose-response curves were generated using XLfit 4.1 software. The mean effective drug concentrations that inhibit endogenous HBV polymerase activity by 50% were calculated from several independent experiments.

Cytotoxicity Determination

A standard in vitro cytotoxicity assay was performed in HepG2 cells. Cells were exposed to drug for 9 days. Cell viability was determined via MTS staining using a CellTiter 96 Aqueous One Solution cell proliferation assay according to the manufacturer's instructions.

a) HepG2 cells were seeded in 96-well tissue culture plates in 100 µl fresh growth media at $7 \times 10^3$ cells per well.

b) Drug stock solutions were made up in 100% DMSO as 400× stock solutions and stored at −20° C. until used.

c) Four hours after cells were plated the drug dilutions were prepared and then added to the cells. Cells received up to 100 µM of drug in a total of 200 µl of fresh growth media containing 0.25% DMSO. Control wells received growth media with 0.25% DMSO growth media. Plates were incubated at 37° C., 5% $CO_2$.

d) Cells were treated every-other-day with fresh growth media and fresh drug dilutions for a total of 8 days as described above.

e) On day 9, cell viability of HepG2 cells was determined by adding 20 µl of MTS CellTiter 96 Aqueous One Solution. Following 4 hours of incubation at 37° C., absorbance was measured at $A_{490}$ nm in a Victor V plate reader (Perkin Elmer).

f) The $CC_{50}$ concentrations were determined using XLfit 4.1 software.

The antiviral in vitro activity of PMEA, B261 (hydroxy-tBuSATE N-benzylphosphoramidate derivative of PMEA as shown in Example 10 Table) along with LdT as control was tested in a total of 4 HBV drug susceptibility assays. The table below provides the results:

| HBV Cell Assay (EPA Read-out) | | | |
|---|---|---|---|
| Drug | Cytotoxicity ($CC_{50}$ in µM) | Antiviral Activity * ($EC_{50}$ in µM) | SI |
| PMEA | >100 | 0.328 ± 0.082 | >310 |
| B261 | 19.6 | 0.016 ± 0.004 | 1,225 |
| LdT | >100 | 0.366 ± 0.056 | >273 |

Cytoxicity and efficacy was determined on collagen plates.

Example 41

Determination of Total Metabolism in Liver Subcellular Fractions (Depletion of Parent)

NADPH Incubations.

Figure 2:
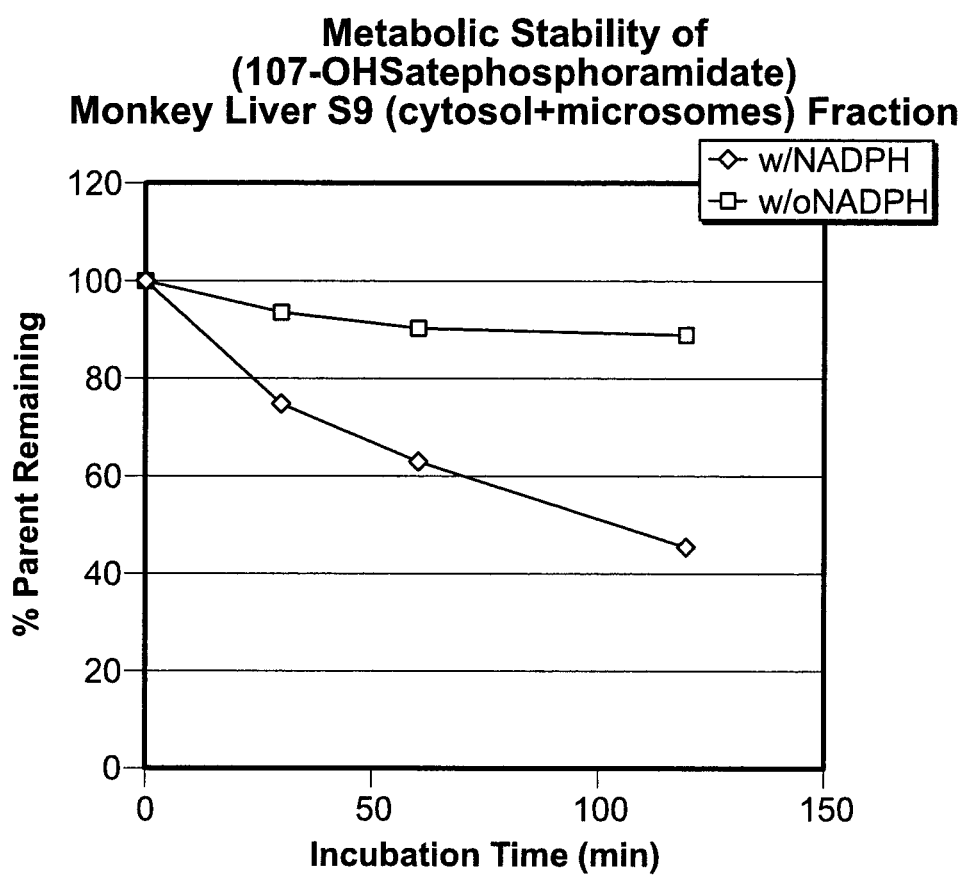
FIG. 2 depicts depletion of NM107 hydroxySATE phosphoramidate (B102) after incubation with and without NADPH in monkey liver S9.

Microsomal or S9 incubations were conducted in a final volume of 0.5 mL. Pooled liver microsomal or S9 protein (1.0 mg/mL), suspended in incubation buffer (100 mM potassium phosphate, pH 7.4, 5 mM $MgCl_2$, and 0.1 mM EDTA) was preincubated for 5 min at 37° C. with 10-50 µM OHSATE phosphoramidate compound from a stock solution in DMSO (final DMSO concentration was 0.1%); the reaction was initiated by the addition of NADPH (3 mM final concentration). Incubations with no NADPH served as controls. At specific times (0-120 min), 0.1 mL samples were taken and the reaction terminated by the addition of 1 volume of stop solution (acetonitrile). The samples were vortex for 30 sec and then centrifuged at 1500 g for 10 min. The supernatant was transferred to HPLC glass vials and analyzed without further processing by HPLC. FIGS. 1 and 2 depict depletion of NM108 SATE phosphoramidate (B299) and NM107 SATE phosphoramidate (B102), respectively, after incubation with NADPH in monkey liver S9.

HPLC System for Medium Samples-Unchanged Prodrug

| HPLC: Agilent 1100 | |
|---|---|
| Column: | Phenomenex Luna C18(2), 20 × 2 mm, |
| Mobile phases (MP): | MP(A) 10 mM $K_2HPO_4$ pH5, MP(B) ACN |
| Gradient elution: | 20 to 63% MP(B) run from 0 to 30 min |
| Runtime: | 20 min |
| Flow rate: | 1 mL/min |
| Injection volume: | 10-20 µL |
| UV: | 252 nm-NM108SATE deriv (B299) |
| | 272 nm-NM107SATE deriv (B102) |

Thus, without being limited to any theory, since the metabolism is NADPH dependent, it is possible that the phosphoroamidate compound is preferentially activated by Cytochrome P450 in the liver.

Example 42

Determination of Triphosphate Levels in Cells

Preparation of Primary Hepatocyte Cultures

Freshly isolated cells from animal and human liver were obtained in suspension on ice. Following receipt, cells were pelleted by centrifugation at 500 rpm (rat) or 700 rpm (monkey and human) and resuspended at 0.8 million cells per mL of platting medium (HPM). Multi-well collagen-coated plates (12-well) were then seeded by addition of 1 mL of cell suspension (0.8 million cells/mL). The plates were gently shaken to evenly distribute the cells and placed in an incubator at 37° C. for approximately 4 to 6 hours to allow cells to attach. Once cells have attached, the platting medium was removed and replaced with hepatocyte culture medium (HCM). Cells were left overnight in an incubator at 37° C. to acclimatize to culture and the medium.

Incubations with Test Article

Hepatocyte incubations were conducted in a final volume of 1.0 mL HCM/well (0.8 million cells/mL). HCM from overnight incubation of cells was removed and replaced with fresh HCM, pre-warmed to 37° C., containing 10 µM test article from a stock solution in DMSO (final DMSO concentration was 0.1%). At specific times (up to 24 hrs), incubation medium was discarded and the cell monolayers were carefully washed two times with ice-cold PBS. Following the last wash, all PBS was carefully removed and 1 mL of extraction buffer (ice-cold 70% methanol) was added. Each well was sealed with parafilm immediately following addition of methanol. Once the entire plate was processed, additional parafilm was placed on entire plate forming a double seal to prevent evaporation during the extraction process. The cover lid was then placed on the plate and sealed with tape. The plates were then stored at −20° C. for a minimum of 24 hrs to allow for extraction of intracellular contents.

Preparation of Huh7 or HepG2 Cultures

HepG2s or Huh7 cells were plated at $0.4 \times 10^6$ cells/well in collagen-coated 12-well plates. Cells were allowed to attach overnight. Culture medium from overnight incubation of cells was removed and replaced with fresh culture medium, pre-warmed to 37° C., containing 10 µM test article from a stock solution in DMSO (final DMSO concentration was 0.1%). After 24-72 hours, incubation medium was discarded and the cell monolayers were carefully washed two times with ice-cold PBS. Following the last wash, all PBS was carefully removed and 1 mL of extraction buffer (ice-cold 70% methanol) was added. Each well was sealed with parafilm immediately following addition of methanol. Once the entire plate was processed, additional parafilm was placed on entire plate forming a double seal to prevent evaporation during the extraction process. The cover lid was then placed on the plate and sealed with tape. The plates were then stored at −20° C. for a minimum of 24 hrs to allow for extraction of intracellular contents.

Sample Preparation for Analysis

Cellular extracts were prepared by transferring 0.9 mL of extract into 2 mL microfuge tubes followed by centrifugation for 5 min at 14,000 rpm. Approximately 1004 of the supernatant was transferred to HPLC vials and triphosphate levels determined by LCMS/MS as described below.

HPLC Conditions: NM107-triphosphate

| HPLC: | |
|---|---|
| Column: | Phenomenex Luna Amino 3 µm 100A, 30 × 2 mm, |
| Mobile phases (MP): | (A) 70% 10 mM NH₄OAc 30% ACN pH 6.0 |
| | (B) 70% 1 mM NH₄OAc 30% ACN pH 10.5 |

| Gradient elution: | | | | |
|---|---|---|---|---|
| Step | Time | Flow | A | B |
| 0 | 0.00 | 400 | 80 | 20 |
| 1 | 0.10 | 400 | 80 | 20 |
| 2 | 0.11 | 400 | 40 | 60 |
| 3 | 0.21 | 400 | 40 | 60 |
| 4 | 2.60 | 400 | 10 | 90 |
| 5 | 2.61 | 400 | 0 | 100 |
| 6 | 5.60 | 400 | 0 | 100 |
| 7 | 5.61 | 400 | 80 | 20 |
| 8 | 9.00 | 400 | 80 | 20 |

| Flow rate to MS: | 0.400 mL/min, no split |
|---|---|
| Injection volume: | 10 µL |

| Compound | Precursor ion | Product ion |
|---|---|---|
| NM107 triphosphate | 498.0 | 112.0 |

Exemplary HPLC Conditions: NM108-triphosphate

| HPLC: | |
|---|---|
| Column: | Phenomenex Luna Amino 3 µm 100A, 30 × 2 mm, |
| Mobile phases (MP): | (A) 70% 10 mM NH₄OAc 30% ACN pH 6.0 |
| | (B) 70% 1 mM NH₄OAc 30% ACN pH 10.5 |

| Gradient elution: | | | | |
|---|---|---|---|---|
| Step | Time | Flow | A | B |
| 0 | 0.00 | 400 | 60 | 40 |
| 1 | 0.10 | 400 | 60 | 40 |
| 2 | 0.11 | 400 | 40 | 60 |
| 3 | 0.21 | 400 | 40 | 60 |
| 4 | 2.60 | 400 | 10 | 90 |
| 5 | 2.61 | 400 | 0 | 100 |
| 6 | 5.61 | 400 | 0 | 100 |
| 7 | 5.61 | 400 | 60 | 40 |
| 8 | 9.00 | 400 | 60 | 40 |

| Flow rate to MS: | 0.400 mL/min, no split |
|---|---|
| Injection volume: | 10 uL |

| Compound | Precursor ion | Product ion |
|---|---|---|
| NM108 triphosphate | 538.0 | 152.0 |

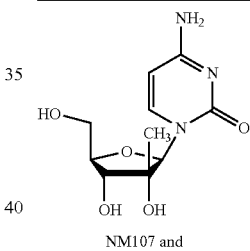

NM107 and

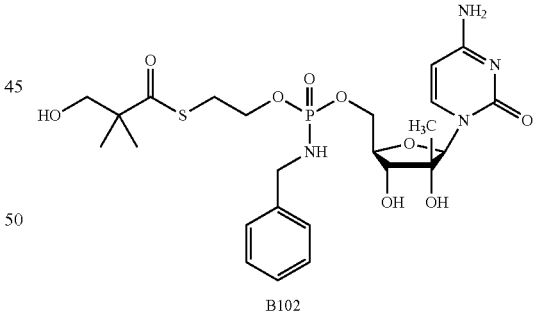

B102

NM107 triphosphate and B102 triphosphate levels in cell extracts were observed as follows:

| | Intracellular Triphosphate (pmol/million cells) | | | |
|---|---|---|---|---|
| drug in culture | Human | Monkey | HepG2* | Huh7* |
| B102 | 991 | 1838 | 1.5 | 9.2 |
| NM107 | 19 | 10 | 17 | 37 |

24 hr incubation in 10 µM drug
*72 hr incubation in 10 µM drug

As seen from the data levels of intracellular triphosphate for B102 were higher compared to those for NM107.

Example 43

Demonstration of Potent Antiviral Activity of Second Generation Nucleoside Inhibitors, B102, in HCV-Infected Chimpanzees Nucleoside analogs such as NM107 (2' methyl cytidine, valopicitabine nucleoside component) have shown efficacy against HCV in the clinical setting and their 5'-triphosphates (TP) can be potent inhibitors of HCV NS5B polymerase. However, their wide systemic distribution and inefficient hepatic conversion to TP may lead to reduced safety and antiviral activity. The in vivo preclinical safety and antiviral activity of the nucleotide prodrugs, B102 were assessed.

Methods: For pharmacokinetic (PK) and toxicology studies, B102 were orally administered to rats or monkeys at doses from 20 to 300 mg/kg/day up to 14 days. Hepatic nucleoside TP levels were determined by LC-MS/MS. Compounds (10 mg/kg/day) were administered once daily by oral gavage for 4 days in chimpanzees chronically infected with HCV genotype 1. HCV viral loads were monitored before, during and after treatment by quantitative RT-PCR.

Results: PK studies in rat and monkey revealed that B102 and has a first-pass hepatic extraction of >95% with low systemic exposure (<1%). Hepatic TP levels were 10-50-fold higher with nucleotide prodrugs versus a nucleoside counterpart. No toxicity was observed after administration of 50 mg/kg/day of A2 to monkeys for 14 days. No initial emesis or G1 toxicity was observed. In HCV-infected chimpanzees, B102 produced a rapid and potent antiviral effect followed by a rebound to baseline after drug discontinuation. Mean viral load reductions ranged from 1.5 log 10 with B102 to over 4 days of drug exposure. An equivalent dose of valopicitabine led to a 0.7 log 10 viral reduction. No lab abnormalities or evidence of toxicities were observed in chimpanzees.

Thus, when orally administered, B102 generates high hepatic levels of triphosphates coupled with low systemic exposure, leading to rapid and potent inhibition of HCV replication in chimpanzees, thus demonstrating a promising in vivo preclinical safety profile and antiviral activity.

Example 44

Compounds were tested in an anti-HBV assay. Determination of anti-HBV activity in HBV virions and nucleocapsids via endoenous polymerase assays (EPA)
Drug Susceptibility Assay Using a Wild-Type HBV Producer Cell Line
1. 12-well collagen-I coated plates were seeded with producer cells expressing wild-type HBV at a density of $0.5\text{-}1\times10^6$ cells per well in 2 ml growth/selection media.
2. Drug stock solutions were made up freshly in 100% DMSO as 200× stocks. Five additional 4-fold dilutions were prepared from these 200× stock in 100% DMSO. For each experiment, 4 aliquots of each drug dilution series were stored at −20° C. until used.
3. Once cells reached confluency (1 day after cells were seeded), drug treatment was initiated by adding 10 µl of drug dilution into 2 ml of fresh growth/selection media. Thus, the final DMSO concentration did not exceed 0.5%. The no-drug control wells received only 10 µl of DMSO in fresh media.
4. Cells were treated every-other-day with 2 ml of fresh drug/medium for a total of 8 days. Cell lysates were then collected on day 10 and subjected to EPA analysis as described below.

Preparation of Nucleocapsid-Containing Lysates for EPA Analysis
1. Cells were grown for 3 to 4 days in 12-well collagen-I coated plates until confluent.
2. Media was carefully aspirated and the cell monolayers were rinsed once with 1 ml of PBS.
3. One ml of lysis buffer (50 mM Tris-HCl pH 7.5/150 mM NaCl/5 mM $MgCl_2$/0.2% NP-40) was added to each well. Plates were stored on ice for 30 min to 4 h.
4. Lysed cells were transferred to 1.5 ml-microfuge tubes.
5. Lysates were clarified by spinning at 14,000 rpm for 5 min at room temperature.
6. Clarified lysates were transferred to fresh tubes and immediately frozen on dry-ice, then stored at −80° C. until endogenous polymerase assays were performed as described below.

Preparation of Secreted Virions from Supernatant for EPA Analysis
1. Cells were grown for 3 to 4 days in 12-well collagen-I coated plates until confluent.
2. Media was carefully aspirated and transferred to 1.5 ml-microfuge tubes.
3. Supernatants were clarified by spinning at 14,000 rpm for 5 min at room temperature.
4. Clarified supernatants were transferred to fresh tubes and immediately frozen on dry-ice, then stored at −80° C. until endogenous polymerase assays were performed essentially as described below.

Endogenous Polymerase Assay (EPA) of Cell Lysates and Supernatants
1. EPAs were performed essentially as described by Seifer et al (1998). Intracellular HBV nucleocapsids were immunoprecipitated from the cytoplasmic lysates overnight at 4° C. with a polyclonal rabbit anti-HBcAg antibody and immobilized on protein A sepharose CL-4B beads. Secreted virions were immunoprecipitated from clarified cell supernatants overnight at 4° C. with a monoclonal mouse anti-LS antibody (MA18/7) in the absence of detergent.
2. Following 3 washes of the immobilized capsids or virions with 1 ml of EPA wash buffer (75 mM $NH_4Cl$, 50 mM Tris-HCl pH 7.4, 1 mM EDTA), endogenous polymerase reactions were initiated by adding 50 µl of detergent-containing EPA cocktail (50 mM Tris-HCl pH7.4, 75 mM $NH_4Cl$, 1 mM EDTA, 20 mM $MgCl_2$, 0.1 mM β-ME, 0.5% NP-40, 100 µM cold dGTP, TTP, dCTP, and 50 nM $^{33}$P-dATP) and incubated overnight at 37° C. The detergent is required to strip the outer envelope from immunoprecipitated virions as well as to enhance permeability of the nucleocapsids.
3. Following digestion with 1 mg/ml of proteinase K for 1 h at 37° C., endogenously $^{33}$P-labeled HBV DNA was liberated via phenol/chloroform extraction.
4. The nucleic acids were precipitated with 1 volume of 5M $NH_4$-acetate and 2.5 volumes of 100% EtOH, and then separated on a 1% native agarose gel in Tris-borate-EDTA buffer.
5. Gels were blotted onto positively charged nylon membrane overnight at room temperature via capillary transfer in 0.4 N NaOH.
6. Dried membranes were exposed to a PhosphorImager screen (GE Healthcare) overnight at room temperature, then scanned (Storm 860, GE Healthcare) and quantitated with ImageQuant software (GE Healthcare).
7. The 50% effective concentration ($EC_{50}$) values were calculated from the resulting best-fit equations determined by Xlfit, version 4.1 (IDBS).

The following results were obtained.
| Compound Ref. No. | Structure | Virion EC$_{50}$ (μM) | RI EC$_{50}$ (μM) |
|---|---|---|---|
| A348 (NM 48) | 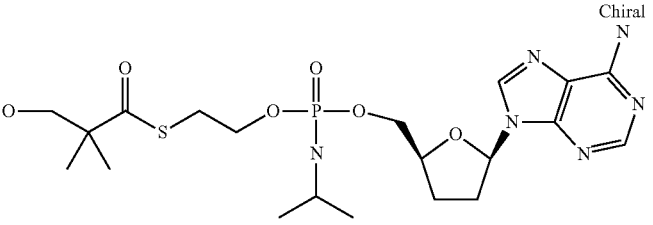 [SMILES: CC(C)NP(=O)(OCCSC(=O)C(C)(C)CO)OC[C@@H]1CC[C@H](n2cnc3c(N)ncnc32)O1] | +++ | |
| A362 (NM 77) | 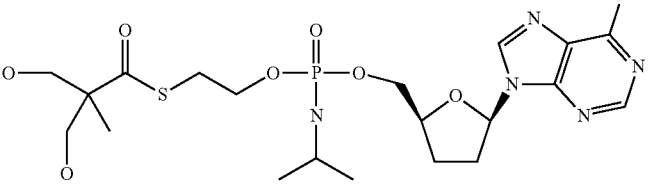 | ++ | ++ |
| A616 (NM 128) | 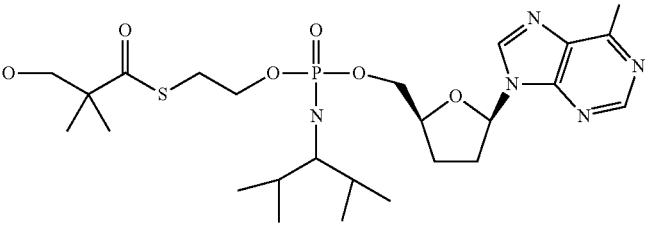 | | ++ |
| C819 (NM 177) | 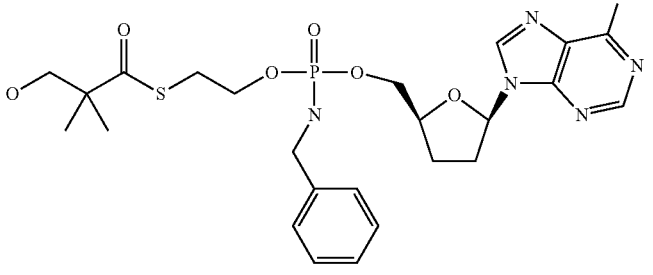 | ++ | ++ |
| A361 (NM 55) | 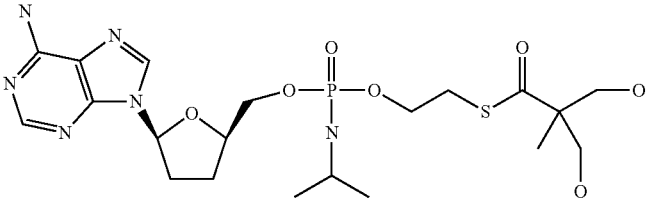 | + | ++ |

-continued

| Compound Ref. No. | Structure | Virion EC$_{50}$ (μM) | RI EC$_{50}$ (μM) |
|---|---|---|---|
| A550 (NM 204) | Chiral | +++ | +++ |
| C791 | Chiral | ++ | |
| B261 | 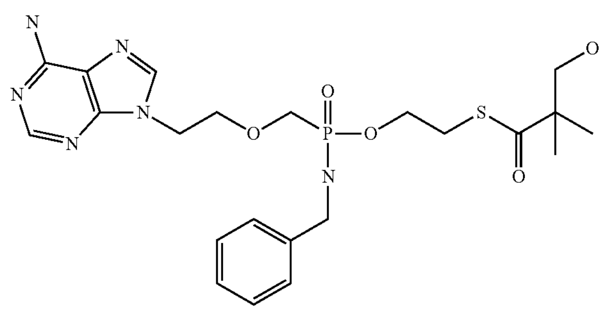 [SMILES: CC(C)(CO)C(=O)SCCOP(=O)(COCCn1cnc2c(N)ncnc21)NCc1ccccc1] | | +++ |
| PMEA | 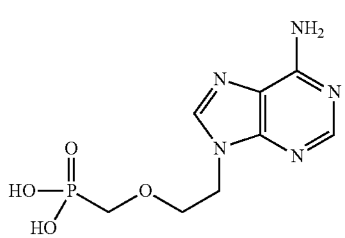 [SMILES: Nc1ncnc2c1ncn2CCOCP(=O)(O)O] | | +++ |
| L-dT | | | +++ |

EC$_{50}$ in HBV virion and Ri is provided as follows:

+++ ≤ 1 μm, ++ > 1-10 μm and + > 10 μm

Example 45

Ethynyl Nucleosides for the Treatment of HCV

Exemplary compound syntheses are described below:

Scheme 6

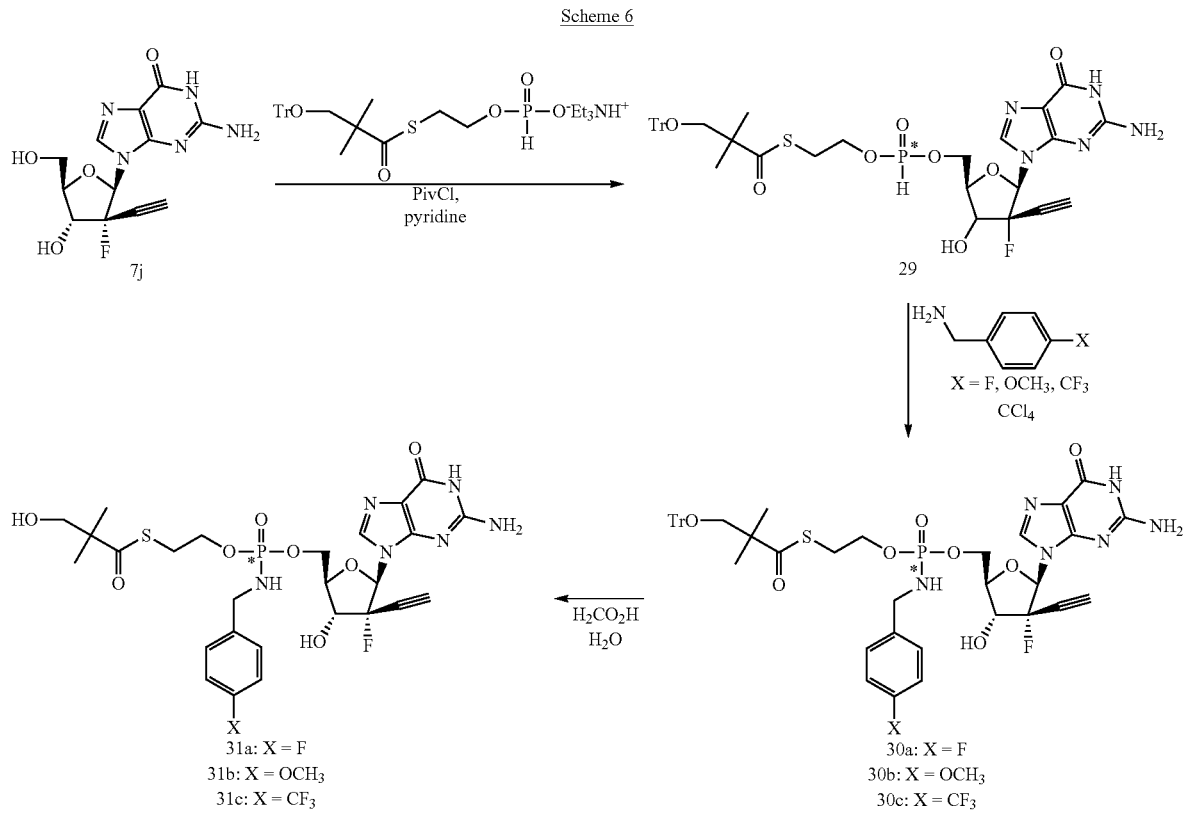

29: {9-[(2R)-2-Deoxy-2-fluoro-2-C-ethynyl-β-D-erythro-furanosyl]-guanin}-5'-yl-O-(triphenylmethyloxy-tert-butyl-5-acyl-2-thioethyl) H-phosphonate To a stirred solution of 7j (0.32 mmol) and S-(2-Phosphite-ethyl) 2,2-dimethyl-3-triphenylmethyloxy-thiopropionate (0.42 mmol) in pyridine (5 ml) at −15° C. was added dropwise pivaloyl chloride (0.64 mmol) under nitrogen. The reaction mixture was stirred at −15° C. for 2 hours. Dichloromethane and NH$_4$Cl solution were added. Organic phase was separated washed with NH$_4$Cl solution, dried over Na$_2$SO$_4$, filtered and concentrated under reduced pressure. The crude material was purified by flash column chromatography (DCM/MeOH) to yield the title compound Brown powder. Molecular Formula C$_{38}$H$_{39}$FN$_5$O$_8$PS $^1$H NMR (DMSO-d$_6$, 400 MHz) δ (ppm) 1.12 (s, 6H), 1.84 (m, 4H) 3.04 (s, 2H), 3.92 (d, J=5.60 Hz, 1H), 4.01-4.10 (m, 3H), 4.33-4.39 (m, 2H), 4.60-4.66 (m, 1H), 6.13 (d, J=18.00 Hz, 1H), 6.67 (s, 2H), 7.21-7.35 (m, 15H), 7.81 (s, 1H), 10.86 (brs, 1H)

30a: N-(4-fluoro-benzylaminyl)-{9-[(2R)-2-deoxy-2-fluoro-2-C-ethynyl-β-D-erythro-furanosyl]-guanin}-5'-yl-O-(triphenylmethyloxy-tert-butyl-5-acyl-2-thioethyl)phosphate To a stirred solution of 29 (0.088 mmol) in anhydrous carbon tetrachloride (880 μL), 4-fluoro-benzylamine (0.44 mmol) was added dropwise. The reaction mixture was stirred at room temperature for 2 h and evaporated to dryness (bath temperature not exceeding 30° C.). The crude mixture was filtered on a silica gel plug, eluting with a gradient 0-10% methanol in dichloromethane to yield the title compound.

White solid. Molecular Formula C$_{45}$H$_{45}$F$_2$N$_6$O$_8$PS $^1$H NMR (DMSO-d$_6$, 400 MHz) δ (ppm) 1.09 (s, 6H), 3.03 (s, 2H), 3.39-3.41 (m, 2H), 3.90-3.93 (m, 5H), 4.05-4.08 (m, 1H), 4.20-4.23 (m, 2H), 4.62-4.65 (m, 1H), 5.74 (m, 1H), 6.08-6.14 (dd, J=17.94 Hz and J=4.22 Hz, 1H), 6.32 (m, 1H), 6.67 (s, 2H), 7.21-7.35 (m, 19H), 7.81 (s, 1H), 10.86 (brs, 1H) $^{31}$P NMR (DMSO-d$_6$, 162 MHz) δ (ppm) 9.83 (s, 1P) $^{19}$F NMR (DMSO-d$_6$, 235 MHz) δ (ppm) −116.24 (s, 1F), −158-0.2 (s, 1F) Scan ES$^+$ 899 (M−H)$^+$, UV λ$_{max}$ 255 nm 31a: N-(4-fluoro-benzylaminyl)-{9-[(2R)-2-deoxy-2-fluoro-2-C-ethynyl-β-D-erythro-furanosyl]guanin}-5'-yl-O-(hydroxy-tert-butyl-5-acyl-2-thioethyl)phosphate 30a (0.09 mmol) was dissolved in dichloromethane (320 μL) and treated with formic acid (32 μL). The mixture was stirred at room temperature for 10 min, filtered through a solid phase extraction column eluting with a gradient 0-30% methanol in dichloromethane, then purified by reverse phase (C18) silica gel column chromatography eluting with a gradient 0-100% acetonitrile in water and lyophilised from a mixture of water/dioxan to yield the title compound. White solid. Molecular Formula C$_{26}$H$_{31}$F$_2$N$_6$O$_8$PS $^1$H NMR (d$_6$-DMSO, 400 MHz) δ (ppm) 1.09 (s, 6H), 3.03 (s, 2H), 3.39-3.41 (m, 2H), 3.90-3.93 (m, 5H), 4.05-4.08 (m, 1H), 4.20-4.23 (m, 2H), 4.62-4.65 (m, 1H), 4.92 (m, 1H), 5.74 (m, 1H), 6.08-6.14 (dd, J=17.94 Hz and J=4.22 Hz, 1H), 6.32 (m, 1H), 6.67 (s, 2H), 7.21-7.35 (m, 4H), 7.81 (s, 1H), 10.86 (brs, 1H) $^{31}$P NMR (DMSO-d$_6$, 162 MHz) δ (ppm) 9.66 (s, 1P) $^{19}$F NMR (DMSO-d$_6$, 235 MHz) δ (ppm) −116.24 (s, 1F), −158.44 (s, 1F) Scan ES$^+$ 657 (M−H)$^+$, UV λ$_{max}$ 254 nm

30b: N-(4-methoxy-benzylaminyl)-{9-[(2R)-2-deoxy-2-fluoro-2-C-ethynyl-β-D-erythro-furanosyl]-guanin}-5'-yl-O-(triphenylmethyloxy-tert-butyl-5-acyl-2-thioethyl)phosphate 30b was synthesized from 29 and 4-methoxy-benzylamine as described for 30a. White solid. Molecular Formula C$_{46}$H$_{48}$FN$_6$O$_9$PS $^1$H NMR (DMSO-d$_6$, 400 MHz) δ (ppm) 1.09 (s, 6H), 3.03 (m, 2H), 3.42 (d, J=5.02 Hz, 2H), 3.71 (d, J=3.60 Hz, 3!H), 3.85-3.90 (m, 5H), 4.06-4.10 (m, 1H), 4.23-4.29 (m, 2H), 4.60-4.66 (m, 1H), 5.54-5.57 (m, 1H), 6.08-6.14 (dd, J=17.94 Hz and J=4.22 Hz, 1H), 6.28-6.33 (m, 1H), 6.60 (s, 2H), 6.80-6.85 (m, 2H), 7.18-7.20 (m, 2H), 7.23-7.25 (m, 15H), 7.82 (s, 1H), 10.56 (brs, 1H))$^{31}$P NMR (DMSO-d$_6$, 162 MHz) δ (ppm) 9.83 (s, 1P) $^{19}$F NMR (DMSO-d$_6$, 235 MHz) δ (ppm) −116.24 (s, 1F), −158.2 (s, 1F) Scan ES$^+$ 911 (M−H)$^+$, UV λ$_{max}$ 255 nm

31b: N-(4-methoxy-benzylaminyl)-{9-[(2R)-2-deoxy-2-fluoro-2-C-ethynyl-β-D-erythro-furanosyl]-guanin}-5'-yl-O-(hydroxy-tert-butyl-5-acyl-2-thioethyl)phosphate 31b was synthesized from 30b as described for 31a. White solid. Molecular Formula C$_{27}$H$_{34}$FN$_6$O$_9$PS $^1$H NMR (d$_6$-DMSO, 400 MHz) δ (ppm) 1.09 (s, 6H), 3.03 (m, 2H), 3.42 (d, J=5.02 Hz, 2H), 3.71 (d, J=3.60 Hz, 3H), 3.85-3.90 (m, 5H), 4.06-4.10 (m, 1H), 4.23-4.29 (m, 2H), 4.60-4.66 (m, 1H), 4.92 (t, J=5.50 Hz, 1H), 5.54-5.57 (m, 1H), 6.08-6.14 (dd, J=17.94 Hz and J=4.22 Hz, 1H), 6.28-6.33 (m, 1H), 6.60 (s, 2H), 6.80-6.85 (m, 2H), 7.18-7.20 (m, 2H), 7.82 (s, 1H), 10.56 (brs, 1H), $^{31}$P NMR (DMSO-d$_6$, 162 MHz) δ (ppm) 9.86 (s, 1P) $^{19}$F NMR (DMSO-d$_6$, 235 MHz) δ (ppm) −158.24 (s, 1F) Scan ES$^+$ 669 (M−H)$^+$, UV λ$_{max}$ 254 nm

30c: N-(4-trifluoro-benzylaminyl)-{9-[(2R)-2-deoxy-2-fluoro-2-C-ethynyl-β-D-erythro-furanosyl]-guanin}-5'-yl-O-(triphenylmethyloxy-tert-butyl-5-acyl-2-thioethyl)phosphate 30c was synthesized from 29 and 4-trifluoromethyl-benzylamine as described for 30a. White solid. Molecular Formula C$_{46}$H$_{45}$F$_4$N$_6$O$_8$PS $^1$H NMR (d$_6$-DMSO, 400 MHz) δ (ppm) 1.09 (s, 6H), 3.03 (t, J=6.44 Hz, 2H), 3.42 (s, 2H), 3.87-3.92 (m, 5H), 4.03-4.08 (m, 1H), 4.24-4.29 (m, 2H), 4.60-4.64 (m, 1H), 5.79-5.82 (m, 1H), 6.08-6.14 (dd, J=17.94 Hz and J=4.22 Hz, 1H), 6.28-6.33 (m, 1H), 6.60 (s, 2H), 7.23-7.25 (m, 15H), 7.50-7.70 (m, 4H), 8.25 (brs, 1H), 10.76 (brs, 1H), $^{31}$P NMR (DMSO-d$_6$, 162 MHz) δ (ppm) 9.86 (s, 1P) $^{19}$F NMR (DMSO-d$_6$, 235 MHz) δ (ppm) −158.20 (s, 1F) Scan ES$^+$ 949 (M−H)$^+$, UV λ$_{max}$ 254 nm

31c: N-(4-trifluoromethyl-benzylaminyl)-{9-[(2R)-2-deoxy-2-fluoro-2-C-ethynyl-β-D-erythro-furanosyl]-guanin}-5'-yl-O-(hydroxy-tert-butyl-5-acyl-2-thioethyl)phosphate 31c was synthesized from 30c as described for 31a. White solid. Molecular Formula C$_{27}$H$_{31}$F$_4$N$_6$O$_8$PS $^1$H NMR (d$_6$-DMSO, 400 MHz) δ (ppm) 1.09 (s, 6H), 3.03 (t, J=6.44 Hz, 2H), 3.42 (s, 2H), 3.87-3.92 (m, 5H), 4.03-4.08 (m, 1H), 4.24-4.29 (m, 2H), 4.60-4.64 (m, 1H), 4.91 (brs, 1H), 5.79-5.82 (m, 1H), 6.08-6.14 (dd, J=17.94 Hz and J=4.22 Hz, 1H), 6.28-6.33 (m, 1H), 6.60 (s, 2H), 7.50-7.70 (m, 4H), 8.25 (brs, 1H), 10.64 (brs, 1H), $^{31}$P NMR (DMSO-d$_6$, 162 MHz) δ (ppm) 9.86 (s, 1P) $^{19}$F NMR (DMSO-d$_6$, 235 MHz) δ (ppm) −158.24 (s, 1F) Scan ES$^+$ 669 (M−H)$^+$, UV λ$_{max}$ 254 nm Further exemplary compounds synthesized using procedures similar to those described herein are listed below. Note the following names for the compounds synthesized in the examples.

6a: 6-Chloro-9-[(2R)-2-deoxy-2-C-ethynyl-2-fluoro-β-D-erythro-pentofuranosyl]purine 6b: N2-Isobutyryl-9-[(2R)-2-deoxy-2-C-ethynyl-2-fluoro-β-D-erythro-pentofuranosyl]-guanine 6c: 1-[(2R)-2-Deoxy-2-C-ethynyl-2-fluoro-β-D-erythro-pentofuranosyl]uracile 6d: 1-[(2R)-2-Deoxy-2-C-ethynyl-2-fluoro-β-D-erythro-pentofuranosyl]thymine 6e: N4-Benzoyl-1-[(2R)-2-deoxy-2-C-ethynyl-2-fluoro-β-D-erythro-pentofuranosyl]cytosine 6f: 5-Fluoro-1-[(2R)-2-deoxy-2-C-ethynyl-2-fluoro-β-D-erythro-pentofuranosyl]uracile 6g: 4-Chloro-7-[(2R)-2-deoxy-2-C-ethynyl-2-fluoro-β-D-erythro-pentofuranosyl]pyrrolo[2,3-d]pyrimidine 7i: 9-[(2R)-2-Deoxy-2-C-ethynyl-2-fluoro-β-D-erythro-pentofuranosyl]adenine 7j: 9-[(2R)-2-Deoxy-2-C-ethynyl-2-fluoro-β-D-erythro-pentofuranosyl]-guanine 7k: 1-[(2R)-2-Deoxy-2-C-ethynyl-2-fluoro-β-D-erythro-pentofuranosyl]cytosine 7l: 4-Amino-7-[(2R)-2-deoxy-2-C-ethynyl-2-fluoro-β-D-erythro-pentofuranosyl]pyrrolo[2,3-d]pyrimidine 11c: 1-[(2R)-2-Deoxy-2-C-ethynyl-2-fluoro-β-D-erythro-pentofuranosyl]-uracil-5'-yl-bis(S-pivaloyl-2-thioethylphosphate 11f: 1-[(2R)-2-Deoxy-2-C-ethynyl-2-fluoro-β-D-erythro-pentofuranosyl]-5-fluorouracil-5'-yl-bis(S-pivaloyl-2-thioethylphosphate)

11k: 1-[(2R)-2-Deoxy-2-C-ethynyl-2-fluoro-β-D-erythro-pentofuranosyl]-cytosin-5'-yl-bis(S-pivaloyl-2-thioethylphosphate)

11l: 1-[(2R)-2-Deoxy-2-C-ethynyl-2-fluoro-β-D-erythro-pentofuranosyl]-4-aminopyrrolo[2,3-d]pyrimidin-5'-yl-bis(S-pivaloyl-2-thioethylphosphate)

16: 9-[(2R)-2,3-Dideoxy-2-C-ethynyl-2-fluoro-β-D-glycero-pentofuranosyl]-guanine 17: 9-[(2R)-2,3-Dideoxy-2-C-ethynyl-2-fluoro-β-D-glycero-pentofuranosyl]-guanin-5'-yl-bis(S-pivaloyl-2-thioethylphosphate)

20: 9-[(2R)-2-Deoxy-2-C-ethynyl-2-fluoro-β-D-erythro-pentofuranosyl]-guanin-5'-yl-bis(S-pivaloyl-2-thioethylphosphate 23: 9-[(2R)-2-Deoxy-3,5-di-O-isobutyryl-2-C-ethynyl-2-fluoro-β-D-erythro-pentofuranosyl]-guanine 24: N2-Isobutyryl-9-[(2R)-2-Deoxy-3,5-di-O-isobutyryl-2-C-ethynyl-2-fluoro-β-D-erythro-pentofuranosyl]-guanine 27i: 9-[(2R)-2-Deoxy-2-C-ethynyl-2-fluoro-β-D-erythro-pentofuranosyl]adenine 5'-triphosphate sodium salt 27j: 9-[(2R)-2-Deoxy-2-C-ethynyl-2-fluoro-β-D-erythro-pentofuranosyl]-guanine 5'-triphosphate sodium salt 28: 9-[(2R)-2,3-dideoxy-2-C-ethynyl-2-fluoro-β-D-glycero-pentofuranosyl]-guanine 5'-triphosphate sodium salt Scheme 1
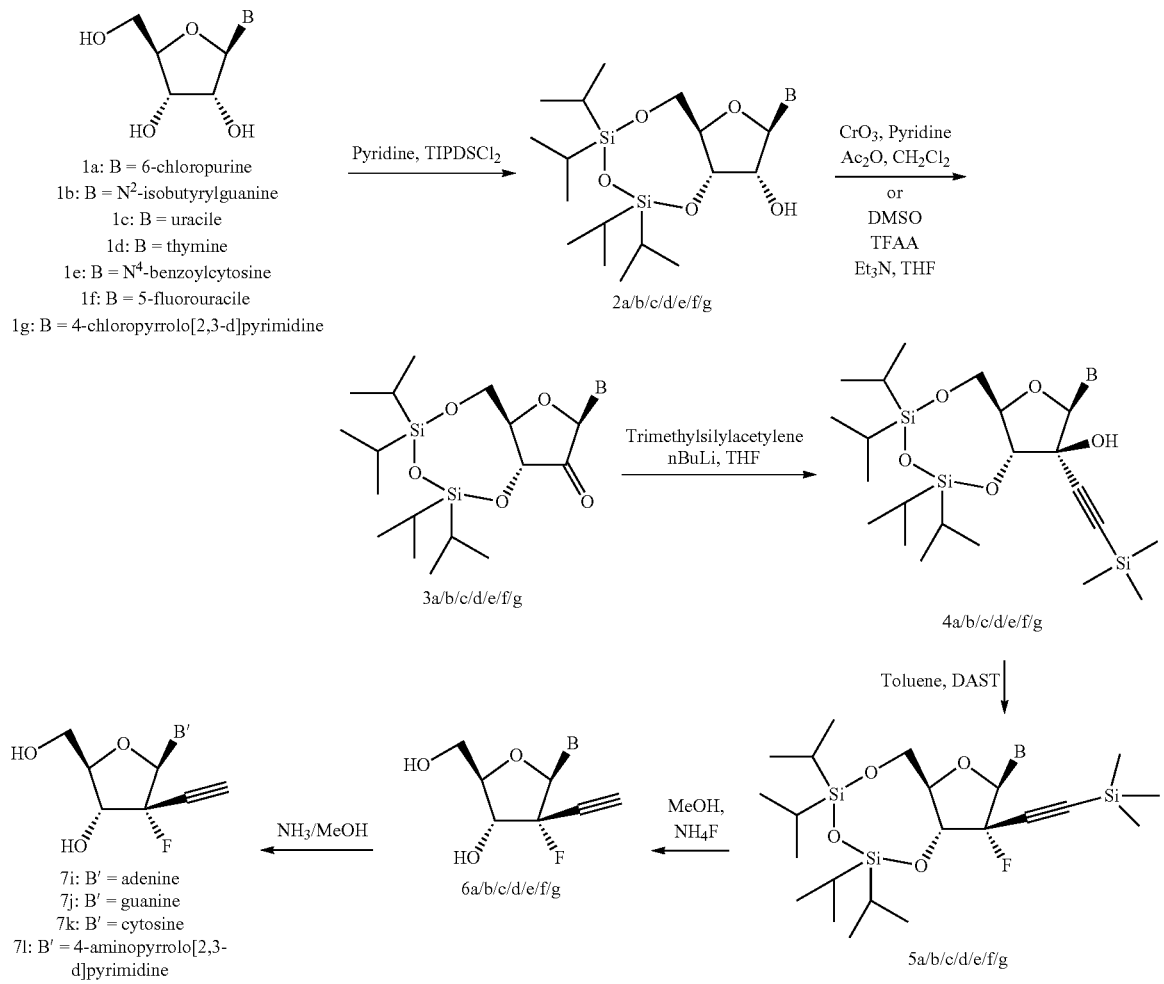
1a: B = 6-chloropurine
1b: B = N²-isobutyrylguanine
1c: B = uracile
1d: B = thymine
1e: B = N⁴-benzoylcytosine
1f: B = 5-fluorouracile
1g: B = 4-chloropyrrolo[2,3-d]pyrimidine
7i: B' = adenine
7j: B' = guanine
7k: B' = cytosine
7l: B' = 4-aminopyrrolo[2,3-d]pyrimidine

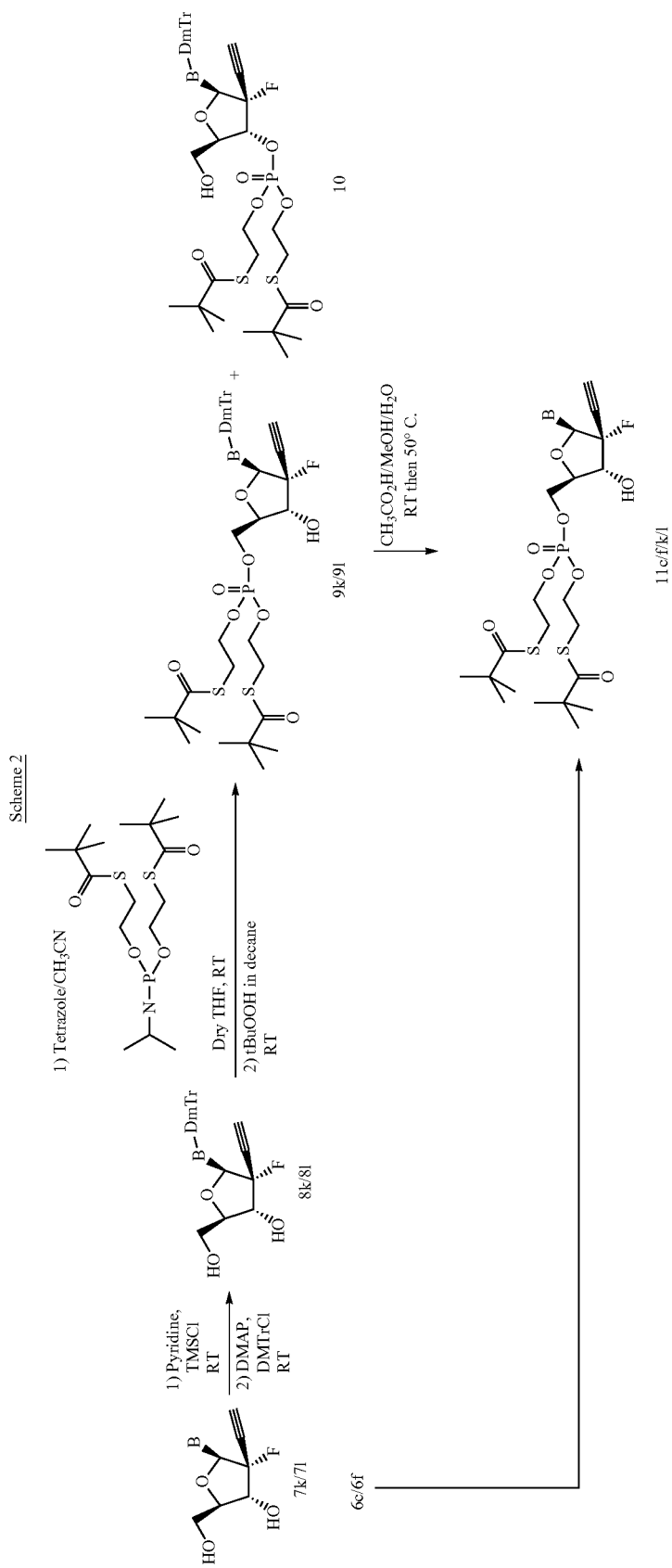

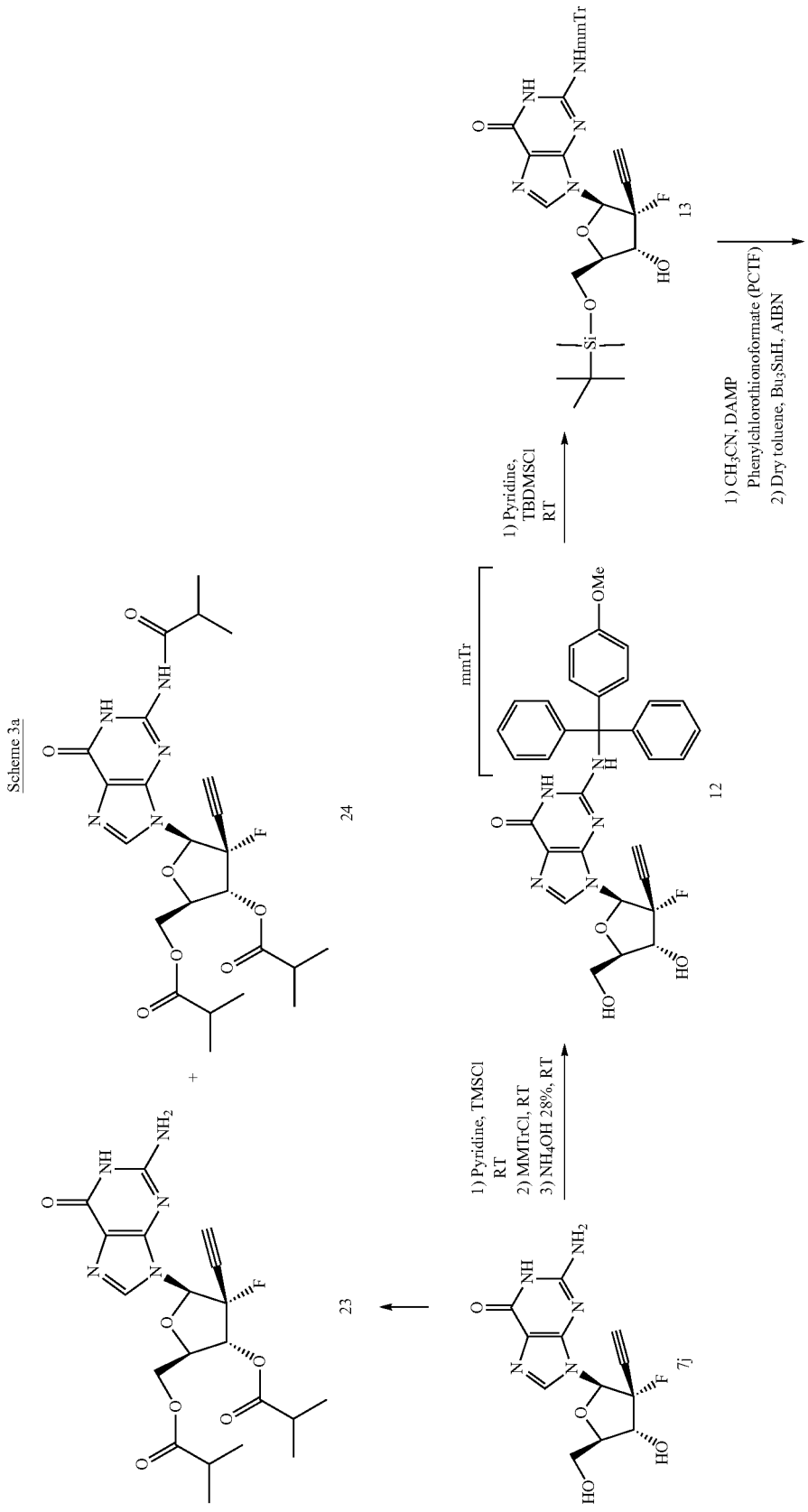

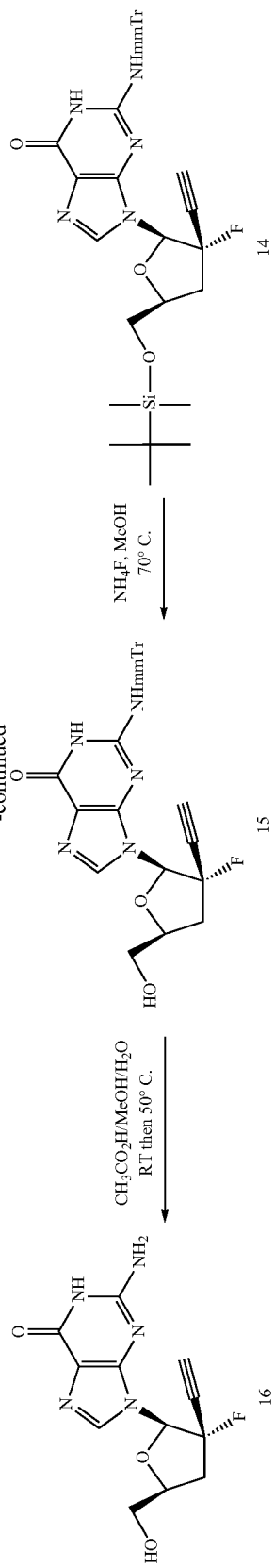

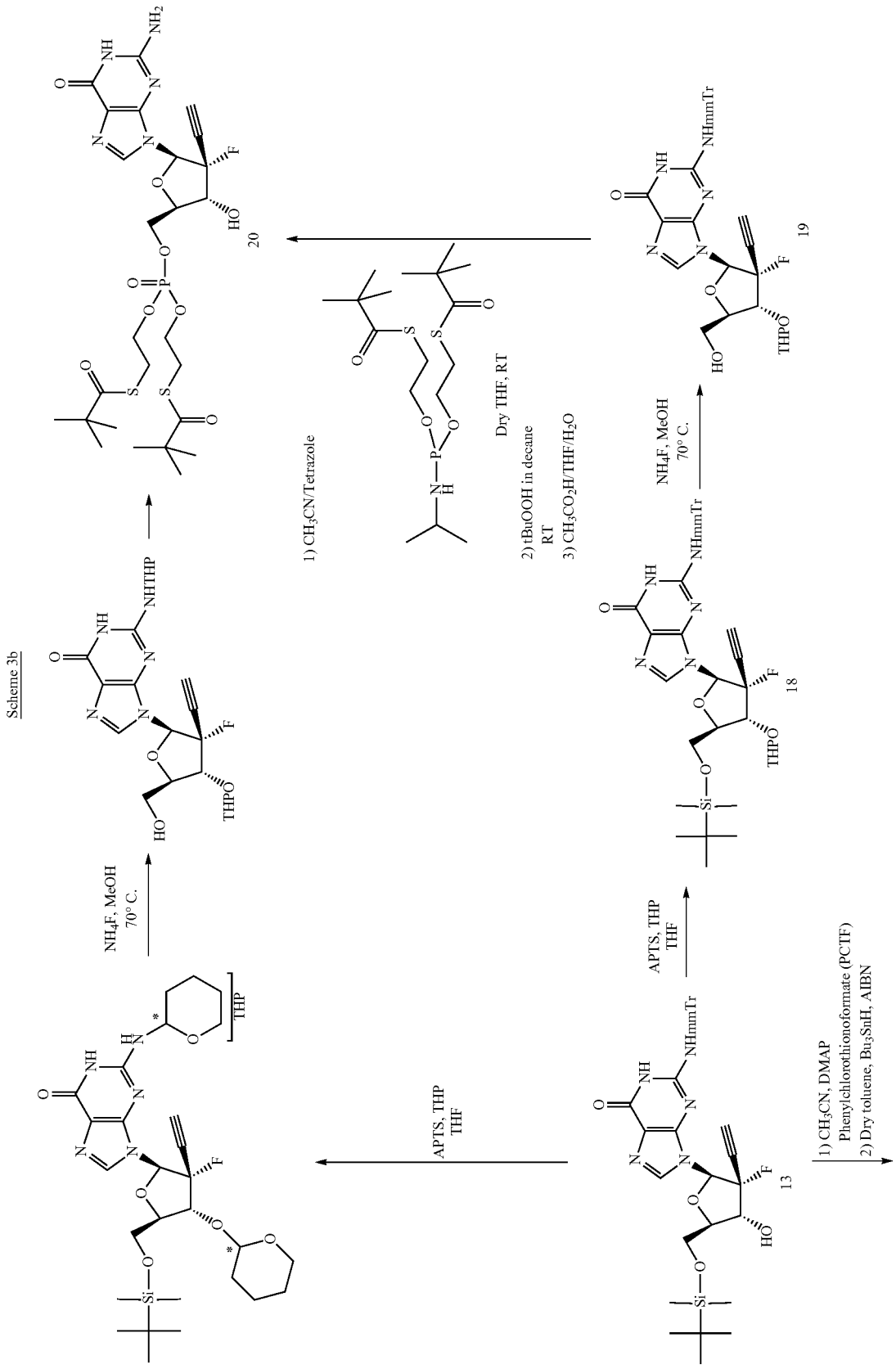

-continued
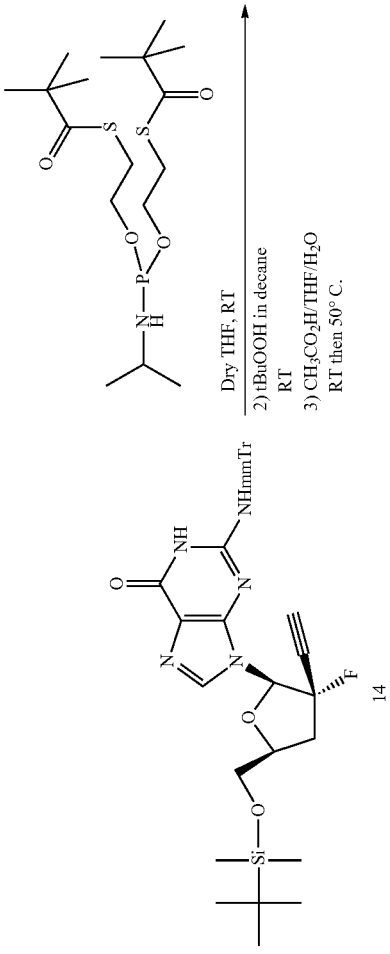

Scheme 4

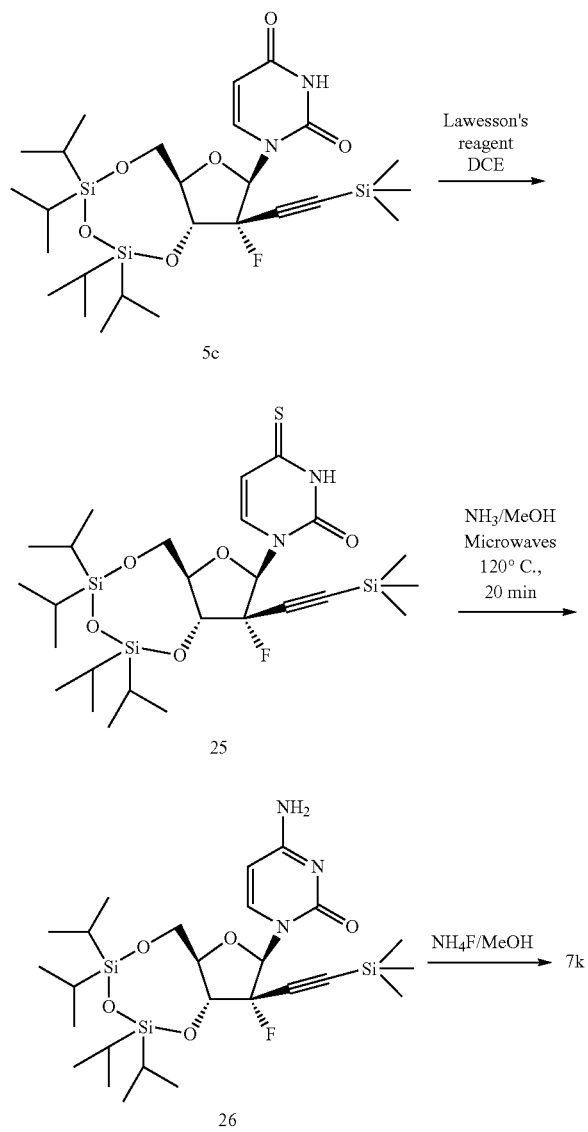

Scheme 5

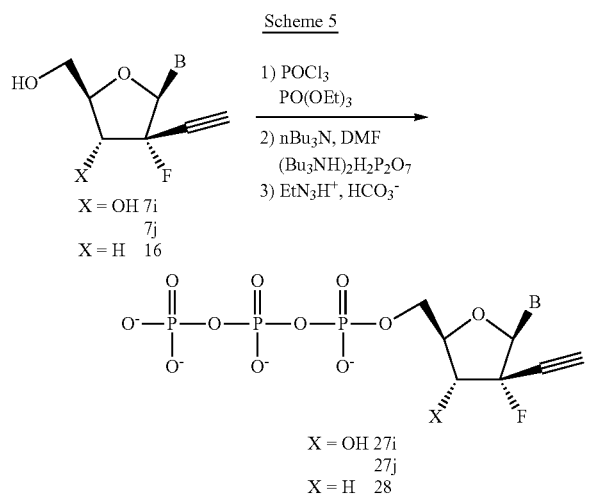

3a: 6-Chloro-9-[2-oxo-3,5-O-(1,3-diyl-1,1,3,3-tetraisopropyldisiloxane)-β-D-ribo-furanosyl]purine 6-Chloro-[3,5-O-(1,3-diyl-1,1,3,3-tetraisopropyldisiloxane)-β-D-ribo-furanosyl]purine (18.84 mmol) was coevaporated twice with THF then dissolved in anhydrous THF (50 mL). Anhydrous DMSO (119.82 mmol) was added and the resulting solution was cooled down to between −40° C. and −30° C. Trifluoroacetic anhydride (36.17 mmol) was added dropwise and the solution was stirred between −40° C. and −30° C. for 2 h after which $EtN_3$ (97.52 mmol) was added. The resulting solution was allowed to warm up to room temperature over 30 min while stirring, then diluted with diethyl ether and washed with $H_2O$, dried ($Na_2SO_4$) and evaporated to dryness. The crude material was purified by column chromatography eluting with 1% ethyl acetate in dichloromethane. The yellow oil obtained was dissolved in DCM and stirred with an excess of $MgSO_4$ at room temperature for 36 h, filtered and concentrated under reduced pressure to give the title compound. Pale yellow foam. Molecular Formula $C_{22}H_{35}ClN_4O_5Si_2$. $^1H$ NMR (DMSO-$d_6$, 250 MHz) δ (ppm) 9.01 (s, 1H, H-8), 8.61 (s, 1H, H-2), 6.35 (s, 1H, H-1'), 5.35 (d, 1H, H-3', $J_{3'-4'}$=9.7 Hz), 4.31 (m, 1H, H-4'), 4.12-4.09 (m, 2H, H-5', H-5"), 1.22-0.94 (m, 28H, iPr). LRFAB-MS (GT): 527 $(M+H)^+$, 525 $(M-H)^-$. UV $λ_{max}$ 263 nm. $R_f$ 0.17 (ethyl acetate/$CH_2Cl$, 10/90, v/v).

4a and 4'a: 6-Chloro-9-[3,5-O-(1,3-diyl-1,1,3,3-tetraisopropyldisiloxane)-2-C-trimethysilylethynyl-β-D-arabino-furanosyl]purine (4a) and 6-chloro-9-[3,5-O-(1,3-diyl-1,1,3,3-tetraisopropyl-disiloxane)-2-C-trimethylsilylethynyl-β-D-ribo-furanosyl]purine (4'a)

Trimethylsilylacetylene (59.20 mmol) was dissolved in anhydrous THF (70 mL). n-Butyllithium (37 mL, 1.6 M in hexanes) was added dropwise at −78° C. The reaction mixture was stirred for 30 min at −78° C. and then allowed to warm up to −55° C. 3a (11.84 mmol) in solution in THF (34 mL) was added dropwise at −78° C. The reaction mixture was stirred for 1 h at −78° C. and then allowed to warm up to −30° C. The reaction was quenched by careful addition of aqueous saturated $NH_4Cl$ (45 mL) at −78° C. After warming to room temperature, the mixture was diluted with diethyl ether, washed with saturated brine, dried ($Na_2SO_4$) and concentrated to dryness. The crude material was purified by silica gel chromatography eluting with 20% $Et_2O$ in petroleum ether to yield two compounds: 4a (4.62 g, 62%). Pale yellow foam. Molecular Formula $C_{27}H_{45}ClN_4O_5Si_3$ $^1H$ NMR (DMSO-$d_6$, 200 MHz) δ (ppm) 8.81 (s, 1H, H-8), 8.64 (s, 1H, H-2), 6.64 (s, 1H, OH-2'), 6.33 (s, 1H, H-1'), 4.57 (d, 1H, H-3', $J_{3'-4'}$=6.6 Hz), 4.20-3.97 (m, 3H, H-4', H-5' and H-5"), 1.20-1.00 (m, 28H, iPr), 0.14 (s, 9H, $Si(CH_3)_3$). LRFAB-MS (GT): 625 $(M+H)^+$. $R_f$ 0.72 (ethyl acetate/$CH_2Cl$, 10/90, v/v);

and 4'a (0.75 g, 10%). Yellow oil. Molecular Formula $C_{27}H_{45}ClN_4O_5Si_3$ $^1H$ NMR (DMSO-$d_6$, 200 MHz) δ (ppm) 8.80 (s, 1H, H-8), 8.73 (s, 1H, H-2), 6.64 (s, 1H, OH-2'), 6.55 (s, 1H, H-1'), 4.62 (d, 1H, H-3', $^3J_{3'-4'}$=9.1 Hz), 4.39 (m, 1H, H-4'), 4.13 (dd, 1H, H-5', $J_{5'-4'}$=3.4 Hz, $^2J_{5'-5"}$=13.2 Hz), 3.90 (dd, 1H, H-5", $J_{5"-4'}$=2.6 Hz, $^2J_{5"-5'}$=13.2 Hz), 1.15-1.00 (m, 28H, iPr), 0.10 (s, 9H, $Si(CH_3)_3$). LRFAB-MS (GT): 625 $(M+H)^+$. $R_f$ 0.64 (ethyl acetate/$CH_2Cl$, 10/90, v/v).

5a: 6-Chloro-9-[(2R)-2-deoxy-2-fluoro-3,5-O-(1,3-diyl-1,1,3,3-tetraisopropyldisiloxane)-2-C-trimethylsilylethynyl-β-D-erythro-pentofuranosyl]purine 4a (6.78 mmol) was dissolved in dried toluene (31.8 mL) under argon and cooled to −20° C. DAST (40.68 mmol) was added dropwise and the cooling bath was removed after the addition was complete. Stirring was continued for 1.5 hour and the mixture was dissolved with ethyl acetate and poured into saturated NaHCO$_3$ and stirred for 5 min. The organic layer was washed with saturated brine, dried (Na$_2$SO$_4$), concentrated, and purified by silica gel chromatography eluting with 20% Et$_2$O in petroleum ether to give the title compound (1.11 g, 26%). Yellow oil. Molecular Formula C$_{27}$H$_{44}$ClN$_4$O$_4$Si$_a$. $^1$H NMR (CDCl$_3$-d$_6$, 200 MHz) δ(ppm) 8.79 (s, 1H, H-8), 8.48 (s, 1H, H-2), 6.48 (d, 1H, H-1', J$_{1'-F}$=16.0 Hz), 4.74 (dd, 1H, H-3', J$_{3'-4}$=9.4 Hz, J$_{3'-F}$=22.4 Hz), 4.36 (d, 1H, H-5', $^2$J$_{5'-5'}$=13.4 Hz), 4.20 (m, 1H, H-4'), 4.10 (dd, 1H, H-5", $^2$J$_{5'-5'}$=13.4 Hz, J$_{5''-4}$=2.6 Hz), 1.30-1.10 (m, 28H, iPr), 0.00 (s, 9H, Si(CH$_3$)$_3$). LRFAB-MS (GT): 627 (M+H)$^+$. UV λ$_{max}$ 263 nm. R$_f$ 0.24 (diethyl ether/petroleum ether, 30/70, v/v).

6a: 6-Chloro-9-[(2R)-2-deoxy-2-C-ethynyl-2-fluoro-β-D-erythro-pentofuranosyl]purine A mixture of 5a (3.65 mmol) and ammonium fluoride (47.45 mmol) in methanol (12.5 mL) was heated at reflux for 2 h. After cooling down to room temperature, the mixture was concentrated to dryness and purified on silica gel chromatography eluting with a stepwise gradient 2-4% of methanol in DCM to provide the title compound (0.89 g, 78%). Yellow solid. Molecular Formula C$_{12}$H$_{10}$ClFN$_4$O$_3$. $^1$H NMR (DMSO-d$_6$, 200 MHz) δ(ppm) 9.02 (s, 1H, H-8), 8.89 (s, 1H, H-2), 6.55 (d, 1H, H-1', J$_{C-F}$=16.1 Hz), 6.34 (1d, 1H, OH-3'), 5.38 (lt, 1H, OH-5'), 4.64 (dt, 1H, H-3', J$_{3'-4}$=9.3 Hz, J$_{3'-F}$=22.5 Hz), 4.07 (m, 1H, H-4'), 3.83 (m, 2H, H-5', H-5"), 3.76 (d, 1H, ethynyl, $^4$J$_{H-F}$=5.3 Hz). $^{13}$C NMR (DMSO-d$_6$, 75 MHz) δ(ppm) 152.0 (C-2), 151.2 (C-4), 149.5 (C-6), 144.7 (C-8), 130.9 (C-5), 95.1 (d, C-2', $^1$J$_{2'-F}$=182.3 Hz), 88.0 (d, C-1', $^2$J$_{1'-F}$=39.8 Hz), 82.9 (d, CCH, J$_{C-F}$=8.2 Hz), 82.5 (C-4'), 75.3 (d, CCH, J$_{C-F}$=31.5 Hz), 72.7 (d, C-3', $^2$J$_{3'-F}$=19.5 Hz), 59.0 (C-5'). $^{19}$F NMR (DMSO-d$_6$, 235 MHz) δ(ppm) −159.0 (m). LC/MS: (M+H$^+$) 313.1 (8.29 min). UV λ$_{max}$ 262 nm. R$_f$ 0.21 (MeOH/CH$_2$Cl, 7/93, v/v).

7i: 9-[(2R)-2-Deoxy-2-C-ethynyl-2-fluoro-β-D-erythro-pentofuranosyl]adenine 6a (2.24 mmol) was dissolved in saturated ammoniacal methanol (80 mL) and heated for 4 h in a steel bomb at 90° C. After cooling down to room temperature the mixture was coevaporated to dryness and purified by silica gel chromatography eluting with a gradient 5-8% of methanol in DCM to yield the title compound (305 mg, 46%). Yellow solid. Molecular Formula C$_{12}$H$_{12}$FN$_5$O$_3$. $^1$H NMR (DMSO-d$_6$, 200 MHz) δ(ppm) 8.40 (s, 1H, H-8), 8.17 (s, 1H, H-2), 7.38 (1s, 2H, NH$_2$) 6.35 (d, 1H, H-1', $^3$J$_{1'-F}$=17.1 Hz), 6.25 (m, 1H, OH-3'), 5.33 (lt, 1H, OH-5'), 4.68 (m, 1H, H-3'), 4.00-3.69 (m, 3H, H-4', H-5', H-5"), 3.77 (d, 1H, ethynyl, $^4$J$_{H-F}$=5.4 Hz). $^{13}$C NMR (DMSO-d$_6$, 75 MHz) δ(ppm) 155.8 (C-4), 152. (C-2), 149.0 (C-6), 138.7 (C-8), 118.5 (C-5), 95.4 (d, C-2', $^1$J$_{2'-F}$=180.8 Hz), 87.6 (d, C-1', $^2$J$_{1'-F}$=40.5 Hz), 82.5 (d, CCH, $^3$J$_{C-F}$=8.0 Hz), 82.0 (C-4'), 74.5 (d, CCH, $^2$J$_{C-F}$=31.0 Hz), 72.8 (d, C-3', $^2$J$_{3'-F}$=19.5 Hz), 59.2 (C-5'). $^{19}$F NMR (DMSO-d$_6$, 235 MHz) δ(ppm) −158.0 (t). LC/MS: (M+H$^+$) 294.1 (5.74 min). UV λ$_{max}$ 258 nm. R$_f$ 0.33 (MeOH/CH$_2$Cl, 15/85, v/v).

4b: N$^2$-Isobutyryl-9-[3,5-O-(1,3-diyl-1,1,3,3-tetraisopropyldisiloxane)-2-C-trimethylsilylethynyl-β-D-arabino-furanosyl]-guanine To a suspension of CrO$_3$ (110.76 mmol) in DCM (220 mL) at 0° C., acetic anhydride (110.76 mmol) and anhydrous pyridine (221.52 mmol) were added. 9-[3,5-O-(1,3-Diyl-1,1,3,3-tetraisopropyldisiloxane)-ribo-furanosyl]-N$^2$-isobutyrylguanine (36.92 mmol) in solution in DCM (110 mL) was added dropwise. The cooling bath was removed and the resulting solution stirred at room temperature for 5 h. The reaction mixture was poured into cold ethyl acetate, filtered through a silica and celite gel plug, concentrated to dryness and coevaporated twice with toluene. The residue obtained was dissolved in DCM and stirred with an excess of MgSO$_4$ overnight, filtered and evaporated to get the ketone. The trimethylsilylacetylene (88.60 mmol) was dissolved in anhydrous THF (98 mL) under argon. n-Butyllithium (55.4 mL, 1.6 M in hexanes) was added dropwise at −78° C. The reaction mixture was stirred for 30 min at −78° C. and then allowed to warm up to −55° C. The ketone in solution in THF (49 mL) was added dropwise at −78° C. The reaction mixture was stirred for 1 h at −78° C. and then allowed to warm up to −30° C. and stirred for 3 h. The reaction was quenched by careful addition of aqueous saturated NH$_4$Cl (72 mL) at −78° C. After warming to room temperature, the mixture was diluted with ethyl acetate, washed twice with saturated brine, dried (Na$_2$SO$_4$) and concentrated to dryness. The crude material was purified using column chromatography eluting with 1.5% MeOH in dichloromethane to give the title compound (8.59 g, 34%, 2 steps). Pale yellow foam. Molecular Formula C$_{31}$H$_{55}$N$_5$O$_6$Si$_3$. $^1$H NMR (DMSO-d$_6$ 250 MHz) δ(ppm) 12.10 (1s, 1H, NH), 11.69 (1s, 1H, NH), 7.91 (s, 1H, H-8), 6.69 (s, 1H, OH), 5.94 (s, 1H, H-1'), 4.29 (d, 1H, H-3', J$_{3'-4}$=5.5 Hz), 3.85-3.95 (m, 3H, H-4', H-5' and H-5"), 2.46 (m, 1H, CH(CH$_3$)$_2$), 0.90-1.08 (m, 30H, iPr and CH(CH$_3$)$_3$), 0.00 (s, 9H, Si(CH$_3$)$_2$). LC/MS: (M+H$^+$) 692.4 (24.96 min). UV λ$_{max1}$ 254 nm, λ$_{max2}$ 281 nm. R$_f$ 0.34 (MeOH/CH$_2$Cl, 15/85, v/v).

5b: N$^2$-Isobutyryl-9-[(2R)-2-deoxy-2-fluoro-3,5-O-(1,3-diyl-1,1,3,3-tetraisopropyldisiloxane)-2-C-trimethyl-silylethynyl-β-D-erythro-pentofuranosyl]-guanine 4b (2.89 mmol) was dissolved in dried DCM (60 mL) under argon and pyridine (18.06 mmol) was added. The reaction mixture was cooled to −20° C. and DAST (31.35 mmol) was added dropwise. The cooling bath was removed after completion of the addition. Stirring was continued for 1 h 15 and the mixture was dissolved with ethyl acetate and poured into saturated NaHCO$_3$ and stirred for 5 min. The organic layer was washed with saturated brine, dried (Na$_2$SO$_4$), concentrated, and purified by silica gel chromatography eluting with ethyl acetate in DCM (2%) to give the title compound (1.41 g, 70%). Yellow oil. Molecular Formula C$_{31}$H$_{54}$FN$_5$O$_5$Si$_3$. $^1$H NMR (DMSO-d$_6$, 250 MHz) δ(ppm) 12.22 (s, 1H, NH), 8.09 (s, 1H, H-8), 6.21 (d, 1H, H-1', J$_{1'-F}$=15.6 Hz), 4.54 (dd, 1H, H-3', J$_{3'-F}$=23.6 Hz, J$_{3'-4}$=9.8 Hz), 4.33 (m, 1H, H-5', $^2$J$_{5'-5''}$=13.1 Hz), 4.16 (m, 1H, H-5"), 2.81 (m, 1H, CH (CH$_3$)$_2$), 1.13-1.03 (m, 34H, iPr and CH(CH$_3$)$_2$), 0.08 (s, 9H, Si(CH$_3$)$_3$, $^3$J$_{H-H}$=6.9 Hz). $^{19}$F NMR (DMSO-d$_6$, 235 MHz) δ(ppm) −160.26 (dd, J$_{F-1'}$=16.1 Hz, J$_{F-3}$=23.3 Hz). LC/MS: (M+H$^+$) 694.7 (24.02 min). LRFAB-MS (GT): 694 (M+H)$^+$, 692 (M−H)$^−$. UV λ$_{max}$ 256 nm. R$_f$ 0.46 (MeOH/CH$_2$Cl, 05/95, v/v).

6b: N$^2$-Isobutyryl-9-[(2R)-2-deoxy-2-C-ethynyl-2-fluoro-β-D-erythro-pentofuranosyl]-guanine 5b (1.89 mmol) was dissolved in methanol (13.8 mL) and ammonium fluoride (24.54 mmol) was added. The resulting solution was stirred at reflux for 1 h and evaporated to dryness. The crude material was purified on silica gel chromatography eluting with a stepwise gradient 6-10% of methanol in DCM to yield the title compound (344 mg, 48%). Pale yellow oil. Molecular Formula $C_{16}H_{20}FN_5O_4Si_3$. $^1H$ NMR (DMSO-$d_6$, 400 MHz) δ(ppm) 12.18 (1s, 1H, NH), 11.77 (1s, 1H, NH), 8.34 (s, 1H, H-8), 6.29 (d, 1H, OH-3', $J_{OH-3'}$=7.5 Hz), 6.20 (d, 1H, H-1', $J_{1'-F}$=16.2 Hz), 5.39 (t, 1H, OH-5', $J_{OH-5'}$=5.1 Hz), 4.52 (dt, 1H, H-3', $J_{3'-F}$=22.9 Hz), 3.98 (m, 1H, H-4'), 3.90-3.85 (m, 2H, H-5' and ethynyl), 3.72 (m, 1H, H-5"), 2.52 (m, 1H, CH(CH$_3$)$_2$), 1.14 (d, 6H, CH(CH$_3$)$_2$, $^3J_{H-H}$=6.9 Hz). $^{13}C$ NMR (DMSO-$d_6$, 100 MHz) δ(ppm) 180.7 (C-6), 155.3 (C-2), 148.9 (C-4), 137.3 (C-8), 120.4 (C-5), 95.8 (d, C-2', $^1J_{2'-F}$=182.1 Hz), 87.7 (d, C-1', $^2J_{1'-F}$=39.2 Hz), 83.4 (d, CCH, $^3J_{C-F}$=9.1 Hz), 82.6 (C-4'), 75.9 (d, CCH, $^2J_{C-F}$=31.2 Hz), 72.9 (d, C-3', $^2J_{3'-F}$=19.1 Hz), 59.3 (C-5'). $^{19}F$ NMR (DMSO-$d_6$, 235 MHz) δ(ppm) –158.9 (m). LC/MS: (M+H$^+$) 380.3 (8.34 min). UV $\lambda_{max1}$ 256 nm, $R_f$ 0.40 (MeOH/CH$_2$Cl, 15/85, v/v).

7j: 9-[(2R)-2-Deoxy-2-C-ethynyl-2-fluoro-β-D-erythro-pentofuranosyl]-guanine 6b (1.33 mmol) was dissolved in saturated methanolic ammonia (62 mL) and stirred at room temperature for 20 h. The reaction mixture was then evaporated to dryness under reduced pressure. The residue was dissolved in water and washed twice with ethyl acetate. The aqueous layer was evaporated and purified on reverse phase column chromatography (C18) eluting with a gradient 2-15% of acetonitrile in water. The residue obtained was then dissolved in hot ethyl acetate, filtered and dried to give the title compound (134 mg, 33%). Yellow solid. Molecular Formula $C_{12}H_{12}FN_5O_4$ $^1H$ NMR (DMSO-$d_6$, 400 MHz) δ(ppm) 10.70 (1s, 1H, NH), 7.98 (s, 1H, H-8), 6.60 (1s, 2H, NH$_2$), 6.21 (d, 1H, OH-3', $J_{OH-3'}$=7.6 Hz), 5.83 (d, 1H, H-1', $J_{1'-F}$=16.9 Hz), 5.29 (t, 1H, OH-5', $J_{OH-5'}$=5.2 Hz), 4.50 (td, 1H, H-3', $J_{3'-F}$=22.8 Hz, $J_{3'-4'}$=9.2 Hz), 3.93-3.81 (m, 3H, H-4', H-5' and ethynyl), 3.70 (m, 1H, H-5"). $^{13}C$ NMR (DMSO-$d_6$, 100 MHz) δ(ppm) 157.2 (C-6), 154.3 (C-2), 151.05 (C-4), 135.1 (C-8), 116.7 (C-5), 96.4 (d, C-2', $^1J_{C-F}$=182.1 Hz), 87.4 (d, C-1', $^2J_{C-F}$=39.2 Hz), 83.1 (d, CCH, $J_{C-F}$=9.1 Hz), 82.4 (C-4'), 76.2 (d, CCH, $^2J_{C-F}$=31.2 Hz), 73.2 (d, C-3', $^2J_{C-F}$=20.1 Hz), 59.5 (C-5'). $^{19}F$ NMR (DMSO-$d_6$, 235 MHz) δ(ppm) –158.5 (m). LC/MS (A): (M+H$^+$) 310.1 (5.55 min). LRFAB-MS (GT): 619 (2M+H)$^+$, 310 (M+H)$^+$, 152 (B+H)$^+$, 617 (2M–H)$^-$, 308 (M–H)$^-$. UV $\lambda_{max}$ 253 nm 3c: 1-[2-oxo-3,5-O-(1,3-diyl-1,1,3,3-tetraisopropyldisiloxane)-β-D-ribo-furanosyl]uracile 3c was synthesized from 1-[3,5-O-(1,3-diyl-1,1,3,3-tetraisopropyldisiloxane)-ribo-furanosyl]uracile as described for 3a. Pale yellow foam. Molecular Formula $C_{21}H_{36}N_2O_7Si_2$ $^1H$ NMR (DMSO-$d_6$, 400 MHz) δ(ppm) 11.58 (1s, 1H, NH), 7.74 (d, 1H, H-6, $J_{6-5}$=8.0 Hz), 5.68 (d, 1H, H-5, $J_{5-6}$=8.0 Hz), 5.45 (s, 1H, H-1'), 4.97 (d, 1H, H-3', $J_{3'-4'}$=9.2 Hz), 4.06-3.90 (m, 3H, H-4', H-5'), 1.14-0.87 (m, 28H, iPr). LR LC/MS: (M+H$^+$) 485.1 (M–H$^-$) 483.1 (5.53 min). UV $\lambda_{max}$ 262 nm. $R_f$ 0.40 (MeOH/CH$_2$Cl, 05/95, v/v).

4c: 1-[3,5-O-(1,3-diyl-1,1,3,3-tetraisopropyldisiloxane)-2-C-trimethylsilylethynyl-β-D-arabino-furanosyl]uracile
Yoshimura, Y.; Iino, T.; Matsuda, A. *Tetrahedron Lett.* 1991, 32, 6003-6006.

Molecular Formula $C_{26}H_{46}N_2O_7Si_3$ $^1H$ NMR (DMSO-$d_6$, 400 MHz) δ(ppm) 11.35 (1s, 1H, NH), 7.44 (d, 1H, H-6, $J_{6-5}$=8.0 Hz), 6.54 (s, 1H, OH), 6.02 (s, 1H, H-1'), 5.54 (d, 1H, H-5, $J_{6-5}$=8.0 Hz), 4.13-3.93 (m, 3H, H-3', H-5'), 3.75 (m, 1H, H-4'), 1.03-0.96 (m, 28H, iPr), 0.00 (s, 9H, Si(CH3)3). $^{13}C$ NMR (DMSO-$d_6$, 100 MHz) δ(ppm) 163.4 (C-4), 150.8 (C-2), 141.6 (C-6), 103.6 (CCSi), 101.2 (C-5), 92.5 (CCSi), 87.3 (C-1'), 80.9 (C-4'), 77.9 (C-2'), 75.9 (C-3'), 61.8 (C-5'), 17.7-17.1 (8C, 4 SiC(CH$_3$)$_2$), 13.3-12.6 (4C, 4 SiC(CH$_3$)$_2$), 0.2 (3C, Si(CH$_3$)$_3$). LR LC/MS: (M+H$^+$) 583.2 (M–H$^-$) 581.2 (6.72 min). UV $\lambda_{max}$ 261 nm. $R_f$ 0.27 (Ethyl acetate/CH$_2$Cl, 10/90, v/v).

5c: 1-[(2R)-2-Deoxy-2-fluoro-3,5-O-(1,3-diyl-1,1,3,3-tetraisopropyldisiloxane)-2-C-trimethylsilylethynyl-β-D-erythro-pentofuranosyl]uracile 5c was synthesized from 4c as described for 5a. Yellow oil. Molecular Formula $C_{27}H_{49}FN_2O_6Si_3$ $^1H$ NMR (DMSO-$d_6$, 400 MHz) δ(ppm) 11.62 (s1, 1H, NH), 7.43 (d1, 1H, H-6, $J_{6-5}$=8.0 Hz), 6.12 (d, 1H, H-1', $J_{F-F}$=16.8 Hz), 5.68 (d, 1H, H-5, $J_{5-6}$=8.0 Hz), 4.22-3.85 (m, 4H, H-3', H-4', H-5'), 1.16-1.00 (m, 28H, iPr), 0.00 (s, 9H, Si(CH$_3$)$_3$). $^{19}F$ NMR (DMSO-$d_6$, 376 MHz) δ(ppm) –159.7. LR LC/MS: (M+H$^+$) 585.2 (M–H$^-$) 583.3 (6.47 min). UV $\lambda_{max}$ 261 nm. $R_f$ 0.52 (Ethyl acetate/CH$_2$Cl, 15/85, v/v).

6c: 1-[(2R)-2-Deoxy-2-C-ethynyl-2-fluoro-β-D-erythro-pentofuranosyl]uracile

A mixture of 5c (0.56 mmol) and ammonium fluoride (7.31 mmol) were dissolved in methanol (10 mL) stirred at reflux for 1 h and evaporated to dryness. The resulting residue was purified on silica gel flash column chromatography eluting with a gradient 0-20% methanol in DCM and then, on reverse phase column chromatography eluting with a gradient 0-100% acetonitrile in water to give the desired product which was lyophilised from water (47 mg, 31%). White lyophilised powder. Molecular Formula $C_{11}H_{11}FN_2O_5$. $^1H$ NMR (DMSO-$d_6$, 400 MHz) δ(ppm) 11.49 (s1, 1H, NH), 7.87 (d, 1H, H-6, $J_{6-5}$=8.0 Hz), 6.18 (d, 1H, OH-3', $J_{OH-3}$=7.2 Hz), 6.10 (d, 1H, H-1', $J_{1'-F}$=18.0 Hz), 5.69 (d, 1H, H-5, $J_{5-6}$=8.0 Hz), 5.32 (m, 1H, OH-5'), 4.19-4.10 (m, 2H, H-3' and ethynyl), 3.85-3.75 (m, 2H, H-4' H-5'), 3.60 (m, 1H, H-5"). $^{13}C$ NMR (DMSO-$d_6$, 100 MHz) δ(ppm) 163.3 (C-4), 150.6 (C-2), 140.1 (C-6), 102.5 (C-5), 95.5 (d, C-2', $J_{2'-F}$=186.1 Hz), 87.1 (d, C-1', $^2J_{1'-F}$=40.2 Hz), 83.2 (d, CCH, $^2J_{C-F}$=8.0 Hz), 82.1 (C-4'), 76.5 (d, CCH, $^4J_{C-F}$=30.1 Hz), 73.3 (d, C-3', $^2J_{C-F}$=19.1 Hz), 58.7 (C-5'). $^{19}F$ NMR (DMSO-$d_6$, 376 MHz) δ(ppm) –158.2. LR LC/MS: (M+H$^+$) 271.1 (M–H$^-$) 269.2 (1.12 min). HRFAB-MS $C_{11}H_{12}O_5N_2F$. (M+H$^+$) calculated 271.0730. found 271.0739. UV $\lambda_{max}$ 261 nm. $R_f$ 0.33 (MeOH/CH$_2$Cl, 20/80, v/v).

2d: 1-[3,5-O-(1,3-diyl-1,1,3,3-tetraisopropyldisiloxane)-β-D-ribo-furanosyl]thymine The 1-(β-D-ribo-furanosyl)thymine (40.9 mmol) was dissolved in pyridine (435 ml) and the mixture was cooled down to 0° C. with an ice-bath for 25 minutes. Then, TIPSCl$_2$ (16.2 ml) was added and after complete addition, the mixture was allowed to warm up to room temperature. The reaction mixture was stirred at room temperature for 3 hrs, diluted with dichloromethane and water, washed with a saturated aqueous solution of NaHCO$_3$. The organic phases were combined, dried over Na$_2$SO$_4$, filtered and evaporated. The residue was coevaporated with toluene to remove pyridine. The resulting residue was purified by flash column chromatography eluting with a gradient 0-2% of methanol in dichloromethane to give the title compound. Off-white powder. Molecular Formula $C_{22}H_{40}N_2O_7Si_2$. $^1H$ NMR (DMSO-$d_6$, 400 MHz) δ(ppm)

0.94-1.04 (m, 28H), 1.73 (s, 3H), 3.86-3.96 (m, 1H), 4.06-4.13 (m, 2H), 4.14-4.20 (m, 1H), 5.44-5.48 (m, 1H), 5.53 (brs, 1H), 5.77 (brs, 1H) 7.42 (s, 1H), 11.35 (brs, 1H). UV $\lambda_{max}$ 212 nm, 266 nm.

3d: 1-[2-oxo-3,5-O-(1,3-diyl-1,1,3,3-tetraisopropyld-isiloxane)-β-D-ribo-furanosyl]thymine To a suspension of $CrO_3$ (60 mmol) in dichloromethane (200 mL) at 0° C., acetic anhydride (59 mmol) and anhydrous pyridine (120 mmol) were added. 2d (20 mmol) in solution in DCM was added dropwise. The cooling bath was removed and the resulting solution stirred at room temperature for 3 h. The reaction mixture was poured into cold ethyl acetate, filtered through a silica and celite gel plug, concentrated to dryness and coevaporated twice with toluene to give the title compound. Colorless oil. Molecular Formula $C_{22}H_{38}N_2O_7Si_2$

4d: 1-[3,5-O-(1,3-diyl-1,1,3,3-tetraisopropyldisilox-ane)-2-C-trimethylsilylethynyl-β-D-arabino-furano-syl]thymine 4d was synthesized from 3d and trimethylacetylene as described for 4a. Brown solid. Molecular Formula $C_{27}H_{48}N_2O_7Si_3$. Scan ES$^+$ 597 (M+H)$^+$, UV $\lambda_{max}$ 265 nm.

5d: 1-[(2R)-2-Deoxy-2-fluoro-3,5-O-(1,3-diyl-1,1,3,3-tetraisopropyldisiloxane)-2-C-trimethyl-silyleth-ynyl-β-D-erythro-pentofuranosyl]thymine 5d was synthesized from 4a as described for 5a. Brown solid. Molecular Formula $C_{27}H_{47}FN_2O_6Si_3$ $^1H$ NMR (CDCl$_3$-d$_6$, 400 MHz) δ(ppm) 0.1 (s, 9H), 1.05-1.14 (m, 28H), 1.92 (s, 3H), 3.99-4.13 (m, 1H), 4.44-4.9 (m, 3H), 6.35 (d, 1H, J=16.44 Hz), 7.2 (s, 1H), 8.86 (s, 1H). Scan ES$^+$ 599 (M+H)$^+$,

6d: 1-[(2R)-2-Deoxy-2-C-ethynyl-2-fluoro-β-D-erythro-pentofuranosyl]thymine 6d was synthesized from 5d as described for 7i. Molecular Formula $C_{12}H_{13}FN_2O_5$. $^1H$ NMR (CDCl$_3$-d$_6$, 400 MHz) δ(ppm) 1.75 (s, 3H), 3.6-3.65 (m, 1H), 3.82-3.84 (m, 2H), 4.07 (d, 1H, J=5.27 Hz), 4.19 (m, 1H), 5.4 (brs, 1H), 6.08 (d, 1H, J=17.8 Hz), 6.17 (brs, 1H), 7.8 (s, 1H), 11.46 (brs, 1H). Scan ES$^+$ 285 (M+H)$^+$, UV $\lambda_{max}$ 266 nm.

4e: N$^4$-Benzoyl-1-[3,5-O-(1,3-diyl-1,1,3,3-tetraiso-propyldisiloxane)-2-C-trimethylsilylethynyl-β-D-arabino-furanosyl]cytosine 4e was synthesized from 3e and trimethylacetylene as described for 4a. Brown solid. Molecular Formula $C_{33}H_{51}N_3O_7Si_3$ Scan ES$^+$ 686 (M+H)$^+$, UV $\lambda_{max}$ 260 nm, 310 nm.

5e: N$^4$-benzoyl-1-[(2R)-2-Deoxy-2-fluoro-3,5-O-(1,3-diyl-1,1,3,3-tetraisopropyldisiloxane)-2-C-trim-ethyl-silylethynyl-β-D-erythro-pentofuranosyl]cy-tosine 5e was synthesized from N$^4$-benzoyl-1-[3,5-O-(1,3-diyl-1,1,3,3-tetraisopropyldisiloxane)-2-C-trimethyl-silylethy-nyl-D-arabino-furanosyl]cytosine as described for 5a. Yellow solid. Molecular Formula $C_{30}H_{42}FN_3O_6Si_2$. Scan ES$^+$ 688 (M+H)$^+$, UV $\lambda_{max}$ 260 nm, 310 nm.

6e: N$^4$-benzoyl-1-[(2R)-2-Deoxy-2-C-ethynyl-2-fluoro-β-D-erythro-pentofuranosyl]cytosine 6e was synthesized from 5e as described for 7i. White powder. Molecular Formula $C_{18}H_{16}FN_3O_5$. $^1H$ NMR (DMSO-d$_6$, 400 MHz) δ(ppm) 3.63-3.69 (m, 1H), 3.82-3.93 (m, 2H), 4 (d, 1H, J=5.27 Hz), 4.13-4.24 (m, 1H), 5.38 (brs, 1H), 6.23-6.28 (m, 2H), 7.32-7.36 (m, 1H), 7.49-7.53 (m, 2H), 7.6-7.64 (m, 1H), 7.99-8.01 (m, 2H), 8.34 (d, 1H, J=7.32 Hz), 11.30 (brs, 1H). Scan ES$^+$ 374 (M+H)$^+$, UV $\lambda_{max}$ 262 nm, 303 nm.

7k: 1-[(2R)-2-Deoxy-2-C-ethynyl-2-fluoro-β-D-erythro-pentofuranosyl]cytosine Molecular Formula $C_{11}H_{12}FN_3O_4$. $^1H$ NMR (DMSO-d$_6$, 400 MHz) δ(ppm) 3.57-3.62 (m, 1H), 3.77-3.80 (m, 2H), 3.95 (d, 1H, J=5.53 Hz), 4.03-4.16 (m, 1H), 5.2 (brs, 1H), 5.73 (d, 1H, J=7.19 Hz), 6.06 (d, 1H, J=7.19 Hz), 6.14-6.25 (m, 1H), 7.17-7.3 (2brs, 2H), 7.74 (d, 1H, J=7.74 Hz). Scan ES$^+$ 270 (M+H)$^+$, UV $\lambda_{max}$ 271 nm.

8k: N$^4$-dimethoxytrityl-1-[(2R)-2-Deoxy-2-C-ethy-nyl-2-fluoro-β-erythro-pentofuranosyl]cytosine To a stirred solution of 7k (2.34 mmol) in pyridine (7.2 ml) was added trimethylsilyl chloride (9.36 mmol) at room temperature. The reaction mixture was stirred at room temperature for 2 hours. 4-dimethylamino pyridine (1.17 mmol) and dimethoxytrityl chloride (3.51 mmol) were then added. The mixture was stirred at room temperature for 16 hours. The reaction mixture was diluted with DCM and sat NaHCO$_3$ solution. The organic phase was washed twice with sat NaHCO$_3$ solution, dried over Na$_2$SO$_4$, filtered and evaporated. The crude material was dissolved in a solution NH4OH/dioxin (2:1) and stirred for 4 hrs. Solvent was evaporated and the residue purified by silica gel chromatography (DCM/EtOH) to yield the title compound. White foam. Molecular Formula $C_{32}H_{30}FN_3O_6$. Scan ES$^-$ 570 (M+H)$^-$, UV $\lambda_{max}$ 277 nm

9k: 1-[(2R)-2-Deoxy-2-C-ethynyl-2-fluoro-βD-erythro-pentofuranosyl]-4-N-dimethoxytrityl-cy-tosin-5'-yl-bis(S-pivaloyl-2-thioethylphosphate To a stirred solution of 8k (0.35 mmol) in anh THF/tetrazole solution (1.05 mmol) was added bis(S-pivaloyl-2-thio-ethyl) N,N-diisopropylphosphoramidite (0.42 mmol) at 0° C. The reaction mixture was stirred at room temperature for 3 hrs. The reaction mixture was cooled down to 0° C. and tert-butyl hydroperoxide (0.7 ml/mmol) was added. The reaction mixture was stirred at room temperature for 2 hours. The mixture was diluted with DCM, neutralized with sat Na$_2$S$_2$O$_3$ solution. The organic phase was washed twice with H$_2$O, extracted, dried over Na$_2$SO$_4$, filtered and evaporated. The crude material was purified by silica gel chromatography (DCM/EtOH) to yield the title compound. Glassy compound. Molecular Formula $C_{47}H_{59}FN_3O_{11}PS_2$. Scan ES$^+$ 938 (M+H)$^+$, UV $\lambda_{max}$ 277 nm

11k: 1-[(2R)-2-Deoxy-2-C-ethynyl-2-fluoro-β-D-erythro-pentofuranosyl]-cytosin-5'-yl-bis(S-pivaloyl-2-thioethylphosphate 9k (34 mmol) was stirred in AcOH/MeOH/H$_2$O (3/6/1) solution for 2 hrs and at 50° C. for 4 hours. The reaction mixture was then evaporated and purified by silica gel chromatography (DCM/EtOH) to yield the title compound. White lyophilized powder. Molecular Formula $C_{25}H_{37}FN_3O_9PS_2$. $^1H$ NMR (DMSO-$d_6$, 400 MHz) δ (ppm) 1.17 (s, 18H), 3.08-3.11 (t, J=6.07 Hz, 4H), 3.99-4.08 (m, 7H), 4.22-4.28 (m, 2H), 5.73-5.75 (d, J=7.30 Hz, 1H), 6.30 (brs, 2H), 7.26-7.31 (d, J=17.30 Hz, 2H), 7.47-7.48 (d, J=7.30 Hz, 1H) $^{19}F$ NMR (DMSO-$d_6$, 376 MHz) δ (ppm) −156.48 (s, 1F) $^{31}P$ NMR (DMSO-$d_6$, 162 MHz) δ (ppm) −1.96 (s, 1P). Scan ES$^+$ 638 (M+H)$^+$, UV $\lambda_{max}$ 271 nm 12: $N^2$-Methoxytrityl-9-[(2R)-2-deoxy-2-C-ethynyl-2-fluoro-β-D-erythro-pentofuranosyl]-guanine To a stirred solution of a (5.18 mmol) in pyridine (7 ml/mmol) was added trimethylsilyl chloride at room temperature. The mixture was stirred at room temperature for 6 hours. Methoxytrityl chloride (6.21 mmol) was then added and the reaction mixture was stirred at room temperature for 16 hours and 2 hours with NH$_4$OH (4 ml/mmol). The mixture was diluted with ethyl acetate, washed with H$_2$O, sat NaHCO$_3$ solution and sat NaCl solution, dried over Na$_2$SO$_4$, filtered and evaporated. The crude material was purified by silica gel chromatography (DCM/MeOH) to yield the title compound. Yellowish oil. Molecular Formula $C_{32}H_{28}FN_5O_5$.

13: $N^2$-Methoxytrityl-9-[(2R)-2-deoxy-2-C-ethynyl-2-fluoro-5-O-tert-butyldimethylsilyl-β-D-erythro-pentofuranosyl]-guanine To a stirred solution of 12 (2.29 mmol) in pyridine (5 ml) at 0° C., was added tert-butyldimethylsilyl chloride (2.75 mmol). The reaction mixture was stirred at room temperature for 24 hours. It was then diluted in DCM and washed twice with H$_2$O. The organic phase was extracted, dried over Na$_2$SO$_4$, filtered and evaporated. The crude material was purified by silica gel chromatography (DCM/MeOH) to yield the title compound. Yellowish oil. Molecular Formula $C_{38}H_{44}FN_5O_5Si$. Scan ES$^+$ 696 (M+H)$^+$, $\lambda_{max}$ 260 nm. Scan ES$^-$ 694 (M+H)$^-$, UV $\lambda_{max}$ 260 nm

14: $N^2$-Methoxytrityl-9-[(2R)-2,3-dideoxy-2-C-ethynyl-2-fluoro-5-O-tert-butyldimethylsilyl-β-D-glycero-pentofuranosyl]-guanine To a stirred solution of 13 (0.14 mmol) in acetonitrile (47 ml/mmol) was added 4-dimethylamino pyridine (0.56 mmol) and phenyl chlorothionoformate (0.43 mmol) at room temperature. The reaction mixture was stirred at room temperature for 16 hours and was concentrated under reduced pressure. The residue obtained was dissolved in DCM, the organic phase was washed with H$_2$O, HCl (1N), dried over Na$_2$SO$_4$, filtered evaporated and co-evaporated with toluene.

The crude material was dissolved in toluene (12 ml/mmol), azo-bis-isobutyronitrile (0.02 mmol) and tributylstannane (0.24 mmol) were added at room temperature. The reaction mixture was stirred at 125° C. for 2 hours and concentrated under reduced pressure. The crude material was purified by silica gel chromatography (DMC/MeOH) to yield the title compound. Yellowish oil. Molecular Formula $C_{38}H_{44}FN_5O_4Si$. Scan ES$^+$ 680 (M+H)$^+$, UV $\lambda_{max}$ 260 nm

15: $N^2$-Methoxytrityl-9-[(2R)-2,3-dideoxy-2-C-ethynyl-2-fluoro-β-D-glycero-pentofuranosyl]-guanine 14 (0.35 mmol) was dissolved in MeOH (20 ml/mmol). Ammonium fluoride (3.55 mmol) was then added at room temperature and the reaction mixture was stirred at 70° C. for 2 hours. After concentration under reduced pressure, the crude material was purified by silica gel chromatography (DCM/MeOH) to yield the title compound. Beige foam. Molecular Formula $C_{32}H_{30}FN_5O_4$. $^1H$ NMR (CDCl$_3$-$d_6$, 400 MHz) δ (ppm) 2.38-2.45 (m, 2H), 2.75 (brs, 2H), 3.64-3.67 (d, J=12.20 Hz, 2H), 3.77 (s, 4H), 4.20-4.23 (d, J=11.7 Hz, 1H), 4.41-4.42 (d, J=8.4 Hz, 1H), 5.83-5.87 (d, J=16.24 Hz, 1H), 6.80-6.82 (d, J=8.12 Hz, 4H), 7.26-7.31 (m, 11H), 7.84 (brs, 1H), 9.26 (brs, 1H)

16: 9-[(2R)-2,3-Dideoxy-2-C-ethynyl-2-fluoro-β-D-glycero-pentofuranosyl]guanine 15 (0.09 mmol) was stirred in AcOH/THF/H$_2$O (3/6/1) solution at 50° C. for 1 day. The reaction mixture was then concentrated under reduced pressure and purified by silica gel chromatography, C18 (H$_2$O/ACN) Beige lyophilisated powder. Molecular Formula $C_{12}H_{12}FN_5O_5$. $^1H$ NMR (DMSO-$d_6$, 400 MHz) δ (ppm) 2.57-2.74 (m, 2H), 3.56 (s, 1H), 3.61-3.64 (d, J=12.10 Hz, 1H), 3.79-3.82 (d, J=12.10 Hz, 1H), 3.91-3.93 (d, J=5.40 Hz, 1H), 4.32-4.35 (m, 1H), 5.25 (s, 1H), 6.06-6.10 (d, J=18.20 Hz, 1H), 6.64 (s, 1H), 8.01 (s, 1H), 10.82 (s, 1H) $^{19}F$ NMR (DMSO-$d_6$, 376 MHz) δ (ppm) −138.4 (s, 1F). Scan ES$^-$ 292 (M+H)$^-$, Scan ES$^+$ 316 (M+Na)$^+$, UV $\lambda_{max}$ 251 nm

17: 9-[(2R)-2,3-Dideoxy-2-C-ethynyl-2-fluoro-β-D-erythro-pentofuranosyl]-guanin-5'-yl-bis(S-pivaloyl-2-thioethylphosphate)

17 was synthesized from 14 (0.35 mmol) as described for 9. The crude material was then stirred in AcOH/THF/H$_2$O (4/2/1) at 50° C., for 3 hours. The reaction mixture was concentrated under reduced pressure and purified by silica gel chromatography (DCM/MeOH) to yield the title compound. Beige solid. Molecular Formula $C_{26}H_{37}FN_5O_8PSi_2$ $^1H$ NMR (DMSO-$d_6$, 400 MHz) δ (ppm) 2.48 (s, 18H), 2.65-2.68 (m, 2H), 3.06-3.10 (q, J=3.71 Hz, and J=6.02 Hz, 4H), 3.97-4.04 (m, 5H), 4.31-4.35 (m, 2H), 4.50-4.52 (m, 1H), 6.13-6.18 (d, J=17.60 Hz, 1H), 6.63 (s, 2H), 7.82 (s, 1H), 10.85 (s, 1H). $^{19}F$ NMR (DMSO-$d_6$, 376 MHz) δ (ppm) −139.2 (s, 1F). Scan ES$^+$ 662 (M+H)$^+$, UV $\lambda_{max}$ 254 nm. HPLC (0-100% ACN over a period of 8 min) $t_R$=5.65 min.

18: $N^2$-Methoxytrityl-9-[(2R)-2-deoxy-2-C-ethynyl-2-fluoro-5-O-tert-butyldimethylsilyl-3-O-tetrahydropyranyl-β-D-erythro-pentofuranosyl]-guanine To a stirred solution of 13 (0.8 mmol), in anh THF (20 ml/mmol), at room temperature, was added p-toluen sulfonic acid (0.12 mmol) and dihydropyran (2 ml/mmol). The reaction mixture was stirred at room temperature for 3 days and neutralized with TEA. The mixture was diluted with DCM, washed twice with H$_2$O. The organic phase was dried over Na$_2$SO$_4$, filtered and evaporated. The crude material was purified by silica gel chromatography (DCM/MeOH) to yield the title compound. Molecular Formula $C_{43}H_{52}FN_5O_6Si$. Scan ES$^+$ 780 (M+H)$^+$

19: $N^2$-Methoxytrityl-9-[(2R)-2-deoxy-2-C-ethynyl-2-fluoro-3-O-tetrahydropyranyl-β-D-erythro-pentofuranosyl]-guanine 19 was synthesized from 18, as described for 15. Molecular Formula $C_{37}H_{38}FN_5O_6$. Scan ES$^+$ 666 (M+H)$^+$.

21: $N^2$-Tetrahydropyranyl-9-[(2R)-2-deoxy-2-C-ethynyl-2-fluoro-5-O-tert-butyldimethylsilyl-3-O-tetrahydropyranyl-β-D-erythro-pentofuranosyl]-guanine 21 was obtained from the purification of 18. Molecular Formula $C_{28}H_{42}FN_5O_6Si$. Scan ES$^+$ 592 (M+H)$^+$, UV $\lambda_{max}$ 273 nm

22: $N^2$-Tetrahydropyranyl-9-[(2R)-2-deoxy-2-C-ethynyl-2-fluoro-3-β-tetrahydropyranyl-β-D-erythro-pentofuranosyl]-guanine 22 was synthesized from 21 (0.46 mmol), as described for 15. Molecular Formula $C_{22}H_{28}FN_5O_6$

20: 9-[(2R)-2-Deoxy-2-C-ethynyl-2-fluoro-β-D-erythro-pentofuranosyl]-guanin-5'-yl-bis(S-pivaloyl-2-thioethylphosphate 20 was synthesized from 19 (0.09 mmol), as described for 9k. The crude material was then stirred at room temperature in AcOH/THF/H$_2$O (4/2/1) solution overnight. The reaction mixture was concentrated under reduced pressure and purified by silica gel chromatography (DCM/MeOH) to yield the title compound. White lyophilized powder. Molecular Formula $C_{26}H_{37}FN_5O_9PS_2$ $^1$H NMR (DMSO-d$_6$, 400 MHz) δ (ppm) 1.16 (s, 20H), 3.06-3.09 (m, 4H), 3.90-3.91 (d, J=5.40 Hz, 1H), 3.99-4.10 (q, J=6.70 Hz and J=7.00 Hz, 4H), 4.32-4.38 (m, 2H), 4.63 (m, 1H), 6.10-6.14 (d, J=16.93 Hz, 1H), 6.69 (s, 2H), 7.79 (s, 1H), 10.96 (s, 1H) $^{31}$P NMR (DMSO-d$_6$, 162 MHz) δ (ppm) −1.91 (s, 1P) $^{19}$F NMR (DMSO-d$_6$, 376 MHz) δ (ppm) −156.82 (s, 1F) Scan ES$^+$ 678 (M+H)$^+$.

25: 1-[(2R)-2-Deoxy-2-fluoro-3,5-O-(1,3-diyl-1,1,3,3-tetraisopropyldisiloxane)-2-C-trimethylsilylethynyl-β-D-erythro-pentofuranosyl]-4-thiouracile 5c (820 mg, 1.40 mmol) was dissolved in anhydrous 1,2-dichloroethane (35 mL) and treated with Lawesson's reagent (1.13 g, 2.80 mmol). The reaction mixture was stirred at reflux overnight and evaporated to dryness. The resulting residue was filtered on a silica gel plug eluting with a gradient 0-5% of ethyl acetate in dichloromethane to give the title compound. Yellow oil. Molecular Formula $C_{26}H_{45}FN_2O_5SSi_3$ LR LC/MS: (M+H$^+$) 601.3 (M−H$^-$) 599.3 (7.03 min). UV $\lambda_{max}$ 332 nm. R$_f$ 0.71 (Ethyl acetate/CH$_2$Cl$_2$ 7/93, v/v).

26: 1-[(2R)-2-Deoxy-2-fluoro-3,5-O-(1,3-diyl-1,1,3,3-tetraisopropyldisiloxane)-2-C-ethynyl-β-D-erythro-pentofuranosyl]cytosine Crude 25 was dissolved in saturated ammoniacal methanol (9 mL). The resulting solution was heated by micro-waves at 120° C. for 20 min and concentrated under reduced pressure to give the title compound. Oily residue. Molecular Formula $C_{26}H_{46}FN_3O_5Si_3$ LR LC/MS (B): (M+H$^+$) 512.3 (M−H$^-$) 510.3 (5.33 min). UV $\lambda_{max1}$ 242 nm, $\lambda_{max2}$ 273 nm.

27i: 9-[(2R)-2-Deoxy-2-C-ethynyl-2-fluoro-β-D-erythro-pentofuranosyl]adenine 5'-triphosphate sodium salt To a solution of 7i (0.286 mmol) in triethylphosphate (750 µL), phosphoryle chloride (75 µL, 0.807 mmol) was added at 0° C. This reaction mixture A was stirred overnight at 5° C. Tributylammonium pyrophosphate (PPi/Bu$_3$N 1/1.5, 1 g, 2.19 mmol) was dissolved in anhydrous DMF (2 mL). Tributylamine (420 µL, 1.76 mmol) was added to the PPi and the resulting mixture was stirred for 15 min at 0° C. 2.4 mL of this solution were added to the reaction mixture A. The reaction mixture was stirred at 0° C. for 1 min. The reaction was carefully quenched with TEAB 1M (pH=7.5, 10 mL), stirred 20 min at 0° C., then diluted with water and ethyl acetate. The aqueous phase was concentrated under reduced pressure. The crude material was subjected to DEAE-Sephadex chromatography eluting with a gradient 10$^{-3}$-1 M of TEAB). The desired fractions were combined, concentrated under reduced pressure and coevaporated with a mixture of water/methanol, and finally coevaporated with water. The resulting residue was purified on semipreparative HPLC. Fractions containing the expected product were concentrated under reduced pressure, coevaporated with a mixture of water/methanol and lyophilised from water. The triethylammonium salt triphosphate was eluted three times with water on a Dowex Na$^+$ resin column to yield after lyophilisation from water to the sodium salt.

Molecular Formula $C_{12}H_{11}FN_5O_{12}P_3$ 3Na. $^1$H NMR (D$_2$O, 300 MHz) δ (ppm) 8.31 (s, 1H, H-8), 8.14 (s, 1H, H-2), 6.28 (d, 1H, H-1', $^3J_{1'-F}$=15.6 Hz), 4.64 (m, 1H, H-3'), 4.42 (m, 1H, H-5'), 4.35-4.25 (m, 2H, H-4' and H-5"), 2.82 (d, 1H, ethynyl, $^4J_{H-F}$=5.5 Hz). $^{31}$P NMR (D$_2$O, 121 MHz) δ(ppm) −10.27 (d, 1P, P$_\gamma$, J$_{P\gamma-P\beta}$=19.4 Hz), −11.03 (d, 1P, P$_\alpha$, J$_{P\alpha-P\beta}$=19.4 Hz), −22.38 (t, 1P, P$_\beta$, J$_{P\beta-P\gamma}$=J$_{P\beta-P\alpha}$=19.4 Hz). $^{19}$F NMR (D$_2$O, 282 MHz) δ (ppm) −160.0 (m). LRFAB-MS (GT): 600 (M+H)$^+$, 578 (M−Na+2H)$^+$, 556 (M−2Na+3H), 598 (M−H)$^-$, 576 (M−Na)$^-$, 554 (M−2Na+H)$^-$, 532 (M−3Na+2H)$^-$.

27i: 9-[(2R)-2-Deoxy-2-C-ethynyl-2-fluoro-β-D-erythro-pentofuranosyl]-guanine 5'-triphosphate sodium salt 27j was synthesized from 7j as described for 27. Molecular Formula $C_{12}H_{11}FN_5O_{13}P_3$ 3Na. $^1$H NMR (D$_2$O, 400 MHz) δ (ppm) 7.97 (s, 1H, H-8), 6.19 (d, 1H, H-1', $^3J_{1'-F}$=16.0 Hz), 4.70 (m, 1H under H$_2$O, H-3'), 4.39 (m, 1H, H-5'), 4.29-4.22 (m, 2H, H-4' and H-5"), 2.98 (d, 1H, ethynyl, $^4J_{H-F}$=5.0 Hz). $^{31}$P NMR (D$_2$O, 162 MHz): −10.50 (d, 1P, P$_\gamma$, J$_{P\gamma-P\beta}$=19.4 Hz), −11.03 (d, 1P, P$_\alpha$, J$_{P\alpha-P\beta}$=19.4 Hz), −22.38 (t, 1P, P$_\beta$, J$_{P\beta-P\gamma}$=J$_{P\beta-P\alpha}$=19.4 Hz). $^{19}$F NMR (DMSO-d$_6$, 376 MHz) δ (ppm) −159.1 (m). LRFAB-MS (GT): 638 (M+Na)$^+$, 616 (M+H)$^+$, 594 (M−Na+2H)$^+$, 572 (M−2Na+3H)$^+$, 550 (M−3Na+4H)$^+$, 592 (M−Na)$^-$, 570 (M−2Na+H)$^-$, 548 (M−3Na+2H)$^-$.

2g 4-Chloro-7-[3,5-O-(1,3-diyl-1,1,3,3-tetraisopropyldisiloxane)-β-D-ribo-furanosyl]pyrrolo[2,3-d]pyrimidine 2g was synthesized from 9-[β-D-ribo-furanosyl]-7-deaza-6-chloropurine, as described for intermediate 12. Yellow oil. Molecular Formula $C_{23}H_{38}ClN_3O_5Si_2$. $^1$H NMR (DMSO-d$_6$, 400 MHz) δ (ppm) 0.96-1.04 (m, 28H), 3.92-3.95 (m, 3H), 4.41-4.58 (m, 2H), 5.65 (s, 1H), 6.08 (s, 1H), 6.71 (s, 1H), 7.83 (s, 1H), 8.62 (s, 1H)

3g: 4-Chloro-7-[2-oxo-3,5-O-(1,3-diyl-1,1,3,3-tetraisopropyldisiloxane)-β-D-erythro-pentofuranosyl]pyrrolo[2,3-d]pyrimidine 3g was synthesized from 2g as described for 3d. Brown solid. Molecular Formula $C_{23}H_{36}ClN_3O_5Si_2$. Scan ES$^+$ (M+H)$^+$ 528, UV $\lambda_{max}$ 271 nm

4g: 4-Chloro-[3,5-O-(1,3-diyl-1,1,3,3-tetraisopropyl-disiloxane)-2-C-trimethylsilylethynyl-β-D-arabino-furanosyl]pyrrolo[2,3-d]pyrimidine 4g was synthesized from 3g as described for 4a. Beige solid. Molecular Formula: $C_{28}H_{46}ClN_3O_5Si_3$. $^1H$ NMR (DMSO-$d_6$, 400 MHz) δ (ppm), 0.12 (s, 9H), 0.95-1.09 (m, 28H), 3.90-3.94 (m, 1H), 4.02-4.03 (m, 2H), 4.37-4.39 (d, J=6.74 Hz, 1H), 6.43 (s, 1H), 6.44 (s, 1H), 6.68 (d, J=3.71 Hz, 1H), 7.71-7.72 (d, J=3.84 Hz, 1H), 8.66 (s, 1H)

5g: 4-Chloro-7-[(2R)-2-deoxy-2-fluoro-3,5-O-(1,3-diyl-1,1,3,3-tetraisopropyldisiloxane)-2-C-trimethyl-silylethynyl-β-D-erythro-pentofuranosyl]pyrrolo[2,3-d]pyrimidine 5g was synthesized from 4g as described for 5a. Yellow oil. Molecular formula $C_{28}H_{45}ClFN_3O_5Si_3$. $^1H$ NMR (DMSO-$d_6$, 400 MHz) δ (ppm) 0.33 (s, 9H), 1.02-1.13 (m, 28H), 4.0-4.03 (d, J=13.42 Hz, 1H), 4.12-4.14 (d, J=9.43 Hz, 1H), 4.27-4.31 (d, J=14.00 Hz, 1H), 4.71 (brs, 1H), 6.58-6.62 (d, J=17.07 Hz, 1H), 6.82-6.83 (d, J=3.80 Hz, 1H), 7.72 (d, J=3.80 Hz, 1H), 8.69 (s, 1H) $^{19}F$ NMR (DMSO-$d_6$, 235 MHz) δ (ppm) −159.6 (s, 1F)

6g: 4-Chloro-7-[(2R)-2-deoxy-2-C-ethynyl-2-fluoro-β-D-erythro-pentofuranosyl]pyrrolo[2,3-d]pyrimidine 6g was synthesized from 5g as described for 6a. Yellow oil. Molecular Formula $C_{13}H_{11}ClFN_3O_3$. $^1H$ NMR (DMSO-$d_6$, 400 MHz) δ (ppm) 3.60-3.65 (d, J=5.44 Hz, 1H), 3.68-3.71 (d, J=12.35 Hz, 1H), 3.85-3.88 (d, J=12.35 Hz, 1H), 3.95-3.97 (d, J=8.90 Hz, 1H), 4.46-4.54 (dd, J=23.23 Hz and J=9.39 Hz, 1H), 5.38 (s, 1H), 6.28 (s, 1H), 6.57-6.61 (d, J=16.47 Hz, 1H), 6.79 (d, J=3.82 Hz, 1H), 8.04 (d, J=3.78 Hz, 1H), 8.70 (s, 1H) $^{19}F$ NMR (DMSO-$d_6$, 235 MHz) δ (ppm) −158.30 (s, 1F). Scan ES$^+$ 312 (M+H)$^+$. Scan ES$^-$ 356 (M+HCO$_2$)$^-$.

7l: 4-Amino-7-[(2R)-2-deoxy-2-C-ethynyl-2-fluoro-β-D-erythro-pentofuranosyl]pyrrolo[2,3-d]pyrimidine 7l was synthesized from 6g as described for 6a. White lyophilised powder. Molecular Formula $C_{13}H_{13}FN_4O_3$. $^1H$ NMR (DMSO-$d_6$, 400 MHz) δ (ppm) 3.61 (d, J=5.52 Hz, 1H), 3.63-3.67 (m, 1H), 3.80-3.83 (d, J=12.14 Hz, 1H), 3.86-3.88 (d, J=9.38 Hz, 1H), 4.46-4.54 (dd, J=23.23 Hz and J=9.39 Hz, 1H), 5.30 (brs, 1H), 6.1 (brs, 1H), 6.41-6.47 (d, J=16.47 Hz, 1H), 6.57-6.61 (d, J=16.47 Hz, 1H), 7.04 (s, 2H), 7.37-7.38 (d, J=3.65 Hz, 1H), 8.05 (s, 1H) $^{19}F$ NMR (DMSO-$d_6$, 235 MHz) δ (ppm) −157.15 (s, 1F) Scan ES$^+$ 293 (M+H)$^+$, UV $\lambda_{max}$ 275 nm

23: 9-[(2R)-2-Deoxy-3,5-di-O-isobutyryl-2-C-ethynyl-2-fluoro-β-D-erythro-pentofuranosyl]-guanine A solution of 9-[(2R)-2-Deoxy-2-C-ethynyl-2-fluoro-β-D-erythro-furanosyl]-guanine (0.16 mmol), 4-dimethylaminopyridine (0.01 mmol), triethylamine (0.48 mmol) and isobutyric anhydride (0.48 mmol), in acetonitrile (1 ml) was stirred at room temperature for 6 hours. The reaction mixture was hydrolysed with a NaHCO$_3$ saturated solution. Ethyl acetate was added. The organic phase was separated, washed with NaCl saturated solution, dried over Na$_2$SO$_4$, filtered and concentrated under reduced pressure. The crude material was purified by flash column chromatography (DCM/EtOH) to yield the title compound White powder. Molecular Formula $C_{20}H_{24}FN_5O_6$ $^1H$ NMR (DMSO-$d_6$, 400 MHz) δ (ppm) 1.02-1.22 (m, 12H), 2.53-2.59 (m, 1H), 2.65-2.70 (m, 1H), 4.04 (d, J=4.77 Hz, 1H), 4.35-4.40 (m, 3H), 5.88-5.94 (dd, J=9.39 Hz and J=8.21 Hz, 1H), 6.21-6.25 (d, J=17.28 Hz, 1H), 6.58 (s, 2H), 7.09 (s, 1H), 10.82 (s, 1H). Scan ES$^+$ 450.0 (M+H)$^+$, UV $\lambda_{max}$ 251 nm

24: N-2-Isobutyryl-9-[(2R)-2-deoxy-3,5-di-O-isobutyryl-2-C-ethynyl-2-fluoro-β-D-erythro-pentofuranosyl]-guanine 24 was obtained from the purification of 23. White powder. Molecular Formula $C_{24}H_{30}FN_5O_7$ $^1H$ NMR (DMSO-$d_6$, 400 MHz) δ (ppm) 1.02-1.22 (m, 18H), 2.53-2.59 (m, 1H), 2.65-2.70 (m, 1H), 2.74-2.80 (m, 1H), 4.04 (d, J=4.90 Hz, 1H), 4.35-4.40 (m, 3H), 5.73-5.80 (dd, J=10.14 Hz and J=7.80 Hz, 1H), 6.29-6.34 (d, J=17.36 Hz, 1H), 8.23 (s, 1H), 11.80 (brs, 1H), 12.3 (brs, 1H). Scan ES$^+$ 520 (M+H)$^+$, UV $\lambda_{max}$ 257 nm

4f: 5-Fluoro-1-[3,5-O-(1,3-diyl-1,1,3,3-tetraisopropyldisiloxane)-2-C-trimethylsilylethynyl-β-D-arabino-furanosyl]uracile 4f was synthesized from 3f as described for 4a. Orange solid. Molecular Formula $C_{26}H_{45}FN_2O_7Si_3$ $^1H$ NMR (DMSO-$d_6$, 400 MHz) δ (ppm) 0.13 (s, 9H), 0.94-1.06 (m, 28H), 3.75 (m, 1H), 3.96-4.09 (m, 3H), 5.99 (d, J=1.53 Hz, 1H), 6.53 (s, 1H), 7.58-7.60 (d, J=6.76 Hz, 1H), 11.8 (brs, 1H) Scan ES$^-$ 599 (M−H)$^-$, UV $\lambda_{max}$ 271 nm

5f: 5-Fluoro-1-[(2R)-2-deoxy-2-fluoro-3,5-O-(1,3-diyl-1,1,3,3-tetraisopropyldisiloxane)-2-C-trimethyl-silylethynyl-β-D-erythro-pentofuranosyl]uracile 5f was synthesized from 4f as described for 5a. White solid. Molecular Formula $C_{26}H_{44}F_2N_2O_6Si_3$. $^1H$ NMR (DMSO-$d_6$, 400 MHz) δ (ppm) 0.13 (s, 9H), 0.94-1.06 (m, 28H), 3.92-3.95 (d, J=12.47 Hz, 1H), 3.96-4.09 (m, 1H), 4.21 (d, J=12.22 Hz, 1H), 5.20 (brs, 1H), 6.10-6.15 (d, J=16.53 Hz, 1H), 7.56 (s, 1H), 12.23 (brs, 1H) $^{19}F$ NMR (DMSO-$d_6$, 235 MHz) δ (ppm) −160.06 (s, 1F), −165.94 (s, 1F) Scan ES$^+$ 603 (M−H)$^+$, UV $\lambda_{max}$ 272 nm

6f: 5-Fluoro-1-[(2R)-2-deoxy-2-C-ethynyl-2-fluoro-β-D-erythro-pentofuranosyl]uracile 6f was synthesized from 5f as described for 6a. White solid. Molecular Formula $C_{11}H_{10}F_2N_2O_5$. $^1H$ NMR (DMSO-$d_6$, 400 MHz) δ (ppm) 3.61-3.64 (d, J=12.55 Hz, 1H), 3.81-3.85 (m, 2H), 4.11 (d, J=4.91 Hz, 1H), 4.14-4.20 (m, 1H), 5.50 (s, 1H), 6.04-6.09 (d, J=16.91 Hz, 1H), 6.20 (d, J=7.64 Hz, 1H), 8.29 (d, J=7.09 Hz, 1H), 12.05 (s, 1H) $^{19}F$ NMR (DMSO-$d_6$, 235 MHz) δ (ppm) −158.74 (s, 1F), −166.27 (s, 1F) Scan ES$^+$ 289.0 (M−H)$^+$, UV $\lambda_{max}$ 270 nm.

11f: 1-[(2R)-2-deoxy-2-C-ethynyl-2-fluoro-β-D-eryhro-pentofuranosyl]-5-fluorouracil-5'-yl-bis(S-pivaloyl-2-thioethylphosphate)

11f was synthesized from 6f as described 9k. White solid. Molecular Formula $C25H_{35}F_2N_2O_{10}PS_2$. $^1H$ NMR (DMSO-$d_{6+D2O}$, 400 MHz) δ (ppm) 1.15-1.17 (m, 18H), 3.10 (t, J=6.40 Hz, 4H), 4-4.08 (m, 5H), 4.19 (d, J=5.39 Hz, 1H), 4.24-4.39 (m, 3H), 6.12 (d, J=16.82 Hz, 1H), 6.39 (d, J=6.07 Hz, 1H), 7.86 (brs, 1H), 12.12 (brs, 1H).

28: 9-[(2R)-2,3-dideoxy-2-C-ethynyl-2-fluoro-β-D-glycero-pentofuranosyl]-guanine 5'-triphosphate sodium 28 was synthesized from 16 as described for 27i. White powder. Molecular Formula $C_{12}H_{12}FN_5Na_3O_{12}P_3$. $^1$H NMR ($D_2O$, 400 MHz) δ(ppm) 2.61-2.72 (m, 2H), 2.95-2.96 (m, 1H), 4.16-4.22 (m, 1H), 4.35-4.40 (m, 1H), 4.6-4.7 (m, 1H), 6.17 (d, J=16 Hz, 1H), 8.02 (s, 1H). $^{19}$F NMR ($D_2O$, 235 MHz) δ (ppm) (-138.95)-(-138.74) (m, 1F), $^{31}$P NMR ($D_2O$, 162 MHz) δ (ppm) -10.66 (d, J=19.44 Hz, 1P), -11.14 (d, J=19.44 Hz, 1P), -22.82 (t, J=19.44 Hz, 1P). Scan $ES^+$ 599.6 $(M-3Na)^{3+}$, UV $λ_{max}$ 253 nm.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed is:

1. A method for the treatment of a host infected with a Flaviviridae virus or hepatitis B virus, comprising administering an effective treatment amount of a compound of formula:

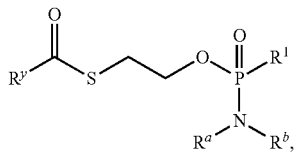

or a pharmaceutically acceptable salt, a tautomeric or polymorphic form thereof, wherein:
  $R^y$ is optionally substituted alkyl, alkenyl, alkynyl, aryl, arylalkyl, cycloalkyl, cycloalkenyl, hydroxyalkyl, amino, heterocyclyl or heteroaryl;
  $R^a$ and $R^b$ are selected as follows:
    i) $R^a$ and $R^b$ are each independently hydrogen or optionally substituted alkyl, carboxyalkyl, hydroxyalkyl, hydroxyarylalkyl, acyloxyalkyl, aminocarbonylalkyl, alkoxycarbonylalkyl, aryl, arylalkyl, cycloalkyl, heteroaryl or heterocyclyl; or
    ii) $R^a$ and $R^b$ together with the nitrogen atom on which they are substituted form a 3-7 membered heterocyclic or heteroaryl ring; and
  $R^1$ is ribavirin, viramidine, valopicitabine, 2'-β-methyl-cytidine, 2'-β-methyl-guanosine, 2'-β-methyl-uridine, 2'-β-methyl-thymidine, 2'-β-methyl-adenosine, 2'-β-methyl-inosine, L-ddA, PSI-6130, MK-0608, resiquimod, celgosivir, lamivudine, entecavir, telbivudine, racivir, emtricitabine, clevudine, amdoxovir, or valtorcitabine.

2. The method of claim 1, wherein the virus is hepatitis C.
3. The method of claim 2, wherein the host is a human.
4. The method of claim 2 wherein the compound is

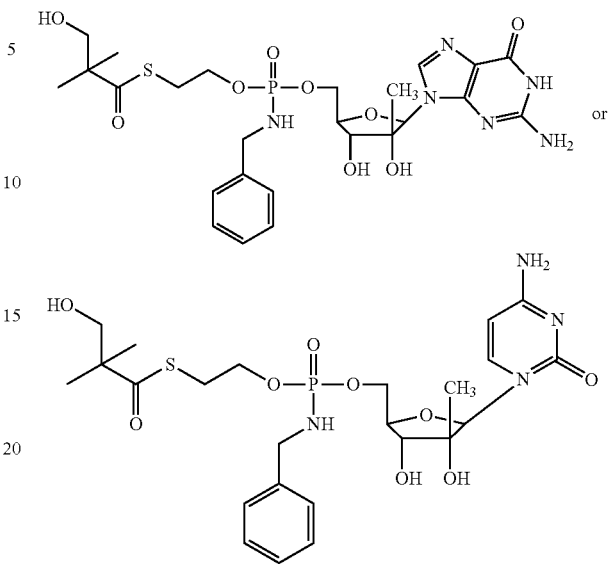

or a pharmaceutically acceptable salt thereof.

5. The method of claim 2, wherein said administration directs a substantial amount of said compound or pharmaceutically acceptable salt thereof to the liver of said host.

6. The method of claim 2, wherein said compound or pharmaceutically acceptable salt thereof is administered in combination or alternation with an interferon, a ribavirin, an interleukin, a NS3 protease inhibitor, a cysteine protease inhibitor, a phenanthrenequinone, a thiazolidine derivative, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, or a ribozyme.

7. The method of claim 5, wherein said compound or pharmaceutically acceptable salt thereof is administered in combination or alternation with an interferon, a ribavirin, an interleukin, a NS3 protease inhibitor, a cysteine protease inhibitor, a phenanthrenequinone, a thiazolidine derivative, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, or a ribozyme.

8. The method of claim 7, wherein the interferon is pegylated interferon alpha 2a, interferon alphacon-1, natural interferon, albuferon, interferon beta-1a, omega interferon, interferon alpha, interferon gamma, interferon tau, interferon delta or interferon γ-1b.

9. The method of claim 5, wherein the host is a human.

10. The method of claim 9, wherein said administration directs a substantial amount of said compound or pharmaceutically acceptable salt thereof to the liver of said host.

11. The method of claim 1, comprising treating a human host infected with hepatitis B virus.

12. A method for the treatment of a host infected with a Flaviviridae virus or hepatitis B virus, comprising administering an effective treatment amount of a compound of formula:

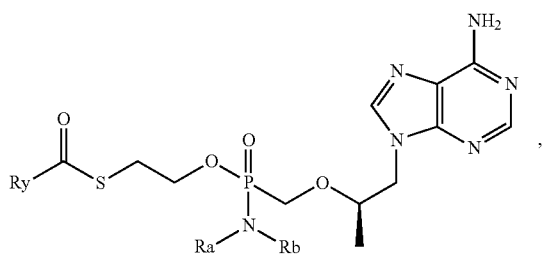

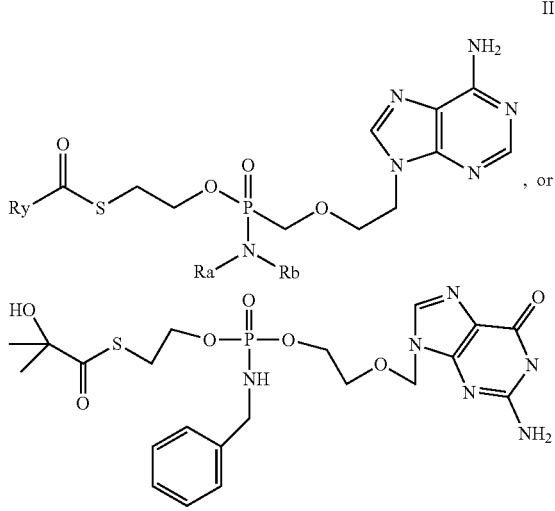

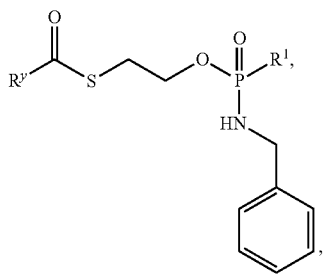

wherein $R^y$ is hydroxyalkyl or —C(CH$_3$)$_2$CH$_2$OH; and $R^a$ and $R^b$ are independently hydrogen, alkyl, substituted alkyl, benzyl or substituted benzyl;

and wherein optionally said compound or pharmaceutically acceptable salt thereof is administered in combination or alternation with interferon alfa-2b, Peginterferon alfa-2a, lamivudine, entecavir, telbivudine, racivir, emtricitabine, clevudine, amdoxovir, valtorcitabine, tenofovir or adefovir.

13. The method of claim 12, wherein said administration directs a substantial amount of said compound or pharmaceutically acceptable salt thereof to the liver of said host.

14. The method of claim 1, wherein the compound is administered in combination or alternation with ribavirin.

15. The method of claim 14, wherein the compound has the formula:

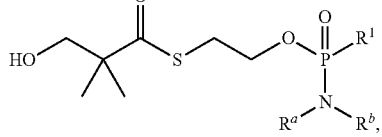

or a pharmaceutically acceptable salt, a tautomeric or polymorphic form thereof.

16. The method of claim 14, wherein the compound has the formula:

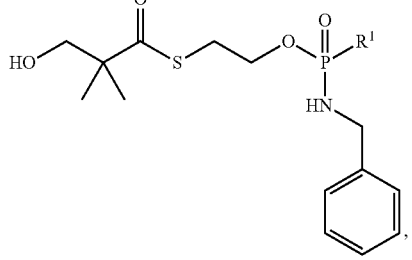

or a pharmaceutically acceptable salt, a tautomeric or polymorphic form thereof.

17. The method of claim 14, wherein the compound has the formula:

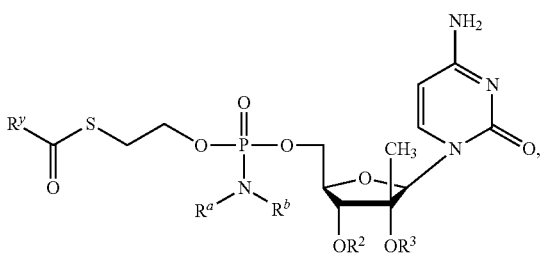

or a pharmaceutically acceptable salt, a tautomeric or polymorphic form thereof.

18. The method of claim 1, wherein the compound has the formula:

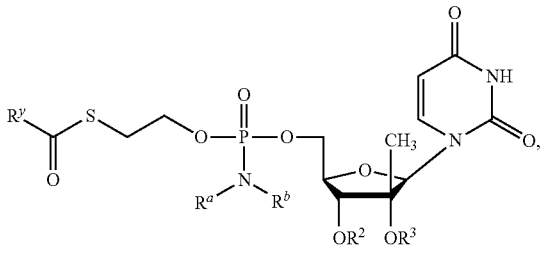

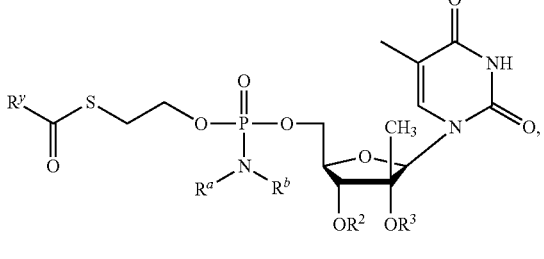

-continued

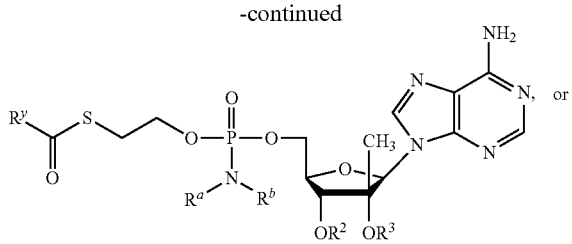

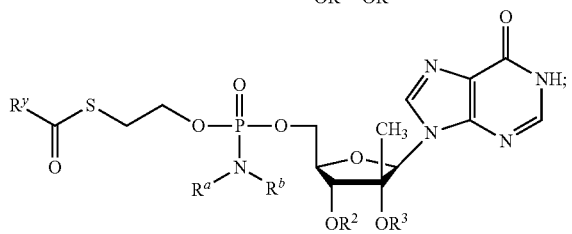

wherein $R^2$ and $R^3$ are each independently H, or $R^2$ and $R^3$ are linked to form a cyclic group by an alkyl, ester or carbamate linkage;
or a pharmaceutically acceptable salt, a tautomeric or polymorphic form thereof.

19. The method of claim 14 having the formula:

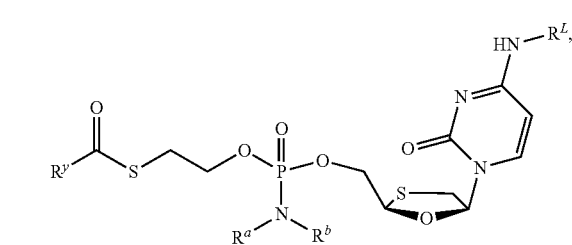

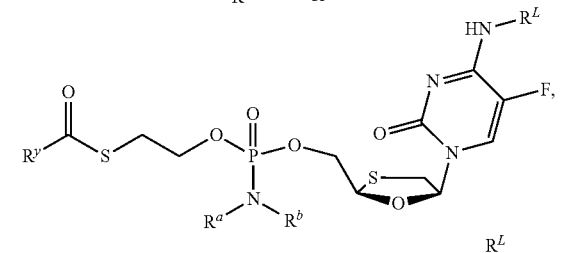

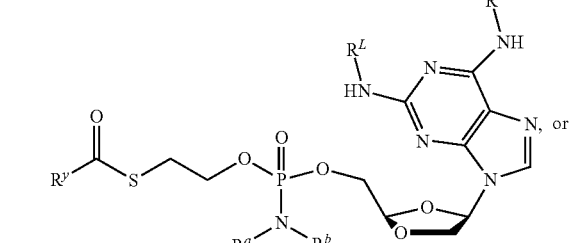

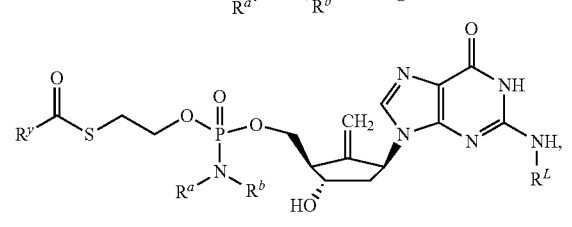

wherein
each $R^L$ is independently H, carbamyl, straight chained, branched or cyclic alkyl; acyl; CO-alkyl, CO-aryl, CO-alkoxyalkyl, CO-aryloxyalkyl, CO-substituted aryl, sulfonate ester, a lipid, an amino acid; an amino acid residue; or a carbohydrate;
or a pharmaceutically acceptable salt, a tautomeric or polymorphic form thereof.

20. The method of claim 1, wherein the compound is selected from:

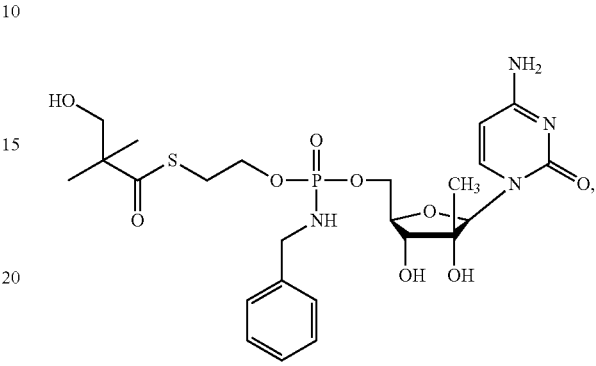

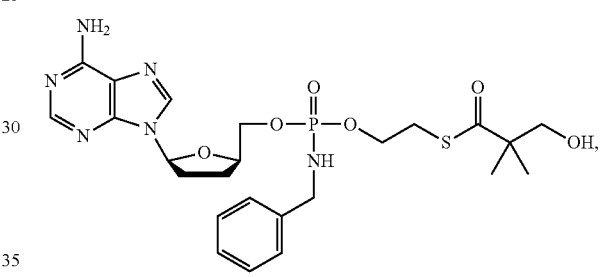

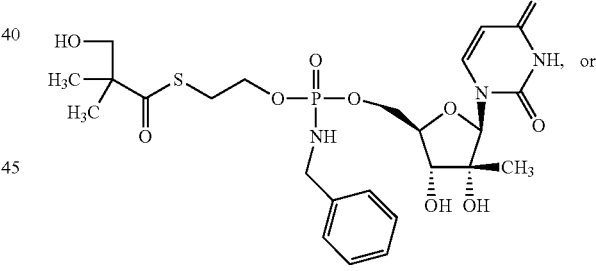

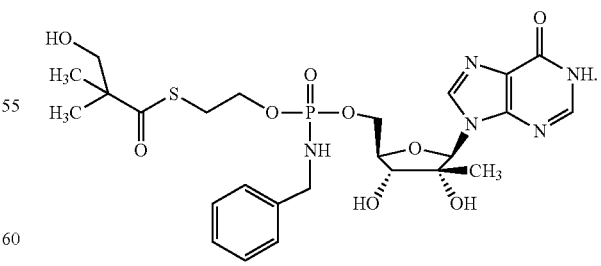

21. The method of claim 20, wherein the virus is hepatitis C.

22. The method of claim 21, wherein the host is a human.

23. The method of claim 12, wherein the compound has the formula:
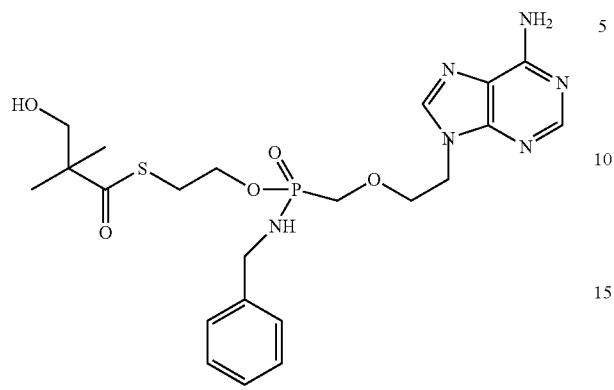
or a pharmaceutically acceptable salt thereof.
* * * * *